United States Patent
Swinnen et al.

(10) Patent No.: US 7,947,851 B2
(45) Date of Patent: May 24, 2011

(54) 1,1'-(1,2-ETHYNEDIYL)BIS-BENZENE DERIVATIVES AS PTP 1-B INHIBITORS

(75) Inventors: Dominique Swinnen, Beaumont (FR); Catherine Jorand-Lebrun, Contamine-Sarzin (FR); Patrick Gerber, Etoy (CH); Jerome Gonzalez, Annemasse (FR); Agnes Bombrun, Chambesy (CH)

(73) Assignee: Merck Serono SA, Vaud (CH)

( * ) Notice: Subject to any disclaimer, the term of this patent is extended or adjusted under 35 U.S.C. 154(b) by 848 days.

(21) Appl. No.: 11/547,861

(22) PCT Filed: Mar. 29, 2005

(86) PCT No.: PCT/EP2005/051426
§ 371 (c)(1),
(2), (4) Date: Nov. 26, 2007

(87) PCT Pub. No.: WO2005/097773
PCT Pub. Date: Oct. 20, 2005

(65) Prior Publication Data
US 2009/0029903 A1    Jan. 29, 2009

Related U.S. Application Data

(60) Provisional application No. 60/566,280, filed on Apr. 29, 2004.

(30) Foreign Application Priority Data

Apr. 7, 2004   (EP) .................................... 04101445

(51) Int. Cl.
| C07D 333/34 | (2006.01) |
| C07C 65/03 | (2006.01) |
| C07C 211/44 | (2006.01) |
| C07C 233/65 | (2006.01) |
| C07C 311/15 | (2006.01) |
| A61K 31/165 | (2006.01) |
| A61P 3/10 | (2006.01) |

(52) U.S. Cl. ......... 562/458; 562/422; 514/595; 514/576
(58) Field of Classification Search ........................ None
See application file for complete search history.

(56) References Cited

U.S. PATENT DOCUMENTS

| 4,439,617 A | 3/1984 | Sestanj et al. |
| 4,927,831 A | 5/1990 | Malamas |
| 6,479,524 B1 * | 11/2002 | Priepke et al. ................. 514/352 |

FOREIGN PATENT DOCUMENTS

| WO | WO 98/16503 | 4/1998 |
| WO | WO 00/15213 | 3/2000 |
| WO | 00 35859 | 6/2000 |
| WO | 02 04459 | 1/2002 |
| WO | 03 032999 | 4/2003 |
| WO | 03 064376 | 8/2003 |

OTHER PUBLICATIONS

Rexford S. Ahima, et al., "LEPTIN", Annu. Rev. Physiol., vol. 62, 2000, pp. 413-437.
Jeffery D. Bjorge, et al., "Identification of Protein-tyrosine Phosphatase 1B as the Major Tyrosine Phosphatase Activity Capable of Dephosphorylating and Activating c-Src in Several Human Breast Cancer Cell Lines", The Journal of Biological Chemistry, vol. 275, No. 52, Dec. 29, 2000, pp. 41439-41446.
Alan Cheng, et al., "Attenuation of Leptin Action and Regulation of Obesity by Protein Tyrosine Phosphatase 1B" Developmental Cell, vol. 2, Apr. 2002, pp. 497-503.
Ralph A. Defronzo, et al., "Insulin Resistance A Multifaceted Syndrome Responsible for NIDDM, Obesity, Hypertension, Dyslipidemia, and Atherosclerotic Cardiovascular Disease", Diabetes Care, vol. 14, No. 3, Mar. 1991, pp. 173-194.
Evanthia Diamanti-Kandarakis, et al., "Therapeutic effects of metformin on insulin resistance and hyperandrogenism in polycystic ovary syndrome", European Journal of Endocrinology, vol. 138, 1998, pp. 269-274.
Siegfried E. Drewes, et al., "Reaction of Diazomethane with Quaternary Nitrogen Compounds to form Betaines", J. Chem. Soc. Perkin Trans 1, 1975, pp. 1283-1284.
Andrea Dunaif, "Insulin Resistance and the Polycystic Ovary Syndrome: Mechanism and Implications for Pathogenesis", Endocrine Reviews, vol. 18, No. 6, 1997, pp. 774-800.
Mounib Elchebly, et al., "Modulation of insulin signaling by protein tyrosine phosphatases", J Mol Med, vol. 78, 2000, pp. 473-482.
Adrian Folkes, et al., "Synthesis and in Vitro Evaluation of a Series of Diketopiperazine Inhibitors of Plasminogen Activator Inhibitor-1", Bioorganic & Medicinal Chemistry Letters, vol. 11, 2001, pp. 2589-2592.
R. J. Jarrett, "Cardiovascular Disease and Hypertension in Diabetes Mellitus", Diabetes/Metabolism Reviews, vol. 5, No. 7, 1989, pp. 547-558.

(Continued)

*Primary Examiner* — Daniel M Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

The present invention is related to carboxylic acids of Formula (I) and use thereof for the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). In particular, the present invention is related to the use of carboxylic acids of Formula (I) to modulate, notably to inhibit the activity of PTPs.

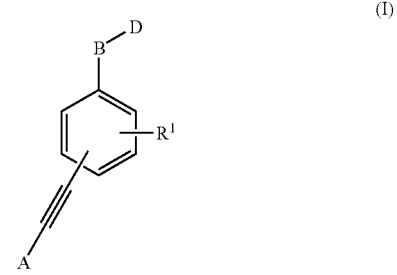

21 Claims, No Drawings

OTHER PUBLICATIONS

Brian P. Kennedy, et al., "Protein Tyrosine Phosphatase-1B in Diabetes", Biochemical Pharmacology, vol. 60, 2000, pp. 877-883.

Lori D. Klaman, et al., "Increased Energy Expenditure, Decreased Adiposity, and Tissue-Specific Insulin Sensitivity in Protein-Tyrosine Phosphatase 1B-Deficient Mice", Molecular and Cellular Biology, vol. 20, No. 15, pp. 5479-5489, year: 2000.

Jonathan H. Marriott, et al., "Synthesis of the farnesyl ether 2,3,5-trifluoro-6-hydroxy-4-[(E,E)-3,7,11-trimethyldodeca-2,6,10-trien-1-yloxy]nitrobenzene, and related compounds containing a substituted hydroxytrifluorophenyl residue: novel inhibitors of protein farnesyltransferase, geranylgeranyltransferase I and squalene synthase", J. Chem. Soc., Perkin Trans. 1, 2000, pp. 4265-4278.

N. Soundararajan, et al., "Descriptive Photochemistry of Polyfluorinated Azide Derivatives of Methyl Benzoate", J. Org. Chem, vol. 55, 1990, pp. 2034-2044.

Mary C. McGuire, et al., "Abnormal Regulation of Protein Tyrosine Phosphatase Activities in Skeletal Muscle of Insulin-Resistant Humans", Diabetes, vol. 40, Jul. 1991, pp. 939-942.

Joseph Meyerovitch, et al., "Hepatic Phosphotyrosine Phosphatase Activity and Its Alterations in Diabetic Rats", J. Clin. Invest, vol. 84, Sep. 1989, pp. 976-983.

Niels Peter Hundahl Møller, et al., "Protein tyrosine phosphatases (PTPs) as drug targets: Inhibitors of PTP-1B for the treatment of diabetes", Current Opinion in Drug Discovery & Development, vol. 3, No. 5, 2000, pp. 527-540.

Purnima Pathre, et al., "PTP1B Regulates Neurite Extension Mediated by Cell-Cell and Cell-Matrix Adhesion Molecules", Journal of Neuroscience Research, vol. 63, 2001, pp. 143-150.

Gerald M. Reaven, et al., "Nonketotic Diabetes Mellitus: Insulin Deficiency or Insulin Resistance?", The American Journal of Medicine, vol. 60, Jan. 1976, pp. 80-88.

Lisa P. Shock, et al., "Protein tyrosine phosphatases expressed in developing brain and retinal Müller glia", Molecular Brain Research, vol. 28, 1995, pp. 110-116.

Janet Sredy, et al., "Insulin Resistance Is Associated With Abnormal Dephosphorylation of a Synthetic Phosphopeptide Corresponding to the Major Autophosphorylation Sites of the Insulin Receptor", Metabolism, vol. 44, No. 8, Aug. 1995, pp. 1074-1081.

Robert W. Stout, "Overview of the Association Between Insulin and Atherosclerosis", Metabolism, vol. 34, No. 12, Dec. 1985, pp. 7-12.

Zhong-Yin Zhang, "Protein tyrosine phosphatases: prospects for therapeutics", Current Opinion in Chemical Biology, vol. 5, 2001, pp. 416-423.

* cited by examiner

1,1'-(1,2-ETHYNEDIYL)BIS-BENZENE DERIVATIVES AS PTP 1-B INHIBITORS

FIELD OF THE INVENTION

The present invention is related to carboxylic acids of formula (I), in particular for the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia, polycystic ovary syndrome (PCOS). The compounds of this invention are particularly useful in the treatment of type II diabetes, obesity or the regulation of appetite. Specifically, the present invention is related to carboxylic acids for the modulation, notably the inhibition of the activity of PTPs, in particular of PTP1B.

BACKGROUND OF THE INVENTION

The prevalence of insulin resistance in glucose intolerant subjects is well known. Reaven et al (*American Journal of Medicine*, 60, 80 (1976)) used a continuous infusion of glucose and insulin (insulin/glucose clamp technique) and oral glucose tolerance tests to demonstrate that insulin resistance exists in a diverse group of non-obese, non-ketotic subjects. These subjects ranged from borderline glucose tolerant to overt, fasting hyperglycemia. The diabetic groups in these studies included both insulin dependent (IDDM) and non-insulin dependent (NIDDM) subjects.

Coincident with sustained insulin resistance is the more easily determined hyperinsulinemia, which may be measured by accurate determination of circulating plasma insulin concentration in the plasma of subjects. Hyperinsulinemia may be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia and insulin resistance with obesity and with ischemic diseases of the large blood vessels (e.g. atherosclerosis) has been well established by numerous experimental, clinical and epidemiological studies (Stout, *Metabolism*, 34, 7 (1985)). Statistically significant plasma insulin elevations at 1 and 2 hours after oral glucose load correlate with an increased risk of coronary heart disease.

Since most of these studies actually excluded diabetic subjects, data relating the risk of atherosclerotic diseases to the diabetic condition are not as numerous, but point in the same direction as for non-diabetic subjects. However, the incidence of atherosclerotic diseases in morbidity and mortality statistics in the diabetic population exceeds that of the nondiabetic population (Pyorala et al; Jarrett *Diabetes/Metabolism Reviews*, 5,547 (1989)).

The association of hyperinsulinemia and insulin resistance with Polycystic Ovary Syndrome (PCOS) is also well acknowledged (Diamanti-Kandarakis et al.; Therapeutic effects of metformin on insulin resistance and hyperandrogenism in polycystic ovary syndrome; *European Journal of Endocrinology* 138, 269-274 (1998), Andrea Dunaif; Insulin Resistance and the Polycystic Ovary Syndrome: Mechanism and Implications for Pathogenesis; *Endocrine Reviews* 18(6), 774-800 (1997)).

The independent risk factors obesity and hypertension for atherosclerotic diseases are also associated with insulin resistance. Using a combination of insulin/glucose clamps, tracer glucose infusion and indirect calorimetry, it was demonstrated that the insulin resistance of essential hypertension is located in peripheral tissues (principally muscle) and correlates directly with the severity of hypertension (DeFronzo and Ferrannini, *Diabetes Care*, 14, 173 (1991)). In hypertension of obese people, insulin resistance generates hyper-insulinemia, which is recruited as a mechanism to limit further weight gain via thermogenesis, but insulin also increases renal sodium re-absorption and stimulates the sympathetic nervous system in kidneys, heart, and vasculature, creating hypertension.

It is assumed that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (Mounib Elchebly, Alan Cheng, Michel L. Tremblay; Modulation of insulin signaling by protein tyrosine phosphatases; *J. Mol. Med.* 78, 473-482 (2000)).

Protein-tyrosine phosphatases (PTPs) play an important role in the regulation of phosphorylation of proteins and represent the counterparts of kinases. Among classical PTPs, there are two types: (i) non-receptor or intracellular PTPs and (ii) receptor-like PTPs. Most intracellular PTPs contain one catalytic domain only, whereas most receptor-like enzymes contain two. The catalytic domain consists of about 250 amino acids (Niels Peter Hundahl Moller et al. Protein tyrosine phosphatases (PTPs) as drug targets: Inhibitors of PTP-1B for the treatment of diabetes; *Current Opinion in Dog Discovery & Development* 3(5), 527-540 (2000)).

The interaction of insulin with its receptor leads to phosphorylation of certain tyrosine molecules within the receptor protein, thus activating the receptor kinase. PTPs dephosphorylate the activated insulin receptor, attenuating the tyrosine kinase activity. PTPs can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTP-alpha and SH-PTP2 (Lori Klaman et al.; Increased Energy Expenditure, Decreased Adiposity, and Tissue-specific Insulin Sensitivity in Protein-Tyrosine Phosphatase 1B-Deficient Mice; *Molecular and Cellular Biology*, 5479-5489 (2000)).

PTP1B is a member of the PTP family. This 50 kDa protein contains a conserved phosphatase domain at residues 30-278 and is localized to the cytoplasmic face of the endoplasmic reticulum by its C-terminal 35 residues. Its interactions with other proteins are mediated by proline-rich regions and SH2 compatible sequence. PTP1B is believed to act as a negative regulator in insulin signaling.

McGuire et al. (*Diabetes*, 40, 939 (1991)) demonstrated that non-diabetic glucose intolerant subjects possessed significantly elevated levels of PTP activity in muscle tissue vs. normal subjects, and that insulin infusion failed to suppress PTP activity as it did in insulin sensitive subjects.

Meyerovitch et al. (*J. Clinical Invest.*, 84, 976 (1989)) observed significantly increased PTP activity in the livers of two rodent models of IDDM, the genetically diabetic BB rat, and the STZ-induced diabetic rat. Sredy et al. (*Metabolism*, 44, 1074, (1995)) observed similar increased PTP activity in the livers of obese, diabetic ob/ob mice, which represent a typical rodent model of NIDDM.

Zhang et al (*Curr. Opin. Chem. Biol.*, 5(4), 416-23 (2001)) found that PTPs are also implicated in a wide variety of other disorders, including cancer. Bjorge, J. D. et al. (*J. Biol. Chem.*, 275(52), 41439-46 (2000)) indicates that PTP1B is the primary protein-tyrosine phosphatase capable of dephosphorylating c-Src in several human breast cancer cell lines and suggests a regulatory role for PTP1B in the control of c-Src kinase activity.

Pathre et al (*J. Neurosci. Res.*, 63(2), 143-150 (2001)) describes that PTP1B regulates neurite extension mediated by cell-cell and cell-matrix adhesion molecules. Further, Shock L. P et al. (*Mol. Brain. Res.*, 28(1), 110-16 (1995)) demonstrates that a distinct overlapping set of PTPs is expressed in the developing brain and retinal Mueller glia, including 2 novel PTPs that may participate in neural cell communication.

The insulin receptor (IR) is a prototypical tyrosine kinase receptor whose ligand binding and dimerization results in auto-phosphorylation on multiple tyrosines. This is followed by 25 the recruitment and phosphorylation of IRS1-4 (depending on the tissue) and PI3K. Although vanadium-containing compounds have been known since the 19$^{th}$ century to alleviate diabetes, it was understood only recently that these inhibitors stimulate the insulin signaling pathway by blocking PTP action. Evidence for the involvement of the IR (insulin receptor) and IRS-1 in this phenotype was that both proteins show increased tyrosine phosphorylation in the PTP1B-mutated mice. The available data strongly suggest that in particular PTP1B is a promising target for the development of drugs to treat diabetes and obesity (Brian P. Kennedy and Chidambaram Raamachandran; Protein Tyrosine Phosphatase-1B in Diabetes; *Biochemical Pharmacology*, Vol. 60, 877-883, (2000)).

A further protein involved in obesity is Leptin. Leptin is a peptide hormone that plays a central role in feeding and adiposity (Leptin, *Annu. Rev. Physiol.* 62 p. 413-437 (2000) by Ahima R. S. et al.). Recently, it has been suggested that PTP1B negatively regulates leptin signaling, and provides one mechanism by which it may regulate obesity. Further, it is known that pharmacological inhibitors of PTP1B hold promise as an alternative or a supplement to leptin in the treatment of obesity due to leptin resistance (*Developmental Cell.*, vol. 2, p. 497-503 (2002)).

In numerous patent application small molecules have been proposed as inhibitors of PTPs.

Substituted aryl and heteroaryl derivatives of benzamidines and their use as anti-thrombotics are described in WO 00/35859.

Further background art related to the compounds of the present invention are the following references:
WO 00/15213 claiming sulfonamides in the treatment of congestive heart failure.
WO 98/16503 claims sulfonamide MMP inhibitors (anti-inflammatory activity).
WO 03/032999 relates to amide compounds which are said to be MMP-13 inhibitors, useful in the treatment of cancer and arthritis.

SUMMARY OF THE INVENTION

The present invention relates to carboxylic acids of formula (I).

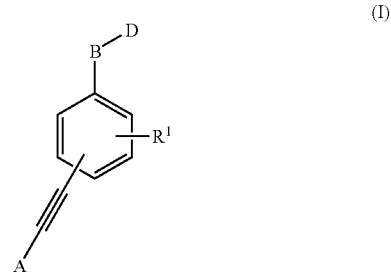

Such compounds are suitable for the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS). In one embodiment, compounds of this invention are inhibitors of PTPs.

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

"PTPs" are protein tyrosine phosphatases or dual specific phosphatases and include for instance PTP1B, TC-PTP, PTP-β, PTP-H1, DEP-1, LAR, SHP-1, SHP-2, GLEPP-1, PTP-μ, VHR, hVH5, LMW-PTP, PTEN, PTP-kappa, Pac-1.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (alkyl, —CH$_2$CH=CH$_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxylic acid" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-hetero)cycloalkyl acyl" refers to 3 to 8 membered cycloalkyl or heterocycloalk groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently is hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —$N^+RR'R''$, where each R, R',R'' is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" optionally substituted with halogens, e.g a —S—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —$NRSO_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_6$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxylic acid", trihalomethyl, cyano, hydroxy, mercapto, nitro, and the like. Alternatively, said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-specified compounds of formula (I). Examples of such salts include, but are not restricted, to base addition salts formed by reaction of compounds of formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), ammonia, or with an organic primary, secondary or tertiary alkyl amine. Amine salts derived from methylamine, dimethylamine, triethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine, arginine, choline, lysine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartric acid, citric acid, succinic acid, malic acid, fumaric acid, maleic acid, ascorbic acid, benzoic acid, tannic acid, palmitic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. Such masking group may be an ester moiety (e.g. obtained by masking a carboxylic acid or an hydroxy moiety of the compounds of formula (I)).

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereoisomers and its racemate forms, as well as pharmaceutically acceptable salts thereof. Preferred pharmaceutically acceptable salts of the formula (I), are base addition salts formed by reaction of compounds of formula (I) with pharmaceutically acceptable bases like N-methyl-D-glucamine, tromethamine, sodium, potassium or calcium salts of carbonates, bicarbonates or hydroxides.

The carboxylic acids according to the present invention are those of formula (I):

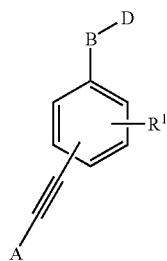

(I)

Formula (I) comprises also the geometrical isomers, the optically active forms, including enantiomers, diastereomers and its racemate forms, as well as pharmaceutically acceptable salts and pharmaceutically active derivatives thereof.

The substituents A, B, D & $R^1$ within formula (I) are defined as follows:

A is selected from the group consisting of substituted or unsubstituted $C_1$-$C_6$-alkyl, substituted or unsubstituted $C_2$-$C_6$-alkenyl, substituted or unsubstituted $C_2$-$C_6$-alkynyl, substituted or unsubstituted $C_1$-$C_6$-alkyl amine, substituted or unsubstituted $C_1$-$C_6$-alkyl alkoxy, substituted or unsubstituted aryl, substituted or unsubstituted heteroaryl; saturated or unsaturated 3-8-membered substituted or unsubstituted cycloalkyl, 3-8-membered substituted or unsubstituted heterocycloalkyl, substituted or unsubstituted $C_1$-$C_6$-alkyl aryl, substituted or unsubstituted $C_1$-$C_6$-alkyl heteroaryl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, substituted or unsubstituted $C_2$-$C_6$-alkynyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl cycloalkyl, substituted or unsubstituted $C_2$-$C_6$-alkenyl heterocycloalkyl, substituted or unsubstituted $C_2$-$C_6$-alkynyl cycloalkyl, substituted or unsubstituted $C_2$-$C_6$-alkynyl heterocycloalkyl.

$R^1$ is selected from the group consisting of H, substituted or unsubstituted $C_1$-$C_6$-alkyl, substituted or unsubstituted $C_1$-$C_6$-alkoxy, halogen. In a specific embodiment $R^1$ is H.

B is either an amine selected from the group consisting of:

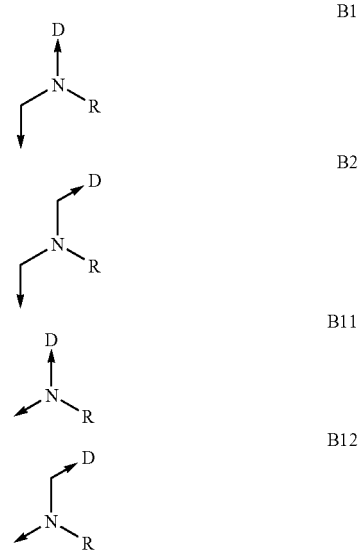

or an ether of the formula

or a carboxamide selected from the group consisting of:

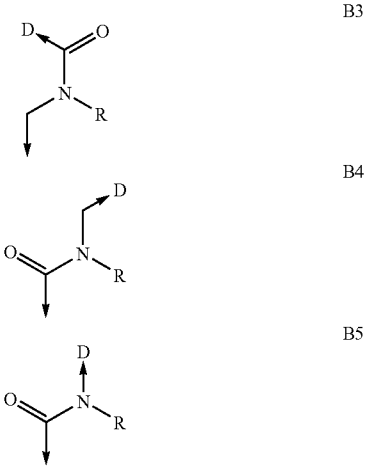

-continued

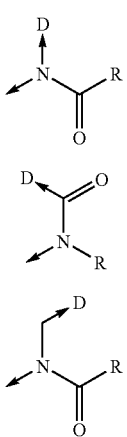

or a sulfonamide selected from the group consisting of:

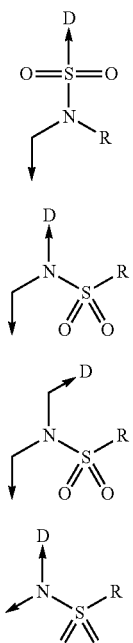

or a urea moiety selected from the group consisting of:

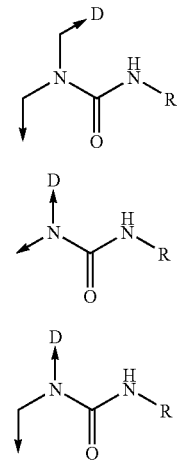

D is either selected from the group consisting of

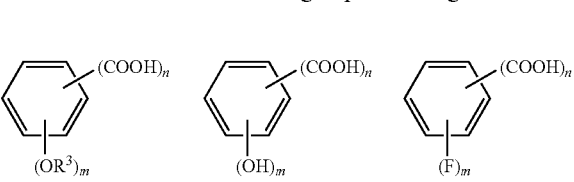

with m being an integer selected from 0, 1 or 2 and n being an integer selected from 1 or 2; or D is

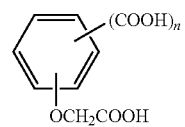

with n being an integer selected from 0 or 1.

R is selected from the group consisting of substituted or unsubstituted $C_1$-$C_8$-alkyl, substituted or unsubstituted $C_2$-$C_6$-alkenyl, substituted or unsubstituted $C_2$-$C_6$-alkynyl, substituted or unsubstituted $C_1$-$C_6$-alkoxy (including ethers or polyethers), substituted or unsubstituted $C_1$-$C_6$-alkyl amine, substituted or unsubstituted $C_1$-$C_6$-alkyl alkoxy, substituted or unsubstituted aryl, substituted or unsubstituted heteroaryl, saturated or unsaturated 3-8-membered substituted or unsubstituted cycloalkyl, 3-8-membered substituted or unsubstituted heterocycloalkyl, substituted or unsubstituted $C_1$-$C_6$-alkyl aryl (e.g. a benzyl group), substituted or unsubstituted $C_1$-$C_6$-alkyl heteroaryl, substituted or unsubstituted $C_2$-$C_6$-alkenyl aryl, substituted or unsubstituted $C_2$-$C_6$-alkenyl heteroaryl, substituted or unsubstituted $C_2$-$C_6$-alkynyl aryl, substituted or -unsubstituted $C_2$-$C_6$-alkynyl heteroaryl, substituted or unsubstituted $C_1$-$C_6$-alkyl cycloalkyl, substituted or unsubstituted $C_1$-$C_6$-alkyl heterocycloalkyl, substituted or unsubstituted $C_2$-$C_6$-alkenyl cycloalkyl, substituted or unsubstituted $C_2$-$C_6$-alkenyl heterocycloalkyl, substituted or unsubstituted $C_2$-$C_6$-alkynyl cycloalkyl, substituted or unsubstituted $C_2$-$C_6$-alkynyl heterocycloalkyl.

Where the moiety B is an amide B3, R could not be a phenyl—optionally fused with a heterocycloalkyl -substituted by one or 2 moieties selected from hydroxy, $C_1$-$C_6$ alkyl, carboxy, $C_1$-$C_6$ alkoxy, $C_1$-$C_3$ alkyl carboxy, $C_2$-$C_3$ alkenyl carboxy, $C_2$-$C_3$ alkynyl carboxy or amino.

$R^3$ is H, or $C_1$-$C_6$-alkyl.

Said aryl or heteroaryl moieties include phenyl, naphthyl, phenantrenyl, pyrrolyl, furyl, thienyl, imidazolyl, pyridyl, oxazolyl, isoxazolyl, thiazolyl, isothiazolyl, pyrazolyl, 1,2,3-triazolyl, 1,2,4-triazolyl, 1,2,3-oxadiazolyl, benzo(1,2,5)oxadiazolyl, 1,2,4-oxadiazolyl, 1,2,5-oxadiazolyl, 1,3,4-oxadiazolyl, tetrazolyl, 1,3,4-triazinyl, 1,2,3-triazinyl, benzopyrimidinyl, benzodioxolyl, benzofuryl, [2,3-dihydro]benzofuryl, isobenzofuryl, benzothienyl, indazolyl, benzotriazolyl, isobenzothienyl, indolyl, isoindolyl, 3H-indolyl, benzimidazolyl, benzothiazolyl, benzoxazolyl, pyridazinyl, pyrimidyl, quinolizinyl, quinazolinyl, phthalazinyl, quinoxalinyl, cinnolinyl, napthyridinyl, quinolyl, isoquinolyl, tetrazolyl, 5,6,7,8-tetrahydroquinolyl, 5,6,7,8-tetrahydroisoquinolyl, purinyl, pteridinyl, xanthenyl, benzoquinolyl, oxolanyl, pyrrolidinyl, pyrazolidinyl, 2H-benzo[d]1,3-dioxolenyl, indanyl, imidazolidinyl, 1,2,4-oxadiazolidinyl, 1,2,5-oxadiazolidinyl, 1,3,4-oxadiazolidinyl or isoxazolidinyl.

In a specific embodiment the aryl or heteroaryl moieties are: phenyl, pyridyl, pyrazolyl, benzodioxolyl, benzofuryl, benzothienyl, indazolyl.

Said cycloalkyl moieties include in particular cyclopentyl, or cyclohexyl groups.

A further specific embodiment is related to compounds of formula (I) wherein the substituent ethynyl-A is in the para-position as set out below:

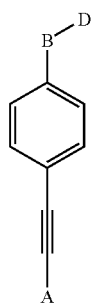

(I)

A specific embodiment consists in carboxylic acid of formula (I) wherein-A is an aryl moiety, in particular a substituted or unsubstituted phenyl group. A specific phenyl would be a phenyl being substituted by a $C_1$-$C_8$-alkyl, more preferably by a $C_1$-$C_4$-alkyl, a halogen or an alkoxy group, e.g. a butyl, trifluoromethyl group or a chlorine.

A further specific embodiment consists in carboxylic acid of formula (I), wherein B is either of

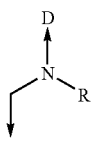

B1

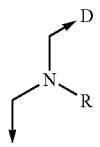

B2

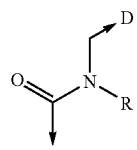

B4

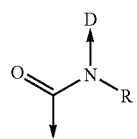

B5

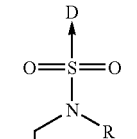

B6

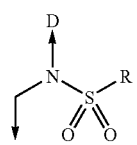

B7

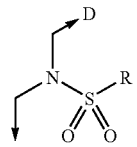

B8

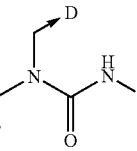

B9

B10

In one embodiment B is either B1 or B2, in particular B1.
In one embodiment B is either of B 12, B 16, B 17, B20 or B22.

A further specific embodiment consists in carboxylic acid of formula (I), wherein D is either of:

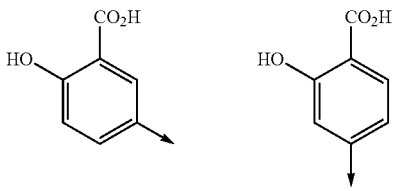

In a further further specific embodiment D is

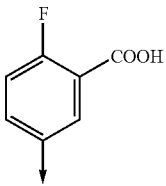

In still a further specific embodiment R is a $C_4$-$C_6$-alkyl, e.g. a hexyl group.

Preferred compounds of the invention are those of formula (I), wherein A is a phenyl group substituted by a $C_1$-$C_4$-alkyl or a halogen, B is either B1, R is a $C_4$-$C_6$-alkyl and D is

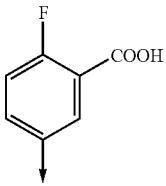

Specific carboxylic acid derivatives according to formula (I) comprise the following:

5-[{4-[(4-Butylphenyl)ethynyl]benzyl}(hexyl)amino]-2-hydroxybenzoic acid, N-methyl-D-glucamine (i.e. 1-deoxy-1-(methylamino)glucitol) salt 5-[{4-[(4-Butylphenyl)ethynyl]benzyl}(hexyl)amino]-2-hydroxybenzoic acid, hydrochloride salt 5-[{4-[(4-Butylphenyl)ethynyl]benzyl}(hexyl)amino]-2-hydroxybenzoic acid, lysine salt 5-({4-[(4-Butylphenyl)ethynyl]benzyl}{[(E)-2-phenylvinyl]sulfonyl}amino)-2-hydroxybenzoic acid 4-({{4-[(4-Butylphenyl)ethynyl]benzyl}[2-(4-chlorophenyl)ethyl]amino}-methyl)benzoic acid, hydrochloride salt {4-[({[(4-tert-Butylphenyl)amino]carbonyl}{4-[(4-butylphenyl)ethynyl]-benzyl}amino)-methyl]phenoxy}acetic acid 5-[{4-[(4-Butylphenyl)ethynyl]benzyl}(3-phenylpropyl)amino]-2-hydroxy-benzoic acid, hydrochloride salt {4-[({4-[(4-Butylphenyl)ethynyl]benzyl}{[(E)-2-phenylvinyl]sulfonyl}-amino)methyl]-phenoxy}acetic acid 5-[{4-[(4-Butylphenyl)ethynyl]benzyl}(1-naphthylmethyl)amino]-2-hydroxybenzoic acid, hydrochloride salt

[4-({{4-[(4-Butylphenyl)ethynyl]benzyl}[(cyclohexylamino)carbonyl]amino}methyl)-phenoxy]acetic acid

[4-({{4-[(4-Butylphenyl)ethynyl]benzyl}[(cyclohexylamino)carbonyl]-amino}methyl)-phenoxy]acetic acid, N-methyl-D-glucamine (i.e. 1-deoxy-1-(methylamino)glucitol) salt

[4-({{4-[(4-Butylphenyl)ethynyl]benzyl}[(propylamino)carbonyl]-amino}methyl)-phenoxy]acetic acid {4-[({4-[(4-Butylphenyl)ethynyl]benzyl}{[(4-cyanophenyl)amino]carbonyl}amino)-methyl]phenoxy}acetic acid 5-((4-tert-Butylbenzyl){4-[(4-butylphenyl)ethynyl]benzyl}amino)-2-hydroxybenzoic acid, hydrochloride salt (4-{[{4-[(4-Butylphenyl)ethynyl]benzyl}(2-thienylsulfonyl)amino]methyl}phenoxy)acetic acid 5-[(1-{-[(4-Butylphenyl)ethynyl]phenyl}pentyl)oxy]-2-hydroxybenzoic acid 7-[(1-{4-[(4-Butylphenyl)ethynyl]phenyl}pentyl)oxy]-2,2-dimethyl-4H-1,3-benzodioxin-4-one, N-methyl-D-glucamine (i.e. 1-deoxy-1-(methylamino)-glucitol) salt (4-{[{4-[(4-Butylphenyl)ethynyl]benzyl}(ethylsulfonyl)amino]-methyl}phenoxy)acetic acid 5-{[{4-[(4-Butylphenyl)ethynyl]benzyl}(hexyl)amino]carbonyl}-2-hydroxy-benzoic acid, N-methyl-D-glucamine (i.e. 1-deoxy-1-(methylamino)-glucitol) salt 5-{[{4-[(4-Butylphenyl)ethynyl]benzoyl}(hexyl)amino]methyl}-2-hydroxybenzoic acid, N-methyl-D-glucamine (i.e. 1-deoxy-1-(methyl-amino)glucitol) salt 5-{[{4-[(4-Butylphenyl)ethynyl]benzyl}(hexyl)amino]sulfonyl}-2-hydroxy-benzoic acid, N-methyl-D-glucamine (i.e. 1-deoxy-1-(methylamino)-glucitol) salt 4-[{4-[(4-Butylphenyl)ethynyl]benzyl}(hexyl)amino]-2-hydroxybenzoic acid, N-methyl-D-glucamine (i.e. 1-deoxy-1-(methylamino)glucitol) salt 5-[{4-[(4-Butylphenyl)ethynyl]benzyl}(hexyl)amino]-2-fluorobenzoic acid 5-[{4-[(4-Butylphenyl)ethynyl]benzyl}(hexyl)amino]-2-fluorobenzoic acid, N-methyl-D-glucamine (i.e. 1-deoxy-1-(methylamino)glucitol) salt 5-{[{2-[(4-Butylphenyl)ethynyl]benzyl}(hexyl)amino]carbonyl}-2-hydroxybenzoic acid 4-((3-Cyclopentylpropyl){4-[(4-fluorophenyl)ethynyl]benzoyl}amino)-2-hydroxybenzoic acid, N-methyl-D-glucamine (i.e. 1-deoxy-1-(methyl-amino)glucitol) salt 4-[{4-[(4-Butylphenyl)ethynyl]benzoyl}(3-cyclopentylpropyl)amino]-2-hydroxybenzoic acid, N-methyl-D-glucamine (i.e. 1-deoxy-1-(methyl-amino)glucitol) salt 5-{[{4-[(4-Fluorophenyl)ethynyl]benzoyl}(hexyl)amino]methyl}-2-hydroxy-benzoic acid, N-methyl-D-glucamine (i.e. 1-deoxy-1-(methylamino)-glucitol) salt 5-{[{4-[(4-Chlorophenyl)ethynyl]benzoyl}(hexyl)amino]methyl}-2-hydroxybenzoic acid, N-methyl-D-glucamine (i.e. 1-deoxy-1-(methyl-amino)glucitol) salt 2-Fluoro-5-{hexyl[4-(phenylethynyl)benzyl]amino}benzoic acid, N-methyl-D-glucamine (i.e. 1-deoxy-1-(methylamino)glucitol) salt 5-({4-[(4-Chlorophenyl)ethynyl]benzyl}(hexyl)amino)-2-hydroxybenzoic acid, N-methyl-D-glucamine (i.e. 1-deoxy-1-(methylamino)glucitol) salt 5-(Hexyl{4-[(4-methoxyphenyl)ethynyl]benzyl}amino)-2-hydroxybenzoic acid, N-methyl-D-glucamine (i.e. 1-deoxy-1-(methylamino)glucitol)salt 5-[Hexyl(4-{[4-(trifluoromethyl)phenyl]ethynyl}benzyl)amino]-2-hydroxybenzoic acid, N-methyl-D-glucamine (i.e. 1-deoxy-1-(methylamino)glucitol)salt 5-[{4-[(4-Butylphenyl)ethynyl]benzyl}(cyclopentylmethyl)amino]-2-fluorobenzoic acid, N-methyl-D-glucamine (i.e. 1-deoxy-1-(methylamino)glucitol)salt 5-[{4-[(4-Butylphenyl)ethynyl]benzyl}(3,3-dimethylbutyl)amino]-2-fluorobenzoic acid, N-methyl-D-glucamine (i.e. 1-deoxy-1-(methylamino)glucitol)salt 5-((Cyclopentylmethyl){4-[(4-metboxyphenyl)ethynyl]benzyl}amino)-2-hydroxybenzoic acid, N-methyl-D-glucamine (i.e. 1-deoxy-1-(methylamino)glucitol)salt 5-({4-[(4-Butylphenyl)ethynyl]benzyl}(ethyl)amino)-2-fluorobenzoic acid, N-methyl-D-glucamine (i.e. 1-deoxy-1-(methylamino)glucitol) salt 5-(Hexyl{4-[(4-propylphenyl)ethynyl]benzyl}amino)-2-hydroxybenzoic acid, N-methyl-D-glucamine (i.e. 1-deoxy-1-(methylamino)glucitol)salt 5-[{4-[(4-Butylphenyl)ethynyl]benzyl}(hexyl)amino]-2-fluorobenzoic acid, lysine salt 5-[{4-[(4-Butylphenyl)ethynyl]benzyl}(hexyl)amino]-2-fluorobenzoic acid, tromethamine (i.e. (2-amino-2-hydroxymethyl)-1,3-propanediol) salt 5-[{4-[(4-Butylphenyl)ethynyl]benzyl}(pentyl)amino]-2-fluorobenzoic acid, N-methyl-D-glucamine (i.e. 1-deoxy-1-(methylamino)glucitol) salt 5-[{4-[(4-Butylphenyl)ethynyl]benzyl}(methyl)amino]-2-fluorobenzoic acid 5-[{4-[(4-Butylphenyl)ethynyl]benzyl}(cyclopropylmethyl)amino]-2-fluorobenzoic acid, N-methyl-D-glucamine (i.e. 1-deoxy-1-(methylamino)glucitol)salt 5-{Butyl[4-(phenylethynyl)benzyl]amino}-2-fluorobenzoic acid, N-methyl-D-glucamine (i.e. 1-deoxy-1-(methylamino)glucitol) salt 2-Fluoro-5-{[4-(phenylethynyl)benzyl](propyl)amino}benzoic acid, N-methyl-D-glucamine (i.e. 1-deoxy-1-(methylamino)glucitol) salt 2-Fluoro-5-[{4-[(4-fluorophenyl)ethynyl]benzyl}(hexyl)amino]benzoic acid, N-methyl-D-glucamine (i.e. 1-deoxy-1-(methylamino)glucitol)salt 2-Fluoro-5-(hexyl{4-[(4-propylphenyl)ethynyl]benzyl}amino)benzoic acid, N-methyl-D-glucamine (i.e. 1-deoxy-1-(methylamino)glucitol)salt 5-[{4-[(4-Butylphenyl)ethynyl]benzyl}[(2-carboxycyclopropyl)methyl]amino}-2-fluorobenzoic acid, N-methyl-D-glucamine (i.e. 1-deoxy-1-(methylamino)glucitol)salt 5-[{4-[(4-Ethylphenyl)ethynyl]benzyl}(hexyl)amino]-2-fluorobenzoic acid, N-methyl-D-glucamine (i.e. 1-deoxy-1-(methylamino)glucitol)salt 5-[{4-[(4-tert-Butylphenyl)ethynyl]benzyl}(hexyl)amino]-2-fluorobenzoic acid, N-methyl-D-glucamine (i.e. 1-deoxy-1-(methylamino)glucitol)salt 5-{[{4-[(4-Butylphenyl)ethynyl]phenyl}(hexyl)amino]methyl}-2-fluorobenzoic acid, N-methyl-D-glucamine (i.e. 1-deoxy-1-(methylamino)glucitol)salt 4-({(3,3-Dimethylbutanoyl)-4-[(4-hexylphenyl)ethynyl]anilino}methyl)-2-hydroxybenzoic acid, N-methyl-D-glucamine (i.e. 1-deoxy-1-(methylamino)glucitol) salt 5-[{4-[(4-Butylphenyl)ethynyl]benzyl}(isobutyl)amino]-2-fluorobenzoic acid, N-methyl-D-glucamine (i.e. 1-deoxy-1-(methylamino)glucitol)salt 5-{[{4-[(4-Butylphenyl)ethynyl]benzyl}(hexyl)amino]carbonyl}-2-fluorobenzoic acid, N-methyl-D-glucamine (i.e. 1-deoxy-1-(methylamino)glucitol)salt 5-[{4-[(4-Butylphenyl)ethynyl]benzoyl}(hexyl)amino]-2-fluorobenzoic acid, N-methyl-D-glucamine (i.e. 1-deoxy-1-(methylamino)glucitol)salt 5-[({4-[(4-Butylphenyl)ethynyl]phenyl}sulfonyl)(hexyl)amino]-2-fluorobenzoic acid, N-methyl-D-glucamine (i.e. 1-deoxy-1-(methylamino)glucitol)salt 5-{[{4-[(4-Butylphenyl)ethynyl]benzoyl}(hexyl)amino]methyl}-2-fluorobenzoic acid, N-methyl-D-glucamine (i.e. 1-deoxy-1-(methylamino)glucitol)salt 5-{[({4-[(4-Butylphenyl)ethynyl]phenyl}sulfonyl)(hexyl)amino]methyl}-2-fluorobenzoic acid 5-{{4-[(4-Butylphenyl)ethynyl]benzyl}[(propylamino)carbonyl]amino}-2-fluorobenzoic acid 5-{{4-[(4-Butylphenyl)ethynyl]benzyl}[(cyclohexylamino)carbonyl]amino}-2-fluorobenzoic acid 4-[{4-[(4-Chlorophenyl)ethynyl]benzoyl}(3-cyclopentylpropyl)amino]-2-hydroxybenzoic acid, N-methyl-D-glucamine (i.e. 1-deoxy-1-(methylamino)glucitol)salt.

The compounds of formula (I) are useful in the treatment and/or prevention of obesity and/or metabolic disorders mediated by insulin resistance or hyperglycemia, comprising diabetes type I and/or II, inadequate glucose tolerance, insulin resistance, hyperlipidemia, hypertriglyceridemia, hypercholesterolemia or polycystic ovary syndrome (PCOS).

In one embodiment the compounds according to formula (I) are particularly useful in the treatment and/or prevention of diabetes type II, obesity and for the regulation of appetite in mammals.

The compounds according to formula (I) are suitable for the modulation of the activity of PTPs, in particular of PTP1B. It is therefore believed that the compounds of the present invention are therefore useful for the treatment and/or prevention of disorders which are mediated by PTPs, in particular of PTP1B. Said treatment involves the modulation—notably the down regulation or the inhibition—of PTPs, particularly of PTP1B and/or GLEPP-1.

The compounds according to formula (I) are also suitable for the treatment and/or prevention of cardiovascular disorders such as coronary obstruction and heart failure, in particular for the treatment and/or prevention of endothelial dysfunction in chronic heart ID failure. The compounds of this invention are particularly useful in the treatment of increased peripheral vasoconstriction in chronic heart failure. Mainly, heart failure is, defined by the inability of the heart to eject blood and to provide adequate perfusion of the peripheral organs. Heart failure does not only affect the myocardium, but also has many consequences on the peripheral circulation. Especially, heart failure is associated with an increased peripheral vascular resistance, secondary to peripheral vasoconstriction. This vasoconstriction is heterogeneous, and mostly affects the 'non essential' territories such as the skin, the intestine and the skeletal muscle, in order to maintain perfusion in the 'essential' territories such as the brain or the heart in a context of decreased cardiac output. However, this initially adaptive mechanism may on the long term increase cardiac afterload (resistance to ventricular contraction) and cardiac work, and thus aggravate contractile dysfunction and contribute to the transition from compensated to decompensated heart failure. Long term impairment or loss of heart muscle activity leads to the development of Chronic Heart Failure (CHF).

A further aspect of the present invention is related to a pharmaceutical composition a comprising a carboxylic acid according to Formula (I) and at least one further drug (in particular an anti-diabetes agent). In one embodiment the further diabetes agents are selected from the group comprising or consisting of insulin (or insulin mimicks), aldose reductase inhibitors, alpha-glucosidase inhibitors, sulfonyl urea agents, biguanides (e.g. metformin), thiazolidiones (e.g. pioglitazone, rosiglitazone) or PPARs agonists, or c-Jun Kinase or GSK-3 inhibitors.

Insulins useful with the method of the present invention include rapid acting insulins, s intermediate acting insulins, long acting insulins and combination of intermediate and rapid acting insulins.

Aldose reductase inhibitors useful in the method of this invention include those known in the art. These include the non-limiting list of:

a) the spiro-isoquinoline-pyrrolidine tetrone compounds disclosed in U.S. Pat. No. 4,927,831 (Malamas), the contents of which are incorporated herein by reference, which includes ARI-509, also known as minalrestat or Spiro[isoquinoline-4(1H), 3'-pyrrolidine]-1,2',3,5'(2H)-tetrone, and analogs thereof, b) 2-[(4-bromo-2-fluorophenyl)methyl]-6-fluoro-(9CI);

c) the compounds of U.S. Pat. No. 4,439,617, the contents of which are incorporated herein by reference, which includes Tolrestat, also known as Glycine, N-[[6-methoxy-5-(trifluoromethyl)-1-naphtalenyl]thioxomethyl]-N-methyl-(9CI) or AY-27773 and analogs thereof;

d) Sorbinil (Registra No. 68367-52-2) also known as Spiro [4H-1-benzopyran-4,4'-imidazoline]-2',5'-dione, 6-fluoro-2,3-dihydro-, (4S)-(9CI) or CP 45634;
e) Methosorbinil;
f) Zopolrestat, which is 1-Phtalazineacetic acid, 3,44-dihydro-4-oxo-3-[[5-(trifluoromethyl)-2-benzothiazolyl]methyl]-(9CI) (Registry No. 110703-94-1);
g) Epalrestat, which is 3-Thiazolidineacetic acid, 5-[(2E)-2-methyl-3-phenyl-2-propenylidene]-4-oxo-2-thioxo-, (5Z)-(9CI) (Registry No. 82150-09-9);
h) Zenarestat (Registry No. 112733-40-6) or 3-[(4-bromo-2-fluorophenyl)-methyl]-7-chloro-3,4-dihydro-2,4-dioxo-1 (2H)-quinazoline acetic acid;
i) Imirestat, also known as 2,7-difluorospiro(9H-fluorene-9, 4'-imnidazolidine)-2',5'-dione;
j) Ponalrestat (Registry No. 72702-95-5), which is 1-Phtalazineacetic acid, 3-[(4-bromo-2-fluorophenyl)methyl]3,4-dihydro-4-oxo-(9CI) and also known as Stalil or Statyl;
k) ONO-2235, which is 3-Thiazolidineacetic acid, 5-[(2E)-2-methyl-3-phenyl-2-propenylidene]-4-oxo-2-thioxo-, (5Z)-(9CI);
l) GP-1447, which is {3-[(4,5,7-trifluorobenzothiazol-2-yl) methyl]-5-methylphenylacetic acid};
m) CT-112, which is 5-(3-ethoxy-4-pentyloxyphenyl)-2,4-thiazolidinedione;
n) BAL-ARI 8, which is Glycine, N[(7-fluoro-9-oxo-9H-xanthen-2-yl)sulfonyl]-N-methyl-)9CI), Reg.No. 124066-40-6));
o) AD-5467, which is 2,3-dihydro-2,8-bis(1-methylethyl)-3-thioxox-4H-1,4-benzoxazine-4-acetic acid of the chloride salt form (4H-1,4-Benzoxazine-4-acetic acid, 2,3-dihydro-2,8-bis(1-methylethyl)-3-thioxo-(9CI);
p) ZD5522, which is (3',5'-dimethyl-4'-nitromethylsulfonyl-2-(2-tolyl)acetanilide);
q) 3,4-dihydro-2,8-diisopropyl-3-thioxo-2H-1,4-benzoxazine-4-acetic acid;
r) 1-[(3-bromo-2-benzofuranyl)sulfonyl]-2,4-imidazolidinedione (M-16209),
s) NZ-314, which is 1-Imidazolidineacetic acid, 3-[(3-nitrophenyl)methyl]-2,4,5-trioxo-9(CI) (Registry No. 128043-99-2),
t) 1-phtalazineacetic acid, 3,4-dihydro-4-oxo-3-[(5-trifluoromethyl)-2-benzothiazolyl]-methyl];
u) M-79175, which is Spiro[4H-1-benzopyran-4,4'-imidazolidine]-2',5'-dione; 6-fluoro-2,3-dihydro-2-methyl-, (2R, 4S)-(9CI);
v) SPR-210, which is 2H-1,4-Benzothiazine-2-acetic acid, 3,4-dihydro-3-oxo-4-[(4,5,7-trifluoro-2-benzothiazolyl) methyl]-(9CI);
w) Spiro[pyrrolidine-3,6'(5'H)-pyrrolo[1,2,3-de][1,4]benzoxazine]-2,5,5'-trione, 8'-chloro-2'-3'-dihydro-(9CI)(also known as AND 138 or 8-chloro-2',3'-dihydrospiro-[pyrolizine-3,6'(5H)-pyrrolo-[1,2,3-de]-[1,4]benzoxazine]2, 5,5'-trione);
x) 6-fluoro-2,3-dihydro-2',5'-dioxo-(2S-cis)-spiro[4H-1-benzopyran-4,4'-imidazolidine]-2-carboxamide (also known as SNK-860);
or a pharmaceutically acceptable salt form of one or more of these compounds.

Among the more preferred aldose reductase inhibitors of this invention are minalrestat, Tolrestat, Sorbinil, Methosorbinil, Zopolrestat, Epalrestat, Zenarestat, Imirestat and Ponalrestat or the pharmaceutically acceptable salt forms thereof.

The alpha-glucosidase inhibitors useful for the method of the present invention include miglitol or acarbose, or the pharmaceutically acceptable salt form thereof.

Sulfonylurea agents useful with the method of the present invention include glipizide, Glyburide (Glibenclamide) Clorpropamide, Tolbutamide, Tolazamide and Glimepiride, or the pharmaceutically acceptable salt forms thereof.

Preferably, said supplementary pharmaceutically active agent is selected from the group consisting of a rapid acting insulin, an intermediate acting insulin, a long acting insulin, a combination of intermediate and rapid acting insulins, Inalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol, Acarbose, Glipizide, Glyburide, Chlorpropamide, Tolbutamide, Tolazamide, or Glimepiride.

Still a further object of the invention is a process for preparing carboxylic acids according to formula I.

The carboxylic acids of the present invention may be prepared from readily available starting materials using the below general methods and procedures. It will be appreciated that where typical or preferred experimental conditions (i.e. reaction temperatures, time, moles of reagents, solvents, etc.) are given, other experimental conditions may also be used, unless otherwise stated. Optimum reaction conditions may vary with the particular reactants or solvents used, but such conditions can be determined by one skilled in the art by routine optimisation procedures.

By the following set out general methods and procedures compounds of formula (I) are obtained.

The carboxylic acid compounds (I) exemplified in this invention may be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but one skilled in the art can determine such conditions by routine optimisation procedures.

In general, the carboxylic acid compounds according to formula (I) of this invention may be prepared from readily available starting materials. If such starting materials are not commercially available, it may be prepared by standard synthetic techniques. The following general methods and procedures described hereinafter in the Examples may be employed to prepare compounds of formula (I).

Generally, carboxylic acid compounds according to formula (I) may be obtained by initial deprotection of the precursors (I') (see Scheme 1 below), wherein B (more specifically $B_{1-22}$), $R^1$ and A are as above defined and the moiety D' is a protected form of D as above defined, for example use of 2,2-dimethyl-4-oxo-4H-1,3-benzodioxin-4-one for D' when D is ortho-hydroxy benzoic acid moiety.

Scheme 1

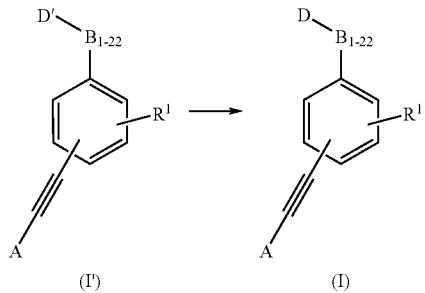

The moiety $B_{1-22}$ is either of the following:
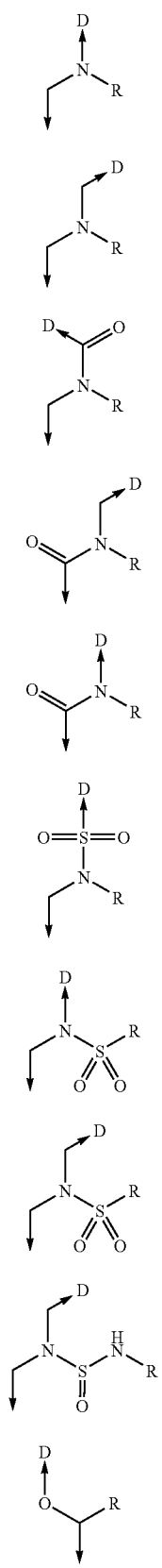
B1
B2
B3
B4
B5
B6
B7
B8
B9
B10
-continued
 B11
 B12
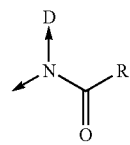 B13
 B14
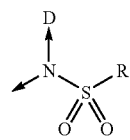 B15
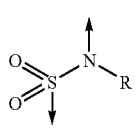 B16
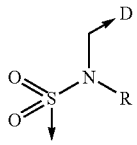 B17
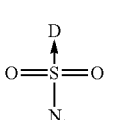 B18
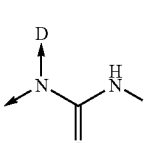 B19
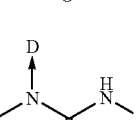 B20
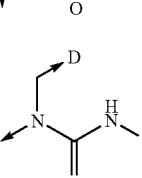 B21

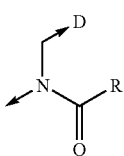
B22

It is recognized by those skilled in the art of organic synthesis that the successful use of these methods and of the methods described below is independent upon the compatibility of substituents on other parts of the molecules. Protecting groups and/or changes in the order of steps described herein may be required.

Those skilled in the art will recognize that certain reactions, for example the preparation of derivatives of formula (II) (Scheme 2), are best carried out when potentially reactive functionality on the molecules is masked or protected, thus avoiding side reactions and/or increasing the yield of the reaction. Examples of protecting groups moieties and all protection and deprotection methods, may be found in Philip J. Kocienski, in "Protecting Groups", Georg Thieme Verlag Stuttgart, New York, 1994 and, Theodora W. Greene and Peter G. M. Wuts in *"Protective Groups in Organic Synthesis"*, $3^{rd}$ edition, John Wiley & Sons Inc., 1999 (NY). The need and choice of protecting groups for a particular reaction is known to those skilled in the art and depends upon the nature of the functional group to be protected (hydroxy, amino, carboxy, etc . . . ), the structure and the stability of the molecule of which the substituent is part of the reaction conditions.

Carboxylic acid derivatives according to formula (I') may be obtained by three different routes. As outlined in Scheme 2, a first route to prepare carboxylic acid derivatives according to formula (I') involves a reductive alkylation by reacting a protected carboxylic acid derivative of formula (II) with an alkylene derivative of formula (III) where FG of derivative (II) being a
  Functional Group FG1 defined as —NH$_2$ (amine) or
  Functional Group FG2 defined as —CH$_2$NH$_2$ (methyleneamine), and FG of derivative (III) being
  Functional Group FG3 defined as —CHO (aldehyde).

The reductive alkylation reaction can be performed by an imine formation in solvents such as toluene under azeotropic removal of water conditions for a few hours, e.g. one hour to 24 hours, followed by reduction reaction with agents such as sodium borohydride, sodium triacetoxyborohydride or sodium cyanoborohydride, preferably sodium borohydride in solvents such as a mixture of toluene and methanol, for a few hours, e.g. one hour to 24 hours, at temperature rising from 0° C. to 50° C. Alternatively the reductive alkylation can be performed in one- or two-step-protocol using agents such as sodium triacetoxyborohydride, sodium cyanoborohydride in solvents such as 1,2-dichloroethane in presence of acetic acid for a few hours, e.g. one hour to 24 hours, at temperature rising from rt to 50° C.

Alternatively derivatives of formula (II) can be substituted by FG3 group and consequently derivatives of formula (III) can be substituted by FG1 or FG2 groups.

Then amine derivatives of formula (IV) can be treated with derivatives of formula (V) to give compounds of formula (I') as shown in Scheme 2. The suitable R' group of derivatives of formula (V) may be chosen by those skilled in the art to prepare the compound of formula (I'). Those skilled in the art may select the adequate R' group to obtain R group as above defined after the reduction step described in the following steps. When derivatives of formula (V) is R'-FG3, reductive alkylation with amino derivatives of formula (IV) can be performed with reducing agents such as sodium triacetoxyborohydride, or sodium cyanoborohydride, preferentially sodium triacetoxyborohydride in solvents such as 1,2-dichloroethane, for a few hours, e.g. one hour to 24 hours, at temperature rising from rt to 70° C. When derivatives of formula (V) is R-FG4 with FG4 is defined as a Leaving Group (LG), e.g. as halogen such as bromide, iodide, chloride, preferentially bromide and chloride or as a sulfonate derivative such as a mesylate or a tosylate derivative, reaction with derivatives of formula (IV) can be performed using sodium hydride in polar aprotic solvents such as DMSO at rt for 2-24 hours. When derivatives of formula (V) are R-FG5 with FG5 is defined as —SO$_2$Cl or R-FG8 with FG8 defined as —COCl, reaction with derivatives of formula (IV) can be performed using a base such as trietoxyl amine, diisopropylethylamine, a polymer supported-amine, e.g. a polymer supported-morpholine, in solvents such as DCM or in pyridine without use of additional base at room temperature for 2-24 hours. When derivatives of formula (V) is R-FG6 with FG6 is defined as R—N=C=O, reaction with derivatives of formula (IV) can be performed with or without a base such as diisopropylethylamine, in solvents such as DCM at rt for 2-24 hours.

Scheme 2

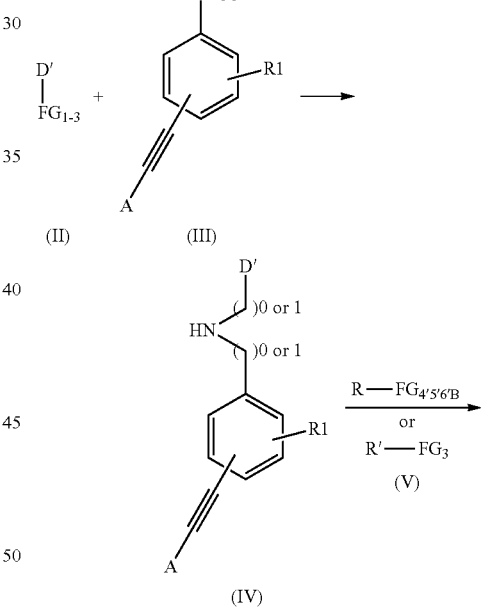

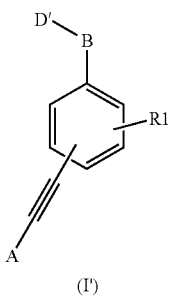

B being either of
B1,B2,B7,B8,B9,B12,B20,B21.B22

A second route to prepare carboxylic acid derivatives according to formula (I') is outlined in Scheme 3. Intermediates of formula (VI) could be obtained by reductive alkylation between a protected carboxylic acid derivative of formula (II) with derivatives of formula (V) where FG of derivative (II) is FG3 and FG of derivative (V) is FG1. The reductive alkylation can be performed in one- or two-step-protocol using reducing agents such as sodium triacetoxyborohydride, sodium cyanoborohydride or sodium borohydride, preferentially sodium triacetoxyborohydride in solvents such as 1,2-dichloroethane in presence of acetic acid for a few hours, e.g. one hour to 24 hours, at rt. Alternatively, the reductive alkylation reaction can be performed by an imine formation in solvents such as toluene under azeotropic removal of water conditions for a few hours, e.g. one hour to 24 hours, followed by reduction reaction with agents such as sodium borohydride, sodium triacetoxyborohydride or sodium cyanoborohydride, preferentially sodium borohydride in solvents such as a mixture of toluene and methanol, for a few hours, e.g. one hour to 24 hours, at temperature rising from 0° C. to 50° C. Alternatively derivatives of formula (II) can be substituted by FG1 or FG2 and consequently derivatives of formula (V) can be substituted by FG3. Alternatively, instead of using a reductive alkylation reaction intermediate of formula (VI) could be prepared in a two-step-protocol by reacting a protected carboxylic acid derivative of formula (II) with a compound of formula (V) to give an amide derivatives of formula (VII), with FG of derivative (II) is FG1 or FG2 and FG of derivative (V) is FG7 defined as —COOH or FG8 defined as —COCl, preferably FG8 in solvents such as DCM in the presence of a base such as diisopropylethylamine for a few hours, e.g. one hour to 24 hours, at temperature rising from 0° C. to rt; followed by reaction with reducing agents such as $BH_3$ in solvents such as THF for a few hours, e.g. one hour to 24 hours, at temperature rising from rt to reflux. Alternatively derivatives of formula (II) can be substituted by FG7 or FG8 and consequently derivatives of formula (V) can be substituted by FG1.

Then derivatives of formula (VI) can be treated with derivatives of formula (III) to give compounds of formula (I') as shown in Scheme 3. When FG substitution of derivatives of formula (III) is FG3, the reductive alkylation with derivatives of formula (VI) can be performed with reducing agents such as sodium triacetoxyborohydride or sodium cyanoborohydride, preferably sodium triacetoxyborohydride in solvents such as 1,2-dichloroethane, for a few hours, e.g. one hour to 24 hours, at temperature rising from rt to is 70° C. When FG substitution of derivatives of formula (III) is FG7, the reaction with derivatives of formula (VI) can be performed with coupling agents such as ED/HOBT in presence of DIEA in solvents such as DCM, for a few hours, e.g. one hour to 24 hours, at temperature rt. When FG substitution of derivatives of formula (III) is FG8 or FG5, the reaction with derivatives of formula (VI) can be performed using a base such as diisopropylethylamine or triethylamine in solvents such as DCM, THF or in pyridine without use of additional base, preferentially in pyridine for a few hours, e.g. one hour to 24 hours, at temperature rising from room temperature to 60° C.

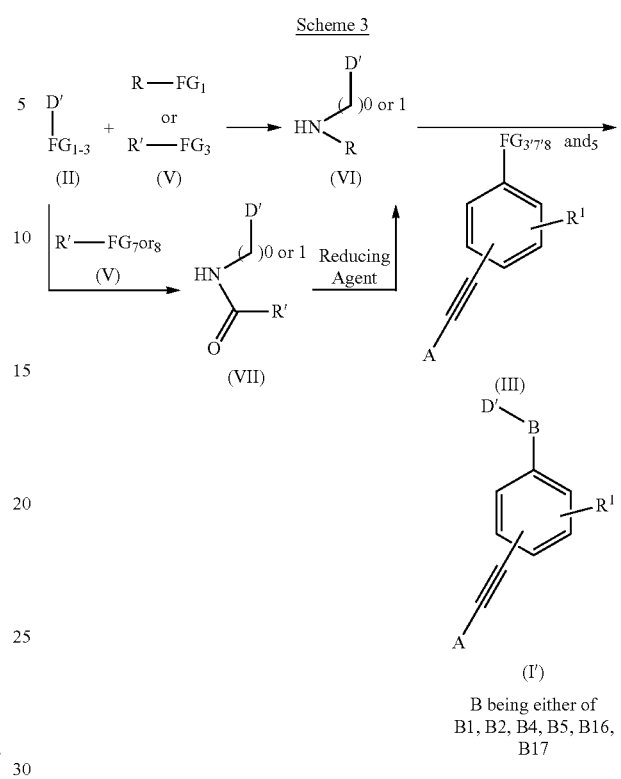

Scheme 3

B being either of B1, B2, B4, B5, B16, B17

A third route to prepare carboxylic acid derivatives according to formula (I') is outlined in Scheme 4. Intermediate of formula (VIII) could be obtained by reductive alkylation between an alkyne derivative of formula (III) with a compound of formula (V), where FG of derivative (III) is FG3 and FG of derivative (V) is FG1. The reductive alkylation can be performed in one- or two-step-protocol using reducing agents such as sodium triacetoxy-borohydride, sodium cyanoborohydride or sodium borohydride, preferably sodium triacetoxyborohydride in solvents such as 1,2-dichloroethane in presence of acetic acid for a few hours, e.g. one hour to 24 hours, at rt. Alternatively, the reductive alkylation reaction can be performed by an imine formation in solvents such as toluene under azeotropic removal of water conditions for a few hours, e.g. one hour to 24 hours, followed by a reduction reaction with agents such as sodium borohydride, sodium triacetoxyborohydride or sodium cyanoborohydride, preferentially sodium borohydride in solvents such as a mixture of toluene and methanol, for a few hours, e.g. one hour to 24 hours, at a temperature rising from 0° C. to 50° C. Alternatively, derivatives of formula (III) can be substituted by FG1 or FG2 and consequently derivatives of formula (V) can be substituted by FG3.

Then derivatives of formula (VIII) can be treated with derivatives of formula (II) to give compounds of formula (I') as shown in Scheme 4. When FG of derivatives of formula (II) is FG3, the reductive alkylation with derivatives of formula (VIII) can be performed with reducing agents such as sodium triacetoxyborohydride or sodium cyanoborohydride, preferably sodium triacetoxy-borohydride in solvents such as 1,2-dichloroethane, for a few hours, e.g. one hour to 24 hours, at temperature rising from rt to 70° C. When FG of derivatives of formula (II) is FG7, the reaction with derivatives of formula (VIII) can be performed with coupling agents such as EDC/HOBT in presence of DIEA in solvents such as DCM, for a few hours, e.g. one hour to 24 hours, at rt. When FG substitution of derivatives of formula (II) is FG8 or FG5, the reaction with derivatives of formula (VIII) can be performed using a base such as diisopropylethylamine or triethylamine in solvents such as DCM, THF or in pyridine without use of additional base, preferentially in pyridine for a few hours, e.g. one hour to 24 hours, at temperature rising from rt to 60° C.; or alternatively using a base such as potassium carbonate in solvents such as a mixture of dioxane and water, e.g. with a 1:1 ratio, for a few hours, e.g. one hour to 24 hours, at room temperature.

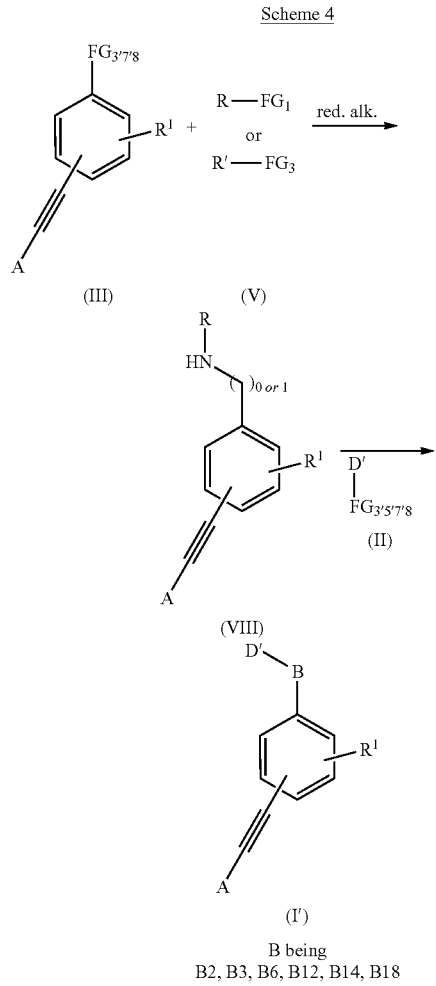

Compounds of formulae (II), (III) and (V) are either commercially available compounds or may be prepared by standard synthetic techniques as hereinafter described in the Examples.

Carboxylic acid derivatives (I') with D' as defined as above can be prepared after deprotection step as described in Scheme 1 by a standard synthetic approach. Carboxylic acid derivatives (I') when containing an ether moiety such as B10 can be prepared after deprotection step as described in Scheme 1, by a standard synthetic approach as hereinafter described in the Examples.

Derivatives of formula (III) and intermediates of formulae (I'), (IV) and (VIII), preferably derivatives of formula (III) can be prepared by Sonogashira cross coupling reaction with a substituted alkyne and an aryl moiety which is substituted by a leaving group such as Br, Cl, I, OMs, OTf, in the presence of additives, such as copper (I) salts in conjunction with palladium catalysts, (e.g. palladium tetrakis (triphenylphosphine), and amines (e.g. triethylamine). Preferred conditions imply use of copper(I) bromide, palladium tetrakis(triphenylphosphine) in triethylamine at e.g. at 90° C.

Novel intermediate compounds of formula (I') are selected from the group consisting of:

6-[{4-[(4-Butylphenyl)ethynyl]benzyl}(hexyl)amino]-2,2-dimethyl-4H-1,3-benzodioxin-4-one Methyl 5-[{4-[(4-butylphenyl)ethynyl]benzyl}(hexyl)amino]-2-hydroxybenzoate (E)-N-{4-[(4-Butylphenyl)ethynyl]benzyl}-N-(2,2-dimethyl-4-oxo-4H-1,3-benzodioxin-6-yl)-2-phenylethylenesulfonamide Methyl 4-({{4-[(4-butylphenyl)ethynyl]benzyl}[2-(4-chlorophenyl)ethyl]amino}methyl)-benzoate Methyl {4-[({[(4-tert-butylphenyl)amino]carbonyl}{4-[(4-butylphenyl)ethynyl]benzyl}-amino)methyl]phenoxy}acetate 6-[{4-[(4-Butylphenyl)ethynyl]benzyl}(3-phenylpropyl)amino]-2,2-dimethyl-4H-1,3-benzodioxin-4-one Methyl {4-[({4-[(4-butylphenyl)ethynyl]benzyl}{[(E)-2-phenylvinyl]sulfonyl}amino)-methyl]phenoxy}acetate 6-[{4-[(4-Butylphenyl)ethynyl]benzyl}(1-naphthylmethyl)amino]-2,2-dimethyl-4H-1,3-benzodioxin-4-one Methyl [4-({{4-[(4-butylphenyl)ethynyl]benzyl}[(cyclohexylamino)carbonyl]amino}-methyl)phenoxy]acetate Methyl [4-({{4-[(4-butylphenyl)ethynyl]benzyl}[(propylamino)carbonyl]amino}-methyl)phenoxy]acetate Methyl [4-({{4-[(4-butylphenyl)ethynyl]benzyl}[(4-cyanoanilino)carbonyl]amino}-methyl)phenoxy]acetate 6-((4-tert-Butylbenzyl){4-[(4-butylphenyl)ethynyl]benzyl}amino)-2,2-dimethyl-4H-1,3-benzodioxin-4-one Methyl (4-{[{4-[(4-butylphenyl)ethynyl]benzyl}(2-thienylsulfonyl)amino]methyl}-phenoxy)acetate 6-[(1-{4-[(4-Butylphenyl)ethynyl]phenyl}pentyl)oxy]-2,2-dimethyl-4H-1,3-benzodioxin-4-one Methyl (4-{[{4-[(4-butylphenyl)ethynyl]benzyl}(ethylsulfonyl)amino]methyl}-phenoxy)-acetate N-{4-[(4-Butylphenyl)ethynyl]benzyl}-N-hexyl-2,2-dimethyl-4-oxo-4H-1,3-benzodioxine-6-carboxamide 4-[(4-Butylphenyl)ethynyl]-N-[(2,2-dimethyl-4-oxo-4H-1,3-benzodioxin-6-yl)methyl]-N-hexylbenzamide 7-[{4-[(4-Butylphenyl)ethynyl]benzyl}(hexyl)amino]-2,2-dimethyl-4H-1,3-benzodioxin-4-one Methyl 5-[{4-[(4-butylphenyl)ethynyl]benzyl}(hexyl)amino]-2-fluorobenzoate N-{2-[(4-Butylphenyl)ethynyl]benzyl}-N-hexyl-2,2-dimethyl-4-oxo-4H-1,3-benzodioxine-6-carboxamide 4-Bromo-N-(3-cyclopentylpropyl)-N-(2,2-dimethyl-4-oxo-4H-1,3-benzodioxin-7-yl)benzamide N-(3-Cyclopentylpropyl)-N-(2,2-dimethyl-4-oxo-4H-1,3-benzodioxin-7-yl)-4-[(4-fluorophenyl)ethynyl]benzamide 4-[(4-Butylphenyl)ethynyl]-N-(3-cyclopentylpropyl)-N-(2,2-dimethyl-4-oxo-4H-1,3-benzodioxin-7-yl)benzamide N-[(2,2-Dimethyl-4-oxo-4H-1,3-benzodioxin-6-yl)methyl]-4-[(4-fluorophenyl)ethynyl]-N-hexylbenzamide 4-[(4-Chlorophenyl)ethynyl]-N-[(2,2-dimethyl-4-oxo-4H-1,3-benzodioxin-6-yl)methyl]-N-hexylbenzamide Methyl 2-fluoro-5-{hexyl[4-phenylethynyl)benzyl]amino}benzoate 6-({4-[(4-Chlorophenyl)ethynyl]benzyl}(hexylamino)-2,2-dimethyl-4H-1,3-benzodioxin-4-one 6-(Hexyl {4-[(4-methoxyphenyl)ethynyl]benzyl}amino)-2,2-dimethyl-4H-1,3-benzodioxin-4-one 6-[Hexyl(4-{[4-(trifluoromethyl)phenyl]ethynyl}benzyl)amino]-2,2-dimethyl-4H-1,3-benzodioxin-4-one 5-{[4-(4-Butyl-phenylethynyl)-benzyl]-cyclopentylmethyl-amino}-2-fluoro-benzoic acid methyl ester
Methyl 5-[{4-[(4-butylphenyl)ethynyl]benzyl}(3,3-dimethylbutyl)amino]-2-fluorobenzoate
6-((Cyclopentylmethyl){4-[(4-methoxyphenyl)ethynyl]benzyl}amino)-2,2-dimethyl-4H-1,3-benzodioxin-4-one
Methyl 5-((cyclopentyhmethyl){4-[(4-methoxyphenyl)ethynyl]-benzyl}amino)-2-hydroxybenzoate
Methyl 5-({4-[(4-butylphenyl)ethynyl]benzyl}(ethyl)amino)-2-fluorobenzoate
6-(Hexyl {4-[(4-propylphenyl)ethynyl]benzyl}amino)-2,2-dimethyl-4H-1,3-benzodioxin-4-one
Methyl 5-(hexyl{4-[(4-propylphenyl)ethynyl]benzyl}amino)-2-hydroxybenzoate
Methyl 5-[{4-[(4-butylphenyl)ethynyl]benzyl}(pentyl)amino]-2-fluorobenzoate
Methyl 5-[{4-[(4-butylphenyl)ethynyl]benzyl}(methyl)amino]-2-fluorobenzoate
Methyl 5-[{4-[(4-butylphenyl)ethynyl]benzyl}(cyclopropylmethyl)amino]-2-fluorobenzoate
Methyl 5-{butyl[4-(phenylethynyl)benzyl]amino}-2-fluorobenzoate
Methyl 2-fluoro-5-{[4-(phenylethynyl)benzyl](propyl)amino}benzoate
Methyl 2-fluoro-5-[{4-[(4-fluorophenyl)ethynyl]benzyl}-(hexyl)amino]benzoate
Methyl 2-fluoro-5-(hexyl{4-[(4-propylphenyl)ethynyl]-benzyl}amino)benzoate
Methyl 5-({4-[(4-butylphenyl)ethynyl]benzyl}{[2-(ethoxycarbonyl) cyclopropyl]methyl}amino)-2-fluorobenzoate
Methyl 5-[{4-[(4-ethylphenyl)ethynyl]benzyl}(hexyl)amino]-2-fluorobenzoate
Methyl 5-[{4-[(4-tert-butylphenyl)ethynyl]benzyl}(hexyl)amino]-2-fluorobenzoate
Methyl 5-{[4-[(4-butylphenyl)ethynyl](hexyl)anilino]methyl}-2-fluorobenzoate
N-[(2,2-Dimethyl4-oxo-4H-1,3-benzodioxin-7-yl)methyl]-N-{4-[(4-hexylphenyl)ethynyl]phenyl}-3,3-dimethylbutanamide
Methyl 5-[{4-[(4-butylphenyl)ethynyl]benzyl}(isobutyl)amino]-2-fluorobenzoate
Methyl 5-{[[{4-[(4-butylphenyl)ethynyl]benzyl}(hexyl)amino]carbonyl}-2-fluorobenzoate
Methyl 5-[{4-[(4-butylphenyl)ethynyl]benzoyl}(hexyl)amino]-2-fluorobenzoate
Methyl 5-[({4-[(4-butylphenyl)ethynyl]phenyl}sulfonyl)(hexyl)amino]-2-fluorobenzoate
Methyl 5-{[{4-[(4-butylphenyl)ethynyl]benzoyl}(hexyl)amino]methyl}-2-fluorobenzoate
Methyl 5-{[({4-[(4-butylphenyl)ethynyl]phenyl}sulfonyl)(hexyl)amino]methyl}-2-fluorobenzoate
Methyl 5-{{4-[(4-butylphenyl)ethynyl]benzyl}[(propylamino)carbonyl]amino}-2-fluorobenzoate
Methyl 5-{{4-[(4-butylphenyl)ethynyl]benzyl}[(cyclohexylamino)carbonyl]amino}-2-fluorobenzoate
4-[(4-Chlorophenyl)ethynyl]-N-(3-cyclopentylpropyl)-N-(2,2-dimethyl-4-oxo-4H-1,3-benzodioxin-7-yl)benzamide Further intermediate compounds suitable to prepare the intermediates (I'), are selected from the group consisting of:
Methyl {4-[({4-[(4-butylphenyl)ethynyl]benzyl}amino)methyl]phenoxy}acetate
2,2-Dimethyl-6-nitro-4H-1,3-benzodioxin-4-one
6-Amino-2,2-dimethyl-4H-1,3-benzodioxin-4-one
6-({4-[(4-Butylphenyl)ethynyl]benzyl}amino)-2,2-dimethyl-4H-1,3-benzodioxin-4-one
{4-[(4-Butylphenyl)ethynyl]benzyl}[2-(4-chlorophenyl)ethyl]amine
1-{4-[(4-Butylphenyl)ethynyl]phenyl}-1-pentanol
2,2-Dimethyl-4-oxo-4H-1,3-benzodioxine-6-carboxylic acid
N-{4-[(4-Butylphenyl)ethynyl]benzyl}-1-hexanamine
2,2-Dimethyl-4-oxo-4H-1,3-benzodioxine-6-carbaldehyde
6-[(Hexylamino)methyl]-2,2-dimethyl-4H-1,3-benzodioxin-4-one
7-[4-(4-Butyl-phenylethynyl)-benzylamino]-2,2-dimethyl-benzo[1,3]dioxin-4-one
Methyl 5-({4-[(4-butylphenyl)ethynyl]benzyl}amino)-2-fluorobenzoate
N-{2-[(4-Butylphenyl)ethynyl]benzyl}-1-hexanamine
3-Cyclopentyl-N-(2,2-dimethyl-4-oxo-4H-1,3-benzodioxin-7-yl)propanamide
7-[(3-Cyclopentylpropyl)amino]-2,2-dimethyl-4H-1,3-benzodioxin-4-one
4-[(4-Chlorophenyl)ethynyl]benzoic acid
Methyl 2-fluoro-5-{[4-(phenylethynyl)benzyl]amino}benzoate
6-({4-[(4-Chlorophenyl)ethynyl]benzyl}amino)-2,2-dimethyl-4H-1,3-benzodioxin-4-one
6-({4-[(4-Methoxyphenyl)ethynyl]benzyl}amino)-2,2-dimethyl-4H-1,3-benzodioxin-4-one
2,2-Dimethyl-6-[(4-{[4-(trifluoromethyl)phenyl]ethynyl}benzyl)amino]-4H-1,3-benzodioxin-4-one
2,2-Dimethyl-6-({4-[(4-propylphenyl)ethynyl]benzyl}amino)-4H-1,3-benzodioxin-4-one
Methyl 2-fluoro-5-(hexylamino)benzoate
4-[(4-Butylphenyl)ethynyl]benzoyl chloride
Methyl 5-[[(4-bromophenyl)sulfonyl](hexyl)amino]-2-fluorobenzoate
Methyl 2-fluoro-5-[(hexylamino) methyl]benzoate
Methyl 5-{[[(4-bromophenyl)sulfonyl](hexyl)amino]methyl}-2-fluorobenzoate
4-[(4-Butylphenyl)ethynyl]aniline
4-[(4-Hexylphenyl)ethynyl]aniline
7-(Dibromomethyl)-2,2-dimethyl-4H-1,3-benzodioxin-4-one
2,2-dimethyl-4-oxo-4H-1,3-benzodioxine-7-carbaldehyde
7-({4-[(4-Hexylphenyl)ethynyl]anilino}methyl)-2,2-dimethyl-4H-1,3-benzodioxin-4-one When employed as pharmaceuticals, carboxylic acids of the present invention are typically administered in the form of a pharmaceutical composition. Hence, pharmaceutical compositions comprising a compound of formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, carboxylic acids of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the carboxylic acid according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, carboxylic acids of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences, 20th* Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples, which are not construed to be viewed as limiting the scope of the invention The following abbreviations are hereinafter used in the accompanying examples: hr(s) (hour(s)), g (gram), mg (milligram), mmol (millimole) mol (mole), m.p. (melting point), eq (equivalents), mL (milliliter), μL (microliters), ESI (Electro-spray ionization), L (liters), EtOAc (Ethyl acetate), Boc (tert-Butoxycarbonyl), CDCl$_3$ (deuterated chloroform), CD$_3$OD (Deuterated methanol), CH$_3$CN (Acetonitrile), DBU (Diazabicyclo [5.4.0]undec-7-ene), DCC (Dicyclohexyl carbodiimide), DCM (Dichloromethane), DIC (Diisopropyl carbodiimide), DIEA (Diisopropylethylamine), DMAP (4-Dimethylaminopyridine), DMF (Dimethylformamide), DMSO (Dimethylsulfoxide), DMSO-d$_6$ (Deuterated dimethylsulfoxide), HOBt (1-Hydroxy-6-trifluoromethyl benzotriazole), EDC (1-(3-Dimethyl-amino-propyl)-3-ethylcarbodiimide), DCE (1,2-dichloroethane), c-Hex (Cyclohexane), Et$_2$O (Diethyl ether), EtOH (Ethanol), Fmoc (9-Fluorenylmethoxycarbonyl), i-PrOH (2-propanol), MeOH (Methanol), min. (minute), MTBE (Methyl tert-butyl ether), NMM (N-methyl-morpholine), MW (micro-wave), Pd/C (palladium on carbon), PPh$_3$ (triphenylphosphine), PetEther (Petroleum ether), rt (room temperature), PyBOP® (Benzotriazole-1-yl-oxy-tris-pyrrolidino-phosphonium hexafluorophosphate), Rt (retention time), SPE (solid phase extraction), TBTU (2-(1-H-benzotriazole-1-yl)-1,1,3,3-tetramethyluromium tetrafluoroborate), TEA (Triethylamine), TFA (Trifluoroacetic acid), TFAA (Trifluoroacetic acid anhydride), THF (Tetrahydrofuran).

The HPLC data provided in the examples described below were obtained as followed. HPLC: Waters Symmetry C$_8$ column 50 mm×4.6 mm; UV detection (maxplot); flow: 2 mL/min; Conditions: 8 min gradient from 0.1% TFA in H$_2$O to 0.07% TFA in CH$_3$CN. The MS data provided in the examples described below were obtained as followed: Mass spectrum: LC/MS Waters ZMD (ESI). The NMR data provided in the examples described below were obtained as followed: $^1$H-NMR: Bruker DPX-300 MHz.

EXAMPLES

Example 1

5-[{4-[(4-butylphenyl)ethynyl]benzyl}(hexyl) amino]-2-hydroxybenzoic acid N-methyl-D-glucamine (i.e. 1-deoxy-1-(methylamino)glucitol) salt Step a) Formation of 2,2-dimethyl-6-nitro-4H-1,3-benzodioxan-4-one

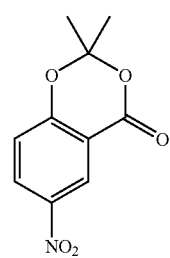

A mixture of 2-hydroxy-5-nitrobenzoic acid (Aldrich, 50.0 g, 0.27 mol), acetone (40 mL, 0.54 mol) and trifluoroacetic anhydride (TFAA) (Aldrich, 100 mL, 0.71 mol) in trifluoroacetic acid (TFA) (Aldrich, 300 mL) was heated at reflux. After 1 hour, an additional amount of acetone (60 mL, 0.82 mol) was added and the resulting reaction mixture was heated under reflux for an additional 48 hrs. The reaction mixture was concentrated under reduced pressure. The residual brown solid was dissolved in DCM (800 mL) and washed with a mixture of an aqueous saturated solution of NaHCO$_3$ (400 mL) and water (400 mL). The aqueous layer was extracted with DCM (2×400 mL). The combined organic layers were dried over MgSO$_4$ and the solvent was removed under reduced pressure. The residual brown oil was taken up in cold pentane (300 mL) at 0° C. and a yellow solid precipitated off. Filtration and washing with pentane gave 53.8 g (88%) of the title compound as a yellow solid. HPLC, Rt: 2.9 min (purity: 99.8%). $^1$H NMR (CDCl$_3$) δ: 8.88 (d, J=2.8 Hz, 1H), 8.44 (dd, J=9.0, 2.8 Hz, 1H), 7.14 (d, J=9.0 Hz, 1H), 1.80 (s, 6H).

Step b) Formation of 6-amino-2,2-dimethyl-4H-1,3-benzodioxin-4-one

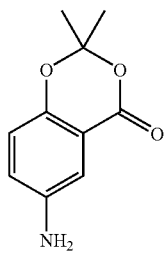

To a solution of 6-nitro-2,2-dimethyl-4H-1,3-benzodioxin-4-one (4.1 g) in EtOH (30 mL) was added Pd/C (1.947 g) under nitrogen atmosphere. Hydrogenation was performed for 12 hrs at rt using 10 bars of H$_2$. The reaction mixture was filtered through X bed of celite, washed with EtOH and THF. The filtrates were concentrated under vacuum to give the title compound as a pale yellow solid (3.5 g, 98%). $^1$H NMR (CDCl$_3$) δ 7.71 (d, J=8.7 Hz, 1H), 7.15 (d, J=2.6 Hz, 1H), 6.83 (dd, J=8.7 Hz, 2.6 Hz, 1H), 3.44 (brs, 2H), 2.63 (s, 6H).

Step c) Formation of 6-({4-[(4-butylphenyl)ethynyl]benzyl}amino)-2,2-dimethyl-4H-1,3-benzodioxin-4-one

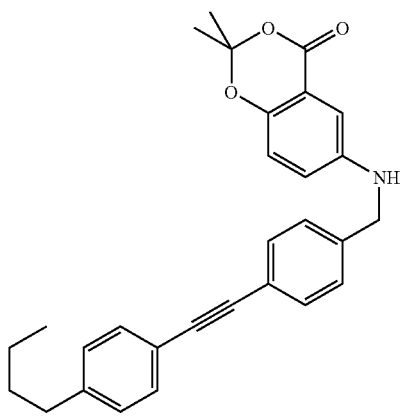

A solution of 4-[(4-butylphenyl)ethynyl]benzaldehyde (5.43 g, 20.7 mmol, intermediate which may be obtained according to methods disclosed in EP03103780.7) and 6-amino-2,2-dimethyl-4H-1,3-benzodioxin-4-one (4.00 g, 20.7 mmol) in toluene (60 mL) was heated at reflux for 3.5 hours with azeotropic removal of water. Then the mixture was cooled down to 0° C. and anhydrous THF (60 mL) and MeOH (60 1L) were added NaBH$_4$ (1.65 g, 43.6 mmol) was added portionwise and the reaction mixture was stirred for 30 min at 0° C. and 45 min at rt. The reaction mixture was poured into a saturated solution of NaCl and extracted with Et$_2$O. The combined organic layers were dried over MgSO$_4$ and the solvents were removed under reduced pressure to give the crude product. Precipitation from a mixture of EtOAc/MeOH gave 7.1 g (75%) of the title compound as a yellow powder. HPLC, Rt: 5.4 min (purity: 97.5%). $^1$H NMR (CDCl$_3$) δ: 7.45 (d, J=8.3 Hz, 2H), 7.39 (d, J=8.3 Hz, 2H), 7.28 (d, J=8.3 Hz, 2H), 7.15-7.06 (m, 3H), 6.80-6.70 (m, 2H), 4.20 (m, 2H), 4.04 (brs, 1H), 2.57 (t, J=7.7 Hz, 2H), 1.65 (s, 6H), 1.61-1.49 (m, 2H), 1.37-1.23 (m, 2H), 0.88 (t, J=7.3 Hz, 3H).

Step d) Formation of 6-[{4-[(4-butylphenyl)ethynyl]benzyl}(hexyl)amino]-2,2-dimethyl-4H-1,3-benzodioxin-4-one

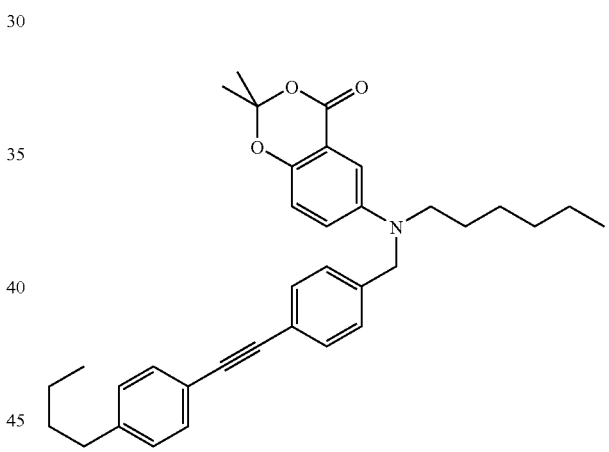

To a solution of 6-({4-[(4-butylphenyl)ethynyl]benzyl}amino)-2,2-dimethyl-4H-1,3-benzodioxin-4-one (4.00 g, 9.1 mmol) in anhydrous DCE (60 mL) were added hexanal (Aldrich, 1.80 mL, 14.6 mmol) and sodium triacetoxyborohydride (6.17 g, 29.1 mmol). The resulting mixture was stirred at 70° C. overnight. Then the reaction mixture was poured into water (60 mL) and extracted with DCM (2×60 mL). The combined organic layers were dried over MgSO$_4$ and the solvents were removed under reduced pressure to give a yellow oil. Purification by flash chromatography on silica-gel (c-Hex/EtOAc (9/1)) gave 4.41 g (92%) of the title compound as a yellow oil. HPLC, Rt: 6.2 min (purity: 100%). LC/MS, M$^+$(ESI): 524.1. $^1$H NMR (CDCl$_3$) δ: 7.48 (d, J=8.3 Hz, 2H), 7.44 (d, J=8.3 Hz, 2H), 7.25 (d, J=3.0 Hz, 1H), 7.20 (d, J=8.3 Hz, 2H), 7.16 (d, J=8.3 Hz, 2H), 6.86 (dd, J=9.0, 3.0 Hz, 1H), 6.79 (d, J=9.0 Hz, 1H), 4.51 (s, 2H), 3.37 (t, J=7.7

Hz, 2H), 2.63 (t, J=7.7 Hz, 2H), 1.71 (s, 6H), 1.61 (m, 4H), 1.40-1.25 (m, 8H), 0.94 (t, J=7.3 Hz, 3H), 0.90 (t, J=6.7 Hz, 3H).

Step e) Formation of methyl 5-[{4-[(4-butylphenyl)ethynyl]benzyl}(hexyl)amino]-2-hydroxybenzoate

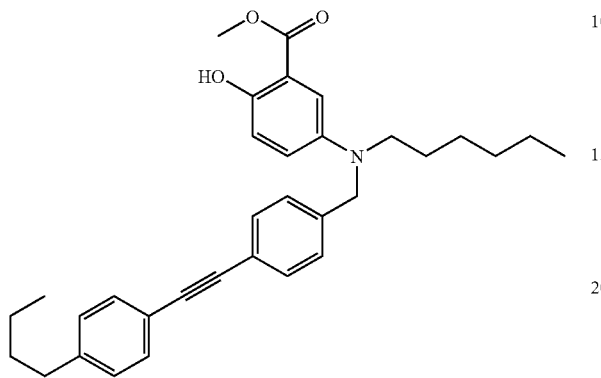

To a solution of 6-[{4-[(4-butylphenyl)ethynyl]benzyl}(hexyl)amino]-2,2-dimethyl-4H-1,3-benzodioxin-4-one (4.41 g, 8.4 mmol) in MeOH (500 mL) and water (30 mL) was added an aqueous solution of NaOH (7.0 mL, 5N). The reaction mixture was stirred at rt for 2 hrs and a yellow powder precipitated out progressively. Filtration and washing with water (2×) gave the title compound as a yellow powder. HPLC, Rt: 5.3 min (purity: 98.7%). LC/MS, M⁺(ESI): 498.3. ¹H NMR (CDCl₃) δ: 10.16 (s, 1H), 7.45 (m, 4H), 7.19 (m, 5H), 6.94 (dd, J=9.0, 3.0 Hz, 1H), 6.86 (d, J=9.0 Hz, 1H), 4.43 (s, 2H), 3.92 (s, 3H), 3.28 (t, J=7.5 Hz, 2H), 2.63 (t, J=7.5 Hz, 2H), 1.60 (m, 4H), 1.30 (m, 8H), 0.92 (m, 6H).

Step f) Formation of 5-[{4-[(4-butylphenyl)ethynyl]benzyl}(hexyl)amino]-2-hydroxybenzoic acid

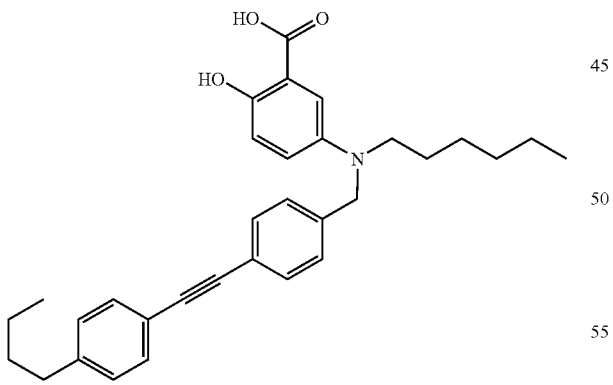

To a solution of methyl 5-[{4-[(4-butylphenyl)ethynyl]benzyl}(hexyl)amino]-2-hydroxybenzoate in MeOH (400 mL) and water (40 mL) was added an aqueous solution of NaOH (6.0 mL, 5N). The reaction mixture was sired at 60° C. overnight. Then an aqueous solution of HCl (10 mL, 5N) was added and the solvents were removed under reduced pressure. The residue was taken up in water and extracted with Et₂O (3×). The combined organic layers were dried over MgSO₄ and the solvent was removed under reduced pressure to give a yellow solid. Precipitation from a DCM/MeOH mixture gave 2.17 g (53%, stop e and f) of the title compound as a beige powder. HPLC, Rt: 4.8 min purity: 99.7%). LC/MS, M⁺(ESI): 484.4, M⁻(ESI): 482.2. ¹H NMR (CDCl₃/CD₃OD (15/1)) δ: 7.39 (m, 4H), 7.18-7.09 (m, 5H), 6.87 (dd, J=9.0, 3.0 Hz, 11), 6.78 (d, J=9.0 Hz, 1H), 4.38 (s, 2H), 3.22 (t, J=7.5 Hz, 2H), 2.57 (t, J=7.8 Hz, 2H), 1.55 (m, 4H), 1.34-1.21 (m, 8H), 0.90-0.75 (m, 6H).

Step g) Formation of 5-[[4-[(4-butylphenyl)ethynyl]benzyl}(hexyl)amino]-2-hydroxybenzoic acid, N-methyl-D-glucamine (i.e. 1-deoxy-1-(methylamino)glucitol) salt

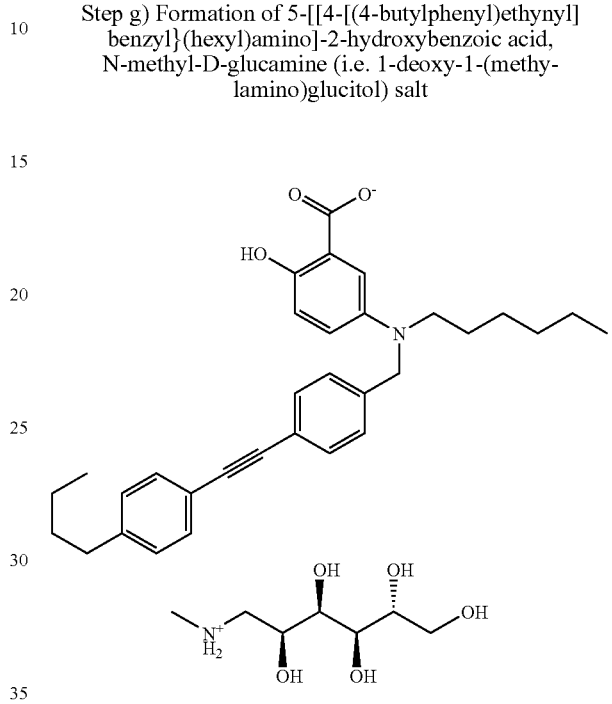

To a solution of the 5-[{4-[(4-butylphenyl)ethynyl]benzyl}(hexyl)amino]-2-hydroxybenzoic acid (1650 mg, 3.41 mmol) in freshly distilled THF (20 mL) was added a solution of N-methyl-D-glucamine (666 mg) in water (4 mL). Water (200 mL) was added and the resulting solution was lyophilized to give 1.93 g (81%) of the title compound as a pale yellow powder. HPLC, Rt: 4.8 min (purity: 98.8%). LC/MS, M⁺(ESI): 484.0, M⁻(ESI): 482.0.

Example 2

5-[{4-[(4-butylphenyl)ethynyl]benzyl}(hexyl)amino]-2-hydroxybenzoic acid hydrochloride salt

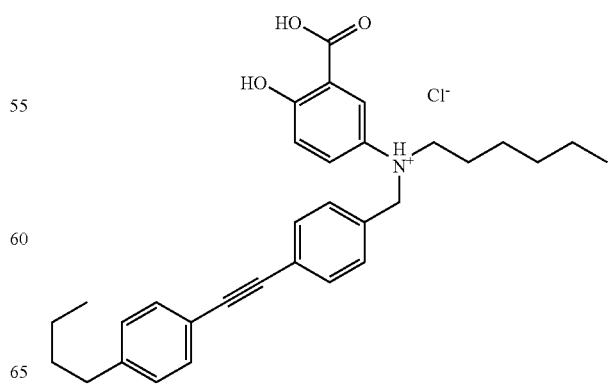

To a solution of 6-[{4-[(4-butylphenyl)ethynyl]benzyl}(hexyl)amino]-2,2-dimethyl-4H-1,3-benzodioxin-4-one (240 mg, 8.4 mmol) in EtOH (15 mL) and water (1 mL) was added an aqueous solution of NaOH (0.5 mL, 5N). The reaction mixture was heated under reflux for 2 hrs. Then an aqueous solution of HCl (2 mL, 5N) was added and the solvents were evaporated under reduced pressure to give a brown oil. The oil was taken up with water (10 mL) and extracted with Et$_2$O (2×10 mL). The combined organic layers were dried over MgSO$_4$ and the volume of solvent was half reduced under reduced pressure. Then a solution of HCl in Et$_2$O (2 mL, 1M) was added and a beige solid precipitated out. The solid was filtrated off, washed with Et$_2$O and dried under vacuum to give 155 mg (65%) of the title compound as a beige powder. HPLC, Rt: 4.7 min (purity: 99.7%). LC/MS, M$^-$(ESI): 482.3. $^1$H NMR (CD$_3$OD) δ: 7.87 (d, J=3.0 Hz, 1H), 7.61 (dd, J=9.0, 3.0 Hz, 1H), 7.49 (d, J=8.3 Hz, 2H), 7.44 (d, J=8.3 Hz, 2H), 7.30 (d, J=8.3 Hz, 2H), 7.24 (d, J=8.3 Hz, 2H), 7.13 (d, J=9.0 Hz, 1H), 4.82 (s, 2H), 3.77 (t, J=8.1 Hz, 2H), 2.67 (t, J=7.5 Hz, 2H), 1.63 (m, 4H), 1.45-1.33 (m, 8H), 0.96 (m, 6H).

Example 3

5-[{4-[(4-butylphenyl)ethynyl]benzyl}(hexyl)amino]-2-hydroxybenzoic acid, lysine salt

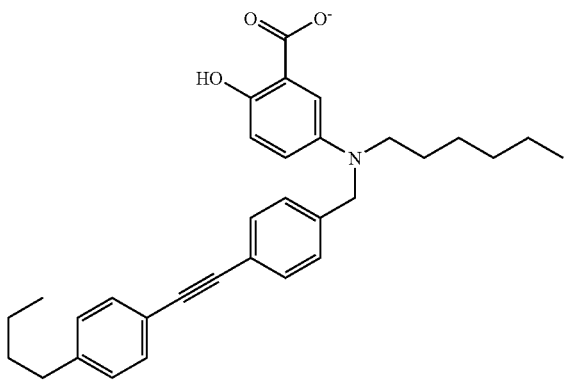

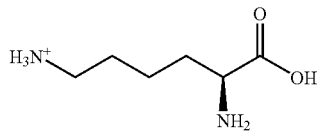

To a solution of the 5-[{4-[(4-butylphenyl)ethynyl]benzyl}(hexyl)amino]-2-hydroxybenzoic acid (90 mg, 0.19 mmol) in freshly distilled THF (1 mL) was added a solution of L-lysine (Aldrich, 27 mg) in water (1 mL). Water (20 mL) was added and the resulting solution was lyophilized to give 87 mg (74%) of the title compound as a pale yellow powder. HPLC, Rt: 4.9 min purity: 99.4%). LC/MS, M$^+$(ESI): 483.7, M$^-$(ESI): 482.1.

Example 4

5-({4-[(4-butylphenyl)ethynyl]benzyl}{[(E)-2-phenylvinyl]sulfonyl}amino)-2-hydroxybenzoic acid Step a) Formation of (E)-N-{4-[(4-butylphenyl)ethynyl]benzyl}-N-(2,2-dimethyl-4-oxo-4H-1,3-benzodioxin-6-yl)-2-phenylethylenesulfonamide

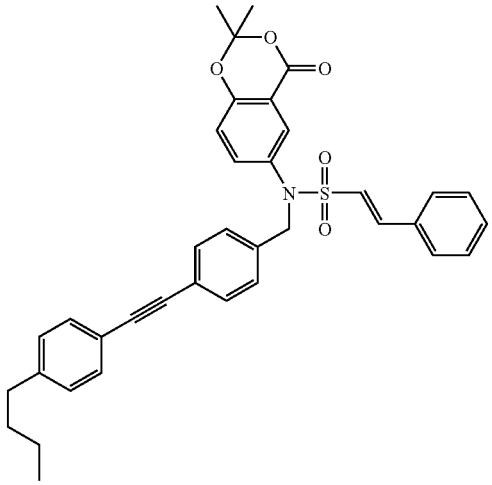

A solution of 6-({4-[(4-butylphenyl)ethynyl]benzyl}amino)-2,2-dimethyl-4H-1,3-benzodioxin-4-one (33 mg, 0.08 mmol), β-styrene sulfonyl chloride (Aldrich, 18 mg, 0.09 mmol) and TEA (26 μl, 0.19 mmol) in DCM (2 mL) was stirred at rt overnight. Trisamine resin (0.5 eq, Novabiochem, 3.5 mmol/g) was added and the mixture was stirred at rt for an additional 2 hrs. It was then filtrated and the filtrate was washed twice with an aqueous saturated solution of ammonium chloride and with brine. It was dried over MgSO$_4$, filtrated and concentrated to give 24 mg (53%) of the title compound. HPLC, Rt: 5.90 min purity: 88.9%). $^1$H NMR (CDCl$_3$) δ: 7.84 (d, J=2.4 Hz, 1H), 7.36-7.54 (m, 11H), 7.23 (d, J=8.3 Hz, 2H), 7.13 (d, J=8.3 Hz, 2H), 6.85 (d, J=8.7 Hz, 1H), 6.78 (d, J=8.7 Hz, 1H), 4.76 (s, 2H), 2.59 (t, J=7.9 Hz, 2H), 1.68 (s, 6H), 1.57 (m, 2H), 1.32 (m, 2H), 0.90 (t, J=7.3 Hz, 3H).

Step b) Formation of 5-([4-[(4-butylphenyl)ethynyl]benzyl}{[(E)-2-phenylvinyl]sulfonyl}-amino)-2-hydroxybenzoic acid

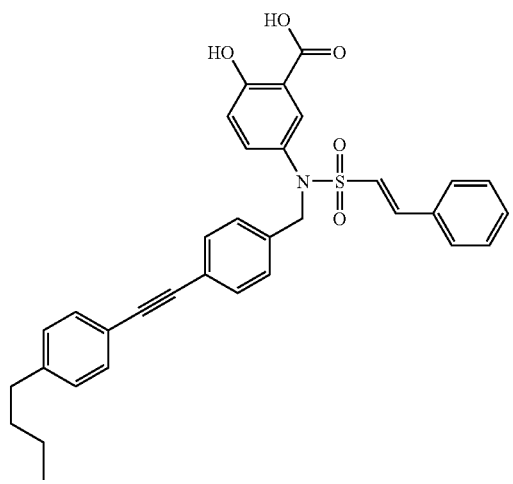

To a solution of (E)-N-{4-[(4-butylphenyl)ethynyl]benzyl}-N-(2,2-dimethyl-4-oxo-4H-1,3-benzodioxin-6-yl)-2-phenylethylenesulfonamide (24 mg, 0.04 mmol) in EtOH (1 mL) and is THF (1 mL) was added an aqueous solution of NaOH (0.5 mL, 5N) and the resulting mixture was heated at 70° C. for 2 hrs. Solvents were concentrated under reduced pressure. The residue was taken up in DCM and washed with an aqueous saturated solution of NH$_4$Cl and brine. The combined organic layers were dried over MgSO$_4$, filtrated and the solvents were removed under reduced pressure. The crude (29 mg) was purified on a SPE column (Sorbent NH$_2$, Isolute® Ig, 0.71 mmol/g) as follows: the column was equilibrated with DCM (2×10 mL) and the crude product (diluted in 1 mL DCM) was poured onto the column. The column was washed with DCM (2×5 mL) then with dioxane (2×5 mL) and the title compound was finally eluted with a solution of HCl in dioxane (2×2 mL, 2N).

Evaporation of the HCl-containing fractions under vacuum gave the title compound (8 mg). HPLC, Rt: 5.54 min (purity: 66.5%). M$^+$(ESI): 564.2.

Example 5

4-({{4-[(4-butylphenyl)ethynyl]benzyl}[2-(4-chlorophenyl)ethyl]amino}-methyl)benzoic acid, hydrochloride salt Step a) Formation of {4-[(4-butylphenyl)ethynyl]benzyl}[2-(4-chlorophenyl)ethyl]amine

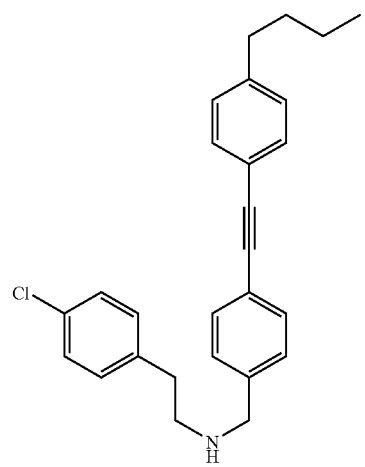

A solution of 4-[(4-butylphenyl)ethynyl]benzaldehyde (2.62 g, 10.0 mmol, intermediate to which may be obtained according to methods disclosed in EP03103780.7) and 2-(4-chlorophenyl)ethylamine (Aldrich, 1.56 g, 10 mmol) was heated at reflux in toluene (50 mL) for 12 hrs with azeotropic removal of water. The mixture was evaporated under vacuum and the residue was taken up in MeOH (60 mL) and chilled at 0° C. NaBH$_4$ (567 mg, 15.0 mmol) was added portionwise and the reaction mixture was stirred for 30 min at 0° C. and 3 hrs at rt. The reaction mixture was poured into a saturated solution of NaCl and extracted with Et$_2$O. The combined organic layers were dried over MgSO$_4$ and the solvents were removed under reduced pressure to give the crude product. Purification by chromatography on silicagel (EtOAc/c-hex 30/70) gave 2.96 g (54%) of the title compound as a white solid. HPLC, Rt: 5.0 min (purity: 99.9%).

Step b) Formation of methyl 4-({{4-[(4-butylphenyl)ethynyl]benzyl}[2-(4-chlorophenyl)-ethyl]amino}methyl)benzoate

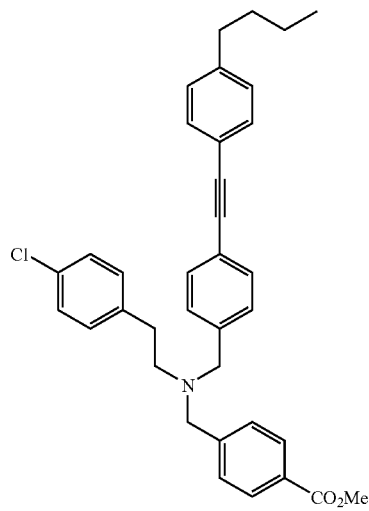

To a solution of {4-[(4-butylphenyl)ethynyl]benzyl}[2-(4-chlorophenyl)ethyl]amine (2.85 g, 7.1 mmol) and methyl 4-formylbenzoate (1.16 g, 7.1 mmol) in DCE (24 mL) was added at once sodium triacetoxyborohydride (2.25 g, 10.6 mmol) and the resulting reaction mixture was stirred 12 hrs at rt. The reaction mixture was poured into water and extracted with DCM. The combined organic layers were dried over MgSO$_4$ and the solvents were removed under reduced pressure to give the crude product. Purification by chromatography on silicagel (EtOAc/c-hex (5/95)) gave 2.8 g (73%) of the title compound as a white solid. HPLC, Rt: 5.0 min (purity: 99.9%). $^1$H NMR (CDCl$_3$) δ: 7.98 (d, J=8.3 Hz, 2H), 7.51-7.43. (m, 4H), 7.36 (d, J=8.3 Hz, 2H), 7.29-7.15 (m, 6H), 7.00 (d, J=8.3 Hz, 2H), 3.94 (s, 3H), 3.68 (s, 2H), 3.64 (s, 2H), 2.83-2.59 (m, 6H), 1.69-1.55 (m, 2H), 1.44-1.30 (m, 2H), 0.95 (J=7.2 Hz, 3H).

Step c) Formation of 4-({{4-[(4-butylphenyl)ethynyl]benzyl}[2-(4-chlorophenyl)ethyl]-amino}methyl)benzoic acid, hydrochloride salt

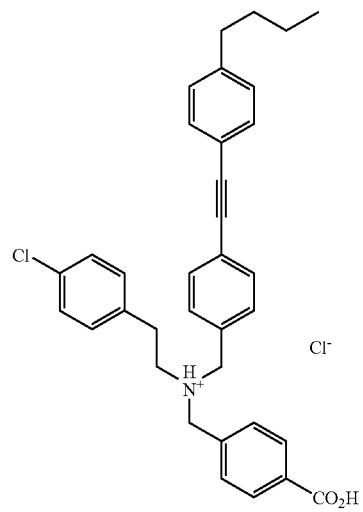

To a solution of methyl 4-({{4-[(4-butylphenyl)ethynyl]benzyl}[2-(4-chlorophenyl)-ethyl]amino}methyl)benzoate (980 mg, 1.78 mmol) in MeOH (15 mL) was added an aqueous solution of NaOH (4.5 mL, 1N) and the resulting mixture was stirred at rt for 12 hrs. An aqueous solution of HCl (1N) was added and the resulting mixture was extracted with Et₂O. The combined organic layers were dried over MgSO₄ and evaporated to give 929 mg of 4-({{4-[(4-butylphenyl)ethynyl]benzyl}[2-(4-chlorophenyl)ethyl]amino}-methyl)benzoic acid as a colorless oil. This product was dissolved in Et₂O (30 mL) and a solution of HCl in dioxane (2 mL, 4N) was added. The precipitate was filtered, washed with Et₂O and dried under vacuum to give 985 mg (97%) of the title compound as a white powder. HPLC, Rt: 4.7 min (purity: 98.9%). M⁻(ESI): 534.3; M⁺(ESI): 536,2. ¹H NMR (DMSO-d₆) δ: 13.4 (brs, 1M), 11.3 (brs, 1H), 8.35-7.28 (m, 16H), 4.82-4.45 (m, 2H), 3.96-4.58 (m, 6H), 2.81 (t, J=7.9 Hz, 2H), 1.84-1.68 (m, 2H), 1.60-1.41 (m, 2H), 1.10 (t, J=7.2 Hz, 3H).

Example 6

{4-[({[(4-tert-butylphenyl)amino]carbonyl}{4-[(4-butylphenyl)ethynyl]-benzyl}amino)methyl]phenoxy}acetic acid Step a) Formation of methyl [4-[(E)-hydroxyimino)methyl]phenoxy]acetate

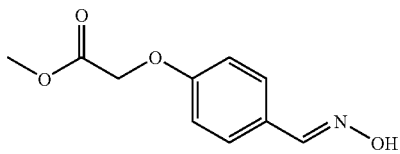

A solution of hydroxylamine hydrochloride (54 g) and sodium acetate (64 g) in water (500 mL) was added drop-wise to a solution of methyl (4-formylphenoxy)acetate (100 g, 0.515 mol, intermediate which may be obtained according to methods described in *Bioorg. Med. Chem. Lett.*, 2001,11(19), 2589-92) in methanol (500 mL) at 0-5° C. The reaction mixture was stirred at rt for 6 hrs, then diluted with water and filtrated. The solid obtained was washed with water and dried under vacuum to give the title compound (80 g; 74%).

Step b) Formation of methyl-[4-(aminomethyl)phenoxy]acetate, acetic acid salt

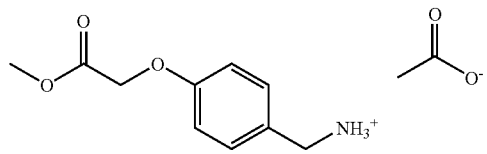

To a solution of methyl [4-[(E)-hydroxyimino)methyl]phenoxy] acetate (30 g, 0.14 mol) in MeOH (650 mL) was added glacial acetic acid (6.8 g). The solution was degassed with N₂ for 30 min before the addition of Pd/C (10%, 3 g) and hydrogenated for 12 hrs under 2 bars of H₂. The reaction mixture was concentrated under vacuum. The crude product was taken up with EtOAc (500 mL). A solid precipitated out which was filtered off and dried under vacuum to give 29 g (81%) of the title compound as a white solid. ¹H NMR (DMSO-d₆) δ: 7.28 (d, J=8.5 Hz, 2H), 6.88 (d, J=8.6 Hz, 2H), 5.76 (brs, 2H), 4.77 (s, 2H), 3.73 (s, 2H), 3.68 (s, 3H), 1.81 (s, 3H).

Step c) Formation of Methyl {4-[({4-[(4-butylphenyl)ethynyl]benzyl}amino)methyl]-phenoxy}acetate

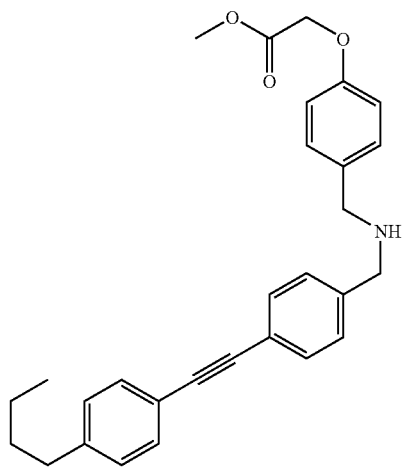

The title compound was prepared following procedure described in Example 1, step c) from methyl [4-(aminomethyl)phenoxy]acetate, acetic acid salt (2.0 g, 7.87 mmol) and 4-[(4-butylphenyl)ethynyl]benzaldehyde (2.06 g, 7.87 mmol, intermediate which may be obtained according to methods disclosed in EP03103780.7). The crude (2.76 g) was purified by flash chromatography (EtOAc/c-Hex (1/4)) to give 1.26 g (36%) of the title compound as a yellow solid. HPLC, Rt: 4.16 min (purity: 94.9%). LC/MS, M⁺(ESI): 442.3. ¹H NMR (CDCl₃) δ: 0.91 (t, J=7.2 Hz, 3H), 1.34 (qt, J=7.6 Hz, 2H), 1.58 (qt. J=7.7 Hz, 2H), 1.83 (brs, 1H), 2.59 (t, J=7.7 Hz, 2H), 3.72 (s, 2H), 3.78 (s, 2H), 3.79 (s, 3H), 4.60 (s, 2H), 6.86 (d, J=8.7 Hz, 2H), 7.13 (d, J=8.3 Hz, 2H), 7.25 (d, J=8.7 Hz, 2H), 7.29 (d, J =8.3 Hz, 2H), 7.42 (d, J=8.3 Hz, 2H), 7.46 (d, J=8.1 Hz, 2H).

Step d) Formation of Methyl {4-[({[(4-tert-butylphenyl)amino]carbonyl}{4-[(4-butylphenyl)ethynyl]benzyl)amino)methyl]phenoxy}acetate

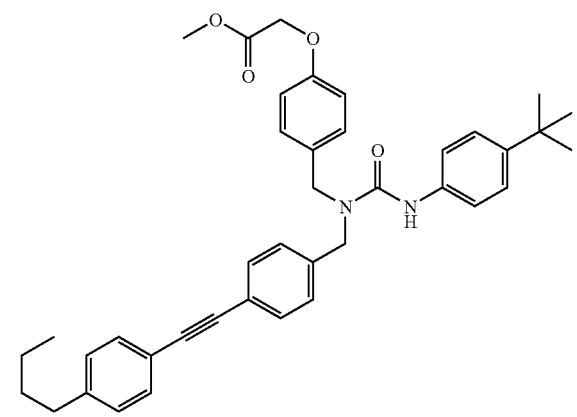

A solution of methyl {4-[({4-[(4-butylphenyl)ethynyl]benzyl}amino)methyl]phenoxy}acetate (45 mg, 0.10 mmol) and 4-tert-butylphenylisocyanate (Aldrich, 27 mg, 0.15 mmol) in DCM (2 mL) was stirred at rt overnight in presence of a morpholine resin (1.5 eq., Novabiochem HL, 3.8 mmol/g). Trisamine resin (1.2 eq, Novabiochem, 3.5 mmol/g) was then added and the mixture was stirred at rt for an additional 2 hrs. The reaction mixture was then filtrated and the solvent was removed under reduced pressure to give quantitatively the title compound. HPLC, Rt: 5.97 min purity: 96.3%). M⁺(ESI): 619.6, M⁻(ESI): 616.9.

Step e) Formation of {4-[({[(4-tert-butylphenyl)amino]carbonyl}{4-[(4-butylphenyl)-ethynyl]benzyl}amino)methyl]phenoxy}acetic acid

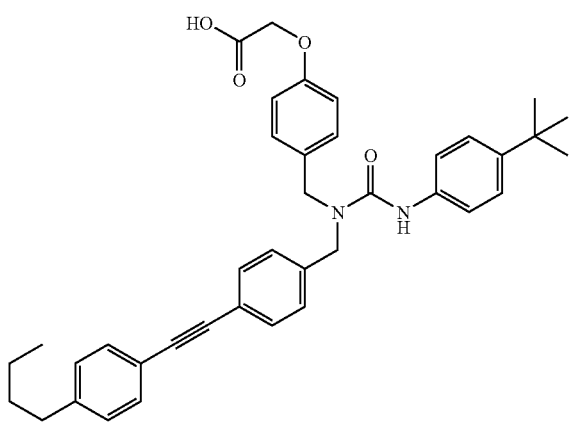

To a solution of methyl {4-[({[(4-tert-butylphenyl)amino]carbonyl}{4-[(4-butylphenyl)-ethynyl]benzyl}amino)methyl]phenoxy}acetate (70 mg, 0.11 mmol) in MeOH (1 mL) and THF (1 mL) was added an aqueous solution of NaOH (0.5 mL, 5N) and the resulting mixture was stirred at it for 3 hrs. Then the solvents were removed under reduced pressure. The residue was taken up in EtOAc and washed with an aqueous solution of HCl (1N) and brine. The organic layer was dried over MgSO₄ and the solvent was removed to give 46 mg (67%) of the title compound. HPLC, Rt: 5.67 min (purity: 97.4%). ¹H NMR (CD₃OD) δ: 7.48 (d, J=8.3 Hz, 2H), 7.40 (d, J=7.5 Hz, 2H), 7.18-7.33 (m, 10H), 6.93 (d, J=8.7 Hz, 2H), 4.66 (s, 2H), 4.66 (s, 2H), 4.54 (s, 2H), 2.63 (t, J=7.5 Hz, 2H), 1.60 (m, 2H), 1.37 (m, 2H), 1.30 (s, 9H), 0.95 (t, J=7.2 Hz, 3H). M⁺(ESI): 603.4, M⁻(ESI): 601.3.

Example 7

5-[{4-[(4-butylphenyl)ethynyl]benzyl}(3-phenylpropyl)amino]-2-hydroxy-benzoic acid, hydrochloride salt Step a) Formation of 6-[{4-[(4-butylphenyl)ethynyl]benzyl}(3-phenylpropyl)amino]-2,2-dimethyl-4H-1,3-benzodioxin-4-one

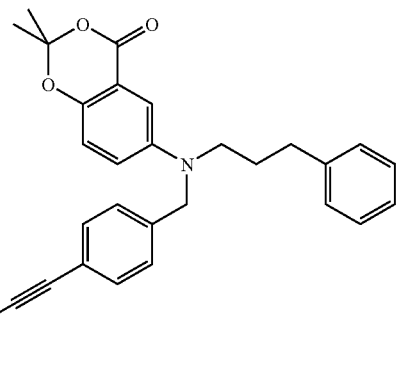

To a solution of 6-({4-[(4-butylphenyl)ethynyl]benzyl}amino)-2,2-dimethyl-4H-1,3-benzodioxin-4-one (150 mg, 0.34 mmol) in anhydrous DCE (3 mL) were added 3-phenylpropionaldehyde (Aldrich, 75 μL, 0.51 mmol) and sodium triacetoxyborohydride (110 mg, 0.51 mmol). The reaction mixture was stirred at rt for 24 hrs. The solvent was removed under reduced pressure. The residue was taken up with an aqueous solution of NaOH (2 mL) and extracted with Et₂O (6 ml). The organic layer was dried over Na₂SO₄ and the solvent was removed under reduced pressure. Purification by flash chromatography on silicagel (pentane/DCM (2/3)) gave 147 mg (77%) of the title compound as a yellow oil. HPLC, Rt: 6.3 min (purity: 99.1%). ¹H NMR (CDCl₃) δ: 7.45 (m, 4H), 7.32-7.15 (m, 10H), 6.91 (m, 1H), 6.80 (m, 1H), 4.49 (s, 2H), 3.42 (t, J=7.4 Hz, 2H), 2.65 (m, 4H), 1.71 (s, 6H), 1.61 (m, 2H), 1.37 (m, 2H), 0.94 (t, J=7.2 Hz, 3H)

Step b) Formation of 5-[{4-[(4-butylphenyl)ethynyl]benzyl}(3-phenylpropyl)amino]-2-hydroxybenzoic acid, hydrochloride salt

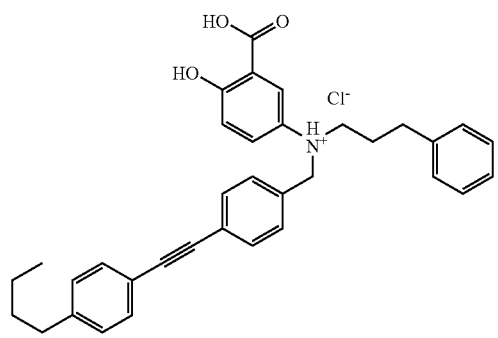

To a solution of 6-[{4-[(4-butylphenyl)ethynyl]benzyl}(3-phenylpropyl)amino]-2,2-dimethyl-4H-1,3-benzodioxin-4-one (147 mg, 0.26 mmol) in MeOH/THF (9 ml, (2/1)) was added an aqueous solution of NaOH (0.3 mL, 5N). The reaction mixture was stirred at rt for 48 hrs. Then a solution of HCl in MeOH (2.5 mL, 1.25M) was added and the solvents were removed under reduced pressure. The residue was taken up with water (5 mL), extracted with Et₂O (2×5 mL) and the combined organic layers were dried over Na₂SO₄. The solvent was removed under reduced pressure. The residue was dissolved in a solution of HCl in Et₂O (2 mL, 1N). Evaporation of the solvent gave 60 mg (32%) of the title compound as a brown foam. HPLC, Rt: 4.8 min (purity: 78.1%). LC/MS, M⁺(ESI): 518.4, M⁻(ESI): 516.3.

Example 8

{4-[({4-[(4-butylphenyl)ethynyl]benzyl}{[(E)-2-phenylvinyl]sulfonyl}-amino)methyl]phenoxy}acetic acid Step a) Formation of methyl {4-[({4-[(4-butylphenyl)ethynyl]benzyl}{[(E)-2-phenylvinyl]-sulfonyl}amino)methyl]phenoxy}acetate acid

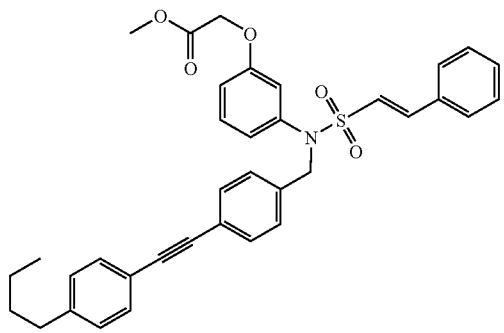

A solution of methyl {4-[({4-[(4-butylphenyl)ethynyl]benzyl}amino)methyl]phenoxy}-acetate (42 mg, 0.10 mmol) and β-styrene sulfonyl chloride (Aldrich, 23 mg, 0.11 mmol) in DCM (2 mL) was stirred at rt overnight in presence of a morpholine resin (1.5 eq., Novabiochem HL, 3.8 mmol/g) (1.5 eq). Trisamine resin (1 eq, Novabiochem, 3.5 mmol/g) was then added and the mixture stirred at rt for an additional 2 hrs. The reaction mixture was then filtrated and the solvent was removed under reduced pressure to give 55 mg (95%) of the title compound. HPLC, Rt: 5.8 min (purity: 83%). M⁺(ESI): 608.2.

Step b) Formation of {4-[({4-[(4-butylpheny Z)ethynyl]benzyl}{[(E)-2-phenylvinyl]sulfonyl}-amino)methyl]phenoxy}acetic acid

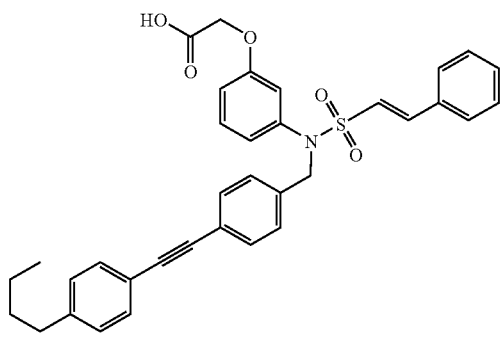

The title compound was prepared following the procedure described in example 6, step f) from methyl {4-[({4-[(4-butylphenyl)ethynyl]benzyl}{[(E)-2-phenylvinyl]sulfonyl}-amino)methyl]phenoxy}acetate (70 mg, 0.12 mmol). The crude was purified by preparative HPLC using a supelcosil ABZ⁺ column. HPLC, Rt: 5.48 min (purity: 89.9%) M⁺(ESI): 594.18, M⁻(ESI): 592.09.

Example 9

5-[{4-[(4-butylphenyl)ethynyl]benzyl}(1-naphthylmethyl)amino]-2-hydroxybenzoic acid hydrochloride salt Step a) Formation of 6-[{4-[(4-butylphenyl)ethynyl]benzyl}(1-naphthylmethyl)amino]-2,2-dimethyl-4H-1,3-benzodioxin-4-one

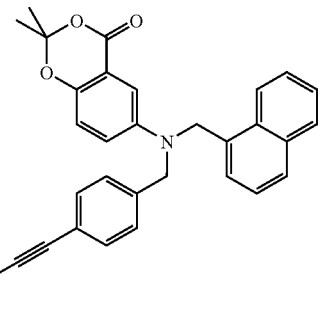

To a solution of 6-({4-[(4-butylphenyl)ethynyl]benzyl}amino)-2,2-dimethyl-4H-1,3-benzodioxin-4-one (150 mg, 0.34 mmol) in anhydrous DCE (3 mL) were added 1-naphtaldehyde (Fluka, 70 µL, 0.51 mmol) and sodium triacetoxyborohydride (110 mg, 0.51 mmol). The reaction mixture was stirred at rt for 72 hrs. The solvent was removed under reduced pressure. The residue was taken up with an aqueous solution of NaOH (2 mL, 1N) and extracted with Et₂O (6 ml). The organic layer was dried over Na₂SO₄ and the solvent was removed under reduced pressure. Purification by flash chromatography on silicagel (pentane/DCM (2/3)) gave 72 mg (36%) of the title compound as a yellow oil. HPLC, Rt: 6.2 min (purity: 100%). ¹H NMR (CDCl₃) δ: 7.91-7.80 (m, 3H), 7.54-7.27 (m, 11H), 7.17 (d, J=7.9 Hz, 2H), 7.08 (m, 1H), 6.78 (d, J=8.7 Hz, 1H), 5.20 (s, 2H), 4.70 (s, 2H), 2.63 (t, J=7.7 Hz, 2H), 1.69 (s, 6H), 1.61 (m, 2H), 1.37 (m, 2H), 0.94 (t, J=7.4 Hz, 3H).

Step b) Formation of 5-[{4-[(4-butylphenyl)ethynyl]benzyl}(1-naphthylmethyl)amino]-2-hydroxybenzoic acid, hydrochloride salt

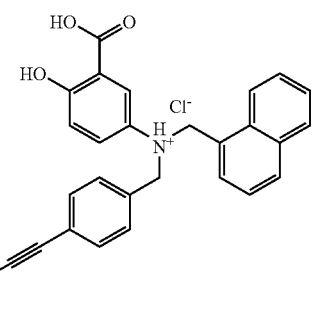

To a solution of 6-[{4-[(4-butylphenyl)ethynyl]benzyl}(1-naphthylmethyl)amino]-2,2-dimethyl-4H-1,3-benzodioxin-4-one (72 mg, 0.12 mmol) in dioxane (2 ml) was added a solution of LiOH hydrate (25 mg, 0.60 mmol) in water (0.2 mL). The reaction mixture was heated at 80° C. for 2 hrs. Then a solution of HCl in dioxane (1 mL, 4N) and a saturated aqueous solution of NaCl (5 mL) were added and extracted with Et$_2$O (2×10 mL). The combined organic layers were dried over Na$_2$SO$_4$ and the solvents were removed under reduced pressure. The residue was dissolved in a solution of HCl in Et$_2$O (1 mL, 1N) and DCM (1 mL). Evaporation of the solvent under reduced pressure gave 41 mg (51%) of the title compound as a beige foam. HPLC, Rt: 5.8 min (purity: 82.7%). LC/MS, M$^+$(ESI): 540.3, M$^-$(ESI): 538.3. $^1$H NMR (CD$_3$OD) δ: 7.97 (m, 3H), 7.72 (m, 1H), 7.58-7.41 (m, 11H), 7.23 (d, J=8.3 Hz, 2H), 6.92 (d, J=9.0 Hz, 1H), 5.42 (s, 2H), 5.11 (s, 2H), 2.67 (t, J=7.5 Hz, 2H), 1.64 (m, 2H), 1.38 (m, 2H), 0.98 (t, J=7.4 Hz, 3H).

Example 10

[4-({{4-[(4-butylphenyl)ethynyl]benzyl}[(cyclohexylamino)carbonyl]amino}methyl)phenoxy]acetic acid Step a) Formation of methyl [4-({{4-[(4-butylphenyl)ethynyl]benzyl)[(cyclohexylamino)-carbonyl]amino}methylphenoxy]acetate

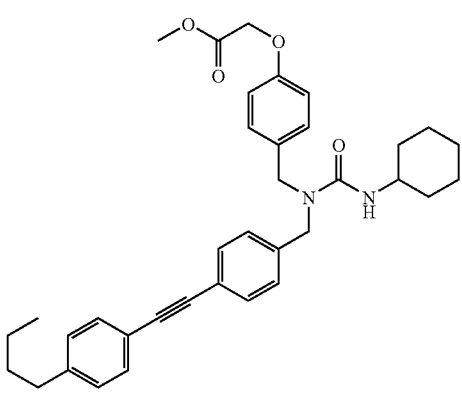

To a suspension of methyl {4-[({4-[(4-butylphenyl)ethynyl]benzyl}amino)methyl]-phenoxy}acetate hydrochloride (500 mg, 1.05 mol) in anhydrous DCM (10 ml) was added DIEA (0.2 mL, 1.18 mmol) and cyclohexyl isocyanate (Aldrich, 0.28 mL, 2.20 mmol). The reaction mixture was stirred at rt for 15 hrs. Then PS-trisamine resin (670 mg, Novabiochem, 3.5 mmol/g) was added and the resulting mixture was stirred at rt for 5 additional hrs. The resin was removed by filtration, washed with DCM and the solvent was evaporated off under reduced pressure. Purification by flash chromatography on silicagel (c-Hex/EtOAc (2/1)) gave 500 mg (84%) of the title compound as a pale yellow oil. HPLC, Rt: 5.9 min (purity: 100%). LC/MS, M$^+$(ESI): 567.4. $^1$H NMR (DMSO-d6) δ: 7.48 (d, J=8.3 Hz, 2H), 7.44 (d, J=8.3 Hz, 2H), 7.24 (d, J=8.3 Hz, 2H), 7.20 (d, J=8.3 Hz, 2H), 7.11 (d, J=8.6 Hz, 2H), 6.88 (d, J=8.6 Hz, 2H), 6.18 (d, J=7.6 Hz, 1H), 4.76 (s, 2H), 4.37 (s, 2H), 4.31 (s, 2H), 3.68 (s, 3H), 3.48 (m, 1H), 2.60 (t, J=7.5 Hz, 2H), 1.75-1.01 (m, 14H), 0.89 (t, J=7.4 Hz, 3H).

Step b) Formation of [4-({{4-[(4-butylphenyl)ethynyl]benzyl}[(cyclohexylamino)carbonyl]-amino}methylphenoxy acetic acid

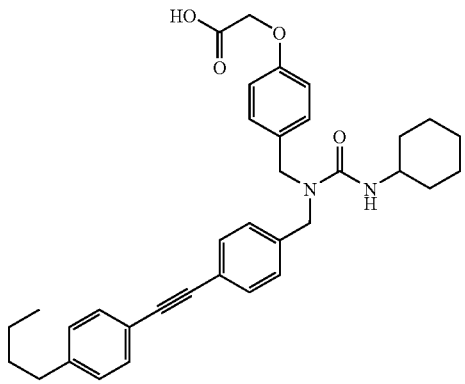

To a solution of methyl [4({{4-[(4-butylphenyl)ethynyl]benzyl}[(cyclohexylamino)-carbonyl]amino}methyl)phenoxy]acetate (500 mg, 0.88 mmol) in MeOH/THF (8 ml, (1/1)) was added an aqueous solution of NaOH (5 mL, 5N). The reaction mixture was stirred at rt for 2 hrs. Then the solution was acidified with an aqueous solution of HCl (1N) and extracted with Et$_2$O (2×). The combined organic layers were dried over MgSO$_4$ and the solvents were removed under reduced pressure to give 459 mg (99%) of the title compound as a pale yellow oil: HPLC, Rt: 5.6 min (purity: 100%). LC/MS, M$^+$(ESI): 553.3, M$^-$(ESI): 551.2. $^1$H NMR (DMSO-d6) δ: 7.48 (d, J=8.3 Hz, 2H), 7.45 (d, J=8.2 Hz, 2H), 7.22 (m, 4H), 7.02 (d, J=8.5 Hz, 2H), 6.71 (d, J=8.5 Hz, 2H), 6.15 (d, J=8.3 Hz, 1H), 4.35 (s, 2H), 4.27 (s, 2H), 3.98 (s, 2H), 3.48 (m, 1H), 2.60 (t, J=7.5 Hz, 2H), 1.80-1.00 (m, 14H), 0.89 (t, J=7.4 Hz, 3H).

Example 11

[4-({{4-[(4-butylphenyl)ethynyl]benzyl}[(cyclohexylamino)carbon-yl]-amino}methyl)phenoxy]acetic acid, N-methyl-D-glucamine (i.e. 1-deoxy-1-(methylamino)glucitol)salt

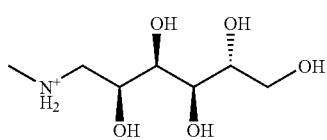

-continued

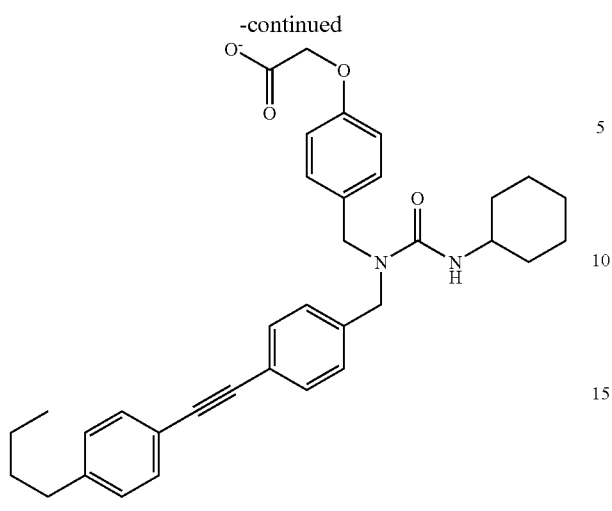

To a solution of the [4-({{4-[(4-butylphenyl)ethynyl]benzyl}[(cyclohexylamino)carbamoyl]-amino}methyl)phenoxy]acetic acid (219 mg, 0.40 mmol) in MeOH (7 mL) was added a solution of N-methyl-D-glucamine (78 mg, 0.40 mmol) in water (2 mL). Water (50 mL) was added and the resulting solution was lyophilized to give 224 mg (76%) of the title compound as a white powder. HPLC, Rt: 5.5 min (purity: 99.8%). LC/MS, M⁺(ESI): 553.8, M⁻(ESI): 551.4.

Example 12

[4-({{4-[(4-butylphenyl)ethynyl]benzyl}[(propylamino)carbonyl]-amino}methyl)phenoxy]acetic acid Step a) Formation of methyl [4-({{4-[(4-butylphenyl)ethynyl]benzyl}[(propylamino)-carbonyl]amino}methyl)phenoxy]acetate

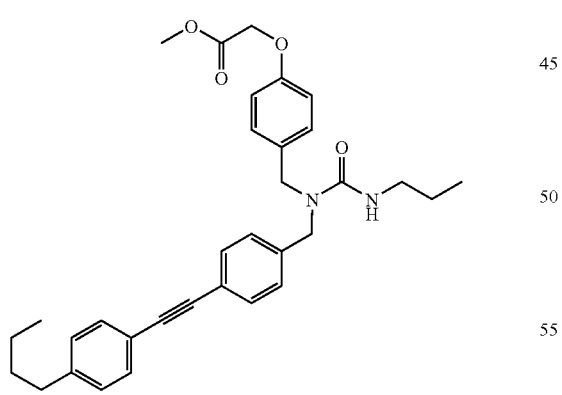

To a solution of methyl {4-[({4-[(4-butylphenyl)ethynyl]benzyl}amino)methyl]-phenoxy}acetate (36 mg, 0.082 mmol) in anhydrous DCM (2 ml) was added n-propyl isocyanate (Aldrich, 16 μL, 0.17 mmol) and the reaction mixture was stirred at rt for 18 hrs.

Then PS-trisamine resin (80 mg, Novabiochem, 3.5 mmol/g) was added and the resulting mixture was stirred at rt for 5 additional hrs. Removal of the resin by filtration followed by the evaporation of the solvent gave 47 mg (99%) of the title compound as a yellow oil. HPLC, Rt: 5.5 min (purity: 96.9%).

Step b) Formation of [4-({{4-[(4-butylphenyl)ethynyl]benzyl}[(propylamino)carbonyl]-amino}methyl)phenoxy]acetic acid

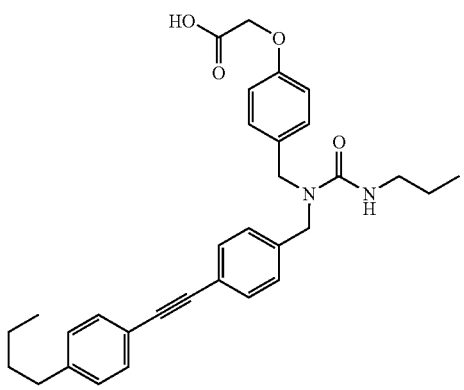

To a solution of methyl [4-({{4-[(4-butylphenyl)ethynyl]benzyl}[(propylamino)carbonyl]-amino}methyl)phenoxy]acetate (47 mg, 0.089 mmol) in MeOH/THF (2 ml, (1/1)) was added an aqueous solution of NaOH (2 mL, 1N). The reaction mixture was stirred at rt for 2 hrs. Then an aqueous solution of HCl (7 mL, 1N) was added and extracted with Et₂O (2×7 mL). The combined organic layers were dried over Na₂SO₄ and the solvents were removed under reduced pressure to give 42 mg (77%) of the title compound as a yellow oil. HPLC, Rt: 5.1 min (purity: 83.9%). LC/MS, M⁺(ESI): 513.4, M⁻(ESI): 511.4. ¹H NMR (DMSO-d6) E: 7.49 (d, J=8.3 Hz, 2H), 7.44 (d, J=7.9 Hz, 2H), 7.22 (m, 4H), 7.11 (d, J=8.8 Hz, 2H), 6.86 (d, J=8.8 Hz, 2H), 6.53 (t, J=5.3 Hz, 1H), 4.63 (s, 2H), 4.37 (s, 2H), 4.31 (s, 2H), 3.03 (m, 2H), 2.60 (t, J=7.7 Hz, 2H), 1.58-1.22 (m, 6H), 0.89 (t, J=7.3 Hz, 3H), 0.78 (t, J=7.4 Hz, 3H).

Example 13

{4-[({4-[(4-butylphenyl)ethynyl]benzyl}{[(4-cyanophenyl)amino]carbonyl}amino)methyl]phenoxy}acetic acid Step a) Formation of methyl [4-({{4-[(4-butylphenyl)ethynyl]benzyl}[(4-cyanoanilino)-carbonyl]amino}methyl)phenoxy]acetate

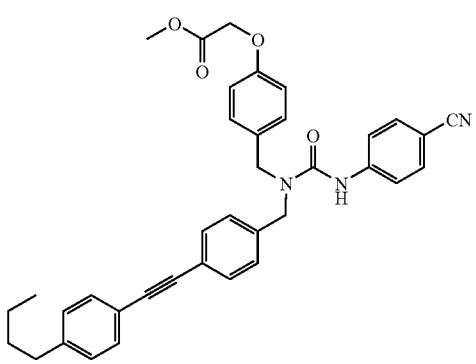

To a solution of methyl {4-[({4-[(4-butylphenyl)ethynyl]benzyl}amino)methyl]-phenoxy}acetate (37 mg, 0.084 mmol) in anhydrous DCM (2 ml) was added 4-cyanophenyl isocyanate (Aldrich, 45 mg, 0.31 mmol) and the reaction mixture was stirred at rt for 18 hrs. Then PS-trisamine resin (75 mg, Novabiochem, 3.5 mmol/g) and DMF (1 mL) were added and the resulting mixture was stirred at rt for 5 additional hrs. Removal of the resin by filtration followed by evaporation of the solvents gave 65 mg (97%) of the title compound as a pale yellow oil. HPLC, Rt: 5.7 min (purity: 74.1%).

Step b) Formation of {4-[({4-[(4-butylphenyl)ethynyl]benzyl}{[(4-cyanophenyl)amino]-carbonyl}amino)methyl]phenoxy}acetic acid

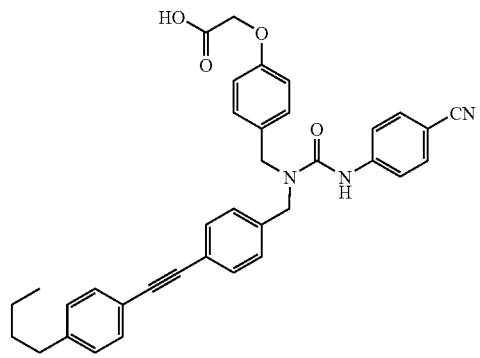

To a solution of methyl [4-({{4-[(4-butylphenyl)ethynyl]benzyl}[(4-cyanoanilino)-carbonyl]amino}methyl)phenoxy]acetate (65 mg) in MeOH/THF (2 ml, (1/1)) was added an aqueous solution of NaOH (2 mL, 1N). The reaction mixture was stirred at rt for 3 hrs. Then an aqueous solution of HCl (7 mL, 1N) was added and extracted with. Et$_2$O (2×7 mL). The combined organic layers were dried over Na$_2$SO$_4$ and the solvents were removed under reduced pressure to give 48 mg of the title compound as a yellow powder. HPLC, Rt: 5.2 min (purity: 75.0%). LC/MS, M$^+$(ESI): 572.4, M$^-$(ESI): 570.4. $^1$H NMR (DMSO-d6) δ: 7.70 (m, 5H), 7.51 (d, J=7.9 Hz, 2H), 7.44 (d, J=7.9 Hz, 2H), 7.28-7.16 (m, 6h), 6.89 (d, J=8.7 Hz, 2H), 4.64 (s, 2H), 4.56 (s, 2H), 4.51 (s, 2H), 2.60 (t, J=7.7 Hz, 2H), 1.55 (m, 2H), 1.28 (m, 2H), 0.89 (t, J=7.2 Hz, 3H).

Example 14

5-((4-tert-butylbenzyl){4-[(4-butylphenyl)ethynyl]benzyl}amino)-2-hydroxybenzoic acid, hydrochloride salt Step a) Formation of 6-((4-tert-butylbenzyl){4-[(4-butylphenyl)ethynyl]benzyl}amino)-2,2-dimethyl-4H-1,3-benzodioxin-4-one

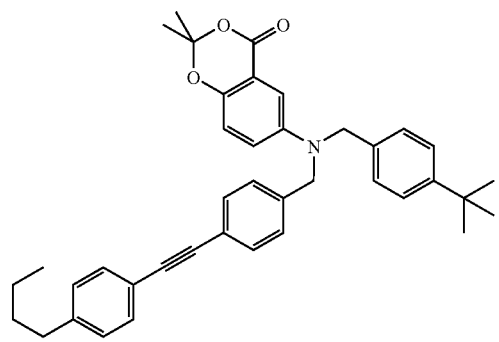

To a solution of 6-({4-[(4-butylphenyl)ethynyl]benzyl}amino)-2,2-dimethyl-4H-1,3-benzodioxin-4-one (150 mg, 0.34 mmol) in anhydrous DCE (3 mL) were added 4-tert-butylbenzaldehyde (Aldrich, 85 µL, 0.51 mmol) and sodium triacetoxyborohydride (110 mg, 0.51 mmol). The reaction mixture was stirred at rt for 72 hrs. The solvent was removed under reduced pressure. The residue was taken up with an aqueous solution of NaOH (2 mL, 1N) and extracted with Et$_2$O (6 ml). The organic layer was dried over Na$_2$SO$_4$ and the solvent was removed under reduced pressure. Purification by flash chromatography on silicagel (pentane/DCM (2/3)) gave 71 mg (31%) of the title compound as a yellow oil. HPLC, Rt: 6.4 min (purity: 86.3%). $^1$H NMR (CDCl$_3$) δ: 7.85-6.90 (m, 15H), 4.62 (brs, 4H), 2.62 (t, J=7.6 Hz, 2H), 1.70 (s, 6H), 1.61 (m, 2H), 1.33 (m, 2H), 1.30 (s, 9H), 0.93 (t, J=7.2 Hz, 3H).

Step b) Formation of 5-((4-tert-butylbenzyl){4-[(4-butylphenyl)ethynyl]benzyl}amino)-2-hydroxybenzoic acid, hydrochloride salt

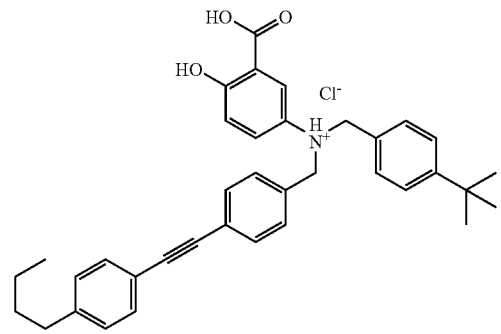

To a solution of 6-((4-tert-butylbenzyl){4-[(4-butylphenyl)ethynyl]benzyl}amino)-2,2-dimethyl-4H-1,3-benzodioxin-4-one (71 mg, 0.12 mmol) in dioxane (2 ml) was added a solution of LiOH hydrate (25 mg, 0.60 mmol) in water (0.2 mL). The reaction mixture was heated at 80° C. for 3 hrs. Then a solution of HCl in dioxane (1 mL, 4N) and a saturated aqueous solution of NaCl (5 mL) were added and extracted with Et$_2$O (2×10 mL). The combined organic layers were dried over Na$_2$SO$_4$ and the solvents were removed under reduced pressure. The residue was dissolved in a solution of HCl in Et$_2$O (1 mL, 1N) and DCM (1 mL). Evaporation of the solvent under reduced pressure gave 57 mg (64%) of the title compound as a beige solid. HPLC, Rt: 5.7 min (purity: 79.0%). $^1$H NMR (CDCl$_3$) δ: 8.08-6.85 (m, 15H), 4.69 (brs, 4H), 2.61 (t, J=7.7 Hz, 2H), 1.59 (m, 2H), 1.34 (m, 2H), 1.24 (s, 9H), 0.93 (t, J=7.3 Hz, 3H).

Example 15

(4-{[{4-[(4-butylphenyl)ethynyl]benzyl}(2-thienyl-sulfonyl)amino]methyl}phenoxy)acetic acid Step a) Formation of methyl (4-{[{4-[(4-butylphenyl)ethynyl]benzyl}(2-thienylsulfonyl)-amino]methyl}phenoxy)acetate

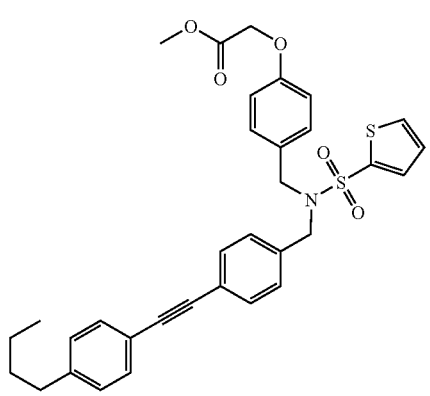

To a cold solution (0° C.) of methyl {4-[({4-[(4-butylphenyl)ethynyl]benzyl}amino)methyl]-phenoxy}acetate (40 mg, 0.091 mmol) in anhydrous pyridine (2 ml) was added 2-thiophenesulfonyl chloride (Aldrich, 82 mg, 0.45 mmol) and the reaction mixture was stirred at 0° C. for 4 hrs and at rt for an additional 15 hours. The reaction mixture was diluted with an aqueous solution of HCl (1N) and extracted with DCM (3×). The combined organic layers were dried over Na$_2$SO$_4$ and the solvent was removed under reduced pressure to give 30 mg (56%) of the title compound as a yellow oil. HPLC, Rt: 5.9 un purity: 92.5%). $^1$H NMR (CDCl$_3$) δ: 7.61 (dd, J=5.3, 1.5 Hz, 1H), 7.58 (dd, J=3.8, 1.5 Hz, 1H), 7.44 (d, J=8.3 Hz, 2H), 7.39 (d, J=7.9 Hz, 2H), 7.17 (d, J=8.3 Hz, 2H), 7.12 (dd, J=5.3, 3.8 Hz, 1H), 7.04 (m, 4H), 6.78 (d, J=8.7 Hz, 2H), 4.61 (s, 2H), 4.33 (s, 2H), 4.30 (s, 2H), 3.81 (s, 3H), 2.63 (t, J=7.7 Hz, 2H), 1.61 (m, 2H), 1.37 (m, 2H), 0.94 (t, J=7.2 Hz, 3H).

Step b) Formation of (4-{[(4-[(4-butylphenyl)ethynyl]benzyl}(2-thienylsulfonyl)amino]-methyl}phenoxy)acetic acid

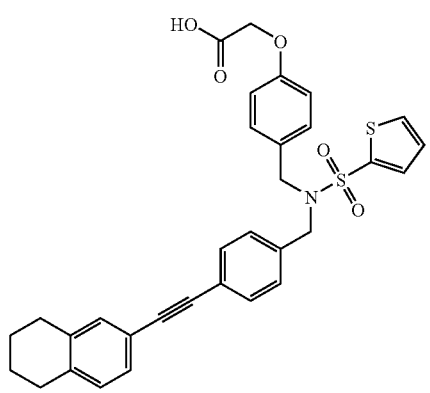

To a solution of methyl (4-{[{4-[(4-butylphenyl)ethynyl]benzyl}(2-thienylsulfonyl)amino]-methyl}phenoxy)acetate (30 mg, 0.051 mmol) in MeOH/THF (4 ml, (1/1)) was added an aqueous solution of NaOH (2 mL, 1N). The reaction mixture was stirred at rt for 2 hrs. Then an aqueous solution of HCl (9 mL, 1N) was added and extracted with Et$_2$O (2×10 mL). The combined organic layers were dried over Na$_2$SO$_4$ and the solvents were removed under reduced pressure to give 30 mg (97%) of the title compound as a green oil. HPLC, Rt: 5.3 min (purity: 95.3%). LC/MS, M$^+$(ESI): 574.2, M$^-$(ESI): 572.3. $^1$H NMR (CDCl$_3$) δ: 7.60 (m, 2H), 7.44 (d, J=8.3 Hz, 2H), 7.38 (d, J=7.9 Hz, 2H), 7.17 (d, J=7.9 Hz, 2H), 7.12 (m, 1H), 7.05 (m, 4H), 6.80 (d, J=8.7 Hz, 2H), 4.66 (s, 2H), 4.33 (s, 2H), 4.31 (s, 2H), 2.63 (t, J=7.5 Hz, 2H), 1.61 (m, 2H), 1.37 (m, 2E), 0.94 (t, J=7.4 Hz, 3H).

Example 16

5-[(1-{4-[(4-butylphenyl)ethynyl]phenyl}pentyl)oxy]-2-hydroxybenzoic acid

Step a) Formation of 1-{4-[(4-butylphenyl)ethynyl]phenyl}-1-pentanol

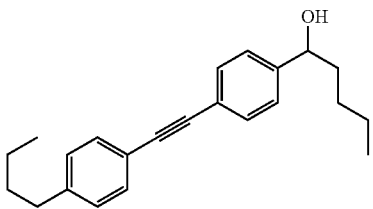

To a cold (−78° C.) solution of 4-[(4-butylphenyl)ethynyl]benzaldehyde (2.6 g, 10.0 mmol, intermediate which may be obtained according to methods disclosed in EP03103780.7) in anhydrous THF (40 mL) was added dropwise a solution of butylmagnesim chloride in THF (7.5 mL, 15.00 mmol, 2N). The resulting solution was stirred at −78° C. for 1 hr, then allowed to reach rt and stirred at rt for 5 hrs. An aqueous solution of HCl (10 mL, 1N) was added and the resulting mixture was extracted with Et$_2$O (3×). The combined organic layers were washed with water and brine, dried over MgSO$_4$ and the solvents were removed under reduced pressure to give 2.45 g (76%) of the title compound as a white solid. HPLC, Rt: 5.4 min (purity: 100%). $^1$H NMR (CDCl$_3$) δ: 7.51 (d, J=8.2 Hz, 2H), 7.44 (d, J=8.3 Hz, 2H), 7.32 (d, J=8.2 Hz, 2H), 7.16 (d, J=8.3 Hz, 2H), 4.68 (t, J=7.2 Hz, 1H), 2.62 (t, J=7.9 Hz, 2H), 1.88-1.19 (m, 10H), 0.98-0.83 (m, 6H).

Step b) Formation of 7-[(1-{4-[(4-butylphenyl)ethynyl]phenyl}pentyl)oxy]-2,2-dimethyl-4H-1,3-benzodioxin-4-one

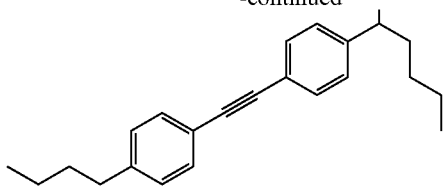

A solution of 7-hydroxy-2,2-dimethyl-4H-1,3-benzodioxin-4-one (363 mg, 1.87 mmol, described in *J. Chem. Soc., Perkin Trans.* 1, 2000, 4265-4278) and tri-n-butylphosphine (378 mg, 1.87 mmol) in anhydrous toluene (10 mL) was chilled at 0° C. To this solution was added N,N,N',N'-tetramiethylazodicarboxamide (322 mg, 1.87 mmol) at once and the resulting reaction mixture was stirred 10 min at 0° C. Then 1-{4-[(4-butylphenyl)ethynyl]phenyl}-1-pentanol (461.5 mg; 1.44 mmol; 1.0 eq.) was added and the resulting mixture was stirred overnight at rt. The solvent was removed under reduced pressure and the crude mixture was purified by chromatography on silicagel (EtOAc/c-Hex (1/9)) to give 456 mg (64%) of the title compound. HPLC, Rt: 6.2 min (purity: 97.0%). $^1$H NMR (CDCl$_3$) δ 7.78 (d, J=8.7 Hz, 1H), 7.50 (d, J=8.3 Hz, 2H), 7.42 (d, J=8.2 Hz, 2H), 7.29 (d, J=8.3 Hz, 2H), 7.15 (d, J=8.3 Hz, 2H), 6.61 (dd, J=2.4 Hz, J=9.0 Hz, 1H), 6.29 (d, J=2.3 Hz, 1H), 5.16-5.07 (m, 1H), 2.61 (t, J=7.8 Hz, 2H), 2.08-1.93 (m, 1H), 1.91-1.75 (m, 1H), 1.73-1.24 (m, 14H), 0.98-0.84 (m, 6H).

Step c) Formation of 4-[(1-{4-[(4-butylphenyl)ethynyl]phenyl}pentyl)oxy]-2-hydroxybenzoic acid

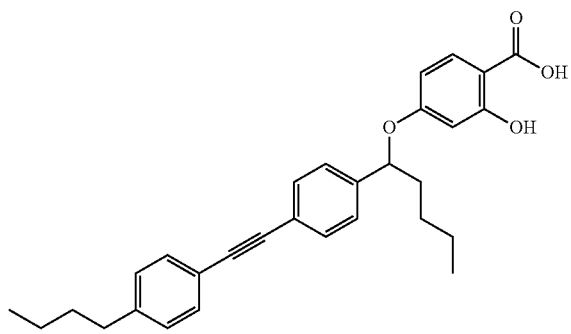

To a solution of 7-[(1-{4-[(4-butylphenyl)ethynyl]phenyl}pentyl)oxy]-2,2-dimethyl-4H-1,3-benzodioxin-4-one (370 mg, 0.74 mmol) in EtOH (10 mL) was added an aqueous solution of NaOH (0.75 mL, 3.75 mmol, 5N) and the resulting mixture was stirred overnight at rt. An aqueous solution of HCl (10 mL, 1N) was added and the resulting reaction mixture was extracted with Et$_2$O (3×). The combined organic layers were washed with water and brine, dried over MgSO$_4$ and the solvents were removed under reduced pressure to give 320 mg (94%) of the title compound as a colorless oil. HPLC, Rt: 6.8 min (purity: 99.8%). LC/MS, M$^-$(ESI): 455.3. $^1$H NMR (CDCl$_3$) δ:10.5 (s, 1H); 9.66 (brs, 1H), 7.72 (d, J=9.0 Hz, 1H), 7.48 (d, J=8.3 Hz, 2H), 7.41 (d, J=8.3 Hz, 2H), 7.28 (d, J=8.3 Hz, 2H), 7.15 (d, J=8.3 Hz, 2H), 6.45 (dd, J=2.3 Hz, J=9.0 Hz, 1H), 6.35 (d, J=2.3 Hz, 1H), 5.14 (t, J=7.8 Hz, 1H), 2.61 (t, J=7.9 Hz, 2H), 2.09-1.93 (m, 1H), 1.90-1.75 (m, 1H), 1.66-1.75 (m, 1H), 1.66-1.19 (m, 8H), 0.96-0.84 (m, 6H).

Example 17

7-[(1-{4-[(4-butylphenyl)ethynyl]phenyl}pentyl)oxy]-2,2-dimethyl-4H-1,3-benzodioxin-4-one, N-methyl-D-glucamine (i.e. 1-deoxy-1-(methylamino)-glucitol) salt

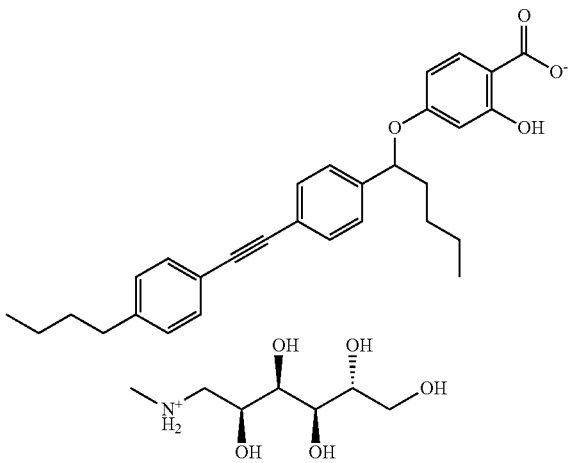

To a solution of 7-[(1-{4-[(4-butylphenyl)ethynyl]phenyl}pentyl)oxy]-2,2-dimethyl-4H-1,3-benzodioxin-4-one (354 mg, 0.78 mmol) in EtOH (5 mL) was added N-methyl-D-glucamine (151 mg, 0.78 mmol) and the resulting reaction mixture was stirred until complete dissolution. After evaporation of most of the solvent (ca. 80%), water (10 mL) was added to the solution and the resulting mixture was lyophilized to give 461 mg (91%) of the title compound as a white powder. HPLC, Rt: 6.0 min (purity: 99.7%). M$^-$(ESI): 455.2.

Example 18

(4-{[{4-[(4-butylphenyl)ethynyl]benzyl}(ethylsulfonyl)amino]-methyl}phenoxy)acetic acid Step a) Formation of methyl (4-{[{4-[(4-butylphenyl)ethynyl]benzyl}(ethylsulfonyl)-amino]methyl}phenoxy)acetate

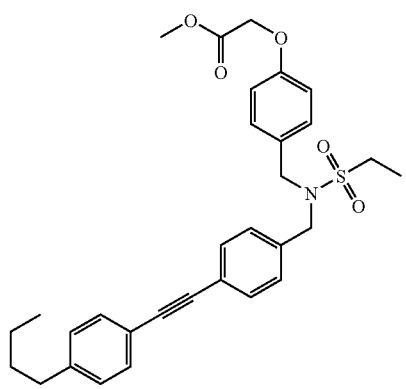

To a cold solution (0° C.) of methyl {4-[({4-[(4-butylphenyl)ethynyl]benzyl}amino)-methyl]phenoxy}acetate (38 mg, 0.086 mmol) in anhydrous pyridine (2 mL) was added ethanesulfonyl chloride (Fluka, 40 ∞l, 0.43 mmol) and the reaction mixture was stirred at 0° C. for 4 hrs and at rt for an additional 15 hours. The reaction mixture was diluted with an aqueous solution of HCl (1N) and extracted with DCM (3×). The combined organic layers were dried over MgSO$_4$ and the solvent was removed under reduced pressure. Purification by flash chromatography on silicagel (cHex/EtOAc) gave 7 mg (15%) of the title compound as a colorless oil. LC/MS, M$^+$(ESI): 534.3 (purity: 94.5%).

Step b) Formation of (4-{[{4-[(4-butylphenyl)ethynyl]benzyl}(ethylsulfonyl)amino]-methyl}phenoxy) acetic acid

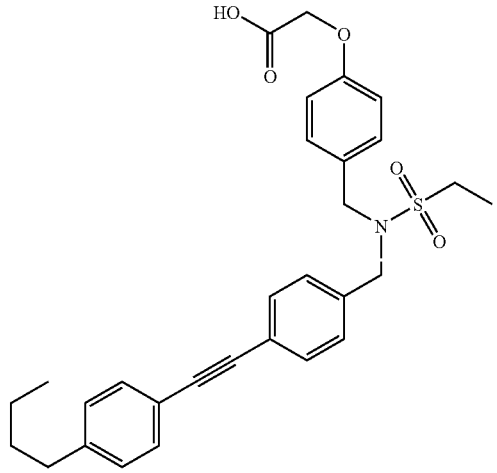

To a solution of methyl (4-{[{4-[(4-butylphenyl)ethynyl]benzyl}(ethylsulfonyl)amino]-methyl}phenoxy)acetate (7 mg, 0.013 mmol) in EtOH (1 mL) was added an aqueous solution of NaOH (20 µL, 5N). The reaction mixture was stirred at 70° C. for 2 hrs. Then an aqueous solution of HCl (1N) was added and extracted with EtOAc (2×). The combined organic layers were dried over Na$_2$SO$_4$ and the solvents were removed under reduced pressure to give 6 mg (90%) of the title compound as a pale yellow oil. HPLC, Rt: 5.0 min (purity: 75.0%). LC/MS, M$^+$(ESI): 520.5, M$^-$(ESI): 518.3.

Example 19

5-[{{4-[(4-butylphenyl)ethynyl]benzyl}(hexyl)amino]carbonyl}-2-hydroxybenzoic acid, N-methyl-D-glucamine (i.e. 1-deoxy-1-(methylamino)-glucitol) salt Step a) Formation of 2,2-dimethyl-4-oxo-4H-1,3-benzodioxine-6-carboxylic acid

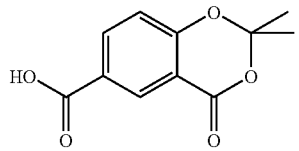

A suspension of 4-hydroxyisophtalic acid (Aldrich, 5.0 g, 27.5 mmol) in acetone (10 mL), TFA (30 mL) and TFAA (10 mL) was heated at 100° C. for 24 hrs. The reaction mixture was concentrated under reduced pressure. The residue was taken up with an aqueous solution of HCl (100 mL, 1N) and extracted with EtOAc (3×200 L); The combined organic layers were dried over MgSO$_4$ and the solvents were removed under reduced: pressure. The crude compound was recrystallized in Et$_2$O (50 mL) to give 4.67 g (77%) of the title compound as a beige powder. $^1$H NMR (DMSO-d$_6$) δ: 8.37 (d J=1.9 Hz, 1H), 8.19 (dd, J=2.2 and 8.7 Hz, 1H), 7.23 (d, J=8.3 Hz, 1H), 1.72 (s, 6H). HPLC, Rt: 2.40 min (purity: 95.7%).

Step b) Formation of N-{4-[(4-butylphenyl)ethynyl]benzyl}-1-hexanamine

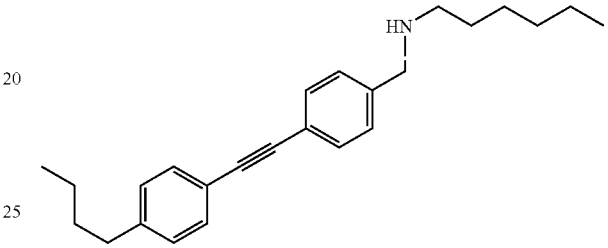

To a solution of 4-[(4-butylphenyl)ethynyl]benzaldehyde (334 mg, 1.27 mmol, intermediate which may be obtained according to methods disclosed in EP03103780.7) and hexylamine (Aldrich, 98 µL, 1.53 mmol) in DCE (15.00 mL) was added acetic acid (110 mL) and sodium triacetoxyborohydride (405 mg, 1.91 mmol) and the resulting mixture was stirred at rt for 3 hrs. The reaction mixture was then diluted with DCM and washed with a saturated aqueous solution of NaHCO$_3$ and brine. The organic layer was dried over MgSO$_4$ and the solvents were removed under reduced pressure. The crude product was purified by flash chromatography on silicagel (DCM, DCM/MeOH/NH$_4$OH 98:2:1 then 95:5:1) to give 144 mg (32%) of the title compound. HPLC, Rt: 4.59 min (purity: 98.7%). $^1$H NMR (CD$_3$Cl$_3$) δ: 0.87 (t, J=6.9 Hz, 3H), 0.91 (t, J=7.3 Hz, 3H), 1.28-1.64 (m, 13H), 2.6 (t, J=7.3 Hz, 4H), 3.78 (s, 2H), 7.14 (d, J=8.1 Hz, 2H), 7.28 (d, J=8.3 Hz, 2H), 7.42 (d, J=8.3 Hz, 2H), 7.47 (d, J=8.1 Hz, 2H).

Step c) Formation of N-{4-[(4-butylphenyl)ethynyl]benzyl}-N-hexyl-2,2-dimethyl-4-oxo-4H-1,3-benzodioxine-6-carboxamide

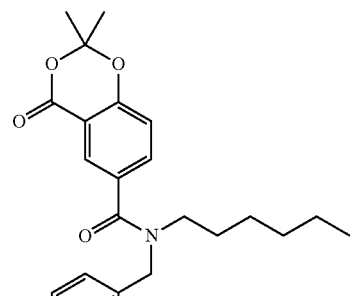

A solution of N-{4-[(4-butylphenyl)ethynyl]benzyl}-1-hexanamine (144 mg, 0.41 mmol), 2,2-dimethyl-4-oxo-4H-1,3-benzodioxine-6-carboxylic acid (92 mg, 0.41 mmol), EDC.HCl (87 mg, 0.46 mmol), HOBT (61 mg, 0.46 mmol) and DIEA (105 µL, 0.62 mmol) in DCM (10 mL) was stirred at rt overnight. Then the reaction mixture was diluted with DCM and washed with a saturated aqueous solution of NaHCO$_3$, a saturated aqueous solution of NH$_4$Cl and brine. The organic layer was dried over MgSO$_4$ and the solvent was removed under reduced pressure. The crude product was purified by flash chromatography on silicagel (EtOAc/c-Hex (20/80)) to give 108 mg (47%) of the title compound as a colorless oil. HPLC, Rt: 6.14 min (purity: 99.9%). $^1$H NMR (CD$_3$Cl$_3$) δ: 0.82 (m, 3H), 0.91 (t, J=7.3 Hz, 3H), 1.32-1.40 (m, 10H), 1.57 (m, 2H), 1.72 (s, 6H), 2.59 (t, J=7.6 Hz, 2H), 3.16-3.41 (m, 2H), 4.40-4.72 (m, 2H), 7.00 (m, 2H), 7.14 (d, J=8.3 Hz, 2H), 7.25 (m, 1H), 7.42 (d, J=8.1 Hz, 2H), 7.48 (d, J=8.1 Hz, 2H), 7.61 (m, 1H), 8.03 (s, 1H).

Step d) Formation of 5-{[{4-[(4-butylphenyl)ethynyl]benzyl}(hexyl)amino]carbonyl)-2-hydroxybenzoic acid

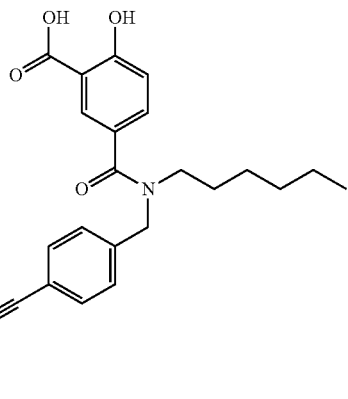

A solution of N-{4-[(4-butylphenyl)ethynyl]benzyl}-N-hexyl-2,2-dimethyl-4-oxo-4H-1,3-benzodioxine-6-carboxamide (108 mg, 0.20 mmol) and lithium hydroxide (120 mg, 2.9 mmol) in THF (1 mL) and water (1 mL) was heated at 70° C. overnight. The solvents were removed under reduced pressure. The residue was taken up in EtOAc and washed with an aqueous solution of HCl (1N) and brine, dried over MgSO$_4$ and the solvent was removed under reduced pressure to give 91 mg (91%) of hte title compound. HPLC, Rt: 5.72 min (purity: 98.9%).

Step e) Formation of 5-{[{4-[(4-butylphenyl)ethynyl]benzyl}(hexyl)amino]carbonyl}-2-hydroxybenzoic acid N-methyl-D-glucamine (i.e. 1-deoxy-1-(methylamino)glucitol) salt

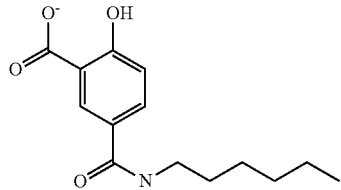

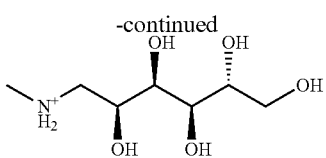

To a solution of 5-{[{4-[(4-butylphenyl)ethynyl]benzyl}(hexyl)amino]carbonyl}-2-hydroxybenzoic acid (91 mg, 98 mmol) in MeOH (2 mL) was added a solution of N-methyl-D-glucamine (35 mg, 0.18 mmol) in water (2 mL). Water (20 mL) was added and the resulting solution was lyophilized to give 103 mg of the title compound as a white powder. HPLC, Rt: 5.73 min (purity: 99.6%). LC/MS, M$^+$(ESI): 512.2, M$^-$(ESI). 510.2. $^1$H NMR (CD$_3$OD) δ: 0.84 (m, 3H), 0.94 (t, J=7.3 Hz, 3H), 1.28-1.40 (m, 8H), 1.60 (m, 4H), 2.62 (t, J=7.7 Hz, 2H), 2.69 (s, 3H), 3.15 (d, J=6.0 Hz, 2H), 3.31 (m, 2H), 3.63-3.83 (m, 5H), 4.03 (m, 1H), 4.72 (m, 2H), 6.86 (d, J=8.3 Hz, 1H), 7.18 (d, J=8.3 Hz 2H), 7.19 (m, 1H), 7.40 (d, J=7.9 Hz, 2H), 7.48 (d, J=7.9 Hz, 2H), 7.99 (d, J=2.3 Hz, 1H). M$^+$(ESI): 512.2, M$^-$(ESI): 510.2.

Example 20

5-{[{4-[(4-butylphenyl)ethynyl]benzoyl}(hexyl)amino]methyl}-2-hydroxybenzoic acid N-methyl-D-glucamine (i.e. 1-deoxy-1-(methyl-amino)glucitol) salt Step a) Formation of 2,2-dimethyl-4-oxo-4H-1,3-benzodioxine-6-carbaldehyde

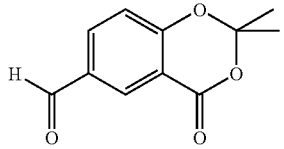

A suspension of 5-formylsalicylic acid (Aldrich, 4.12 g, 24.8 mmol) in TFA (30 ml), TFAA (10 ml) and acetone (10 ml) was heated at 90° C. overnight. The reaction mixture was concentrated under reduced pressure. The residual oil was taken up in EtOAc and washed with a saturated aqueous solution of NaHCO$_3$ and brine. The organic layer was dried-over MgSO$_4$ and the solvent was removed under reduces pressure. The crude product was purified by flash chromatography on silicagel (EtOAc/c-Hex (80/20)) to give 1.8 g (35%) of the title compound as a white powder. $^1$H NMR (CDCl$_3$) δ: 1.80 (s, 6H), 7.09 (d, J=8.7 Hz, 1H), 8.09 (dd, J=8.7, 2.3 Hz, 1H), 8.45 (d, J=1.9 Hz, 1H).

Step b) Formation of 6-[(hexylamino)methyl]-2,2-dimethyl-4H-1,3-benzodioxin-4-one

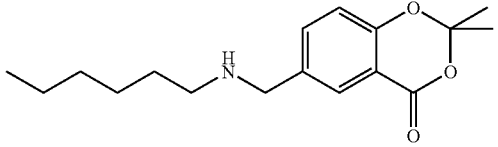

To a solution of 2,2-dimethyl-4-oxo-4H-1,3-benzodioxine-6-carbaldehyde (510 mg, 2.47 mmol) in anhydrous DCE (20 mL) was added n-hexylamine (392 µL, 2.97 mmol), acetic acid (212 µL) and sodium triacetoxyborohydride (786 mg, 3.71 mmol) and the resulting mixture was stirred at rt for 3 hrs. The reaction mixture was diluted with DCM and washed with a saturated aqueous solution of NaHCO$_3$ and brine. The organic layer was dried over MgSO$_4$ and the solvents were removed under reduced pressure. Purification by flash chromatography on silicagel (EtOAc/c-Hex (20/80)) gave 627 mg (87%) of the title compound. HPLC, Rt: 2.70 min purity: 86.4%). $^1$H NMR (CDCl$_3$) δ: 0.85 (t, J=6.8 Hz, 3H), 1.28 (m, 6H), 1.48 (m, 2H), 1.70 (s, 6H), 2.41 (m, 1H), 2.58 (t, J=7.3 Hz, 2H), 3.74 (s, 2H), 6.90 (d, J=8.5 Hz, 1H), 7.53 (dd, J=8.5, 2.3 Hz, 1H), 7.86 (d, J=2.1 Hz, 1H).

Step c) Formation of Methyl 4-[(4-butylphenyl)ethynyl]benzoate

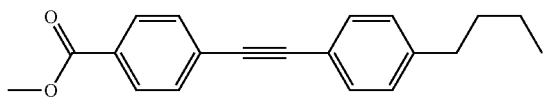

To a solution of 1-butyl-4-ethynylbenzene (Aldrich, 25.0 g, 0.157 mol) and methyl 4-bromobenzoate (Aldrich, 30.9 g, 0.143 mol) in dry acetonitrile (300 mL) under nitrogen was added cuprous iodide (1.36 g, 7.18 mmol), TEA (43.6 g, 0.431 mol) followed by Pd(PPh$_3$)$_2$Cl$_2$ (5.0 g, 7.18 mmol) and the reaction mixture was stirred at 85° C. for 20 hrs. The solvent was removed under reduced pressure. The residue was taken up with Et$_2$O (300 ml) and washed with water and brine. The organic layer was dried over MgSO$_4$ and the solvent was removed under reduced pressure. Purification by flash chromatography on silicagel (PetEther) gave 23.0 g (55%) of the title compound.

Step d) Formation of 4-(4-butylphenylethynyl)benzoic acid

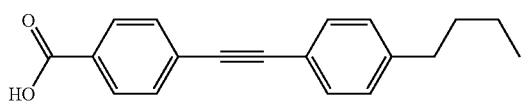

To a solution of methyl 4-[(4-butylphenyl)ethynyl]benzoate (23.0 g, 0.078 mol) in MeOH (200 ml) was added LiOH (3.6 g, 0.157 mol) followed by water (50 mL) and the reaction mixture was stirred for 5 hrs at rt. The solvents were removed under reduced pressure. The residue was acidified with an aqueous solution of HCl (1.5M) and a solid precipitated out. The precipitate was filtered and dried to yield 19.5 g (89%) of the title compound. 1H NMR (DMSO-d$_6$) δ: 13.1 (brs, 1H), 7.96 (dd, J=1.6 and 6.7 Hz, 2H), 7.64 (d, J=6.8 Hz, 2H), 7.49 (d, J=8.1 Hz, 2H), 7.25 (d, J=8.2 Hz, 2H), 2.60 (t, J=7.5 Hz, 2H), 1.55 (m, 2H), 1.29 (m, 2H), 0.88 (t, J=7.3 Hz, 3H).

Step e) Formation of 4-[(4-butylphenyl)ethynyl]-N-[(2,2-dimethyl-4-oxo-4H-1,3-benzodioxin-6-yl)methyl]-N-hexylbenzamide

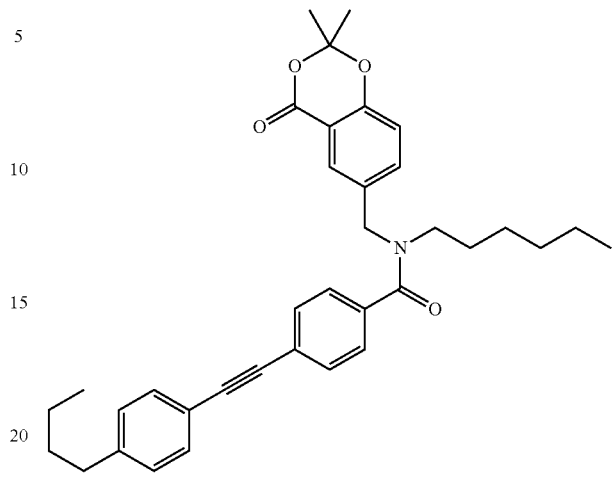

A solution of 4-(4-butylphenylethynyl)benzoic acid (330 mg, 1.19 mmol), EDC.HCl (231 mg, 1.21 mmol), HOBT (163 mg, 1.21 mmol) and DIEA (256 µl, 1.51 mmol) in DCM (15 mL) was stirred 10 min at rt. Then a solution of 6-[(hexylamino)methyl]-2,2-dimethyl-4H-1,3-benzodioxin-4-one (293 mg, 1.01 mmol) in DCM (5 mL) was added and the resulting mixture was stirred 3 hrs at rt. The reaction mixture was diluted with DCM and washed with a saturated aqueous solution of NaHCO$_3$, an aqueous solution of HCl (1N) and brine. Organic layer was dried over MgSO$_4$ and the solvent was removed under reduced pressure. Purification by flash chromatography on silica gel (EtOAc/c-Hex (20/80)) gave 420 mg (73%) of the title compound. HPLC, Rt: 6.18 min (purity: 92.3%). A second purification by preparative HPLC with a X-Terra column allowed the isolation of the title compound (300 mg, 54% yield) as a white powder. HPLC, Rt: 6.15 min (purity: 99.1%). LC/MS, M$^+$(ESI): 552.7. $^1$H NMR (CDCl$_3$) δ: 0.82 (m, 3H), 0.91 (t, J=7.3 Hz, 3H), 1.09-1.41 (m, 8H), 1.53 (m, 4H), 1.72 (s, 6H), 2.60 (t, J=7.6 Hz, 2H), 3.16-3.45 (m, 2H), 4.50-4.70 (m, 2H), 6.96 (d, J=8.5 Hz, 1H), 7.15 (d, J=8.1 Hz, 2H), 7.37 (d, J=8.3 Hz, 2H), 7.42 (d, J=7.9 Hz, 2H), 7.52-7.84 (m, 4H).

Step f) Formation of 5-{[{4-[(4-butylphenyl)ethynyl]benzoyl}(hexyl)amino]methyl}-2-hydroxybenzoic acid

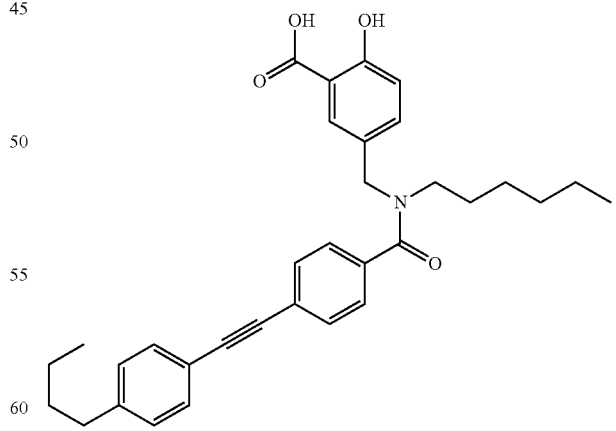

The title compound was prepared following procedure described in example 19, step c) from 4-[(4-butylphenyl)ethynyl]-N-[(2,2-dimethyl-4-oxo-4H-1,3-benzodioxin-6-yl)methyl]-N-hexylbenzamide (300 mg, 0.54 mmol) to give 253 mg (91%) of a white powder. HPLC, Rt: 5.74 min (purity: 99.6%). LC/MS, M-(ESI): 509.9.

Step g), Formation of 5-{[{4-[(4-butylphenyl)ethynyl]benzoyl}(hexyl)amino]methyl}-2-hydroxybenzoic acid, N-methyl-D-glucamine (i.e. 1-deoxy-1-(methylamino)glucitol) salt

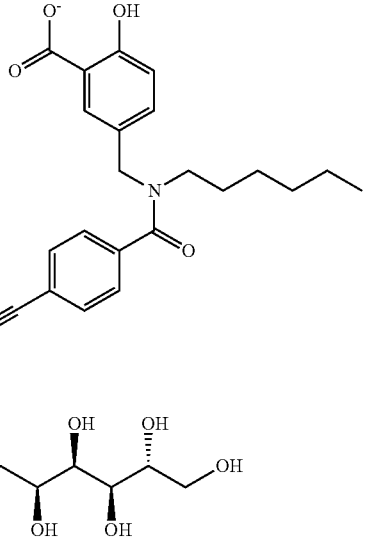

To a solution of 5-{[{4-[(4-butylphenyl)ethynyl]benzoyl}(hexyl)amino]methyl}-2-hydroxybenzoic acid (253 mg, 0.49 mmol) in MeOH (5 mL) was added a solution of N-methyl-D-glucamine (97 mg, 0.49 mmol) in water (2 mL). Water (20 mL) was added and the resulting solution was lyophilized to give 306 mg of the title compound as a white powder. HPLC, Rt: 5.75 min (purity: 99.8%). LC/MS, M$^+$(ESI): 512.0, M$^-$(ESI): 509.9. $^1$H NMR (CD$_3$OD) δ: 0.81 (m, 3H), 0.94 (t, J=7.4 Hz, 3H), 1.07 (m, 3H), 1.37 (m, 5H), 1.58-1.71 (m, 4H), 2.63 (t, J=7.7 Hz, 2H), 2.69 (s, 3H), 3.14 (d, J=6.0 Hz, 2H), 3.29 (m, 1H), 3.43 (m, 1H), 3.61-3.83 (m, 5H), 4.04 (t, J=6.4 Hz, 1H), 4.69 (s, 1H), 4.85 (s, 1H), 6.80 (m, 1H), 7.08 (m, 0.5H), 7.19 (d, J=8.3 Hz, 2H), 7.41-7.47 (m, 4.5H), 7.57 (m, 2H), 7.72 (m, 0.5H), 7.85 (m, 0.5H). Analysis calculated for C$_{33}$H$_{37}$NO$_4$.C$_7$H$_{17}$NO$_5$.1.5 H$_2$0: C, 65.46; H, 7.83; N, 3.82%. Found: C, 65.50; H, 7.69; N, 3.80%

Example 21

5-{[{4-[(4-butylphenyl)ethynyl]benzyl}(hexyl)amino]sulfonyl}-2-hydroxybenzoic acid, N-methyl-D-glucamine (i.e. 1-deoxy-1-(methylamino)-glucitol) salt Step a) Formation of 5-{[{4-[(4-butylphenyl)ethynyl]benzyl}(hexyl)amino]sulfonyl}-2-hydroxybenzoic acid

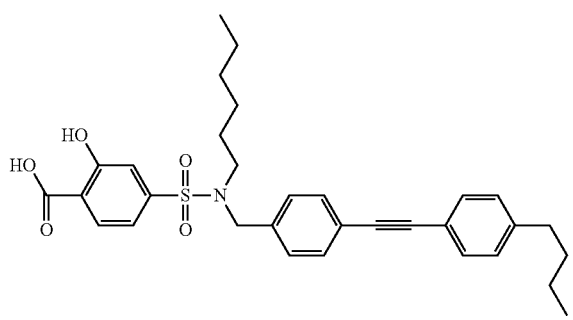

A solution of N-{4-[(4-butylphenyl)ethynyl]benzyl}-1-hexanamine (323 mg, 0.93 mmol), 3-hydroxy-4-carboxybenzene sulfonyl chloride (231 mg, 0.98 mmol) arid K$_2$CO$_3$ (385 mg, 2.79 mmol) in dioxane (5 mL) and water (5 mL) was stirred at room temperature-overnight. The solvent was removed under reduced pressure. The residue was diluted with an aqueous solution of HCl (1N) and extracted with EtOAc. The organic layer was washed with brine, dried over MgSO$_4$ and the solvents were removed under reduced pressure. Purification by preparative HPLC using a X-Terra column gave 287 mg (56%) of the title compound as a white powder. HPLC Rt: 6.01 min (purity: 97.8%). LC/MS, M$^-$(ESI): 546.7. $^1$H NMR (CD$_3$OD) δ: 0.82 (t, J=7.00 Hz, 3H), 0.94 (t, J=7.3 Hz, 3H), 1.12 (m, 6H), 1.38 (m, 4H), 1.61 (qt, J=7.6 Hz, 2H), 2.63 (t, J=7.7 Hz, 2H), 3.14 (t, J=7.5 Hz, 2H), 4.39 (s, 2H), 7.19 (d, J=7.2 Hz, 2H), 7.33-7.48 (m, 8H), 8.06 (d, J=7.9 Hz, 1H).

Step b) Formation of 5-{[{4-[(4-butylphenyl)ethynyl]benzyl}(hexyl)amino]sulfonyl}-2-hydroxybenzoic acid, N-methyl-D-glucamine (i.e. 1-deoxy-1-(methylamino)glucitol) salt

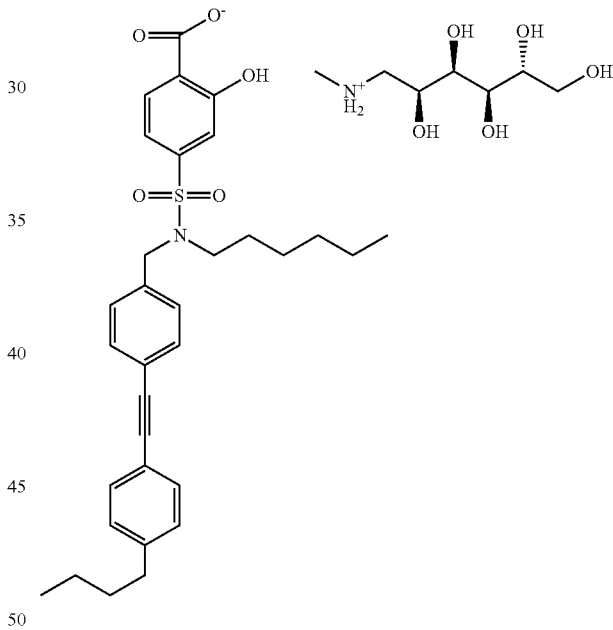

To a solution of 5-{[{4-[(4-butylphenyl)ethynyl]benzyl}(hexyl)amino]sulfonyl}-2-hydroxybenzoic acid (287 mg, 0.52 mmol) in MeOH (5 mL) was added a solution of N-methyl-D-glucamine (102 mg, 0.52 mmol) in water (4 mL). Water (20 mL) was added and the resulting solution was lyophilized to give 300 mg of the title compound as a white powder. HPLC, Rt: 5.98 min (purity: 99.9%). LC/MS, M(ESI): 545.9. $^1$H NMR (CD$_3$OD) δ: 0.79 (t, J=7.0 Hz, 3H), 0.92 (t, J=7.2 Hz, 3H), 1.28 (m, 6H), 1.33 (m, 4H), 1.58 (m, 2H), 2.60 (t, J=7.3 Hz, 2H), 2.70 (s, 3H), 3.08 (t, J=7.2 Hz, 2H), 3.16 (m, 2H), 3.68-3.83 (m, 4H), 4.33 (m, 1H), 4.33 (s, 2H), 7.15-7.45 (m, 10H), 8.02 (d, J=7.9 Hz, 1H). Analysis calculated for C$_{32}$H$_{37}$NO$_5$S.C$_7$H$_{17}$NO$_5$.H$_2$O: C 61.56; H 7.42; N 3.68%. Found: C, 61.70; H 7.30; N, 3.71%

Example 22

4-[{4-[(4-butylphenyl)ethynyl]benzyl}(hexyl)amino]-2-hydroxybenzoic acid, N-methyl-D-glucamine (i.e. 1-deoxy-1-(methylamino)glucitol) salt Step a) Formation of 7-[4-(4-butyl-phenylethynyl)-benzylamino]-2,2-dimethyl-benzo[1,3]dioxin-4-one

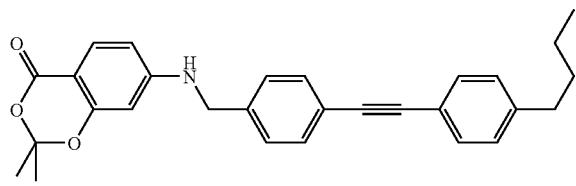

A solution of 4-[(4-butylphenyl)ethynyl]benzaldehyde (2.0 g, 7.63 mmol, intermediate which may be obtained according to methods disclosed in EP03103780.7) and 7-amino-2,2-dimethyl-4H-1,3-benzodioxine-4-one (1.47 g, 7.63 mmol) in toluene (30 mL) was heated at reflux for 96 hrs with azeotropic removal of water. The reaction mixture was concentrated off under reduced pressure. MeOH (15 mL) and THF (15 mL) were then added, and the resulting mixture chilled at 0° C. Sodium borohydride (375 mg, 9.9 mmol) was added portionwise and the mixture was stirred for 1 hr at 0° C., then 3 hrs at room temperature. The reaction mixture was diluted with EtOAc (60 mL) and washed with an aqueous solution of NaOH (3×15 mL, 1N). The organic layer was dried over MgSO$_4$ and the solvents were removed under reduced pressure. Et$_2$O (100 mL) was added and the resulting white precipitate was filtered off to give 2.2 g (66%) of the title compound as a white solid. HPLC, Rt: 5.62 min (purity: 93.6%). LC/MS, M$^-$(ESI): 438.3, M$^+$(ESI): 440.2. $^1$H NMR (CDCl$_3$) δ: 7.71 (d, J=8.6 Hz, 1H), 7.50 (d, J=8.3 Hz, 2H), 7.42 (d, J=8.3 Hz, 2H), 7.29 (d, J=7.9 Hz, 2H), 7.14 (d, J=7.9 Hz, 2H), 6.32 (m, 1H), 6.01 (m, 1H), 4.38 (s, 2H), 2.61 (t, J=7.5 Hz, 2H), 1.60 (s, 6H), 1.65-1.50 (m, 2H), 1.42-1.28 (m, 2H), 0.91 (t, J=7.5 Hz, 3H).

Step b) formation of 7-[{4-[(4-butylphenyl)ethynyl]benzyl}(hexyl)amino]-2,2-dimethyl-4H-1,3-benzodioxin-4-one

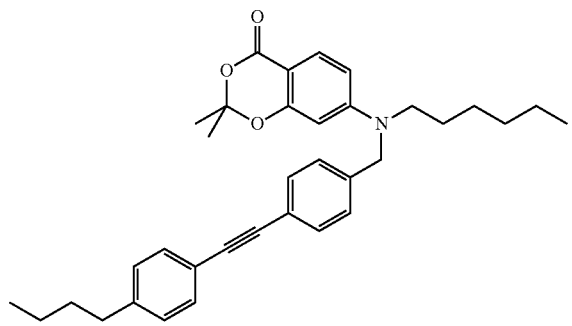

To a solution of 7-[4-(4-butyl-phenylethynyl)-benzylamino]-2,2-dimethyl-benzo[1,3]-dioxin-4-one (1.16 g, 2.64 mmol) in DMSO (32 mL) was added sodium hydride (159 mg, 3.96 mmol, 55-65% in oil) and the resulting mixture was stirred 2 min at rt, then 1-bromohexane (559 µl, 3.96 mmol) was added. The red solution was stirred at rt for 2 hrs. The reaction mixture was poured in EtOAc (70 mL) and washed with an aqueous solution of HCl (2×30 mL, 0.1N) and water (6×30 mL). The organic layer was dried over MgSO$_4$ and the solvents were removed under reduced pressure. The crude mixture was purified by flash chromatography on silicagel (c-Hex/EtOAc (6/1)) to give 795 mg (56%) of the title compound as a yellow oil. HPLC, Rt: 6.4 min (purity: 98.3%). M$^+$(ESI): 524.5. $^1$H NMR (CDCl$_3$) δ: 7.71 (d, J=8.7 Hz, 1H), 7.47 (d, J=8.3 Hz, 2H), 7.41 (d, J=7.9 Hz, 2H), 7.13 (m, 4H), 6.36 (m, 1H), 6.04 (m, 1H), 4.58 (s, 2H), 3.40 (t, J=7.7 Hz, 2H), 2.61 (t, J=7.7 Hz, 2H), 1.76-1.48 (m, 8H), 1.42-1.20 (m, 10H), 0.95-0.82 (m, 6H).

Step c) formation of 4-{[4-(4-butyl-phenylethynyl)-benzyl]-hexyl-amino}-2-hydroxy-benzoic acid

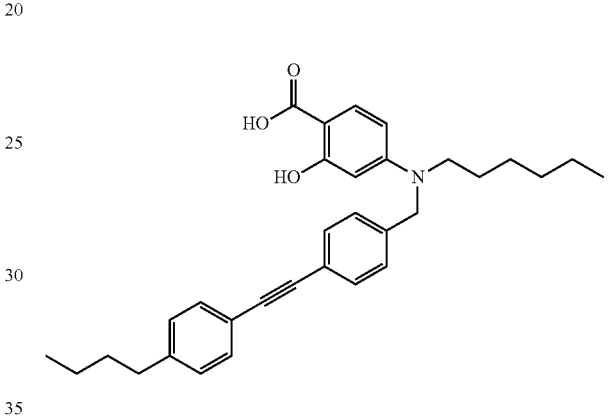

To a solution of 7-[{4-[(4-butylphenyl)ethynyl]benzyl}(hexyl)amino]-2,2-dimethyl-4H-1,3-benzodioxin-4-one (613 mg, 1.2 mmol) in THF (18 mL) was added a suspension of lithium hydroxide monohydrate (1.47 g, 35.1 mmol) in water (5.0 mL). The resulting mixture was refluxed for 48 hrs. The reaction mixture was diluted with Et$_2$O (60 mL) and washed with an aqueous solution of HCl (3×15 mL, 1N) and brine. The organic layer was dried over MgSO$_4$ and the solvents were removed under reduced pressure to give 443 mg (78%) of the title compound as a yellow powder. HPLC, Rt: 6.2 min (purity: 97.7%). LC/MS, M$^-$(ESI): 482.2. $^1$H NMR (CDCl$_3$) δ: 10.59 (s, 1H), 7.66 (d, J=9 Hz, 1H), 7.45 (m, 4H), 7.13 (m, 4H), 6.21 (m, 1H), 6.14 (m, 1H), 4.58 (s, 2H), 3.40 (m, 2H), 2.60 (t, J=7.5 Hz, 2H), 1.72-1.51 (m, 2H), 1.42-1.20 (m, 10H), 0.95-0.82 (m, 6H).

Step d) formation of 4-[{4-[(4-butylphenyl)ethynyl]benzyl}(hexyl)amino]-2-hydroxybenzoic acid, N-methyl-D-glucamine (i.e. 1-deoxy-1-(methylamino)glucitol) salt

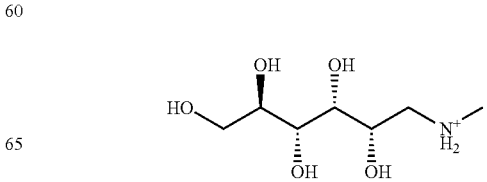

-continued

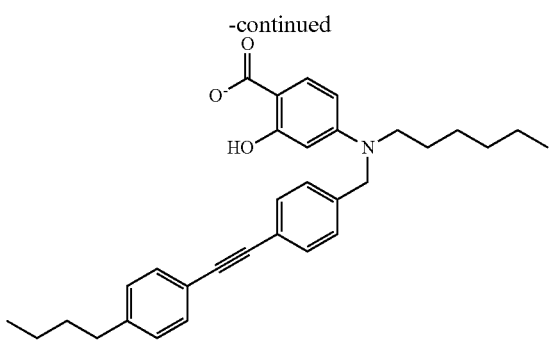

To a solution of 4-[{4-[(4-butylphenyl)ethynyl]benzyl}(hexyl)amino]-2-hydroxybenzoic acid (475 mg, 0.98 mmol) in THF/EtOH (10 mL) was added a solution of N-methyl-D-glucamine (192 mg, 0.98 mmol) in water (50 mL). The resulting solution was lyophilized to give 615 mg (92%) of the title compound as a pale yellow powder. HPLC, Rt: 6.1 min (purity: 98.2%). LC/MS, M⁻(ESI): 482.0

Example 23

5-[{4-[(4-butylphenyl)ethynyl]benzyl}(hexyl)amino]-2-fluorobenzoic acid

Step a) Formation of methyl 5-({4-[(4-butylphenyl)ethynyl]benzyl}amino)-2-fluorobenzoate

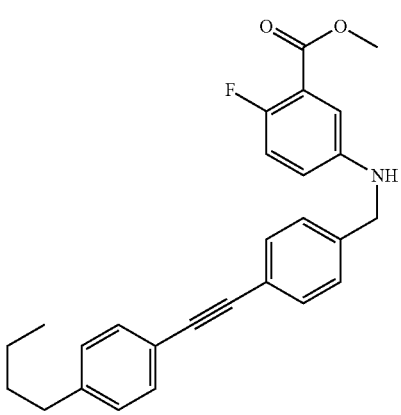

A solution of methyl 5-amino-2-fluorobenzoate (1.20 g, 7.1 mmol, described in *J. Chem. Soc. Perkin Trans. I*, 1975, 1283-1284 and *J. Org. Chem.*, 1990, 2034-2044) and 4-[(4-butylphenyl)ethynyl]benzaldehyde (1.95 g, 7.4 mmol, intermediate which may be obtained according to methods disclosed in EP03103780.7) in toluene (30 ml) was heated under reflux for 2.5 hrs with azeotropic removal of water. The reaction mixture was cooled down to 0° C., then MeOH (30 mL) and sodium borohydride (540 mg, 14.2 mmol) were added. The reaction mixture was stirred at 0° C. for 30 min, then at rt for 1 hr. The reaction mixture was diluted with a saturated aqueous solution of NaCl (100 mL) and water (30 mL) and then extracted with Et₂O (300 mL+50 mL). The combined organic layers were dried over MgSO₄ and the solvents were removed under reduced pressure. The residual brown gummy oil was taken up in MeOH (10 mL) and a white solid precipitated out. Filtration and washing with MeOH (2×) gave 2.23 g (76%) of the title compound as a white powder. HPLC, Rt: 5.8 min (purity: 98.2%). LC/MS, M⁻(ESI): 414.0. ¹H NMR (CDCl₃) δ: 7.51 (d, J=7.9 Hz, 2H), 7.45 (d, J=8.0 Hz, 2H), 7.34 (d, J=8.0 Hz, 2H), 7.17 (m, 3H), 6.97 (m, 1H), 6.76 (m, 1H), 4.35 (s, 2H), 3.92 (s, 3H), 2.63 (t, J=7.8 Hz, 2H), 1.61 (m, 2H), 1.37 (m, 2H), 0.94 (t, J=7.4 Hz, 3H).

Step b) Formation of methyl 5-[{4-[(4-butylphenyl)ethynyl]benzyl}(hexyl)amino]-2-fluorobenzoate

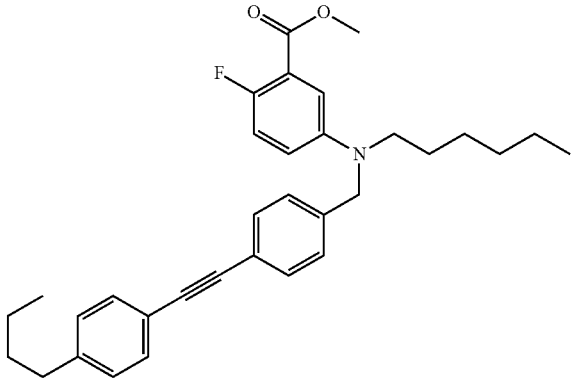

To a suspension of methyl 5-({4-[(4-butylphenyl)ethynyl]benzyl}amino)-2-fluorobenzoate (500 mg, 1.20 mmol) in anhydrous DCE (8 mL) were added hexanal (0.25 mL, 2.07 mmol) and sodium triacetoxyborohydride (825 mg, 3.89 mmol). The reaction mixture was stirred at 70° C. for 3.5 hrs. Then the reaction mixture was diluted with water (10 mL) and extracted with DCM (2×10 mL). The combined organic layers were dried over MgSO₄ and the solvents were removed under reduced pressure. Purification by flash chromatography on silicagel (cHex/EtOAc) gave 460 mg (77%) of the title compound as a pale yellow oil. HPLC, Rt: 6.3 min (purity: 99.9%). ¹H NMR (CDCl₃) δ: 7.47 (d, J=8.3 Hz, 2H), 7.44 (d, J=8.3 Hz, 2H), 7.18 (m, 5H), 6.95 (dd, J=10.1, 9.0 Hz, 1H), 6.74 (m, 1H), 4.52 (s, 2H), 3.91 (s, 3H), 3.38 (t, J=7.7 Hz, 2H), 2.63 (t, J=7.7 Hz, 2H), 1.60 (m, 4H), 1.42-1.25 (m, 8H), 0.92 (m, 6H).

Step c) Formation of 5-[{4-[(4-butylphenyl)ethynyl]benzyl}(hexyl)amino]-2-fluorobenzoic acid

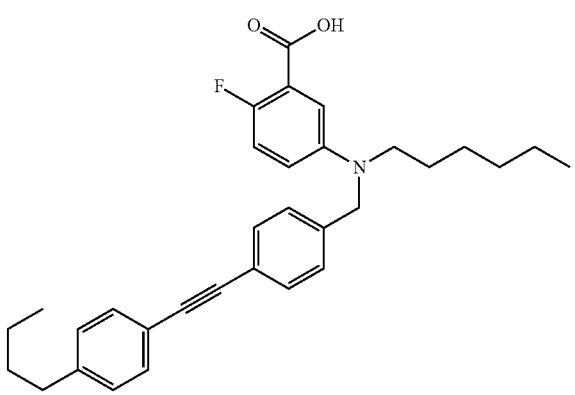

To a solution of methyl 5-[{4-[(4-butylphenyl)ethynyl]benzyl}(hexyl)amino]-2-fluoro-benzoate (454 mg, 0.91 mmol) in MeOH (40 mL) was added an aqueous solution of NaOH (2.7 mL, 1N). The reaction mixture was stirred at 50° C. for 36 hrs. Then an aqueous solution of HCl (5 mL, 1N) was added and the reaction mixture was poured into water (100 mL) and extracted with Et₂O (200 mL+2×100 mL). The combined organic layers were dried over MgSO₄ and the solvents were removed under reduced pressure to give 396 mg (90%) of the title compound as a beige powder. HPLC, Rt: 5.8 min (purity: 99.1%). LC/MS, M⁺(ESI): 486.1, M⁻(ESI): 484.0. ¹H NMR (CDCl₃) δ: 7.48 (d, J=8.3 Hz, 2H), 7.44 (d, J=8.3 Hz, 2H), 7.29 (dd, J=5.6, 3.3 Hz, 1H), 7.17 (m, 4H), 6.97 (dd, J=10.2, 9.0 Hz, 1H), 6.78 (ddd, J=9.0, 3.4, 3.3 Hz, 1H), 4.52 (s, 2H), 3.39 (t, J=7.6 Hz, 2H), 2.62 (t, J=7.6 Hz, 2H), 1.61 (m, 4H), 1.42-1.25 (m, 8H), 0.94 (t, J=7.3 Hz, 3H), 0.90 (t, J=6.8 Hz, 3H).

Example 24

5-[{4-[(4-butylphenyl)ethynyl]benzyl}(hexyl)amino]-2-fluorobenzoic acid, N-methyl-D-glucamine (i.e. 1-deoxy-1-(methylamino)glucitol) salt

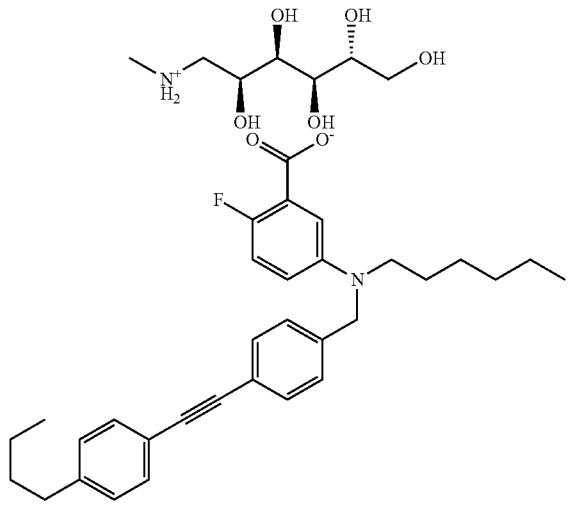

To a solution of 5-[{4-[(4-butylphenyl)ethynyl]benzyl}(hexyl)amino]-2-fluorobenzoic acid (378 mg, 0.78 mmol) in MeOH (3 mL) was added a solution of N-Me-D-glucamine (152 rug, 0.78 mmol) in water (1 mL). Then water (30 mL) was added and the resulting solution was lyophilized to give 493 mg (93%) of the title compound as a pale yellow oil. HPLC, Rt: 5.8 min (purity: 98.0%). LC/MS, M⁺(ESI): 486.1, M⁻(ESI): 483.9.

Example 25

5-{[{2-[(4-butylphenyl)ethynyl]benzyl}(hexyl)amino]carbonyl}-2-hydroxybenzoic acid Step a) Formation of N-{2-[(4-butylphenyl)ethynyl]benzyl}-1-hexanamine

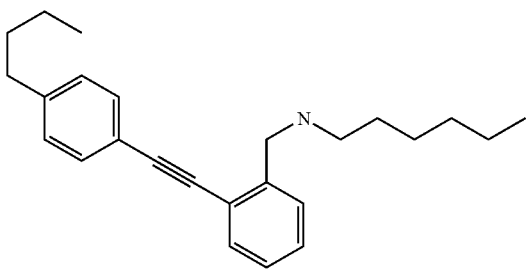

The title compound was prepared following procedure described in example 19, step b) from 2-[(4-butylphenyl)ethynyl]benzaldehyde (1.12 g, 4.28 mmol, intermediate which may be obtained according to methods disclosed in EP03103780.7) and n-hexylamine (Aldrich, 294 μl, 5.13 mmol). Purification of the crude product by flash chromatography on silicagel (DCM/MeOH/NH₄OH 98/2/1) gave 174 mg (12%) of the title compound. HPLC, Rt: 4.39 min purity: 91.6%). LC/MS, M⁺(ESI): 348.4. ¹HNMR (CDCl₃) δ: 0.82 (t, J=6.8 Hz, 3H), 0.91 (t, J=7.3 Hz, 3H), 1.23-1.40 (m, 8H), 1.46-1.64 (m, 4H), 2.25 (m, 1H), 2.62 (t, J=7.5 Hz, 4H), 4.00 (s, 2H), 7.15 (d, J=8.3 Hz, 2H), 7.17-7.26 (m, 2H), 7.39 (m, 1H), 7.42 (d, J=8.3 Hz, 2H), 7.50 (dd, J=7.3, 1.7 Hz, 1H).

Step b) Formation of N-{2-[(4-butylphenyl)ethynyl]benzyl}-N-hexyl-2,2-dimethyl-4-oxo-4H-1,3-benzodioxine-6-carboxamide

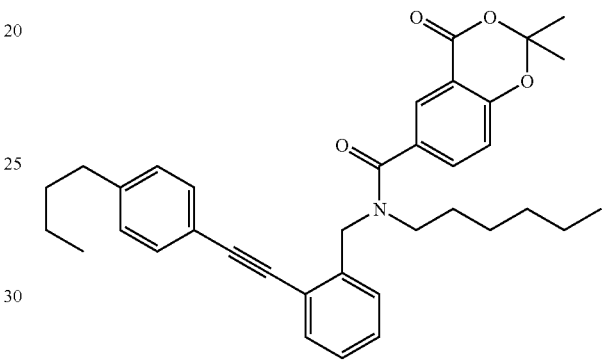

A solution of N-{2-[(4-butylphenyl)ethynyl]benzyl}-1-hexanamine (174 mg, 0.50 mmol), 2,2-dimethyl-4-oxo-4H-1,3-benzodioxine-6-carboxylic acid (122 mg, 0.55 mmol), EDC.HCl (115 mg, 0.60 mmol), DIEA (102 μl, 0.60 mmol) and HOBT (81 mg, 0.60 mmol) in DCM (10 mL) was stirred at rt for 3 hrs. The reaction mixture was diluted with DCM and washed with a saturated aqueous solution of NaHCO₃, an aqueous solution of HCl (1N) and brine. The organic layer was dried over MgSO₄ and the solvent Was removed under reduced pressure. Purification by flash chromatography on silicagel (EtOAc/c-Hex (20/80)) gave 238 mg (87%) of the title compound. HPLC, Rt: 6.14 min (purity: 86.7%).

Step c) Formation of 5-{[{2-[(4-butylphenyl)ethynyl]benzyl}(hexyl)amino]carbonyl]-2-hydroxybenzoic acid

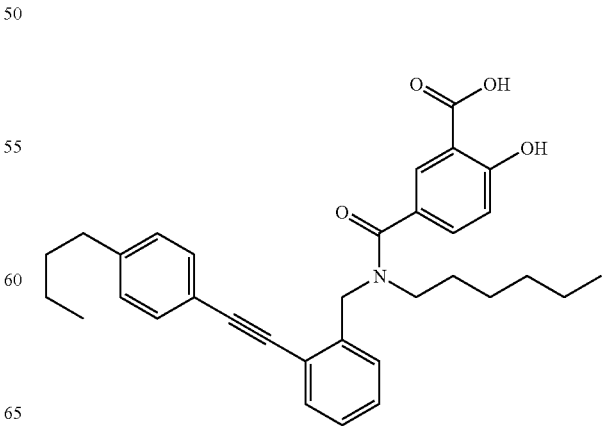

The title compound was obtained following procedure described in example 19, step c) from N-{2-[(4-butylphenyl)ethynyl]benzyl}-N-hexyl-2,2-dimethyl-4-oxo-4H-1,3-benzo-dioxine-6-caxboxamide (238 mg, 0.43 mmol). Purification by preparative HPLC with a X-Terra column gave 110 mg (50%) of the title compound. HPLC, Rt: 5.73min (purity: 96.4%).

Example 26

4-((3-cyclopentylpropyl){4-[(4-fluorophenyl)ethynyl]benzoyl}amino)-2-hydroxybenzoic acid, N-methyl-D-glucamine (i.e. 1-deoxy-1-(methyl-amino)glucitol) salt Step a) Formation of 3-cyclopentyl-N-(2,2-dimethyl-4-oxo-4H-1,3-benzodioxin-7-yl)propanamide

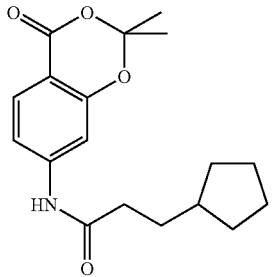

To a cold (0° C.) solution of 7-amino-2,2-dimethyl-4H-1,3-benzodioxine-4-one (1.93 g, 10.0 mmol) and DIEA (1.55 g, 12.00 mmol) in DCM (50 mL) was added drop-wise a solution of 3-cyclopentylpropionyl chloride (Aldrich, 1.93 g, 12.0 mmol) in DCM. The reaction was stirred at 0° C. for 1 hr, then at rt for 3 hrs. The reaction mixture was washed with an aqueous solution of HCl (1N). The organic layer was dried over MgSO$_4$ and the solvent was removed under reduced pressure. Purification by flash chromatography on silicagel (EtOAc/c-Hex (30/70)) gave 3.05 g (96%) of the title compound as a pale yellow oil. HPLC, Rt: 4.26 min (purity: 99.6%). LC/MS, M$^+$(ESI): 318.2, M$^-$(ESI): 316.2. $^1$H NMR (CDCl$_3$) δ: 8.13 (s, 1H), 7.82 (d, J=8.4 Hz, 1H), 7.58 (d, J=1.9 Hz, 1H), 7.05 (dd, J=1.9 Hz, J=8.4 Hz, 1H), 2.41 (t, J=7.6 Hz, 2H), 1.80-1.45 (m, 15H), 1.17-1.00 (m, 2H).

Step b) Formation of 7-[(3-cyclopentylpropyl)amino]-2,2-dimethyl-4H-1,3-benzodioxin-4-one

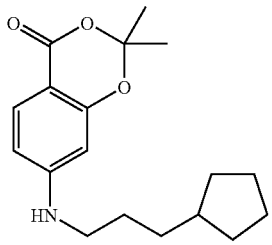

To a solution of 3-cyclopentyl-N-(2,2-dimethyl-4-oxo-4H-1,3-benzodioxin-7-yl)propanamide (2.57 g, 8.08 mmol) in THF (30 mL) was added a solution of borane in THF (24.3 ml, 24.3 mmol, 1M) and the resulting mixture was stirred at rt for 2 hrs. The mixture was then refluxed for 2 hrs. A solution of borane in THF (10.0 ml, 10.0 mmol, 1M) was added again and the mixture was refluxed for an additional 5 hrs. The reaction was quenched with HCl 5 N. Then the solution was made basic by the addition of an aqueous solution of NaOH (5N) and extracted with Et$_2$O (3×). The combined organic layers were dried over MgSO$_4$ and the solvents were removed under reduced pressure. Purification by flash chromatography on silicagel (EtOAc/c-Hex (20/80)) gave 2.1 g (86%) of the title compound as a white solid.

Step c) Formation of 4-bromo-N-(3-cyclopentylpropyl)-N-(2,2-dimethyl-4-oxo-4H-1,3-benzodioxin-7-yl)benzamide

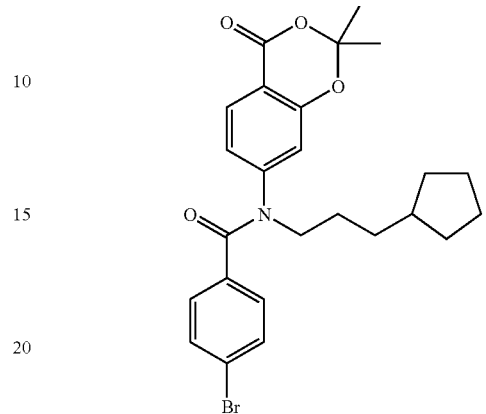

To a cold (0° C.) solution of 7-[(3-cyclopentylpropyl)amino]-2,2-dimethyl-4H-1,3-benzodioxin-4-one (1.70 g, 5.60 mmol) in pyridine (10 mL) was added 4-bromobenzoyl-chloride (Aldrich, 1.47 g, 6.72 mmol) and the resulting reaction mixture was stirred 10 min at 0° C., 30 min at rt and 7 hrs at 60° C. The solvent was removed under reduced pressure. Purification by flash chromatography on silicagel (EtOAc/c-Hex (15/85)) gave 1.6 g (59%) of the title compound as a white solid. HPLC, Rt: 5.2 min (purity: 99.5%). $^1$H NMR (CDCl$_3$) δ: 7.81 (d, J=7.3 Hz, 1H), 7.35 (d, J=8.7 Hz, 2H), 7.18 (d, J=8.7 Hz, 2H), 6.76 (dd, J=1.9 Hz, J=8.3 Hz, 1H), 6.56 (d, J=1.9 Hz, 1H), 3.91 (t, J=7.9 Hz, 2H), 1.80-1.25 (m, 17H), 1.12-0.95 (m, 2H).

Step d) Formation of N-(3-cyclopentylpropyl)-N-(2,2-dimethyl-4-oxo-4H-1,3-benzodioxin-7-yl)-4-[(4-fluorophenyl)ethynyl]benzamide

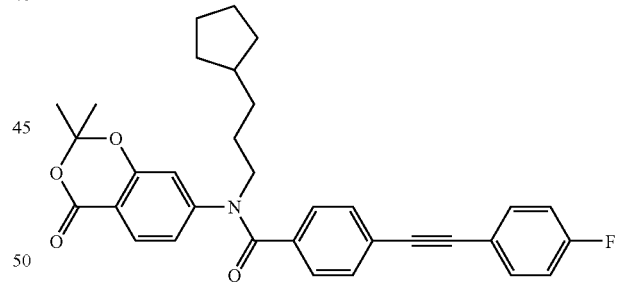

A solution of 4-bromo-N-(3-cyclopentylpropyl)-N-(2,2-dimethyl-4-oxo-4H-1,3-benzodioxin-7-yl)benzamide (355 mg, 0.73 mmol), 4-fluorophenylacetylene (Apollo, 96 mg, 0.80 mmol), bis(triphenylphosphine)palladium(I) chloride (26 mg, 0.04 mmol), triphenylphosphine (38 mg, 0.15 mmol) and cuprous(I) iodide (7 mg, 0.04 mmol) in DMF (3 mL) and TEA (1 mL) was heated under microwave conditions at 120° C. for 25 min. The reaction mixture was then diluted with Et$_2$O and the precipitate obtained was filtered off. Filtrate was then washed with an aqueous solution of HCl (1N) and brine. The organic layer was dried over MgSO$_4$ and the solvents were removed under reduced pressure. Purification by flash chromatography on silicagel (EtOAc/c-Hex (10/90 to 20/80)) gave 321 mg (84%) of the title compound. HPLC, Rt: 5.67 min (purity: 97.9%). $^1$H NMR (CDCl$_3$) δ: 7.78 (d, J=8.3 Hz, 1H), 7.44 (m, 2H), 7.31 (AB, J=8.4, Δ=12 Hz, 4H), 7.01 (t, J=8.5 Hz, 2H), 6.75 (dd, J=8.3, 2.1 Hz, 1H), 6.58 (d, J=2.1 Hz, 1H), 3.91 (t, J=7.7 Hz, 2H), 1.40-1.71 (m, 15H), 1.34 (m, 2H), 1.03 (m, 2H).

Step e) Formation of 4-((3-cyclopentylpropyl){4-[(4-fluorophenyl)ethynyl]benzoyl}amino)-2-hydroxybenzoic acid

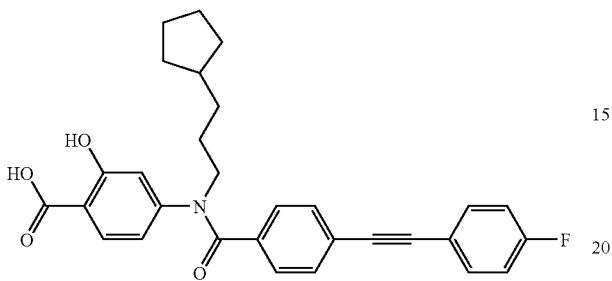

The title compound was prepared following the procedure described in example 19, step c) from N-(3-cyclopentylpropyl)-N-(2,2-dimethyl-4-oxo-4H-1,3-benzodioxin-7-yl)-4-[(4-fluorophenyl)ethynyl]benzamide (850 mg, 1.65 mmol). Purification of the crude (320 mg) by preparative HPLC using a X-Terra column gave 207 mg (70%) of the title compound. HPLC, Rt: 5.28 min (purity: 99.3%). LC/MS, M-(ESI): 484.2. $^1$H NMR (CDCl$_3$) δ: 10.53 (s, 1H), 7.68 (d, J=8.5 Hz, 1H), 7.42 (m, 2H), 7.33 (m, 4H), 7.01 (t, J=8.9 Hz, 2H), 6.71 (d, J=1.9 Hz, 1H), 6.48 (dd, J=8.5, 2.1 Hz, 1H), 3.91 (t, J=7.6 Hz, 2H), 1.56-1.71 (m, 9H), 1.31 (m, 2H), 1.03 (m, 2H).

Step j) Formation of 4-((3-cyclopentylpropyl){4-[(4-fluorophenyl)ethynyl]benzoyl}amino)-2-hydroxybenzoic acid, N-methyl-D-glucamine (i.e. 1-deoxy-1-(methylamino)glucitol) salt

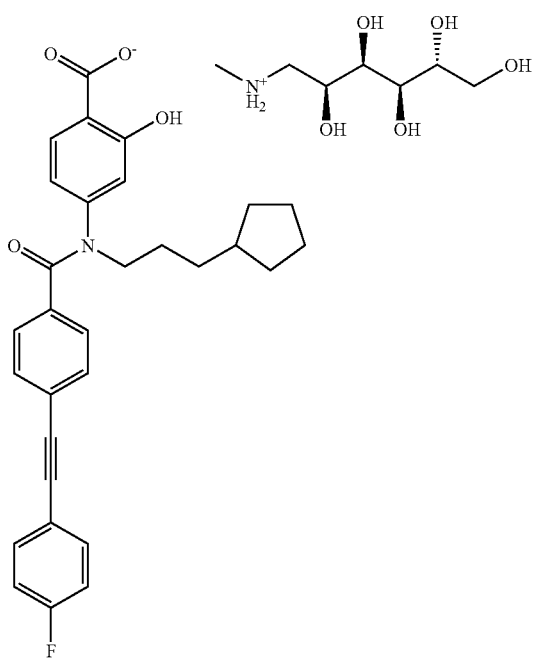

To a solution of 4-((3-cyclopentylpropyl){4-[(4-fluorophenyl)ethynyl]benzoyl}amino)-2-hydroxybenzoic acid (207 mg, 0.43 mmol) in MeOH (20 mL) was added a solution of N-methyl-D-glucamine (83 mg, 0.43 mmol) in water (4 mL). Water (20 mL) was added and the resulting solution was lyophilized to give 268 mg of the title compound as a white powder. HPLC, Rt: 5.31 min (purity: 99.9%). LC/MS, M-(ESI): 545.9. $^1$H NMR (CD$_3$OD) δ: 0.79 (t, J=7.0 Hz, 3H), 0.92 (t, J=7.2 Hz, 3H), 1.28 (m, 6H), 1.33 (m, 4H), 1.58 (m, 2H), 2.60 (t, J=7.3 Hz, 2H), 2.70 (s, 3H), 3.08 (t, J=7.2 Hz, 2H, 3.16 (m, 2H), 3.68-3.83 (m, 4H), 4.33 (m, 1H), 4.33 (s, 2H), 7.15-7.45 (m, 10H), 8.02 (d, J=7.9 Hz, 1H). Analysis calculated for C$_{30}$H$_{28}$NO$_4$F.C$_7$H$_{17}$NO$_5$.1.3 H$_2$O: C 63.11; H 6.81; N 3.98% Found: C 62.99; H, 6.81; N, 4.03%.

Example 27

4-[{4-[(4-butylphenyl)ethynyl]benzyl}(3-cyclopentylpropyl)amino]-2-hydroxybenzoic acid, N-methyl-D-glucamine (i.e. 1-deoxy-1-(methyl-amino)glucitol) salt Step a) Formation of 4-[4-butylphenyl)ethynyl]-N-(3-cyclopentylpropyl)-N-(2,2-dimethyl-4-oxo-4H-1,3-benzodioxin-7-yl)benzamide

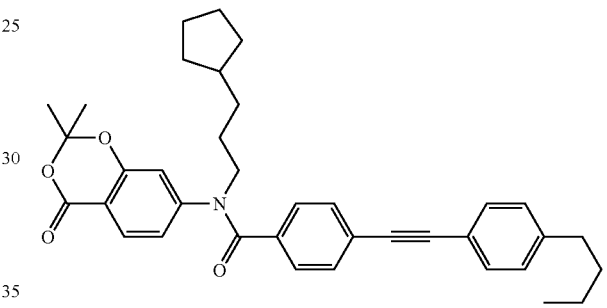

The title compound was prepared following procedure described in example 26, step d) from 4-bromo-N-(3-cyclopentylpropyl)-N-(2,2-dimethyl-4-oxo-4H-1,3-benzodioxin-7-yl)benzamide (437 mg, 0.90 mmol) and 4-butylphenylacetylene (156 mg, 0.99 mmol). Purification by flash chromatography on silicagel (EtOAc/c-Hex (10/90 to 15/85) gave 540 mg (quantitative yield) of the title compound. HPLC, Rt: 6.30 min (purity: 94.3%). LC/MS, M+(ESI): 563.8. $^1$H NMR (CDCl$_3$) δ: 7.78 (d, J=8.3 Hz, 1H), 7.38 (d, J=8.1 Hz, 2H), 7.30 (AB, J=8.5, Δ=14.5 Hz, 4H), 7.13 (d, J=8.3 Hz, 2H), 6.76 (dd, J=8.3, 2.0 Hz, 1H), 6.56 (d, J=2.0 Hz, 1H), 3.91 (t, J=7.6 Hz, 2H), 2.59 (t, J=7.7 Hz, 2H), 1.19-1.67 (m, 21H), 0.99 (m, 2H), 0.85 (t, J=7.3 Hz, 3H).

Step b) Formation of 4-{4-[(4-butylphenyl)ethynyl]benzoyl}(3-cyclopentylpropyl)amino]-2-hydroxybenzoic acid

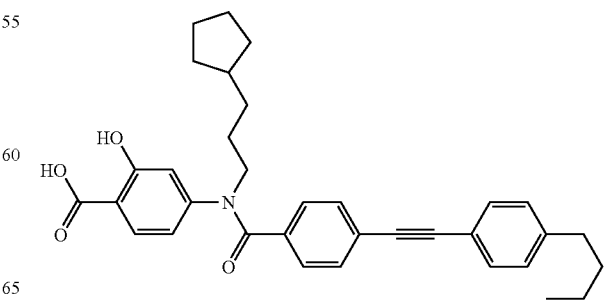

The title compound was prepared following the procedure described in example 19, step c) from 4-[(4-butylphenyl)ethynyl]-N-(3-cyclopentylpropyl)-N-(2,2-dimethyl-4-oxo-4H-1,3-benzodioxin-7-yl)benzamide (460 mg, 0.82 mmol). Purification of the crude by preparative HPLC using a X-Terra column afforded 278 mg (65%) of the title compound. HPLC, Rt: 5.88 min,(purity: 99.9%). LC/MS, M$^-$(ESI): 521.9. $^1$H NMR (CDCl$_3$) δ: 10.58 (s, 1H), 7.69 (d, J=8.7 Hz, 1H), 7.37 (d, J=8.1 Hz, 2H), 7.32 (m, 4H), 7.11 (d, J=8.1 Hz, 2H), 6.71 (d, J=2.1 Hz, 1H), 6.48 (dd, J=8.5, 1.9 Hz, 1H), 3.91 (t, J=7.6 Hz, 2H), 2.58 (t, J=7.6 Hz, 2H), 1.54-1.71 (m, 11H), 1.33 (m, 4H), 1.03 (m, 2H), 0.90 (t, J=7.3 Hz, 3H).

Step c) Formation of 4-[{4-[(4-butylphenyl)ethynyl]benzoyl}(3-cyclopentylpropyl)amino]-2-hydroxybenzoic acid, N-methyl-D-glucamine (i.e. 1-deoxy-1-(methylamino)glucitol) salt

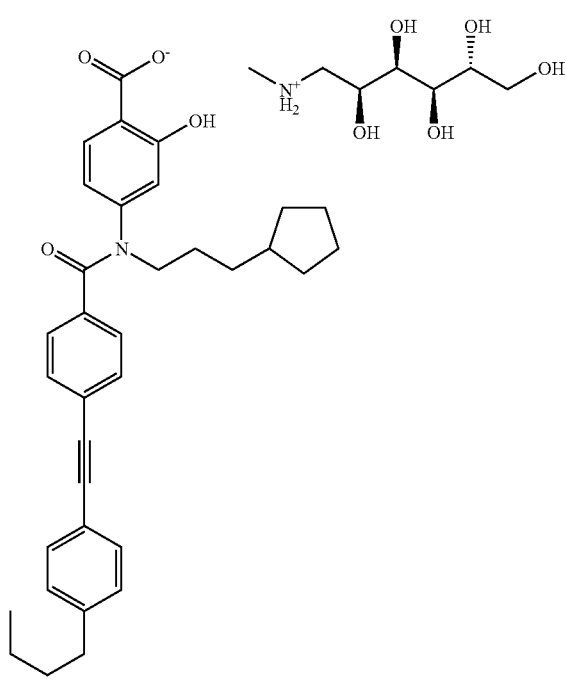

To a solution of 4-((3-cyclopentylpropyl){4-[(4-butylphenyl)ethynyl]benzoyl}amino)-2-hydroxybenzoic acid (278 mg, 0.53 mmol) in MeOH (20 mL) was added a solution of N-methyl-D-glucamine (104 mg, 0.53 mmol) in water (4 mL). Water (20 mL) was added and the resulting solution was lyophilized to give 421 mg of the title compound as a white powder. HPLC, Rt: 5.84 min (purity: 99.9%). LC/MS, M$^-$(ESI): 545.9. Analysis calculated for C$_{34}$H$_{37}$NO$_4$·C$_7$H$_{17}$NO$_5$·4.0 H$_2$O: Calculated C 62.26; H 7.90; N 3.54%. Found: C, 62.36; H, 7.77; N, 3.54%.

Example 28

5-{[{4-[(4-fluorophenyl)ethynyl]benzoyl}(hexylamino]methyl}-2-hydroxy-benzoic acid, N-methyl-D-glucamine (i.e. 1-deoxy-1-(methylamino)-glucitol) salt Step a) Formation of 4-[(4-fluorophenyl)ethynyl]benzoic acid

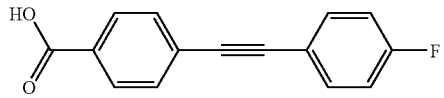

To a solution of 4-[(4-fluorophenyl)ethynyl]benzaldehyde (10.39 g; 46.37 mmol, intermediate which may be obtained according to methods disclosed in EP03 103780.7) in DMF (400 mL) was added potassium peroxomonosulfate (28.5 g, 46.4 mmol) in one portion at rt. The reaction mixture was stirred at rt overnight. The reaction mixture was poured in water (2 L) and the resulting precipitate was filtered off, washed with water and dried under reduced pressure to give 10.45 g (94%) of the title compound as a white powder. HPLC, Rt: 3.98 min (purity: 98.6%). $^1$H NMR (DMSO-d$_6$) δ: 13.15 (brs, 1H), 7.96 (d, J=8.1 Hz, 2H), 7.64 (m, 4H), 7.29 (t, J=8.9 Hz, 2H).

Step b) Formation of N-[(2,2-dimethyl-4-oxo-4H-1,3-benzodioxin-6-yl)methyl]-4-[(4-fluorophenyl)ethynyl]-N-hexylbenzamide

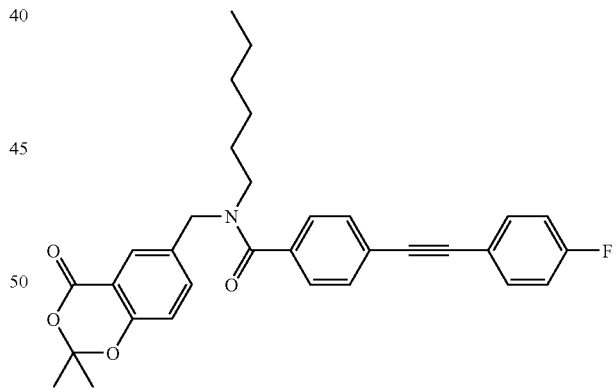

The title compound was prepared following procedure described in example 20, step e) from 6-[(hexylamino)methyl]-2,2-dimethyl-4H-1,3-benzodioxin-4-one (490 mg, 1.68 mmol) and 4-[(4-fluorophenyl)ethynyl]benzoic acid (484 mg, 2.02 mmol). Purification of the crude product by flash chromatography on silicagel (EtOAc/c-Hex (20/80) gave 850 mg (98%) of the title compound. HPLC, Rt: 5.54 min (purity: 99.9%). LC/MS, M$^+$(ESI): 514.1. $^1$H NMR (CDCl$_3$) δ: 7.45-7.90 (m, 6H), 7.37 (d, J=8.1 Hz, 2H), 7.00 (t, J=8.8 Hz, 2H), 6.94 (d, J=8.5 Hz, 1H), 4.69 (s, 1.5H), 4.45 (s, 0.5H), 3.39 (s, 0.5H), 3.14 (s, 1.5H), 1.07-1.77 (m, 14H), 0.80 (m, 3H).

Step c) Formation of 5-{[{[(4-fluorophenyl)ethynyl]benzoyl}(hexyl)amino]methyl}-2-hydroxybenzoic acid

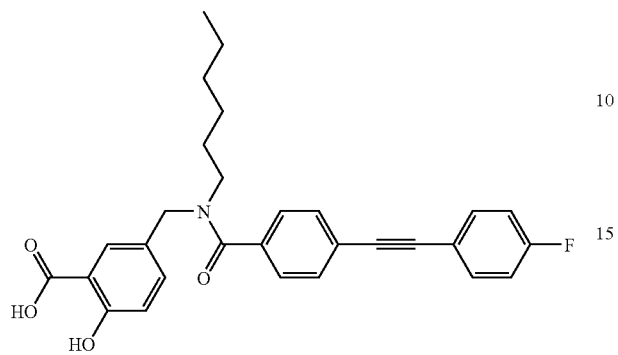

The title compound was prepared following the procedure described in example 19, step-c) from N-[(2,2-dimethyl-4-oxo-4H-1,3-benzodioxin-6-yl)methyl]-4-[(4-fluorophenyl)-ethynyl]-N-hexylbenzamide (850 mg, 1.65 mmol). 680 mg (87%) of the title compound was isolated as a white foam. HPLC, Rt: 5.04 min (purity: 99.0%). LC/MS, M⁺(ESI): 474.1, M⁻(ESI): 471.9. $^1$H NMR (CDCl$_3$) δ: 10.83 (s, 1H), 10.29 (s, 1H), 7.22-7.86 (m, 8H), 6.99 (m, 3H), 4.7 (s, 1.4H), 4.42 (s, 0.6H), 3.47 (s, 0.6H), 3.14 (s, 1.4H), 1.07-1.62 (m, 8H), 0.80 (m, 3H).

Step d) Formation of 5-{[{4-[(4-fluorophenyl)ethynyl]benzoyl}(hexyl)amino]methyl)-2-hydroxybenzoic acid, N-methyl-D-glucamine (i.e. 1-deoxy-1-(methylamino)glucitol) salt

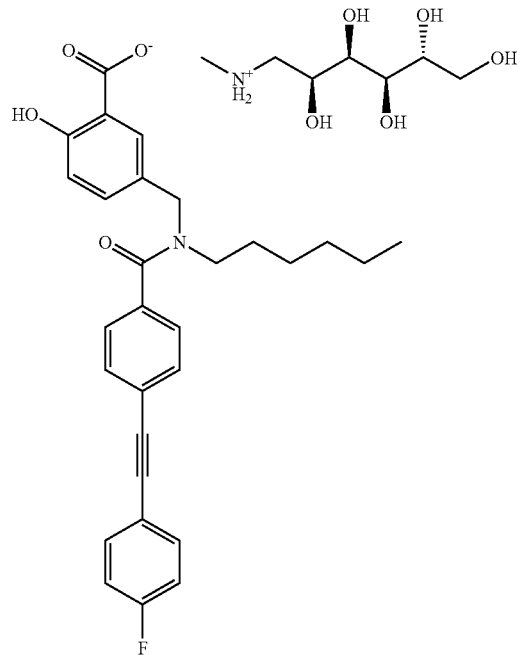

To a solution of 5-{[{4-[(4-fluorophenyl)ethynyl]benzoyl}(hexyl)amino]methyl}-2-hydroxybenzoic acid (680 mg, 1.44 mmol) in MeOH (20 mL) was added a solution of N-methyl-D-glucamine (280 mg, 1.44 mmol) in water (4 mL). Water (20 mL) was added and the resulting solution was lyophilized to give 820 mg of the title compound as a white powder. HPLC, Rt: 5.13 min (purity: 99.4%). LC/MS, M⁺(ESI): 475.5, M⁻(ESI): 471.9. Analysis calculated for C$_{29}$H$_{28}$NO4F.C$_7$H$_{17}$NO$_5$.1.1H$_2$O: Calculated C, 62.80; H, 6.91; N, 4.07%. Found: C, 62.74; H, 6.95; N, 4.06%.

Example 29

5-{[{4-[(4-chlorophenoylethynyl]benzoyl}(hexyl)amino]methyl}-2-hydroxybenzoic acid N-methyl-D-glucamine (i.e. 1-deoxy-1-(methyl-amino)glucitol) salt Step a) Formation of 4-[(4-chlorophenyl)ethynyl]benzoic acid

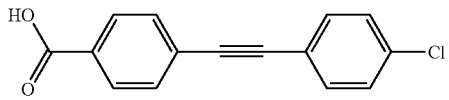

The title compound was prepared following procedure described in Example 28, step a) from 4-[(4-chlorophenyl)ethynyl]benzaldehyde (10.2 g, 42.4 mmol, intermediate which may be obtained according to methods disclosed in EP03103780.7). Purification by trituration of the crude product in isopropyl acetate gave 8.50 g (78%) of the title compound as a cream-powder. HPLC, Rt: 4.23 min (purity: 88.4%). $^1$H NMR (DMSO-d6) δ :13.18 (brs, 1H), 7.96 (d, J=8.3 Hz, 2H), 7.67 (d, J=8.3 Hz, 2H), 7.61 (d, J=8.5 Hz, 2H), 7.51 (d, J=8.5 Hz, 2H).

Step b) 4-[(4-chlorophenyl)ethynyl]-N-[(2,2-dimethyl-4-oxo-4H-1,3-benzodioxin-6-yl)methyl]-N-hexylbenzamide

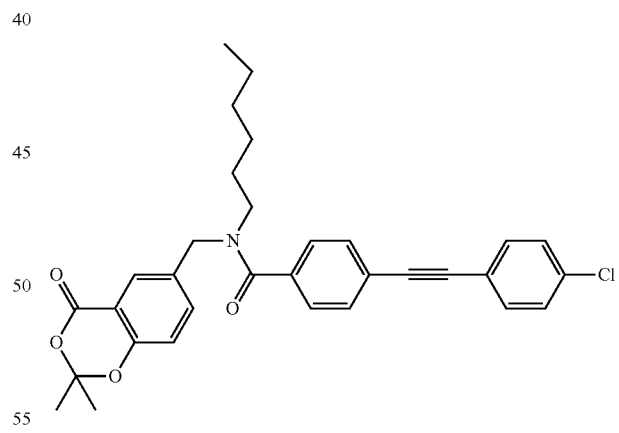

The title compound was prepared following procedure described in example 20, step e) from 6-[(hexylamino)methyl]-2,2-dimethyl-4H-1,3-benzodioxin-4-one (648 mg, 2.22 mmol) and 4-[(4-butylphenyl)ethynyl]benzoic acid (330 mg, 1.19 mmol). Purification of the crude product by flash chromatography on silicagel (EtOAc/c-Hex (20/80)) gave 1.12 g (95%) of the title compound. HPLC, Rt: 5.72 min (purity: 99.2%). LC/MS, M⁺(ESI): 530.1. $^1$H NMR (CDCl$_3$) δ: 7.52-7.85 (m, 4H), 7.44 (d, J=8.5 Hz, 2H), 7.38 (d, J=8.1 Hz, 2H), 7.31 (d, J=8.5 Hz, 2H), 6.96 (d, J=8.5 Hz, 1H), 4.70 (s, 1.5H), 4.47 (s, 0.5H), 3.39 (s, 1.5H), 3.15 (s, 0.5H), 1.21-1.72 (m, 14H), 0.81 (m, 3H).

Step c) Formation of 5-[{{4-[(4-chlorophenyl)ethynyl]benzoyl}(hexyl)amino]methyl}-2-hydroxybenzoic acid

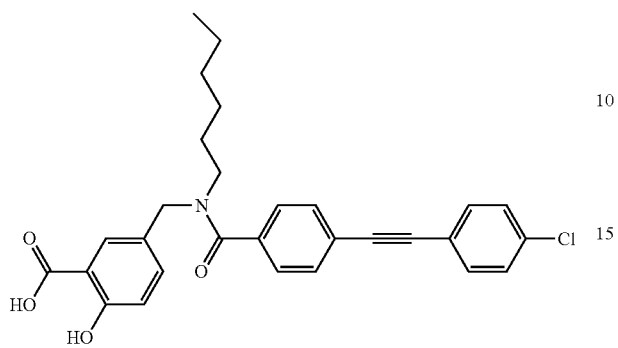

The title compound was prepared following the procedure described in example 19, step c) from N-[(2,2-dimethyl-4-oxo-4H-1,3-benzodioxin-6-yl)methyl]-4-[(4-chlorophenyl)-ethynyl]-N-hexylbenzamide (1.12 g, 2.1 mmol). 930 mg (90%) of the title compound was isolated as a white foam. HPLC, Rt: 5.23 m (purity: 98.8%). LC/MS; $M^+$(ESI): 474.1, $M^-$(ESI): 487.9. $^1$H NMR (CDCl$_3$) δ: 10.72 (s, 1H), 7.38-7.89 (m, 8H), 7.30 (d, J=8.1 Hz, 2H), 6.96 (d, J=8.3 Hz, 1H), 4.69 (s, 1.3H), 4.42 (s, 0.7H), 3.45 (s, 0.7H), 3.15 (s, 1.3H), 1.20-1.63 (m, 8H), 0.81 (m, 3H).

Step d) Formation of 5-{[{4-[(4-chlorophenyl)ethynyl]benzoyl}(hexyl)amino]methyl}-2-hydroxybenzoic acid, N-methyl-D-glucamine (i.e. 1-deoxy-1-(methylamino)glucitol) salt

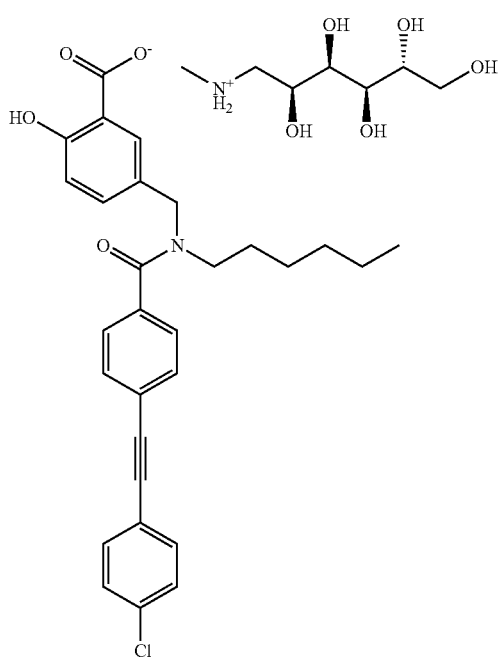

To a solution of 5-{[{4-[(4-chlorophenyl)ethynyl]benzoyl}(hexyl)amino]methyl}-2-hydroxybenzoic acid (930 mg, 1.9 mmol) in MeOH (20 mL) was added a solution of N-methyl-D-glucamine (370 mg, 1.9 mmol) in water (4 mL). Water (20 mL) was added and the resulting solution was lyophilized to give 1.195 g of the title compound as a white powder. HPLC, Rt: 5.28 min (purity: 98.9%). LC/MS, $M^+$(ESI): 489.7 $M^-$(ESI): 488.0. Analysis calculated for $C_{29}H_{28}NO_4Cl \cdot C_7H_{17}NO_5 \cdot 0.6H_2O$: Calculated C, 62.12; H, 6.69; N, 4.02%. Found: C, 62.07; H, 6.78; N, 3.97%.

Example 30

2-fluoro-5-{hexyl[4-(phenylethynyl)benzyl]amino}benzoic acid, N-methyl-D-glucamine (i.e. 1-deoxy-1-(methylamino)glucitol) salt Step a) Formation of methyl 2-fluoro-5-{[4-(phenylethynyl)benzyl]amino}benzoate

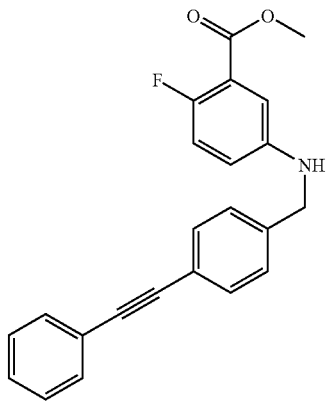

The title compound was prepared following the procedure described in Example 23 step a) using methyl 5-amino-2-fluorobenzoate (500 mg, 2.96 mmol) and 4-(phenylethynyl)benzaldehyde (Fluorochem, 640 mg, 3.10 mmol). The title compound was obtained as a white powder (717 mg, 68%). HPLC, Rt: 4.78 min (purity: 97.4%). LC/MS, $M^-$(ESI): 358.1. $^1$H NMR (CDCl$_3$) δ: 7.52-7.48 (m, 4H), 7.32 (m, 5H), 7.15 (dd, J=5.3, 3.1 Hz, 1H), 6.94 (dd, J=10.5, 9.2 Hz, 1H), 6.72 (m, 1H), 4.33 (s, 2H), 3.89 (s, 3H).

Step b) Formation of methyl 2-fluoro-5-(hexyl[4-(phenylethynyl)benzyl]amino}benzoate

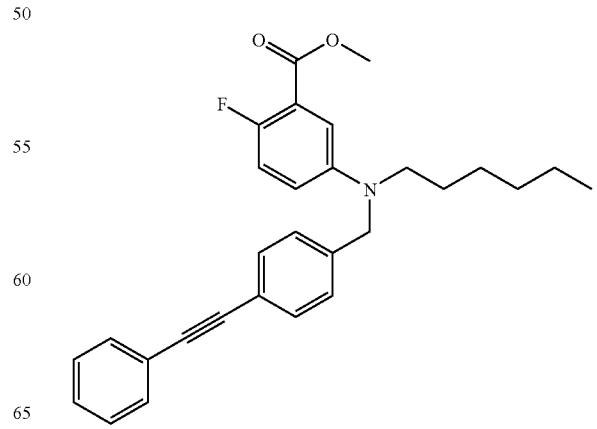

The title compound was prepared following the procedure described in Example 23 step b) using methyl 2-fluoro-5-{[4-(phenylethynyl)benzyl]amino}benzoate (213 mg, 0.59 mmol) and hexanal (Aldrich, 0.11 mL, 0.95 mmol). The title compound was obtained as a pale yellow oil (215 mg, 82%). HPLC, Rt: 6.1 min (purity: 94.5%). LC/MS, M⁺(ESI): 444.2. ¹H NMR (CDCl₃) δ: 7.51-7.44 (m, 4H), 7.32 (m, 3H), 7.17 (m, 3H), 6.92 (dd, J=9.8, 9.7 Hz, 1H), 6.74 (m, 1H), 4.49 (s, 2H), 3.88 (s, 3H), 3.35 (t, J=7.5 Hz, 2H), 1.61 (m, 2H), 1.29 (m, 6H), 0.88 (m, 3H).

Step c) Formation of 2-fluoro-5-{hexyl[4-(phenylethynyl)benzyl]amino}benzoic acid

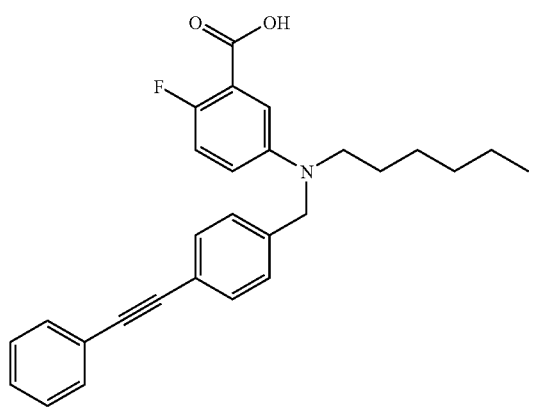

The title compound was prepared following the procedure described in Example 23 step c) using methyl 2-fluoro-5-{hexyl[4-(phenylethynyl)benzyl]amino}benzoate (215 mg, 0.48 mmol). The title compound was obtained as a pale yellow powder (181 mg, 87%). HPLC, Rt: 5.4 min (purity: 94.7%). ¹H NMR (CDCl₃) δ: 7.51-7.44 (m, 4H), 7.32 (m, 4H), 7.20 (d, J=7.9 Hz, 2H), 6.98 (dd, J=9.6, 9.5 Hz, 1H), 6.90 (m, 1H), 4.51 (s, 2H), 3.38 (t, J=7.3 Hz, 2H), 1.63 (m, 2H), 1.29 (m, 6H), 0.87 (t, J=7.0 Hz, 3H).

Step d) Formation of 2-fluoro-5-{hexyl[4-(phenylethynyl)benzyl]amino}benzoic acid, N-methyl-D-glucamine (i.e. 1-deoxy-1-(methylamino)glucitol) salt

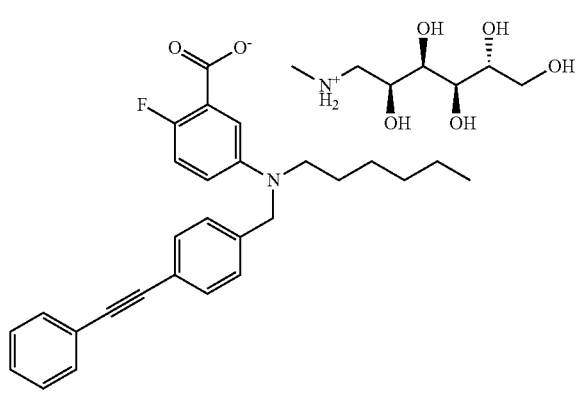

The title compound was prepared following the procedure described in Example 24 using 2-fluoro-5-{hexyl[4-(phenylethynyl)benzyl]amino}benzoic acid (181 mg, 0.42 mmol). The title compound was obtained as a beige powder (223 mg, 85%). HPLCs Rt: 5.4 min (purity: 94.3%). LC/MS, M⁺(ESI): 430.3, M⁻(ESI): 428.2.

Example 31

5-({4-[(4-chlorophenyl)ethynyl]benzyl}(hexyl)amino)-2-hydroxybenzoic acid, N-methyl-D-glucamine (i.e. 1-deoxy-1-(methylamino)glucitol sat Step a) Formation of 6-[((E)-{4-[(4-chlorophenyl)ethynyl]phenyl}methylidene)amino]-2,2-dimethyl-4H-1,3-benzodioxin-4-one

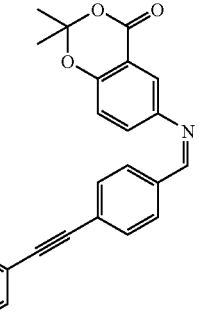

A solution of 4-[(4-chlorophenyl)ethynyl]benzaldehyde (2.60 g, 10.9 mmol, intermediate which may be prepared according to methods disclosed in EP03103780.7) and 6-amino-2,2-dimethyl-4H-1,3-benzodioxin-4-one (2.00 g, 10.36 mmol) in toluene (40 mL) was heated at reflux for 2 hrs with azeotropic removal of water. Then the temperature was cooled down slowly. A yellow solid precipitated out and MeOH (40 mL) was added. The precipitate was filtered, washed with MeOH (2×) and dried under reduced pressure to give 3.98 g (92%) of the title compound as a yellow powder. ¹H NMR (CDCl₃) δ: 8.53 (s, 1H), 7.90 (d, J=8.2 Hz, 2H), 7.85 (d, J=2.5 Hz, 1H), 7.64 (d, J=8.2 Hz, 2H), 7.53 (dd, J=8.6, 2.5 Hz, 1H), 7.50 (d, J=8.5 Hz, 2H), 7.36 (d, J=8.5 Hz, 2H), 7.03 (d, J=8.6 Hz, 1H).

Step b) Formation of 6-({4-[(4-chlorophenyl)ethynyl]benzyl}amino)-2,2-dimethyl-4H-1,3-benzodioxin-4-one

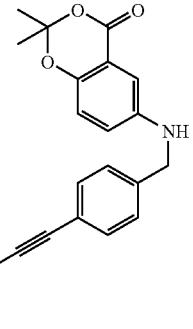

A solution of 6-[((E)-{4-[(4-chlorophenyl)ethynyl]phenyl}methylidene)amino]-2,2-dimethyl-4H-1,3-benzodioxin-4-one (3.73 g, 8.97 mmol), sodium triacetoxyborohydride (5.70 g, 26.9 mmol) and acetic acid (0.77 mL, 13.5 mmol) in anhydrous DCE (120 mL) was stirred for 48 hrs at rt. Then the reaction mixture was diluted with water (150 mL) and an aqueous saturated solution of NaHCO₃ (100 mL) and extracted with DCM (250 mL and 100 mL). The combined organic layers were dried over MgSO$_4$ and evaporated under reduced pressure. The residue was crystallized from a DCM/pentane solution. The solid was filtered, washed with pentane (2×) and dried under reduced pressure to give 3.50 g (93%) of the title compound as a yellow powder. HPLC, Rt: 5.0 min (purity: 98.1%). $^1$H NMR (CDCl$_3$) δ: 7.51 (d, J=8.2 Hz, 2H), 7.46 (d, J=8.5 Hz, 2H), 7.34 (m, 4H), 7.18 (d, J=2.6 Hz, 1H), 6.86 (dd, J=8.8, 2.6 Hz, 1H), 6.81 (d, J=8.8 Hz, 1H), 4.35 (s, 2H), 4.21 (brs, 1H), 1.71 (s, 6H).

Step c) Formation of 6-({4-[(4-chlorophenyl)ethynyl]benzyl}(hexyl)amino)-2,2-dimethyl-4H-1,3-benzodioxin-4-one

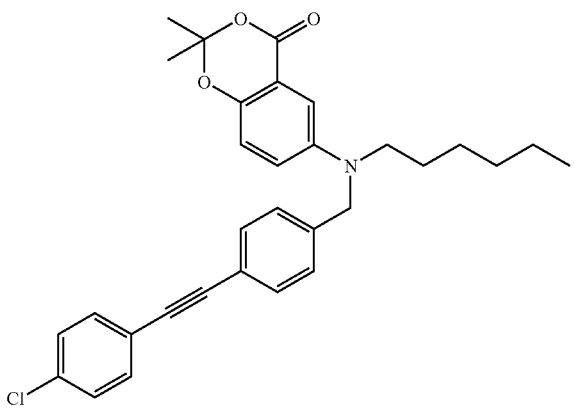

The title compound was prepared following the procedure described in Example 1 step d) using 6-({4-[(4-chlorophenyl)ethynyl]benzyl}amino)-2,2-dimethyl-4H-1,3-benzodioxin-one (3.0 g, 7.18 mmol) and hexanal (1.39 mL, 11.49 mmol). The title compound was obtained as a yellow oil (3.5 g, 97%). HPLC, Rt: 6.3 min (purity: 98.0%). LC/MS, M$^+$(ESI): 502.0. $^1$H NMR (CDCl$_3$) δ: 7.46 (m, 4H), 7.33 (m, 2H), 7.22 (m, 3H), 6.86 (dd, J=9.0, 3.0 Hz, 1H), 6.80 (d, J=9.0 Hz, 1H), 4.52 (s, 2H), 3.37 (t, J=7.5 Hz, 2H), 1.71 (s, 6H), 1.64 (m, 2H), 1.31 (m, 6H), 0.89 (t, J=6.6 Hz, 3H).

Step d) Formation of 5-({4-[(4-chlorophenyl)ethynyl]benzyl}(hexyl)amino)-2-hydroxybenzoic acid

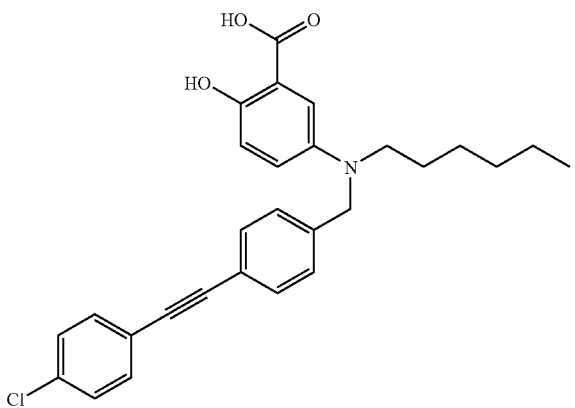

To a solution of 6-({4-[(4-chlorophenyl)ethynyl]benzyl}(hexyl)amino)-2,2-dimethyl-4H-1,3-benzodioxin-4-one (3.40 g, 6.77 mmol) in MeOH (150 mL) was added an aqueous solution of NaOH (5.5 mL, 5N). The reaction mixture was stirred at rt for 1.5 hr and a solid precipitated out. Water (250 mL) was added, and then the precipitate was filtered and washed with water (3×). The solid was taken up with MeOH (150 mL), an aqueous solution of NaOH (5.5 mL, 5N) was added and the resulting mixture was heated at 60° C. for 15 hrs. Then an aqueous solution of HCl (10 mL, 5N) and water (400 mL) were added and the mixture was extracted with Et$_2$O (500+2×250 mL). The combined organic layers were dried over MgSO$_4$ and evaporated under reduced pressure. Purification by crystallization (acetone/water) gave 909 mg (29%) of the title compound as a white powder. HPLC, Rt: 4.5 min (purity: 99.5%). LC/MS, M$^+$(ESI): 462.0, M$^-$(ESI): 459.9. $^1$H NMR (CDCl$_3$) δ: 7.55 (d, J=8.3 Hz, 2H), 7.48 (m, 4H), 7.26 (d, J=7.9 Hz, 2H), 7.00 (d, J=2.8 Hz, 1H), 6.96 (dd, J=9.0, 2.8 Hz, 1H), 6.78 (d, J=9.0 Hz, 1H), 4.47 (s, 2H), 3.30 (m, 2H), 1.51 (m, 2H), 1.24 (m, 6H), 0.83 (m, 3H).

Step e) Formation of 5-({4-[(4-chlorophenyl)ethynyl]benzyl}(hexyl)amino)-2-hydroxybenzoic acid, N-methyl-D-glucamine (i.e. 1-deoxy-1-(methylamino)glucitol) salt

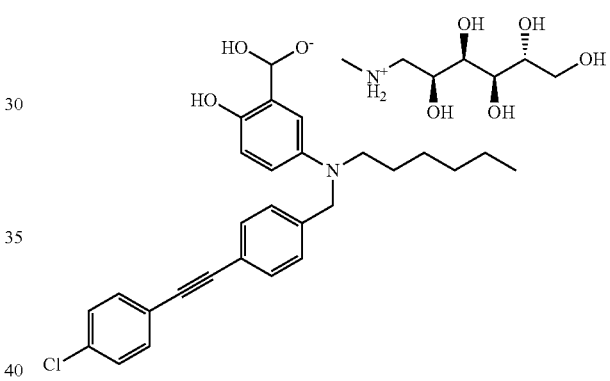

The title compound was prepared following the procedure described in Example 1 step g) using 5-({4-[(4-chlorophenyl)ethynyl]benzyl}(hexyl)amino)-2-hydroxybenzoic acid (882 mg, 1.91 mmol) in THF. The title compound was obtained as a pale yellow powder (1054 mg, 84%). HPLC, Rt: 4.5 min (purity: 99.6%). LC/MS, M$^+$(ESI): 462.0, M$^-$(ESI): 460.

Example 32

5-(hexyl{4-[(4-methoxyphenyl)ethynyl]benzyl}amino)-2-hydroxybenzoic acid, N-methyl-D-glucamine (i.e. 1-deoxy-1-(methylamino)glucitol) salt Step a) Formation of 6-({4-[(4-methoxyphenyl)ethynyl]benzyl}amino)-2,2-dimethyl-4H-1,3-benzodioxin-4-one

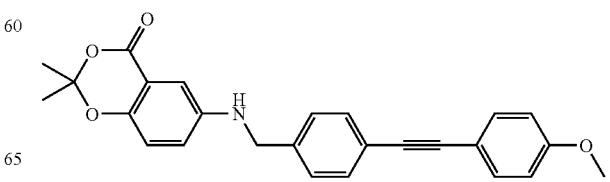

The title compound was prepared following procedure described in Example 1, step c) from 4-[(4-methoxyphenyl)ethynyl]benzaldehyde (1.31 g; 5.53 mmol, intermediate which may be obtained according to methods disclosed in EP03103780.7) and 6-amino-2,2-dimethyl-benzo[1,3]dioxin-4-one (1.07 g; 5.53 mmol). The crude (1.7 g) was purified by recrystallisation from MeOH/EtOAc to give 1.23 g (54%) of the title compound as a yellow powder. HPLC, Rt: 4.77 min (purity: 77%). $^1$H NMR (CDCl$_3$) δ: 7.46 (m, 4H), 7.31 (d, J=7.9 Hz, 2H), 7.15 (d, J=2.6 Hz, 1H), 6.85 (d, J=8.5 Hz, 2H), 6.78 (m, 2H), 4.30 (s, 2H), 3.81 (s, 3H), 1.68 (s, 6H).

Step b) Formation of 6-(hexyl{4-[(4-methoxyphenyl)ethynyl]benzyl}amino)-2,2-dimethyl-4H-1,3-benzodioxin-4-one

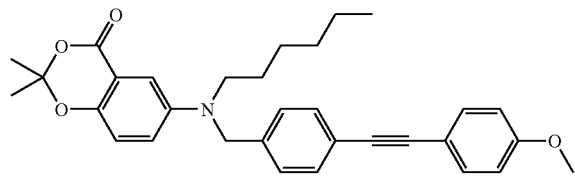

To a solution of 6-({4-[(4-methoxyphenyl)ethynyl]benzyl}amino)-2,2-dimethyl-4H-1,3-benzodioxin-4-one (416 mg; 1.01 mmol) in anhydrous DCE (15 mL) were added hexanal (Aldrich, 181 µl; 1.51 mmol), sodium triacetoxyborohydride (426 mg, 2.01 mmol) and acetic acid (115 µl). The resulting mixture was heated at 70° C. under nitrogen atmosphere for 24 h and poured into a saturated aqueous solution of NaHCO$_3$. The aqueous layer was extracted with DCM (twice) and combined organic layers were washed with brine, dried over magnesium sulfate, filtrated and concentrated. Purification by flash chromatography on silica gel (EtOAc/c-Hex 5:95 then 10:90) gave 520 mg of the title compound (quantitative). HPLC, Rt : 5.82 min (purity: 99.9%). LC/MS, M$^+$(ESI): 498.7. $^1$H NMR (CDCl$_3$) δ: 7.43 (d, J=8.9 Hz, 4H), 7.21 (s, 1H), 7.16 (d, J=8.1 Hz, 2H), 6.74-6.86 (m, 4H), 4.48 (s, 2H), 3.80 (s, 3H), 3.34 (t, J=7.8 Hz, 2H), 1.68 (s, 6H), 1.61 (m, 2H), 1.27 (s, 6H), 0.86 (m, 3H).

Step c) Formation of 5-(hexyl{4-[(4-methoxyphenyl)ethynyl]benzyl}amino)-2-hydroxybenzoic acid

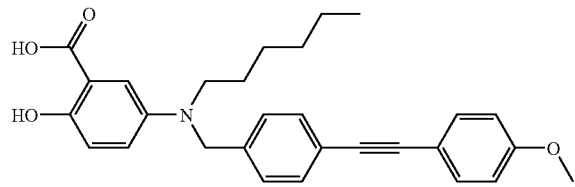

To a solution of 6-(hexyl{4-[(4-methoxyphenyl)ethynyl]benzyl}amino)-2,2-dimethyl-4H-1,3-benzodioxin-4-one (520 mg; 1.05 mmol) in MeOH (20 mL) was added an aqueous solution of NaOH (1.05 mL, 5N). The reaction mixture was stirred at rt for 1 h. The yellow precipitate obtained was filtrated and washed with cola water. It was suspended again in MeOH (20 mL) and aqueous solution of NaOH (2 mL, 5N) and heated at 70° C. overnight. The reaction mixture was poured into an aqueous solution of HCl (1N) and extracted with Et$_2$O. The combined organic layers were washed with brine, dried over magnesium sulfate, filtrated and concentrated. Purification by preparative HPLC using a X-Terra column followed by a recrystallisation in MeOH gave 55 mg (12%) the title compound as a brown powder. HPLC, Rt: 4.24 min purity: 95.0%). LC/MS, M$^+$(ESI): 458.3, M$^-$(ESI): 456.1 $^1$H NMR (CDCl$_3$) δ: 12.70 (brs, 1H), 10.20 (brs, 1H), 7.46 (d, J=5.3 Hz, 2H), 7.44 (d, J=4.5 Hz, 2H), 7.23 (d, J=7.3 Hz, 2H), 6.98 (m, 4H), 6.78 (d, J=9.0 Hz, 1H), 4.46 (s, 2H), 3.78 (s, 3H), 3.31 (m, 2H), 1.51 (m, 2H), 1.25 (m, 6H), 0.84 (m, 3H).

Step d) Formation of 5-hexyl{4-[(4-methoxyphenyl)ethynyl]benzyl}amino)-2-hydroxybenzoic acid, N-methyl-D-glucamine (i.e. 1-deoxy-1-(methylamino)glucitol)salt

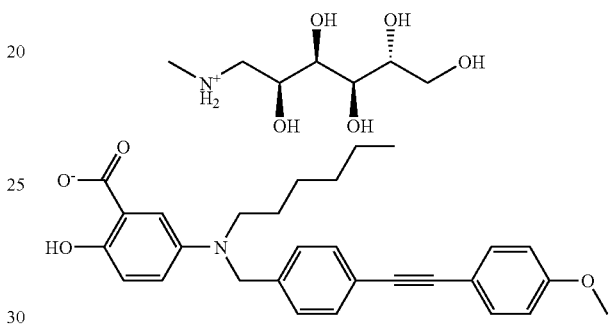

The title compound was prepared following procedure described in Example 1, step g) from 5-(hexyl{4-[(4-methoxyphenyl)ethynyl]benzyl}amino)-2-hydroxybenzoic acid (55 mg; 0.12 mmol) and N-methyl-D-glucamine (23.5 mg; 0.12 mmol). The title compound was isolated as a beige powder (61 mg, quantitative). HPLC, Rt: 4.21 min (purity: 99.8%). LC/MS, M$^+$(ESI): 458.3, M$^-$(ESI): 456.0.

Example 33

5-[hexyl(4-{[4-(trifluoromethyl)phenyl]ethynyl}benzyl)amino]-2-hydroxybenzoic acid N-methyl-D-glucamine (i.e. 1-deoxy-1-(methylamino)glucitol)salt Step a) Formation of 2,2-dimethyl-6-[(4-{[4-(trifluoromethyl)phenyl]ethynyl}benzyl)amino]-4H-1,3-benzodioxin-4-one

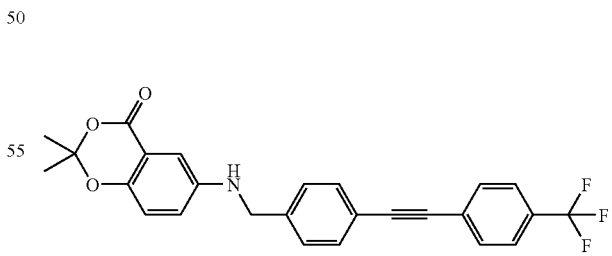

The title compound was prepared following procedure described in example 1, step c) from 4-{[4-(trifluoromethyl)phenyl]ethynyl}benzaldehyde (1.22 g; 4.43 mmol, intermediate which may be obtained according to methods disclosed in EP03103780.7) and 6-amino-2,2-dimethyl-benzo[1,3]dioxin-4-one (855 mg; 4.43 mmol). Purification of the crude (2.6g) by precipitation in DCM upon addition of pentane gave 590 mg (30%) of the title compound as a brown solid. HPLC, Rt: 4.76 min (purity: 76.2%). LC/MS, M⁺(ESI): 452, M⁻(ESI): 450.1, ¹H NMR (CDCl₃) δ 7.59 (s, 4H), 7.51 (d, J=7.5 Hz, 2H), 7.34 (d, J=7.7 Hz, 2H), 7.15 (s, 1H), 6.80 (m, 2H), 4.34 (s, 2H), 1.68 (s, 6H). Purification of the filtrate by flash chromatography on silicagel (EtOAc/c-Hex 10:90 then 20:80) gave another 420 mg of the title compound (21%) as a yellow powder.

Step b) Formation of 6-[hexyl(4-{[4-(trifluoromethyl)phenyl]ethynyl}benzyl)amino]-2,2-dimethyl-4H-1,3-benzodioxin-4-one

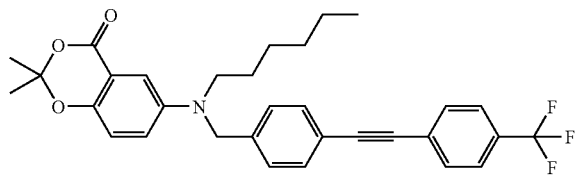

The title compound was prepared following procedure described in Example 32, step c) from 2,2-dimethyl-6-[(4-{[4-(trifluoromethyl)phenyl]ethynyl}benzyl)amino]-4H-1,3-benzodioxin-4-one (427 mg; 0.95 mmol) and hexanal (Aldrich, 170 μl; 1.42 mmol) to give 560 mg of crude. Purification by flash chromatography on silica gel (EtOAc/c-Hexe 5:90 then 10:90) gave 395 mg (78%) of the title compound as a brown powder. HPLC, Rt: 6.21 min (purity: 68.5%). ¹H NMR (CDCl₃) δ: 7.59 (brs, 4H), 7.47 (m, 2H), 7.30.(m 3H), 6.76-6.83 (m, 2H), 4.50 (s, 2H), 3.38 (m, 2H), 1.68 (s, 6H), 1.61 (m, 2H), 1.28 (m, 6H), 0.86 (m, 3H).

Step c) Formation of S-[hexyl(4-{[4-(trifluoromethyl)phenyl]ethynyl}benzyl)amino]-2-hydroxybenzoic acid

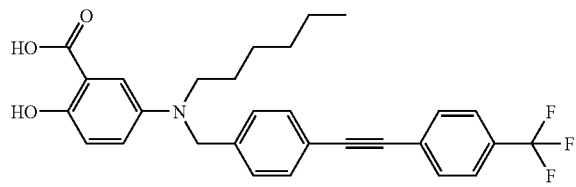

The title compound was prepared following procedure described in Example 32, step c) from 6-[hexyl(4-{[4-(trifluoromethyl)phenyl]ethynyl}benzyl)amino]-2,2-dimethyl-4H-1,3-benzodioxin-4-one (395 mg, 0.74 mmol). Purification by preparative HPLC using a X-Terra column yielded 103 mg (28%) of the title compound. HPLC, Rt: 4.62 min (purity: 96.6%). LC/MS: M⁺(ESI): 496.1, M⁻(ESI): 494.0. ¹H NMR (CDCl₃) δ: 7.86 (s, 1H), 7.56 (m, 5H), 7.37 (d, J=7.9 Hz, 2H), 7.13 (d, J=7.9 Hz, 2H), 6.99 (d, J=9.0 Hz, 1H), 4.59 (brs, 2H), 3.56 (brs, 2H), 1.49 (brs, 2H), 1.19 (m, 6H), 0.80 (m, 3H).

Step d) Formation of 5-[hexyl(4-{[4-(trifluoromethyl)phenyl]ethynyl}benzyl)amino]-2-hydroxybenzoic acid, N-methyl-D-glucamine (i.e. 1-deoxy-1-(methylamino)glucitol)salt

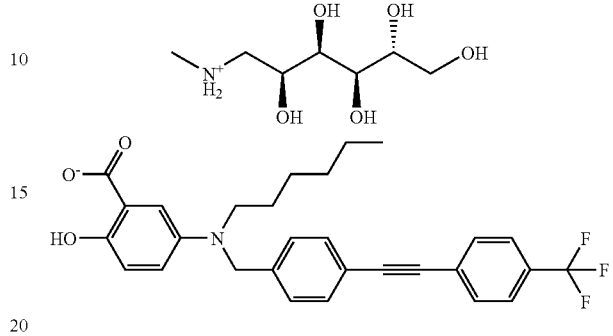

The title compound was prepared following procedure described in example 1, step g) from 5-[hexyl(4-{[4-(trifluoromethyl)phenyl]ethynyl}benzyl)amino]-2-hydroxybenzoic acid (92 mg,; 0.19 mmol) to give 121 mg of a beige powder. Rt: 4.63 min (purity: 98.8%). LC/MS, M⁺(ESI): 496.1, M⁻(ESI): 494.0.

Example 34

5-[{4-[(4-butylphenyl)ethynyl]benzyl}(cyclopentylmethyl)amino]-2-fluorobenzoic acid, N-methyl-D-glucamine (i.e. 1-deoxy-1-(methylamino)glucitol) salt Step a) Formation of 5-{[4-(4-butyl-phenylethynyl)-benzyl]-cyclopentylmethylamino}-2-fluoro-benzoic acid methyl ester

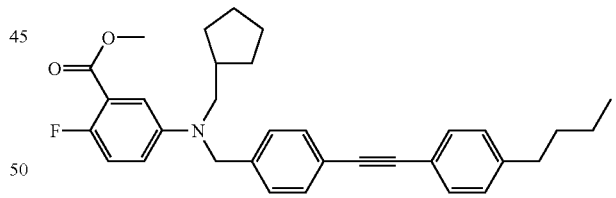

A solution of methyl 5-({4-[(4-butylphenyl)ethynyl]benzyl}amino)-2-fluorobenzoate (800 mg, 1.93 mmol) in DCE (16 mL) was treated with cyclopentanecarboxaldehyde (Aldrich, 283 mg, 2.89 mmol) then with sodium triacetoxyborohydride (1.22 g, 5.78 mmol). The resulting mixture was stirred at 70° C. for 2 h. The reaction mixture was allowed to cool down, dichloromethane (40 mL) was added and the organic layer was washed twice with water and with brine, dried over magnesium sulfate, filtered and concentrated. Purification by flash chromatography on silicagel afforded the title compound as a colorless oil (590 mg, 60%). HPLC, Rt: 6.47 min (purity: 97.1%), LC/MS, M⁺(ESI): 498.1. ¹H NMR (CDCl₃) δ: 7.42 (m, 4H), 7.22 (m, 1M), 7.14 (m, 4H), 6.92 (m, 1H), 6.75 (m, 1H), 4.55 (s, 2H), 3.89 (s, 3H), 3.33 (d, 2H), 2.60 (t, J=7.7 Hz, 2H), 2.29 (m, 1H), 1.65 (m, 2H), 1.70-1.46 (m, 6H), 1.42-1.15 (m, 6H), 0.91 (t, J=7.3 Hz, 3H).

Step b) Formation of 5-{[4-(4-Butyl-phenylethynyl)-benzyl]-cyclopentylmethyl-amino}-2-fluoro-benzoic acid

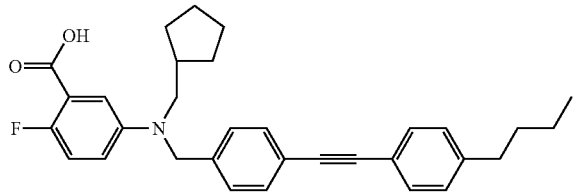

5-{[4-(4-Butyl-phenylethynyl)-benzyl]-cyclopentyl-methyl-amino}-2-fluoro-benzoic acid methyl ester (590 mg, 1.15 mmol) was dissolved in 10 mL of EtOH, sodium hydroxide (692 µl; 5.0 M; 3.56 mmol) was added and the reaction mixture stirred at 65° C for 3 h. The reaction mixture was allowed to cool down and EtOAc (50 mL) was added. The organic layer was washed three times with HCl (1N), dried over magnesium sulfate, filtered and concentrated to give 491 mg (88%) of the title cotmpound as a white solid. HPLC, Rt: 6.03 min (purity: 96.7%), M+(ESI): 484.3, M−(ESI): 482.0. $^1$H NMR (CDCl$_3$) δ: 7.43 (m, 4H), 7.31 (m, 1H), 7.14 (m, 4H), 6.95 (t, J=9.5 Hz, 1H), 6.80 (m, 1H), 4.56 (s, 2H), 3.36 (d, 2H), 2.60 (t, J=7.5 Hz, 2H), 2.30 (m, 1H), 1.76 (m, 2H), 1.70-1.48 (m, 6H), 1.42-1.15 (m, 4H), 0.91 (t, J=7.4 Hz, 3H).

Step c) Formation of 5-[{4-[(4-butylphenyl)ethynyl]benzyl}(cyclopentylmethyl)amino]-2-fluorobenzoic acid, N-methyl-D-glucamine (i.e. 1-deoxy-1-(methylamino)glucitol)salt

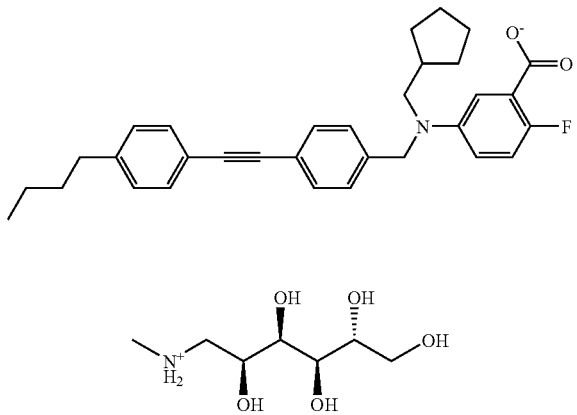

The title compound was prepared following the procedure described in Example 1 step g) using 5-{[4-(4-butyl-phenylethynyl)-benzyl]-cyclopentylmethyl-amino}-2-fluoro-benzoic acid (457 mg, 0.94 mmol). The title compound was obtained as a white powder (576 mg, 90%). HPLC, Rt: 6.20 min (purity: 98.4%). LC/MS, M+(ESI): 484.2, M−(ESI): 482.2.

Example 35

5-[{4-[(4-butylphenyl)ethynylbenzyl}(3,3-dimethyl-butyl)amino]-2-fluorobenzoic acid, N-methyl-D-glucamine (i.e. 1-deoxy-1-(methylamino)glucitol) salt Step a) Formation of methyl 5-[{4-[(4-butylphenyl)ethynyl]benzyl}(3,3 dimethylbutyl)amino]-2-fluorobenzoate

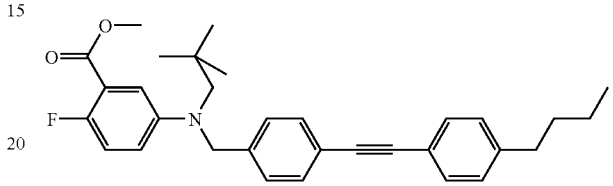

Methyl 5-({4-[(4-butylphenyl)ethynyl]benzyl}amino)-2-fluorobenzoate (800 mg, 1.93 mmol) was dissolved in DCE (15 mL), then 3,3-dimethyl-butyraldehyde (289 mg, 2.89 mmol) was added followed by sodium triacetoxyborohydride (Aldrich, 1224 mg, 5.78 mmol) and the resulting mixture stirred at 70° C. for 2 h. Reaction was allowed to cool down, dichloromethane (40 mL) was added and the organic layer was washed twice with H$_2$O and once with brine, dried over MgSO$_4$, filtered and concentrated under reduced pressure. Purification on silicagel afforded 541 mg (56%) of the title compound as a colorless oil. HPLC, Rt: 6.42 min, purity: 98.3%); LC/MS, M+(ESI): 500.4; $^1$H NMR (CDCl$_3$) δ: 7.44 (m, 4H), 7.17 (m, 5H), 6.93 (t, J=9.6 Hz, 1H), 6.73 (m, 1H), 4.46 (s, 2H), 3.88 (s, 3H), 3.40 (m, 2H), 2.60 (t, J=7.7 Hz, 2H), 1.70-1.46 (m, 4H), 1.34 (m, 2H), 0.99-0.87 (m, 12H).

Step b) Formation of 5-{[4-[(4-butylphenyl)ethynyl]benzyl}(3,3-dimethylbutyl)amino]-2-fluorobenzoic acid

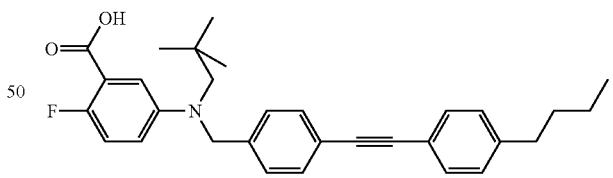

Methyl 5-[{4-[(4-butylphenyl)ethynyl]benzyl}(3,3-dimethylbutyl)amino]-2-fluorobenzoate (541 mg; 1.08 mmol) was dissolved in 10 mL of EtOH and sodium hydroxide (649.63 µl; 5.00 M, 3.25 mmol) was added. The reaction mixture was stirred at 65° C. for 2h30. The reaction mixture was allowed to cool down and EtOAc (50 mL) was added. The organic layer was washed three times with HCl (1M), dried over MgSO$_4$, filtered and concentrated under reduced pressure to afford 450 mg (86%) of the title compound as a yellow solid. HPLC, Rt: 5.97 min (purity: 98.9%); LC/MS M+(ESI): 486.2, M−(ESI)=484.0; $^1$H NMR (CDCl$_3$) δ: 7.44 (m, 4H), 7.32 (m, 1H), 7.20 (d, J=9.8 Hz, 2H,), 7.14 (d, J=8.3 Hz, 2H), 6.97 (m, 1H), 6.91-6.75 (m, 1H), 4.48 (s, 2H), 3.42 (m, 2H), 2.60 (t, J=7.7 Hz, 2H), 1.65-1.46 (m, 4H), 1.40-1.28 (m, 2H), 0.99-0.87 (m, 12H).

Step c) Formation of 5-[{4-[(4-butylphenyl)ethynyl]benzyl}(3,3-dimethylbutyl)amino]-2-fluorobenzoic acid, N-methyl-D-glucamine (i.e. 1-deoxy-1-(methylamino)glucitol)salt

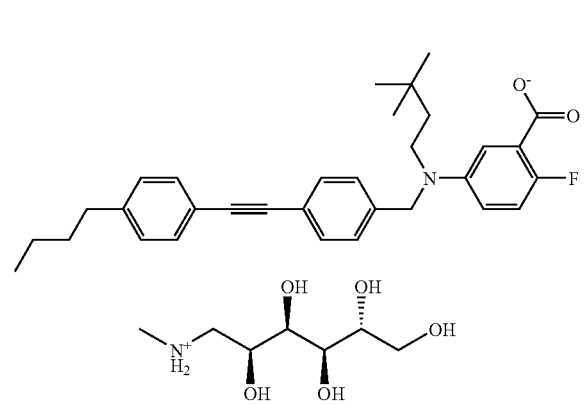

The title compound was prepared following the procedure described in Example 1 step g) using 5-[{4-[(4-butylphenyl)ethynyl]benzyl}(3,3-dimethylbutyl)amino]-2-fluorobenzoic acid (443 mg, 0.91 mmol). The title compound was isolated as a white powder (94%). HPLC, Rt: 6.11 min (purity: 98.5%). LC/MS, M$^+$(ESI): 486.4, M$^-$(ESI): 484.2.

Example 36

5-((cyclopentylmethyl){4-[(4-methoxyphenolyethynyl]benzyl}amino)-2-hydroxybenzoic acid, N-methyl-D-glucamine (i.e. 1-deoxy-1-(methylamino)glucitol)salt Step a) Formation of 6-((cyclopentylmethyl)}4-[(4-methoxyphenyl)ethynyl]benzyl}amino)-2,2-dimethyl-4H-1,3-benzodioxin-4-one

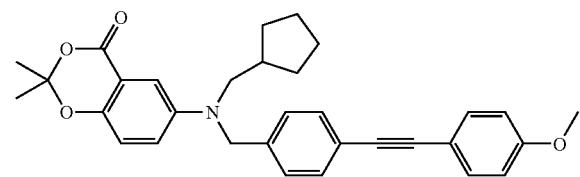

The title compound was prepared following procedure described in example 23, step b) from 6-({4-[(4-methoxyphenyl)ethynyl]benzyl}amino)-2,2-dimethyl-4H-1,3-benzodioxin-4-one (398 mg; 0.96 mmol) and cyclopentanecarboxaldehyde (Aldrich, 141.71 mg; 1.44 mmol). The crude (854 mg) was purified by flash chromatography on silicagel (EtOAc/cHex, gradient 10:90 to 20:80) to give 454 mg (95%) of the title compound as a yellow foam. Rt: 5.85 min (purity: 96.8%). LC/MS, M$^+$(ESI): 496.2. $^1$H NMR (CDCl$_3$) δ: 7.47 (m, 4H), 7.18 (d, J=8.1 Hz, 1H), 6.89 (d, J=8.9 Hz, 2H), 6.87 (m, 3H), 6.79 (d, J=9.0 Hz, 1H), 4.59 (s, 2H), 3.84 (s, 3H), 3.36 (d, J=7.1 Hz, 2H), 2.32 (m, 1H), 1.56-1.65 (m, 6H), 1.45 (s, 6H), 1.26 (m, 2H).

Step b) Formation of methyl 5-((cyclopentylmethyl){4-[(4-methoxyphenyl)ethynyl]-benzyl}amino)-2-hydroxybenzoate

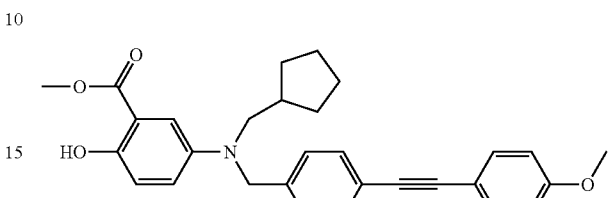

The title compound was prepared following procedure described in example 1, step e) from 6-(cyclopentylmethyl){4-[(4-methoxyphenyl)ethynyl]benzyl}amino)-2,2-dimethyl-4H-1,3-benzodioxin-4-one (438 mg; 0.88 mmol) to give 239 mg (56%) of an orange solid. Rt: 4.71 min (purity: 82.6%).

Step c) Formation of 5-((cyclopentylmethyl)[4-[(4-methoxyphenyl)ethynyl]benzyl}amino)-2-hydroxybenzoic acid

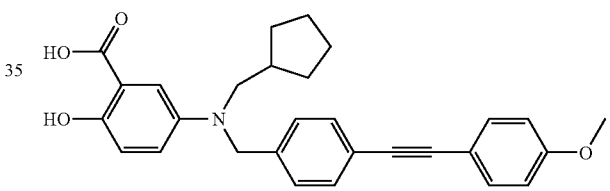

To a solution of ethyl 5-((cyclopentylmethyl){4-[(4-methoxyphenyl)ethynyl]-benzyl}amino)-2-hydroxybenzoate (200 mg; 0.43 mmol) was dissolved in THF (4 mL) and water (1.00 mL) was added LiOH (178 mg; 4.26 mmol). The mixture was then heated in MW for 2500 s at 100° C. It was poured into a 1N solution of HCl and extracted twice with EtOAc. The combined organic layers were dried over magnesium sulfate, filtered and concentrated to give 225 mg of a yellow oil. The oil was suspended in methanol and triturated to give 140 mg (72%) of the title compound as a yellow powder. Rt: 4.08 min (purity: 99.1%), LC/MS: M$^+$(ESI): 456.0, M$^-$(ESI): 454.2.

Step d) Formation of 5-((cyclopentylmethyl){4-[(4-methoxyphenyl)ethynyl]benzyl}amino)-2-hydroxybenzoic acid, N-methyl-D-glucamine (i.e. 1-deoxy-1-(methylamino)glucitol)salt

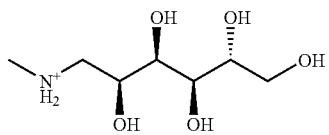

93

-continued

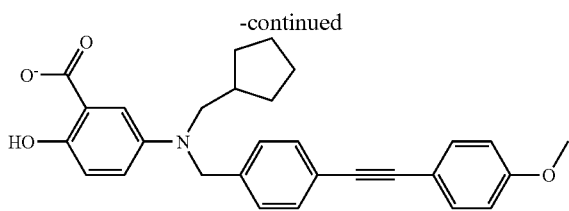

The title compound was prepared following procedure described in Example 1, step g) from 5-((cyclopentylmethyl){4-[(4-methoxyphenyl)ethynyl]benzyl}amino)-2-hydroxybenzoic acid (140 mg; 0.31 mmol) and N-methyl-D-glucamine (60 mg; 0.31 mmol) to give 198 mg of a white powder. Rt: 4.11 min (purity: 100%), LC/MS: M+(ESI): 455.4, M−(ESI): 454.0. Analysis calculated for $C_{29}H_{29}NO_4$—$C_7H_{17}NO_5$-0.5 $H_2O$: calculated C 65.54; H 7.18; N 4.25%; Found: C 65.31; H 7.04; N 4.26%.

Example 37

5-({4-[(4-butylphenyl)ethynyl]benzyl}(ethyl)amino)-2-fluorobenzoic acid, N-methyl-D-glucamine (i.e. 1-deoxy-1-(methylamino)glucitol) salt Step a) Formation of methyl 5-({4-[(4-butylphenyl)ethynyl]benzyl}(ethyl)amino)-2-fluorobenzoate

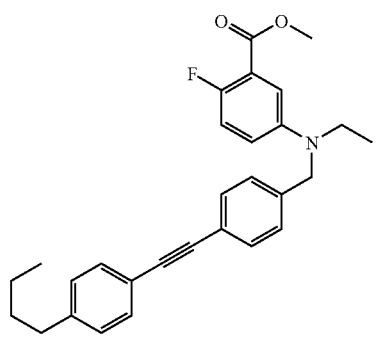

The title compound was prepared following the procedure described in Example 23 step b) using methyl 5-({4-[(4-butylphenyl)ethynyl]benzyl}amino)-2-fluorobenzoate (prepared in Example 23, step a) and ethanol. The title compound was obtained as a pale yellow oil (215 mg). HPLC, Rt: 5.8 min (purity: 98.9%).

Step b) Formation of 5-({4-[(4-butylphenyl)ethynyl]benzyl}(ethyl)amino)-2-fluorobenzoic acid

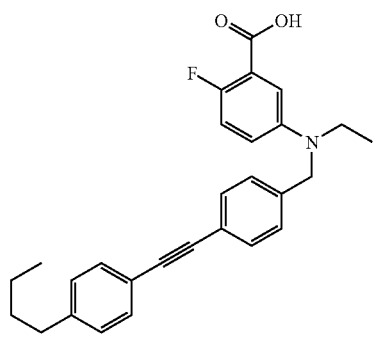

94

The title compound was prepared following the procedure described in Example 23 step c) using methyl 5-({4-[(4-butylphenyl)ethynyl]benzyl}(ethyl)amino)-2-fluorobenzoate (293 mg, 0.66 mmol) in EtOH. The title compound was obtained as a white powder (258 mg, 91%). HPLC, Rt: 5.0 min (purity: 99.2%). LC/MS, M−(ESI): 428.0. $^1$H NMR (CDCl$_3$) δ: 7.48 (d, J=7.9 Hz, 2H), 7.44 (d, J=7.9 Hz, 2H), 7.32 (m, 1H), 7.22 (d, J=7.9 Hz, 2H), 7.16 (d, J=7.9 Hz, 2H), 6.99 (dd, J=10.2, 9.4 Hz, 1H), 6.84 (m, 1H), 4.51 (s, 2H), 3.50 (q, J=6.8 Hz, 2H), 2.62 (t, J=7.6 Hz, 2H), 1.61 (m, 2H), 1.36 (m, 2H), 1.22 (t, J=6.8 Hz, 3H), 0.93 (t, J=7.4 Hz, 3H).

Step c) Formation of 5-({4-[(4-butylphenyl)ethynyl]benzyl}(ethyl)amino)-2-fluorobenzoic acid, N-methyl-D-glucamine (i.e. 1-deoxy-1-(methylamino)glucitol) salt

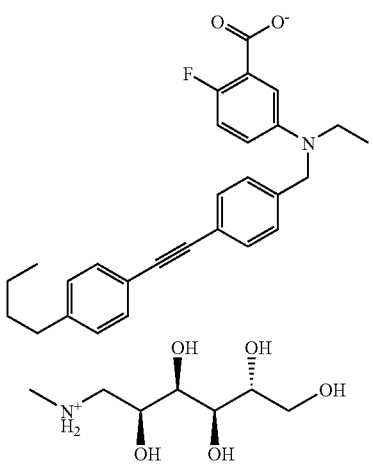

The title compound was prepared following the procedure described in Example 24 using 5-({4-[(4-butylphenyl)ethynyl]benzyl}(ethyl)amino)-2-fluorobenzoic acid (239 mg, 0.56 mmol). The title compound was obtained as a pale yellow powder (267 mg, 77%). HPLC, Rt: 5.0 min (purity: 99.1%). LC/MS, M−(ESI): 428.1.

Example 38

5-(hexyl{4-[(4-propylphenyl)ethyl]benzyl}amino)-2-hydroxybenzoic acid, N-methyl-D-glucamine (i.e. 1-deoxy-1-(methylamino)glucitol)salt Step a) Formation of 2,2-dimethyl-6-({4-[(4-propylphenyl)ethynyl]benzyl}amino)-4H-1,3-benzodioxin-4-one

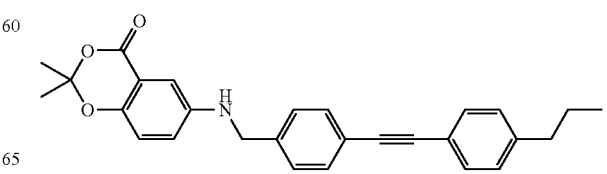

The title compound was prepared following procedure described in Example 1, step c) from 4-[(4-propylphenyl)ethynyl]benzaldehyde (1.53 g; 6.16 mmol) and 6-amino-2,2-dimethyl-benzo[1,3]dioxin-4-one (1.19 g; 6.16 mmol). Purification of the yellow solid (2.4 g) obtained by flash chromatography using silica gel (EtOAc:c-Hex 10:90 to 20:80) gave 660 mg (25%) of the title compound as a yellow solid. HPLC, Rt: 5.48 min (purity: 72.4%), $^1$H NMR (CDCl$_3$) δ: 7.47 (d, J=7.5 Hz, 2H), 7.41 (d, J=8.1 Hz, 2H),: 7.31 (d, J=8.1 Hz, 2H), 7.08 (m, 3H), 6.70-6.79 (m, 2H), 4.25 (s, 2H), 2.57 (t, J=7.6 Hz, 2H), 1.62 (s, 6H), 1.55 (m, 2H), 0.86 (t, J=7.3 Hz, 3H).

Step b) Formation of 6-(hexyl{4-[(4-propylphenyl)ethynyl]benzyl}amino)-2,2-dimethyl-4H-1,3-benzo-dioxin-4-one

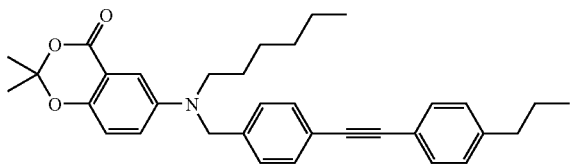

The title compound was prepared following procedure described in Example 23, step b) from 2,2-dimethyl-6-({4-[(4-propylphenyl)ethynyl]benzyl}amino)-4H-1,3-benzo-dioxin-4-one (660 mg; 1.55 mmol) and hexanal (Aldrich, 279.41 μl, 2.33 mmol). Purification of the crude (880 mg) by flash chromatography using silica gel (EtOAc/c-Hex, 5:95 then 10:90) gave 590 mg (75%) of the title compound as a beige powder. HPLC, Rt.: 6.37 min (purity: 61.9%), $^1$H NMR (CDCl$_3$) δ: 7.42 (m, 4H), 7.12-7.19 (m, 5H), 6.78 (m, 2H), 4.48 (s, 2H), 3.34 (t, J=7.6 Hz, 2H), 2.57 (t, J=7.8 Hz, 2H), 1.68 (s, 6H), 1.61 (m, 4H), 1.24 (m, 6H), (0.91 (t, J=7.3 Hz, 3H), 0.86 (t, J=6.7 Hz, 3H).

Step c) Formation of methyl 5-(hexyl{4-[(4-propylphenyl)ethynyl]benzyl}amino)-2-hydroxybenzoate

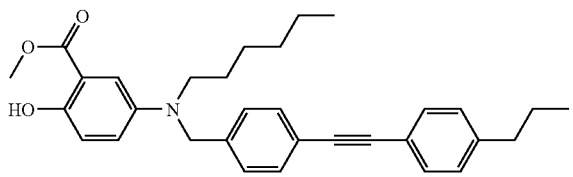

The title compound was prepared following procedure described in example 1, step e) from 6-(hexyl{4-[(4-propylphenyl)ethynyl]benzyl}amino)-2,2-dimethyl-4H-1,3-benzo-dioxin-4-one (590 mg, 1.16 mmol) and isolated as a yellow powder (469 mg, 84%). HPLC, Rt: 5.32 min (purity: 97.1%), LC/MS: M$^+$(ESI): 484.9.

Step d) Formation of 5-(hexyl{4-[(4-propylphenyl)ethynyl]benzyl}amino)-2-hydroxybenzoic acid

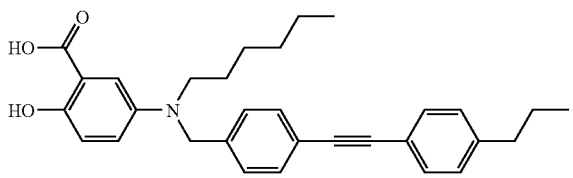

The title compound was prepared following procedure described in example 36, step c) from methyl 5-(hexyl{4-[(4-propylphenyl)ethynyl]benzyl}amino)-2-hydroxybenzoate (450 mg; 0.93 mmol) and isolated as a beige solid (313 mg, 72%). HPLC, Rt: 4.75 min (purity: 97.9%), LC/MS, M$^+$(ESI): 470.5, M$^-$(ESI): 468.1, $^1$H NMR (DMSO) δ: 13.7 (brs, 1H), 11.55 (brs, 1H), 7.44 (m, 4H), 7.24 (m, 4H), 6.99 (m, 2H), 6.78 (d, J=9.0 Hz, 1H), 4.47 (s, 2H), 3.33 (m, 2H), 2.56 (t, J=7.5 Hz, 2H), 1.57 (m, 4H), 1.24 (m, 6H), 0.87 (t, J=7.3 Hz, 3H), 0.85 (m, 3H).

Step e) formation of 5-(hexyl{4-[(4-propylphenyl)ethynyl]benzyl}amino)-2-hydroxybenzoic acid, N-methyl-D-glucamine (i.e. 1-deoxy-1-(methylamino)glucitol) salt

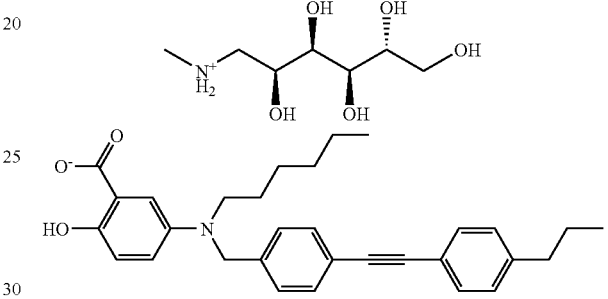

The title compound was prepared following procedure described in example 1, step g) from 5-(hexyl{4-[(4-propylphenyl)ethynyl]benzyl}amino)-2-hydroxybenzoic acid (307 mg; 0.65 mmol) and was isolated as a beige solid (370 mg). HPLC, Rt: 4.74 min (Purity: 99.1%), LC/MS, M$^-$(ESI): 468.2 Analysis calculated for $C_{31}H_{35}NO_3 \cdot C_7H_{17}NO_5 \cdot 0.5 H_2O$: calculated C, 67.73; H, 7.93; N, 4.16%; Found: C, 68.01; H, 7.82; N, 4.03%.

Example 39

5-[{4-[(4-butylphenyl)ethynyl]benzyl}(hexyl)amino]-2-fluorobenzoic acid, lysine salt

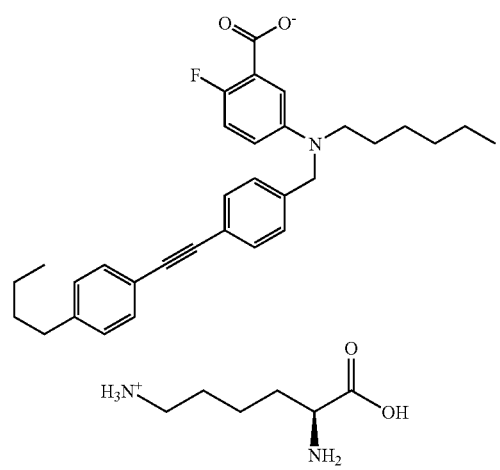

To a solution of 5-[{4-[(4-butylphenyl)ethynyl]benzyl}(hexyl)amino]-2-fluorobenzoic acid (300 mg, 0.62 mmol) in THF (3 mL) was added a solution of L-lysine (91 mg, 0.62 mmol) in water (2 mL). Then water (30 mL) was added and the resulting solution was lyophilized to give 246 mg (63%) of the title compound as a white powder. HPLC, Rt: 6.0 min purity: 98.7%). LC/MS, M$^+$(ESI): 486.3, M$^-$(ESI): 484.3.

Example 40

5-[{4-[4-butylphenyl)ethynyl]benzyl}(hexyl)amino]-2-fluorobenzoic acid, tromethamine (i.e. (2-amino-2-hydroxymethyl)-1,3-propanediol) salt

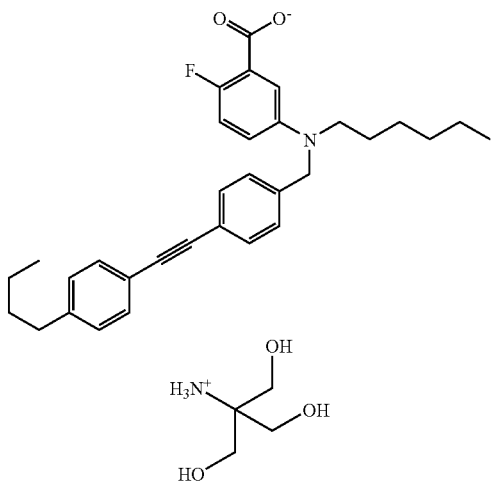

To a solution of 5-[{4-[(4-butylphenyl)ethynyl]benzyl}(hexyl)amino]-2-fluorobenzoic acid (300 mg, 0.62 mmol) in THF (3 mL) was added a solution of tris(hydroxymethyl)amino methane (75 mg, 0.62 mmol) in water (2 mL). Then water (30 mL) was added and the resulting solution was lyophilized to give 362 mg (96%) of the title compound as a white powder. HPLC, Rt: 6.0 min (purity: 98.0%). LC/MS, M$^+$(ESI): 486.3, M$^-$(ESI): 484.2.

Example 41

5-[{4-[(4-butylphenyl)ethynyl]benzyl}(pentyl)amino]-2-fluorobenzoic acid, N-methyl-D-glucamine (i.e. 1-deoxy-1-(methylamino)glucitol) salt Step a) Formation of methyl 5-[{4-[(4-butylphenyl)ethynyl]benzyl}(pentyl)amino]-2-fluorobenzoate

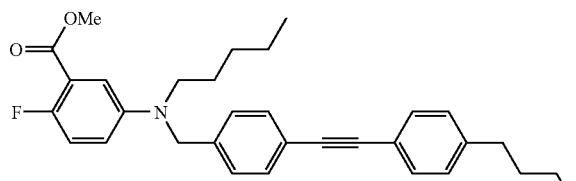

The title compound was prepared following procedure described in example 23, step b) from 5-({4-[(4-butylphenyl)ethynyl]benzyl}amino)-2-fluorobenzoate (305 mg; 0.73 mmol) and valeraldehyde (Aldrich, 195 µl; 1.84 mmol). Purification of the crude by flash chromatography using silicagel (c-Hex-EtOAc, 90:10) gave 230 mg (65%) of the title compound as a yellow oil. HPLC, Rt: 6.44 min (purity=98.4%). $^1$H NMR (CDCl$_3$) δ: 7.44 (d, J=8.7 Hz, 2H), 7.41 (d, J=9.0 Hz, 2H), 7.15 (d, J=7.5 Hz, 2H), 7.13 (d, J=7.9 Hz, 2H), 6.90 (d, J=9.8 Hz, 2H), 6.65 (m, 1H), 4.43 (s, 2H), 3.82 (s, 3H), 3.29 (t, J=7.5 Hz, 2H), 2.54 (t, J=7.7 Hz, 2H), 1.55 (m, 4H), 1.25 (m, 6H), 0.85 (m, 6H).

Step b) Formation of 5-[(4-[(4-butylphenyl)ethynyl]benzyl}(pentyl)amino]-2-fluorobenzoic acid

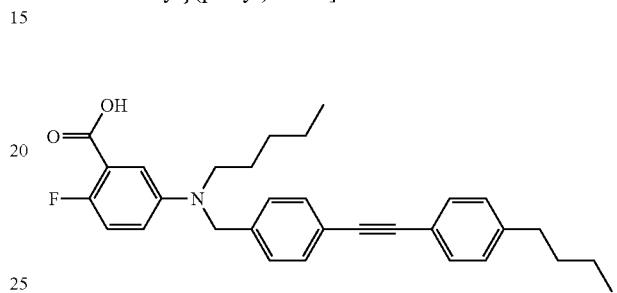

The title compound was prepared following procedure described in example 23, step c) from methyl 5-[{4-[(4-butylphenyl)ethynyl]benzyl}(pentyl)amino]-2-fluorobenzoate (330 mg; 0.68 mmol) and obtained quantitatively (140 mg) as a yellow powder. HPLC, Rt: 5.82 min (purity=97%). LC/MS, M$^-$(ESI): 470.2. $^1$H NMR (CDCl$_3$) δ: 7.46 (d, J=8.2 Hz, 2H), 7.42 (d, J=8.2 Hz, 2H), 7.15 (m, 5H), 6.95 (m, 1H), 6.78 (m, 1H), 4.52 (s, 2H), 3.38 (t, J=7.7 Hz, 2H), 2.61 (t, J=7.5 Hz, 2H), 1.62 (q, J=7.6 Hz, 6H), 1.35 (m, 4H), 0.92 (m, 6H).

Step c) Formation of methyl 5-[{4-[(4-butylphenyl)ethynyl]benzyl}(pentyl)amino]-2-fluorobenzoate, N-methyl-D-glucamine salt (i.e. 1-deoxy-1-(methylamino)glucitol) salt

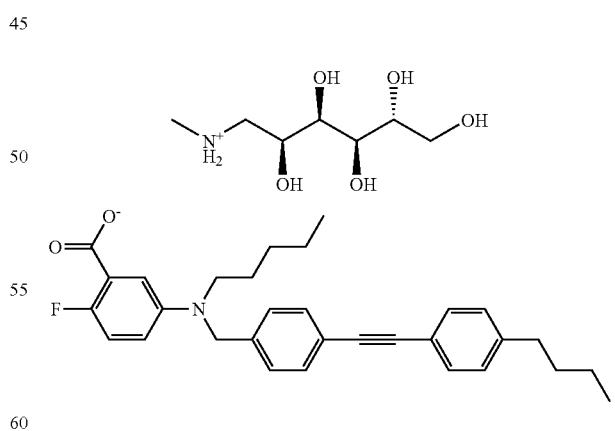

The title compound was prepared following procedure described in example 24 from 5-[{4-[(4-butylphenyl)ethynyl]benzyl}(pentyl)amino]-2-fluorobenzoic acid (130 mg; 0.28 mmol) and N-methyl-D-glucamine (54 mg; 0.28 mmol) and obtained quantitatively as a white powder. HPLC, Rt: 5.79 min (purity=99.5%). LC/MS, M$^-$(ESI): 470.2. Analysis calculated for $C_{31}H_{34}NO_2F—C_7H_{17}NO_5$-2.0 $H_2O$: calculated C, 64.94%, H, 7.89%, N, 3.99%; Found: C, 64.95%, H, 7.46%, N, 3.91%.

Example 42

5-[{4-[(4-butylphenyl)ethynyl]benzyl}(methyl)amino]-2-fluorobenzoic acid

Step a) Formation of methyl 5-[(4-[(4-butylphenyl)ethynyl]benzyl}(methyl)amino]-2-fluorobenzoate

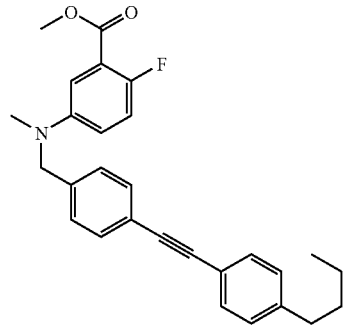

A solution of methyl 5-({4-[(4-butylphenyl)ethynyl]benzyl}amino)-2-fluorobenzoate (305 mg; 0.73 mmol), formaldehyde (Aldrich, 50 μl; 1.84 mmol) and formic acid (2.5 mL) was stirred under microwaves at 100° C. for 5 min. The reaction mixture was then poured into an aqueous solution of NaOH 1M and extracted twice with EtOAc. The combined organic layers were washed with brine, dried over magnesium sulfate, filtrated and concentrated. Purification of the crude (257 mg, yellow oil) by flash chromatography on silicagel afforded 70 mg of the title compound as a yellow powder. HPLC, Rt: 5.84. min (purity=100%). $^1$H NMR ($CDCl_3$) δ: 7.4 (m, 4H), 7.3 (s, 1H), 7.2 (m, 4H), 6.9 (t, J=7.8 Hz, 1H), 6.75 (m, 1H), 4.4 (s, 2H), 2.92 (s, 3H), 2.5 (t, J=7.7 Hz, 2H), 1.5 (m, 2H), 1.25 (m, 2H), 0.8 (t, J=7.53 Hz, 3H).

Step b) Formation of 5-[{4-[(4-butylphenyl)ethynyl]benzyl}(methyl)amino]-2-fluorobenzoic acid

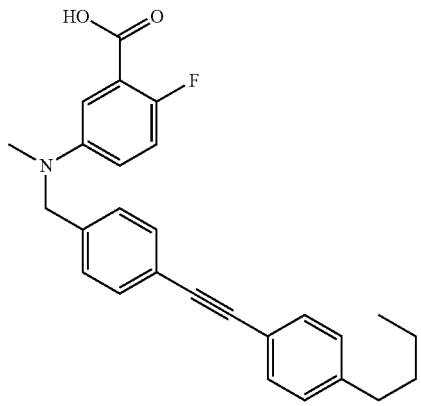

To a solution of methyl 5-[{4-[(4-butylphenyl)ethynyl]benzyl}(methyl)amino]-2-fluorobenzoate (66 mg; 0.15 mmol) in 3 mL of anhydrous THF were added. Lithium Hydroxide monohydrate (65 mg; 1.54 mmol) and water (1 mL). The reaction mixture was stirred under micro waves at 100° C. for 3500 s. Then an aqueous solution of HCl was added; the residue was extracted with EtOAc. The combined organic layers were washed with brine, dried over magnesium sulfate, filtrated and concentrated to give 37 mg of the title compound as a white solid. HPLC, Rt: 5.66 min (purity=93.20%). LC/MS, M$^-$(ESI): 414.5. $^1$H NMR ($CDCl_3$) δ: 7.40 (m, 4H), 7.31 (s, 1H), 7.20 (m, 4H), 6.92 (t, 1H), 6.75 (m, 1H), 4.42 (s, 2H), 2.92 (s, 3H), 2.54 (t, J=7.7 Hz, 2H), 1.50 (m, 2H), 1.25 (m, 2H), 0.82 (t, J=7.5 Hz, 3H).

Example 43

5-[{4-[(4-butylphenyl)ethynyl]benzyl}(cyclopropylmethyl)amino]-2-fluorobenzoic acid N-methyl-D-glucamine (i.e. 1-deoxy-1-(methylamino)glucitol) salt Step a) Formation of methyl 5-[(4-[(4-butylphenyl)ethynyl]benzyl) (cyclopropylmethyl)amino]-2-fluorobenzoate

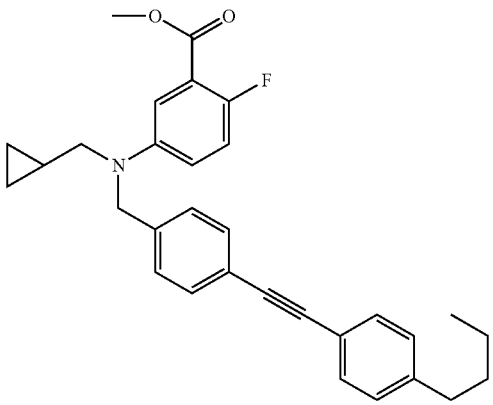

The title compound was prepared following procedure described in example 23, step b) from methyl 5-({4-[(4-butylphenyl)ethynyl]benzyl}amino)-2-fluorobenzoate (326 mg; 0.78 mmol) and cyclopropanecarboxaldehyde (Aldrich, 87.94 μl; 1.18 mmol). Purification of the crude by preparative HPLC using a X-Terra column gave 200 mg (54%) of the title compound as a beige oil. HPLC, Rt: 5.91 min (purity: 99.7%), LC/MS, M$^+$(ESI): 470.4, $^1$H NMR ($CDCl_3$) δ: 7.66 (m, 1H), 7.39 (d, J=7.9 Hz, 4H), 7.00-7.17 (m, 6H), 4.62 (s, 2H), 3.93 (s, 3H), 3.44 (m, 3H), 2.59 (t, J=7.7 Hz, 2H), 1.57 (m, 2H), 1.31 (m, 2H), 0.90 (t, J=7.2 Hz, 3H), 0.53 (d, J=7.2 Hz, 2H), 0.24 (m, 2H).

Step b) Formation of 5-[{4-[(4-butylphenyl)ethynyl]benzyl}(cyclopropylmethyl)amino]-2-fluorobenzoic acid

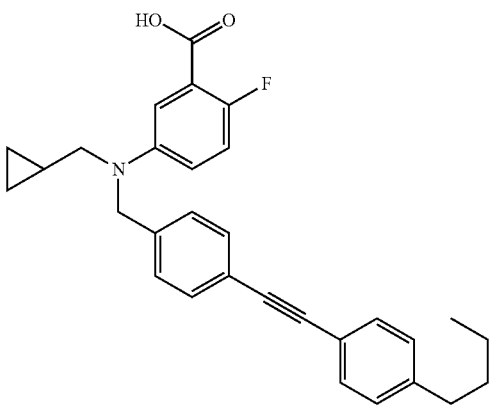

The title compound was prepared following procedure described in example 36, step c) from methyl 5-[{4-[(4-butylphenyl)ethynyl]benzyl}(cyclopropylmethyl)amino]-2-fluorobenzoate (200 mg; 0.43 mmol) and obtained quantitatively (200 mg) as a white powder. HPLC, Rt: 5.45 min (purity: 97.7%), LC/MS, M⁻(ESI): 454.1, ¹H M (MeOD) δ: 7.24-7.42 (m, 5H), 7.22 (d, J=7.9 Hz, 2H), 7.15 (d, J=7.7 Hz, 2H), 7.01 (d, J=7.9 Hz, 2H), 4.64 (s, 2H), 3.36 (d, J=6.4 Hz, 2H), 2.59 (t, J=7.9 Hz, 2H), 1.57 (m, 2H), 1.34 (m, 2H), 1.21 (m, 1H), 0.91 (t, J=7.3 Hz, 3H), 0.50 (m, 2H), 0.21 (m, 2H).

Step c) Formation of 5-[{4-[(4-butylphenyl)ethynyl]benzyl}(cyclopropylmethyl)amino]-2-fluorobenzoic acid, N-methyl-D-glucamine (i.e. 1-deoxy-1-(methylamino)glucitol) salt

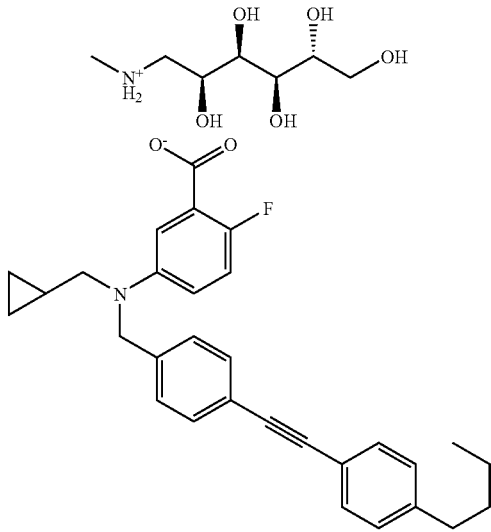

The title compound was prepared following procedure described in example 24 from 5-[{4-[(4-butylphenyl)ethynyl]benzyl}(cyclopropylmethyl)amino]-2-fluorobenzoic acid (200 mg; 0.44 mmol) and N-methyl-D-glucamine (86 mg; 0.44 mmol) and obtained quantitatively as a brown powder. HPLC, Rt: 5.35 min purity: 98.7%), LC/MS, M⁻(ESI): 454.1. Analysis calculated for $C_{30}H_{30}NO_2F—C_7H_{17}NO_5$-0.5 $CH_2Cl_2$-3.0 $H_2O$: calculated C, 60.27%, H, 7.28%, N, 3.75%; Found: C, 60.50%, H, 6.96%, N, 3.92%.

Example 44

5-{butyl[4-(phenylethynyl)benzyl]amino}-2-fluorobenzoic acid, N-methyl-D-glucamine (i.e. 1-deoxy-1-(methylamino)glucitol) salt Step a) Formation of methyl 5-{butyl[4-(phenylethynyl)benzyl]amino}-2-fluorobenzoate

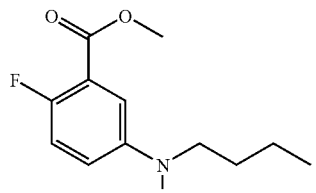

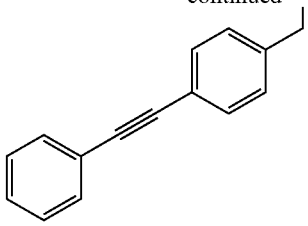

A solution of methyl 5-amino-2-fluorobenzoate (500 mg, 2.96 mmol), 4-(phenylethynyl)benzaldehyde (6 10 mg, 2.96 mmol) and acetic acid (0.25 mL, 4.40 mmol) in toluene (20 mL) was heated under reflux for 3 h with azeotropic removal of water. Then the solvent was removed by distillation at atmospheric pressure and replaced by anhydrous DCE (20 mL). Butanal (Fluka, 0.66 mL, 7.39 mmol), sodium triacetoxyborohydride (1880 mg, 8.87 mmol) and acetic acid (0.25 mL, 4.40 mmol) were added and the resulting mixture was heated at 70° C. After 45 min, an additional amount of sodium triacetoxyborohydride (630 mg, 2.96 mmol) was added. After 45 min, the reaction mixture was diluted with water (40 mL) and extracted with DCM (3×20 mL). The combined organic layers were dried over $MgSO_4$ and the solvents were removed under reduced pressure. Purification by flash chromatography on silicagel (cHex/EtOAc): gave. 924 mg (75%) of the title compound as a colorless oil. HPLC, Rt: 5.6 min (purity: 99.8%). LC/MS, M⁺(ESI): 416.1. ¹H NMR (CDCl₃) δ: 7.51-7.44 (m, 4H), 7.32 (m, 3H), 7.17 (m, 3H), 6.92 (dd, J=9.8, 9.7 Hz, 1H), 6.73 (m, 1H), 4.49 (s, 2H), 3.88 (s, 3H), 3.36 (t, J=7.2 Hz, 2H), 1.60 (m, 2H), 1.34 (m, 2H), 0.93 (t, J=7.2 Hz, 3H).

Step b) Formation of 5-{butyl[4-(phenylethynyl)benzyl]amino}-2-fluorobenzoic acid

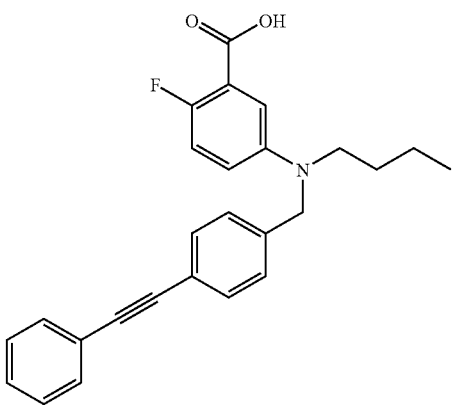

The title compound was prepared following the procedure described in Example 23 step c) using methyl 5-{butyl[4-phenylethynyl)benzyl]amino}-2-fluorobenzoate (924 mg, 2.22 mmol). The title compound was obtained as a sticky colorless oil (776 mg, 87%). HPLC, Rt: 4.9 min (purity: 99.8%). LC/MS, M⁻(ESI): 400.2. ¹H NMR (CDCl₃) δ: 7.54-7.48 (m, 4H), 7.35 (m, 3H), 7.29 (dd, J=5.6, 3.7 Hz, 1H), 7.20

(d, J=8.0 Hz, 2H), 6.98 (dd, J=10.6, 9.3 Hz, 1H), 6.79 (m, 1H), 4.54 (s, 2H), 3.41 (t, J=7.4 Hz, 2H), 1.64 (m, 2H), 1.38 (m, 2H), 0.96 (t, J=7.2 Hz, 3H).

Step c) Formation of 5-{butyl[4-(phenylethynyl)benzyl]amino}-2-fluorobenzoic acid, N-methyl-D-glucamine (i.e. 1-deoxy-1-(methylamino)glucitol) salt

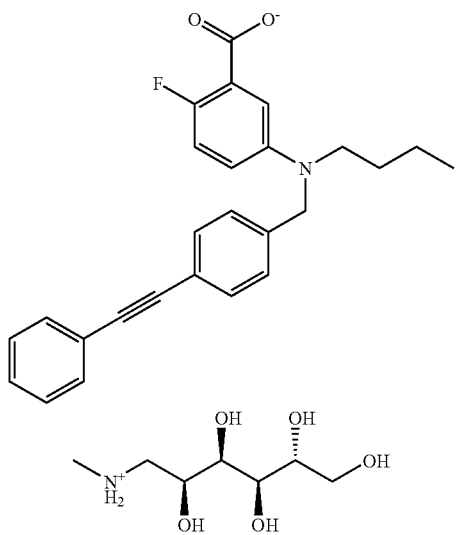

The title compound was prepared following the procedure described in Example 24 using 5-{butyl[4-(phenylethynyl)benzyl]amino}-2-fluorobenzoic acid (762 mg, 1.90 mmol). The title compound was obtained as a white powder (1045 mg, 92%). HPLC, Rt: 4.8 min (purity: 100%). LC/MS, M$^+$(ESI): 402.1, M$^-$(ESI): 400.1.

Example 45

2-fluoro-5-{[4-(phenylethynyl)benzyl](propyl)amino}benzoic acid, N-methyl-D-glucamine (i.e. 1-deoxy-1-(methylamino)glucitol) salt Step a) Formation of methyl 2-fluoro-5-{[4-(phenylethynyl)benzyl](propyl)-amino}benzoate

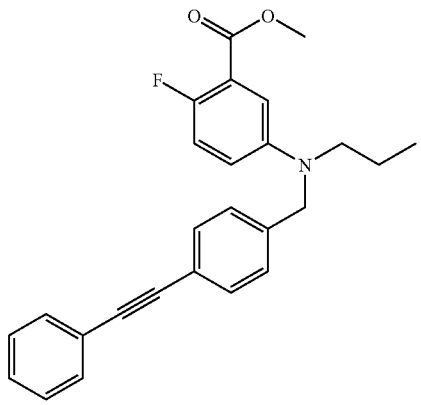

The title compound was prepared following the procedure described in Example 44 step a) using methyl 5-amino-2-fluorobenzoate (500 mg, 2.96 mmol), 4-(phenylethynyl)benzaldehyde (610 mg, 2.96 mmol) and propanal (Aldrich, 540 μL, 7.39 mmol). The title compound was obtained as a sticky colorless oil (628 mg, 53%). HPLC, Rt: 5.4 min (purity: 99.1%). LC/MS, M$^+$(ESI): 402.2. $^1$H NMR (CDCl$_3$) δ: 7.51-7.44 (m, 4H), 7.32 (m, 3H), 7.17 (m, 3H), 6.92 (dd, J=9.8, 9.6 Hz, 1H), 6.74 (m, 1H), 4.50 (s, 2H), 3.88 (s, 3H), 3.33 (t, J=7.3 Hz, 2H), 1.65 (m, 2H), 0.92 (t, J=7.5 Hz, 3H).

Step b) Formation of 2-fluoro-5-{[4-(phenylethynyl)benzyl](propyl)amino}benzoic acid

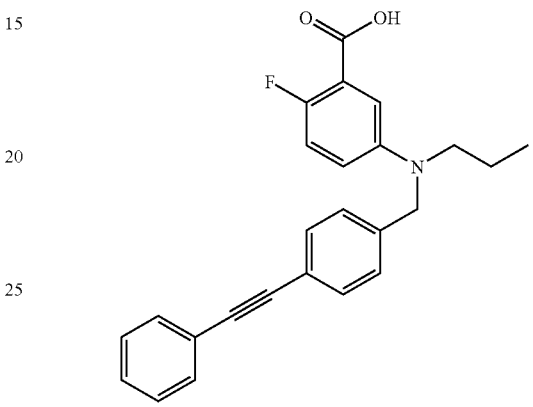

The title compound was prepared following the procedure described in Example 23 step c) using methyl 2-fluoro-5-{[4-(phenylethynyl)benzyl](propyl)amino}benzoate (628 mg, 1.56 mmol). The title compound was obtained as a pale yellow powder (548 mg, 90%). HPLC, Rt: 4.7 min (purity: 98.6%). LC/MS, M$^-$(ESI): 386.2. $^1$H NMR (CDCl$_3$) δ: 7.51-7.45 (m, 4H), 7.33 (m, 3H), 7.26 (dd, J=5.0,.3.3 Hz, 1H), 7.18 (d, J=8.1 Hz, 2H), 6.95 (dd, J=9.8, 9.7 Hz, 1H), 6.79 (m, 1H), 4.52 (s, 2H), 3.35 (t, J=7.5 Hz, 2H), 1.66 (m, 2H), 0.93 (t, J=7.5 Hz, 3H).

Step c) Formation of 2-fluoro-5-{[4-(phenylethynyl)benzyl](propyl)amino}benzoic acid, N-methyl-D-glucamine (i.e. 1-deoxy-1-(methylamino)glucitol) salt

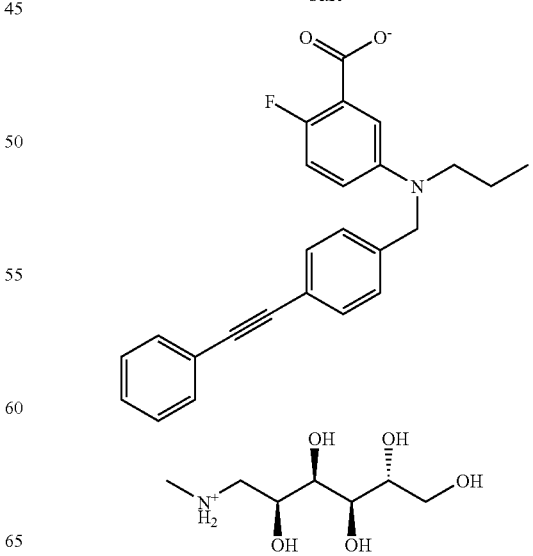

The title compound was prepared following the procedure described in Example 24 using 2-fluoro-5-{[4-(phenylethynyl)benzyl](propyl)amino}benzoic acid (548 mg, 1.41 mmol). The title compound was obtained as a white powder (785 mg, 95%). HPLC, Rt: 4.7 min (purity: 99.2%). LC/MS, M⁻(ESI): 386.2.

Example 46

2-fluoro-5-[{4-[(4-fluorophenyl)ethynyl]benzyl}(hexyl)amino]benzoic acid, N-methyl-D-glucamine (i.e. 1-deoxy-1-(methylamino)glucitol)salt Step a) Formation of methyl 2-fluoro-5-(hexylamino)benzoate

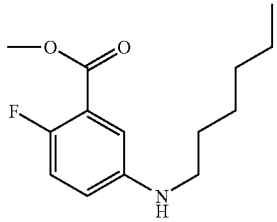

To a solution of methyl 5-amino-2-fluorobenzoate (1.06 g; 6.27 mmol), hexanal (Aldrich, 753 µl; 6.27 mmol) and acetic acid (358.73 µl; 6.27 mmol) in DCE (35 mL) was added sodium triacetoxyborohydride (1.86 g; 8.78 mmol). The reaction mixture was then stirred at r.t under nitrogen atmosphere for 3 h. It was poured in a saturated solution of NaHCO₃ and extracted twice with DCM. The combined organic phases were then washed with brine, dried over MgSO₄, filtrated and concentrated to give 1.654 g of a brown solid. This solid was solubilized in ether and the chlorhydrate was precipitated by addition of Et₂O/HCl. The solid thus obtained (1.06 g) was treated with NaOH (1N), extracted with EtOAc and purified again by flash chromatography using silica gel (c-Hex/EtOAc gradient 95:5 to 90:10) to give 630 mg (40%) of the title compound as a yellow solid. HPLC, Rt: 3.00 min (purity: 98.3%), LC/MS, M⁺(ESI): 255.1, M⁻(ESI): 254.1, ¹H NMR (CDCl₃) δ: 7.06 (dd, J=5.7, 3.1 Hz, 1H), 6.92 (dd, J=10.3, 8.9 Hz, 1H), 6.69 (dt, J=8.9, 3.5 Hz, 1H), 3.89 (s, 3H), 3.60 (brs, 1H), 3.06 (t, J=7.1 Hz, 2H), 1.57 (m, 2H), 1.30 (m, 6H), 0.88 (t, J=6.7 Hz, 3H).

Step b) Formation of methyl 2-fluoro-5-[{4-[(4-fluorophenyl)ethynyl]benzyl)-(hexyl)amino]benzoate

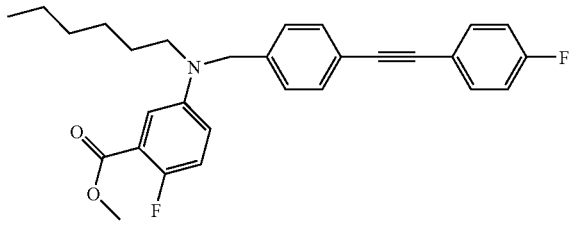

To a solution of methyl 2-fluoro-5-(hexylamino)benzoate (270 mg; 1.07 mmol) and 4-[(4-fluorophenyl)ethynyl]benzaldehyde (358 mg; 1.60 mmol, intermediate which may be obtained according to methods disclosed in EP03103780.7) in anhydrous DCE (15 mL) was added sodium triacetoxyborohydride (678 mg; 3.20 mmol) at rt. The reaction mixture was then heated at 50° C. for 14 h. It was then poured into a solution of saturated NaHCO₃ and extracted twice with DCM. The combined organic phases were then washed with brine, dried over MgSO₄, filtrated and concentrated. The crude brown oil (652 mg) was purified by preparative HPLC using a X-Terra column to give 158 mg (32%) of the title compound as a beige powder. HPLC, Rt: 6.01 min (purity: 96.5%), LC/MS, M⁺(ESI): 462.2, ¹H NMR: (CDCl₃) δ: 7.46 (m, 2H), 7.41 (d, J=8.3 Hz, 2H), 7.37 (m, 1H), 7.13 (d, J=7.9 Hz, 2H), 6.94-7.05 (m, 4H), 4.52 (s, 2H), 3.90 (s, 3H), 3.42 (t, J=7.7 Hz, 2H), 1.56 (m, 2H), 1.26 (m, 6H), 0.85 (t, J=6.6 Hz, 3H).

Step c) Formation of 2-fluoro-5-[{4-[(4-fluorophenyl)ethynyl]benzyl}(hexyl)amino]-benzoic acid

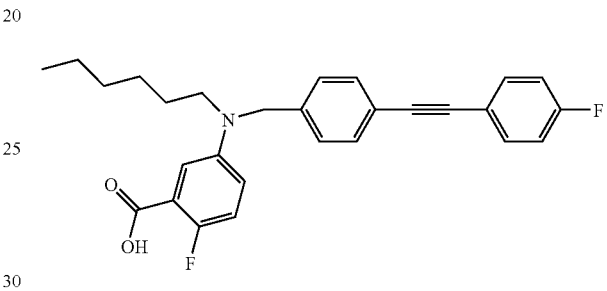

The title compound was prepared following procedure described in Example 36, step c) from methyl 2-fluoro-5-[{4-[(4-fluorophenyl)ethynyl]benzyl}(hexyl)amino]benzoate (300 mg; 0.65 mmol) and was isolated as a beige powder (152 mg, 52%). HPLC, Rt: 5.46 min (purity: 99.0%), LC/MS, M⁺(ESI): 448.1, M⁻(ESI): 446.1, ¹H NMR (CDCl₃): 8.6 (br s, 1H), 7.41-7.49 (m, 4H), 7.34 (m, 1H), 7.16 (d, J=8.3 Hz, 2H), 6.89 (m, 3H), 6.86 (m, 1H), 4.52 (s, 2H), 3.40 (t, J=7.6 Hz, 2H), 1.60 (m, 2H), 1.27 (m, 6H), 0.86 (t, J=6.7 Hz, 3H).

Step d) Formation of 2-fluoro-5-[{4-[(4-fluorophenyl)ethynyl]benzyl}(hexyl)amino-]benzoic acid, N-methyl-D-glucamine (i.e. 1-deoxy-1-(methylamino)glucitol)salt

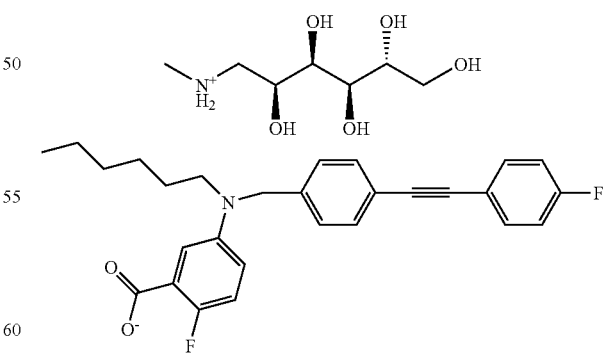

The title compound was prepared following procedure described in Example 24 from 2-fluoro-5-[{4-[(4-fluorophenyl)ethynyl]benzyl}(hexyl)amino]benzoic acid (126 mg; 0.28 mmol) and N-methyl-D-glucamine (55 mg; 0.28 mmol) and isolated as a beige powder (126 mg, quantitative). Rt:

5.83 min (purity: 97.7%), LC/MS: M⁺(ESI): 448.3, M⁻(ESI): 446.0, Rt: 5.45 min (purity: 99.4%). Analysis calculated for $C_{28}H_{27}NO_2F_2$—$C_7H_{17}NO_5 \cdot 3H_2O$: calculated C, 60.33; H, 7.23; N, 4.02%; Found: C, 60.21; H, 6.96; N, 3.84%.

Example 47

2-fluoro-5-(hexyl{4-[(4-propylphenyl)ethynyl] benzyl}amino)benzoic acid, N-methyl-D-glucamine (i.e. 1-deoxy-1-(methylamino)glucitol)salt Step a) Formation of methyl 2-fluoro-5-(hexyl{4-[(4-propylphenyl)ethynyl]-benzyl}amino) benzoate

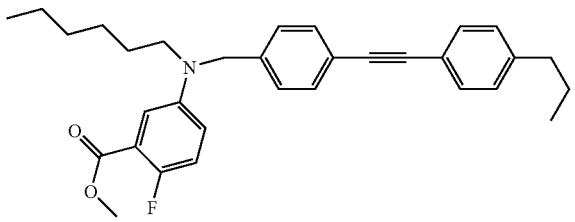

The title compound was prepared following procedure described in Example 46, step b) from methyl 2-fluoro-5-(hexylamino)benzoate (250 mg; 0.99 mmol) and 4-[(4-propylphenyl)ethynyl]benzaldehyde (368 mg; 1.48 mmol, intermediate which may be obtained according to methods disclosed in EP03103780.7). Purification of the crude (407 mg) by preparative HPLC using a X-Terra column yielded to 152 mg (32%) of the title. compound as a beige powder. HPLC, Rt: 6.53 min (purity: 98.6%), LC/MS, M⁺(ESI): 486.5, ¹H NMR (CDCl₃) δ 7.50 (m, 1H), 7.42 (d, J=1.9 Hz, 2H), 7.40 (d, J=2.1 Hz, 2H), 7.13 (d, J=5.5 Hz, 2H), 7.11 (d, J=5.7 Hz, 2H), 6.99 (m, 2H), 4.54 (s, 2H), 3.91 (s, 3H), 3.45 (m, 2H), 2.57 (t, J=7.6 Hz, 2H), 1.55-1.68 (m, 4H), 1.25 (m, 6H), 0.91 (t, J=7.4 Hz, 3H), 0.85 (t, J=6.7 Hz, 3H).

Step b) Formation of 2-fluoro-5-(hexyl{4-[(4-propylphenyl)ethynyl]benzyl}amino)-benzoic acid

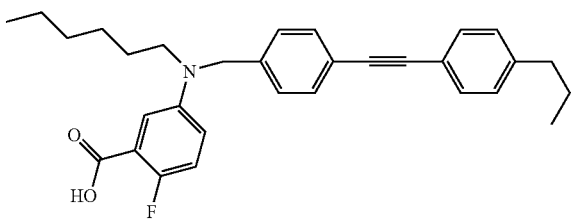

The title compound was prepared following procedure described in Example 36, step c) from methyl 2-fluoro-5-hexyl{4-[(4-propylphenyl)ethynyl]benzyl}amino)benzoate (152 mg; 0.31 mmol) and isolated as a pale yellow powder (120 mg; 97%). HPLC, Rt: 5.93 min (purity: 97.2%), LC/MS, M⁺(ESI): 472.3, M⁻(ESI): 470.2, ¹H NMR (CDCl₃) δ: 7.44 (d, J=8.5 Hz, 2H), 7.41 (d, J=8.1 Hz, 2H), 7.30 (m, 1H), 7.14 (t, J=8.1 Hz, 4H), 6.96 (t, J=9.9 Hz, 1H), 6.80 (m, 1H), 4.51 (s, 2H), 3.39 (t, J=7.6 Hz, 2H), 2.57 (t, J=7.6 Hz, 2H), 1.64 (m, 4H), 1.29 (m, 6H), 0.91 (t, J=7.3 Hz, 3H), 0.87 (t, J=6.4 Hz, 3H).

Step c) Formation of 2-fluoro-5-(hexyl{4-[(4-propylphenyl)ethynyl]benzyl}amino)benzoic acid, N-methyl-D-glucamine (i.e. 1-deoxy-1-(methylamino)glucitol)salt

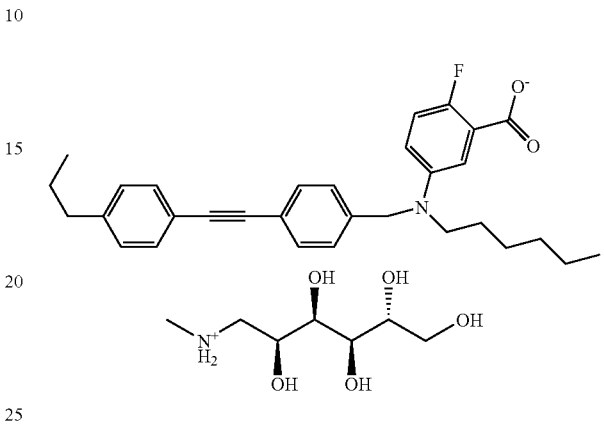

The title compound was prepared following procedure described in Example 24 from 2-fluoro-5-(hexyl{4-[(4-propylphenyl)ethynyl]benzyl}amino)benzoic acid (120 mg; 0.25 mmol) and N-methyl-D-glucamine (49.7 mg; 0.25 mmol) and isolated as a white powder (148 mg, 87%). Rt: 5.83 min (purity: 97.7%), LCFMS: M⁻(ESI): 470.3, Analysis calculated for $C_{31}H_{34}NO_2F$—$C_7H_{17}NO_5 \cdot 1.5\ H_2O$: calculated C, 65.78; H, 7.84; N, 4.04%; Found C, 65.78; H, 7.62; N, 3.99%.

Example 48

5-{{4-[(4-butylphenyl)ethynyl]benzyl}[(2-carboxycyclopropyl)methyl]amino}-2-fluorobenzoic acid, N-methyl-D-glucamine (i.e. 1-deoxy-1-(methylamino)glucitol)salt Step a) Formation of methyl 5-({4-[(4-butylphenyl)ethynyl]benzyl}{[2-(ethoxycarbonyl) cyclopropyl]methyl}amino)-2-fluorobenzoate

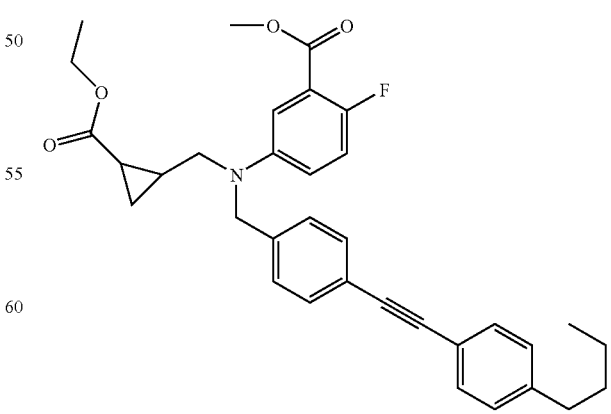

To solution of methyl 5-({4-[(4-butylphenyl)ethynyl] benzyl}amino)-2-fluorobenzoate (500 mg; 1.20 mmol) in anhydrous DCE (30 mL) were added ethyl-2-formyl-1-cyclopropanecarboxylate (Aldrich, 0.40 mL; 3.01 mmol), triacetoxyborohydride (382 mg; 1.81 mmol).The resulting mixture was stirred at 50° C. under $N_2$ atmosphere for 4 hours. The mixture was poured into a saturated solution of $NaHCO_3$ (50 mL) and extracted with DCM (2×50 mL). The combined organic layers were washed with brine (100 mL), dried over magnesium sulfate, filtrated and the solvents were removed under reduced pressure to give 872 mg. Purification of this crude by flash chromatography on silicagel (c-Hex/EtOAc, gradient 95:5 to 90:10) gave 340 mg (65%) of the title compound as a yellow oil. HPLC, Rt: 6.06 min (purity=96.2%). LC/MS, $M^+$(ESI): 542.3. $^1H$ NMR ($CDCl_3$) δ: 7.43 (t, J=8.5 Hz, 4H), 7.32 (m, 1H), 7.22 (d, J=7.9 Hz, 2H), 7.15 (d, J=7.9 Hz, 2H), 6.93 (m, 2H), 4.54 (s, 2H), 4.08 (m, 2H), 3.89 (s, 3H), 3.35 (m, 2H), 2.61 (t, J=7.5 Hz, 2H), 1.32-1.58 (m, 7H), 1.24 (t, J=7.0 Hz, 3H), 0.92 (t, J=7.3 Hz, 3H), 0.88 (m, 1H).

Step b) Formation of: 5-{{4-[(4-butylphenyl)ethynyl]benzyl}[(2-carboxycyclopropyl) methyl]amino}-2-fluorobenzoic acid

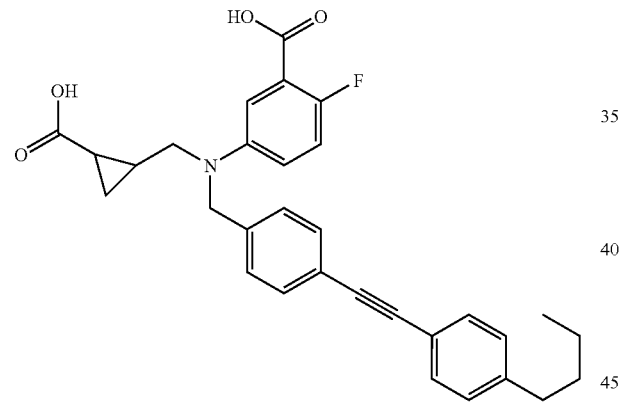

To a solution of methyl 5-({4-[(4-butylphenyl)ethynyl]benzyl}{[2-(ethoxycarbonyl)cyclopropyl]methyl}amino)-2-fluorobenzoate (340 mg; 0.63 mmol) in anhydrous THF (5 mL) were added lithium hydroxide monohydrate (64 mg; 1.54 mmol) and water (7 mL). The reaction mixture was stirred under MW at 100° C. for 2500 s. Then an aqueous solution of HCl (1N) was added, the residue was extracted with EtOAc (2×100 mL). The combined organic layers were washed with brine (60 mL), dried over magnesium sulfate and the solvent was removed under reduced pressure to give 230 mg (73%) of the title compound as a white solid. HPLC, Rt: 4.99 min (purity 99.5%). LC/MS: $M^-$(ESI): 498.2, $^1H$ NMR (MeOD) δ: 7.46 (d, J=8.3 Hz, 2H), 7.41 (d, J=8.3 Hz, 2H), 7.29 (m, 3H), 7.21 (d, J=7.9 Hz, 2H), 4.66 (s, 2H), 3.44 (m, 1H), 2.65 (t, J=7.5 Hz, 2H), 1.65 (m, 3H), 1.35 (m, 3H), 1.15 (m, 1H), 0.95 (m, 4H), 3.59 (m, 1H), 7.05 (m, 2H).

Step c) Formation of 5-{{4-[(4-butylphenyl)ethynyl]benzyl}[(2-carboxycyclopropyl)methyl]amino)-2fluorobenzoate, N-methyl-D-glucamine (i.e. 1-deoxy-1-(methylamino)glucitol)salt

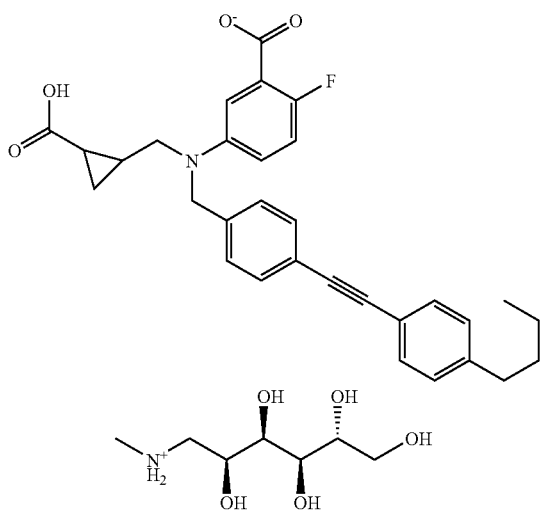

To a solution of 5-{{4-[(4-butylphenyl)ethynyl]benzyl}[(2-carboxy-cyclopropyl)methyl]amino}-2-fluorobenzoic acid (215 mg; 0.43 mmol) in MeOH (10 mL), was added a solution of N-methyl-D-glucamine (84 mg; 0.43 mmol) in water (5 mL). Water (20 mL) was added and the resulting solution was lyophilized to give 240 mg (quantitative) of the title compound as a white powder. HPLC, Rt: 4.99 min purity=99.13%) LC/MS: $M^-$(ESI): 498.3, Analysis calculated for $C_{31}H_{30}NO_4F$—$C_7H_{17}NO_5$-$H_2O$: calculated C, 64.03; H, 6.93; N, 3.93%; Found: C, 64.35; H, 7.17; N, 3.84%.

Example 49

5-[{4-[(4-ethylphenyl)ethynyl]benzyl}(hexyl)amino]-2-fluorobenzoic acid, N-methyl-D-glucamine (i.e. 1-deoxy-1-(methylamino)glucitol)salt Step a) Formation of methyl 5-[{4-[(4-ethylphenyl)ethynyl]benzyl}(hexyl)amino]-2-fluorobenzoate

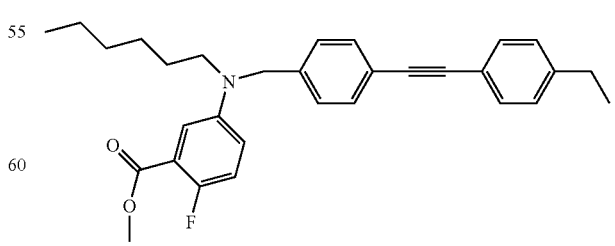

To a solution of 4-[(4-ethylphenyl)ethynyl]benzaldehyde (530 mg; 2.26 mmol, intermediate which may be prepared according to methods disclosed in EP03103780.7) in toluene (35 mL) were added methyl 5-amino-2-fluorobenzoate (382 mg; 2.26 mmol) and AcOH (194 μL) and the reaction mixture was refluxed with azeotropic removal of water until complete consumption of, the aldehyde (determined by $^1$H NMR of aliquots). Toluene was concentrated under reduced pressure and the residue dissolved in DCE (25 mL). Hexanal (Aldrich, 818 μl; 6.79 mmol), acetic acid (194 μL) and sodium triacetoxyborohydride (1,4 g, 6.79 mmol) were added to the solution, which was then heated at 60° C. for 3 hrs. The reaction mixture was poured into a saturated solution of NaHCO$_3$ and extracted twice with DCM. Combined organic layers were washed with brine, dried over magnesium sulfate, filtrated and concentrated to give 1.4 g of a brown solid. Purification by flash chromatography using silica gel (EtOAc/c-Hex, gradient from 97:3 to 95:5) yielded to 330 mg (30%) of the title compound as a white solid. HPLC, Rt: 6.27 min (purity: 61%), LC/MS, M$^+$(ESI): 472.2, $^1$H NMR (CDCl$_3$) δ: 7.43 (t, J=7.7 Hz, 4H), 7.17 (m, 5H), 6.90 (t, J=10.7 Hz, 1H), 6.73 (m, 1H), 4.49 (s, 2H), 3.88 (s, 3H), 3.35 (t, J=7.8 Hz, 2H), 2.63 (qd, J=7.5 Hz, 2H), 1.61 (m, 2H), 1.28 (m, 6H), 1.22 (t, J=7.6 Hz, 3H), 0.85 (t, J=5.1 Hz, 3H).

Step b) Formation of 5-[{4-[(4-ethylphenyl)ethynyl]benzyl}(hexyl)amino]-2-fluorobenzoic acid

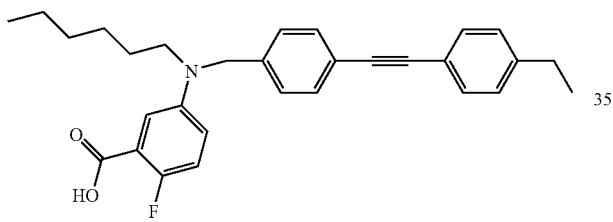

The title compound was prepared following procedure described in Example 36, step c) from methyl 5-[{4-[(4-ethylphenyl)ethynyl]benzyl}(hexyl)amino]-2-fluorobenzoate (320 mg; 0.68 mmol) and isolated as a colorless oil (280 mg, 90%). HPLC,.Rt. 5.67 min (purity: 98.1%), LC/MS, M$^-$(ESI): 456.0, $^1$H NMR (CDCl$_3$) δ: 7.47 (t, J=8.7 Hz, 4H), 7.31 (m, 1H), 7.18 (m, 4H), 6.97 (t, J=9.8 Hz, 1H), 6.60 (m, 1H), 4.52 (s, 2H), 3.39 (t, J=7.5 Hz, 2H), 2.66 (qd, J=7.5 Hz, 2H), 1.65 (m, 2H), 1.33 (m, 6H), 1.24 (t, J=7.5 Hz, 3H), 0.92 (t, J=6.4 Hz, 3H).

Step c) Formation of 5-[{4-[(4-ethylphenyl)ethynyl]benzyl}(hexyl)amino]-2-fluorobenzoic acid, N-methyl-D-glucamine (i.e. 1-deoxy-1-(methylamino)glucitol)salt

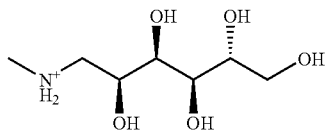

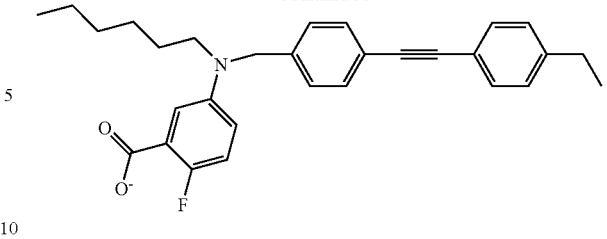

The title compound was prepared following procedure described in Example 24 from 5-[{4-[(4-ethylphenyl)ethynyl]benzyl}(hexyl)amino]-2-fluorobenzoic acid (280 mg; 0.61 mmol) and was isolated as a white powder (173 mg, 43%). HPLC, Rt: 5.55 min (purity: 98.8%), LC/MS, M$^-$(ESI): 456.2, Analysis calculated for C$_{30}$H$_{32}$NO$_2$F—C$_7$H$_{17}$NO$_5$- H$_2$0: calculated C, 66.25; H, 7.66; N, 4.18%; Found: C, 66.31; H, 7.70; N, 4.18%.

Example 50

5-[{4-[(4-tert-butylphenyl)ethynyl]benzyl}(hexyl)amino]-2-fluorobenzoic acid, N-methyl-D-glucamine (i.e. 1-deoxy-1-(methylamino)glucitol)salt Step a) Formation of methyl 5-[{4-[(4-tert-butylphenyl)ethynyl]benzyl}(hexyl)amino]-2-fluorobenzoate

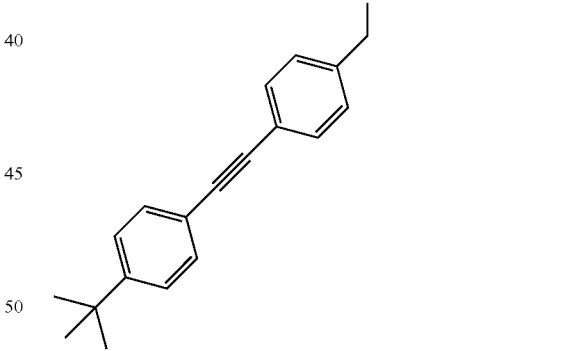

The title compound was prepared following procedure described in Example 49, step a) from 4-[(4-tert-butylphenyl)ethynyl]benzaldehyde (500 mg; 1.91 mmol, intermediate which may be prepared according to methods disclosed in EP0310378.0.7) and methyl 5-amino-2-fluorobenzoate (322 mg; 1.91 mmol) and hexanal (Aldrich, 690 μl; 5.72 mmol). Purification of the crude (700 mg) by preparative HPLC using a X-Terra column afforded 440 mg (46%) of the title compound as a red oil. HPLC, Rt: 6.46 min (purity=89.9%). LC/MS: M$^+$(ESI): 500.3. $^1$H NMR (CDCl$_3$) δ: 7.57 (d, J=1.9 Hz, 2H), 7.54 (d, J=2.3 Hz, 2H), 7.45 (d, J=8.3 Hz, 2H), 7.35-7.20 (m, 3H), 7.04 (t, J=9.6 Hz, 1H), 6.85 (m, 1H), 4.61 (s, 2H), 4.00 (s, 3H), 3.47 (t, J=7.72 Hz, 2H), 1.70 (m, 2H), 1.39 (s, 15H), 0.99 (t, J=6.6Hz, 3H).

Step b) Formation of 5-[{4-[(4-tert-butylphenyl) ethynyl]benzyl}(hexyl)amino]-2-fluorobenzoic acid

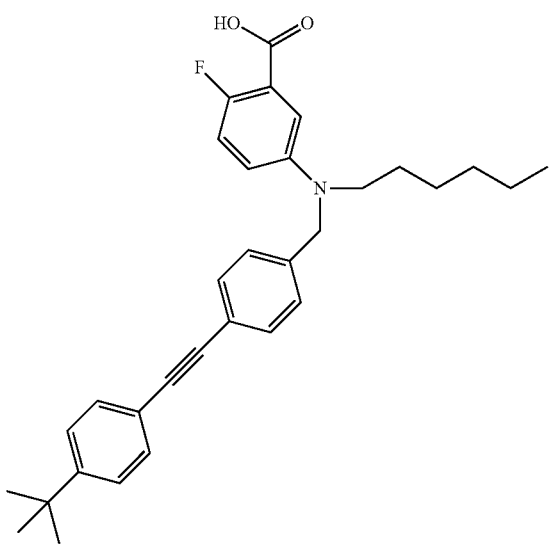

The title compound was prepared following procedure described in Example 36, step c) from methyl 5-[{4-[(4-tert-butylphenyl)ethynyl]benzyl}(hexyl)amino]-2-fluorobenzoate (440 mg; 0.88 mmol) and isolated as a white solid (430 mg, quantitative ). HPLC, Rt: 5.77 min (purity=98.7%). LC/MS: M⁻(ESI): 484.2, $^1$H NMR (CDCl$_3$) δ: 7.38 (m, 5H), 7.29 (m, 3H), 7.12 (d, J=8.6 Hz, 2H), 6.92 (t, J=9.6 Hz, 1H), 4.45 (s, 2H), 3.33 (t, J=7.5 Hz, 2H), 1.55 (m, 2H), 1.25 (m, 15H), 0.80 (t, J=6.9 Hz, 3H).

Step c) Formation of 5-[{4-[(4-tert-butylphenyl)ethynyl]benzyl}(hexyl)amino]-2-fluorobenzoic

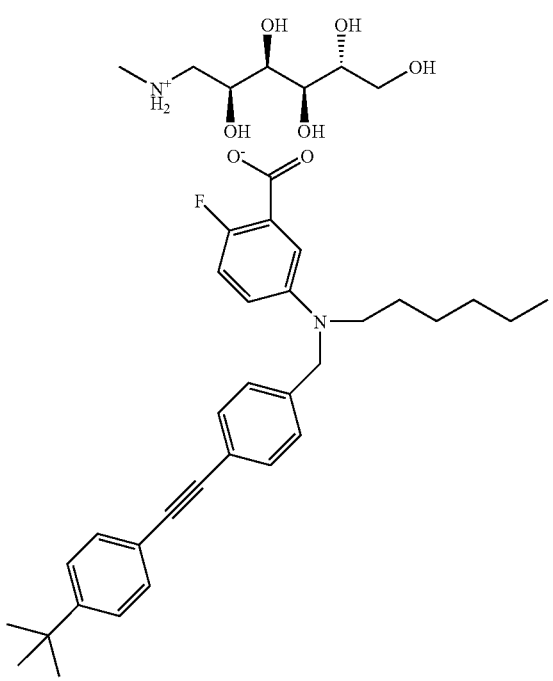

To a solution of 5-[{4-[(4-tert-butylphenyl)ethynyl]benzyl}(hexyl)amino]-2-fluorobenzoic acid (328 mg; 0.68 mmol) in freshly distilled THF (10 mL), was added a solution of N-methyl-D-glucamine (133 mg; 0.68 mmol) in water. Water was added and the resulting solution was lyophilized to give 450 mg (97.9%) of the title compound as a white powder. HPLC, Rt: 5.89 min (purity=98.3%). LC/MS: M⁻(ESI): 484.2, Analysis calculated for $C_{32}H_{36}NO_2F$—$C_7H_{17}NO_5$—$H_2O$: calculated C, 67.03; H, 7.93; N, 4.01%; Found: C, 66.95; H, 7.82; N, 4.04.

Example 51

5-{[{4-[(4-butylphenyl)ethynyl]phenyl}(hexyl) amino]methyl}-2-fluorobenzoic acid, N-methyl-D-glucamine (i.e. 1-deoxy-1-(methylamino)glucitol) salt

Step a) Formation of methyl 2-fluoro-5-formylbenzoate

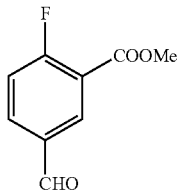

To a solution of 3-bromo-4-fluoro benzaldehyde (Aldrich, 10 g, 0.049 mol) in dry DMF (25 mL) was added dry methanol (40 mL) followed by TEA (9.9 g, 0.0988 mol), dppf (Aldrich, 1.36 g, 0.00246 mol) and palladium acetate (Aldrich, 0.31 g, 0.00138 mol). The reaction mixture was heated to 60° C. under carbon monoxide atmosphere for 20 h. The reaction mixture was cooled and purged with nitrogen to remove dissolved carbon monoxide if any. The solvent was removed under vacuum and the residue was purified by flash chromatography using silicagel (petrol ether/ ethyl acetate, 9:1) to afford 2 g (23%) of the title compound as a solid along with 6 g of unreacted starting material. TLC: Petrol ether/ EtOAc (7:3); R$_f$=0.7; HPLC: purity >98%. $^1$H NMR (DMSO) δ: 10.04 (s, 1H), 8.45 (m, 1H), 8.20 (m, 1H), 7.59 (m, 1H), 3.90 (s, 3H).

Step b) Formation of 4-[(4-butylphenyl)ethynyl]aniline

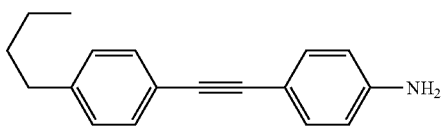

To a stirred solution of 4-iodoaniline (20 g, 91 mmol, Aldrich) and 1-eth-1-ynyl-4-butylbenzene (16.7 g, 105 mmol, Aldrich) in dry acetonitrile (300 mL) under nitrogen was added CuI (0.83 g, 4.3 mmol), TEA (27.7 g, 273 mmol) followed by Pd(PPh$_3$)$_2$Cl$_2$ (3 g, 4.3 mmol). The reaction mixture was stirred at 85° C. for 24 hours and the solvent was removed under reduced pressure. The residue was diluted with Et$_2$O (200 mL) and washed with water, brine and dried (MgSO$_4$). The solvent was removed under reduced pressure and the crude product was purified by chromatography (Pet Ether/EtOAc (4/1) to give 11 g (47%) of the title compound as a solid. TLC-Pet ether/EtOAc (4/1): R$_f$=0.35. HPLC purity >98%.

Step c) Formation of methyl 5-{[4-[(4-butylphenyl)ethynyl](hexyl)anilino]methyl}-2-fluorobenzoate

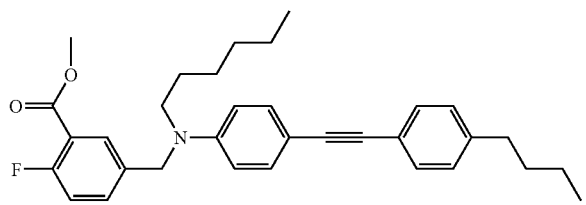

The title compound was prepared following procedure described in Example 49, step a) from 2-fluoro-5-formylbenzoic acid methyl ester (302 mg; 1.66 mmol), 4-(4-butylphenylethynyl)phenylamine (413 mg; 1.66 mmol) and hexanal (Aldrich, 600 μl; 4.97 mmol). Purification of the crude (890 mg) by flash chromatography using silicagel (EtOAc/c-Hex 5:95 then 10:90) afforded 700 mg (85%) of the title compound as a white powder. HPLC, Rt: 6.62 min (purity: 100%), LC/MS, M$^+$(ESI): 500.3, $^1$H NMR(CDCl$_3$) δ: 7.75 (dd, J=6.8, 2.3 Hz, 1H), 7.37 (d, J=8.3 Hz, 2H), 7.32 (d, J=8.9 Hz, 2H), 7.20 (m, 1H), 7.10 (d, J=8.3 Hz, 2H), 7.05 (dd, J=10.5, 8.6 Hz, 1H), 6.58 (d, J=7.9 Hz, 2H), 4.52 (s, 2H), 3.90 (s, 3H), 3.38 (t, J=7.8 Hz, 2H), 2.57 (t, J=7.6 Hz, 2H), 1.57 (m, 4H), 1.30 (m, 8H), 0.87 (m, 6H).

Step d) Formation of 5-{[4-[(4-butylphenyl)ethynyl](hexyl)anilino]methyl}-2-fluorobenzoic acid

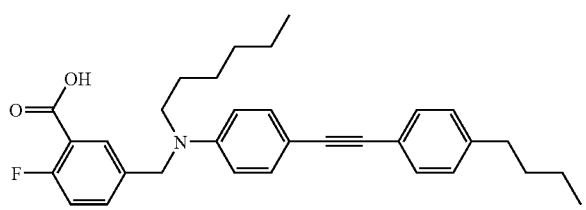

The title compound was prepared following procedure described in Example 36, step c) from methyl 5-{[4-[(4-butylphenyl)ethynyl](hexyl)anilino]methyl}-2-fluorobenzoate (700 mg; 1.40 mmol) and isolated as an orange powder (566 mg, 83%). HPLC, Rt: 6.04 min, (purity: 99.9%). LC/MS, M$^+$(ESI): 486.2, M$^-$(ESI): 484.1. $^1$H NMR (CDCl$_3$) δ: 7.84 (d, J=6.8 Hz, 1H), 7.31 (d, J=8.3 Hz, 2H), 7.32 (d, J=8.7 Hz, 2H), 7.30 (m, 1H), 7.06 (m, 3H), 6.58 (d, J=7.9 Hz, 2H), 4.54 (s, 2H), 3.39 (t, J=7.7 Hz, 2H), 2.57 (t, J=7.7 Hz, 2H), 1.62 (m, 4H), 1.30 (m, 8H), 0.90 (m, 6H).

Step e) Formation of 5-{[4-[(4-butylphenyl)ethynyl](hexyl)anilino]methyl}-2-fluorobenzoic acid, N-methyl-D-glucamine (i.e. 1-deoxy-1-(methylamino)glucitol)salt

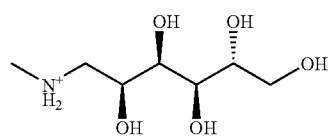

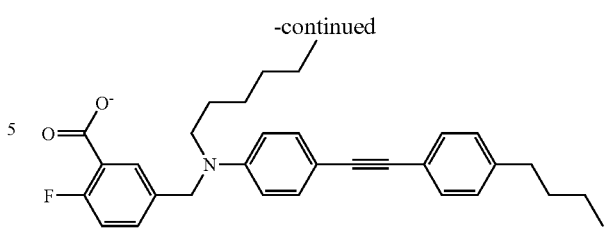

The title compound was prepared following procedure described in Example 1, step g) from 5-{[4-[(4-butylphenyl)ethynyl](hexyl)anilino]methyl}-2-fluorobenzoic acid (566 mg; 1.17 mmol) and N-methyl-D-glucamine (227 mg; 1.17 mmol) and isolated as a white powder (676 mg, 88%). HPLC, Rt: 6.08 min (purity: 100%). LC/MS, M$^+$(ESI): 486.2, M$^-$(ESI): 484.2. Analysis calculated for C$_{32}$H$_{36}$NO$_2$F—C$_7$H$_{17}$NO$_5$—H$_2$O: calculated C, 67.03; H, 7.93; N, 4.01; Found: C, 66.74; H, 7-91; N, 3.98%.

Example 52

4-({(3,3-dimethylbutanoyl)-4-[(4-hexylphenyl)ethynyl]anilino}methyl)-2-hydroxybenzoic acid, N-methyl-D-glucamine (i.e. 1-deoxy-1 (methylamino) glucitol) salt Step a) Formation of 2,2,7-trimethyl-4H-1,3-benzodioxin-4-one

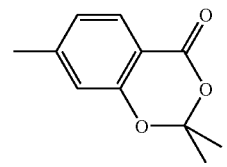

To a stirred suspension of 4-methylsalicylic acid (50 g, Aldrich) in TFA (320 mL) under nitrogen was added TFAA (105 mL) followed by dry acetone (60 mL). The reaction mixture was heated to 65° C. for 5 hours. At this time was added another portion of acetone (50 mL) and heating was continued for 15 hours. The solvent was removed under reduced pressure and the residue was taken up with Et$_2$O (250 mL). The organic layer was washed with a 10% aqueous solution of NaHCO$_3$ (2×100 mL), brine and dried over MgSO$_4$. The solvent was removed under reduced pressure. The residue was purified by chromatography (Pet Ether/EtOAc 98/2) to give 17 g (27%) of the titled compound as a liquid. TLC-Pet. Ether/EtOAc (9/1): R$_f$=0.8.

Step b) Formation of 7-(dibromomethyl)-2,2-dimethyl-4H-1,3-benzodioxin-4-one

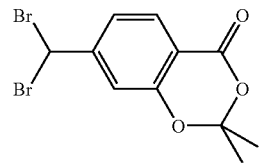

To a solution of 2,2,7-trimethyl-4H-1,3-benzodioxin-4-one (17.0 g, 88 mmol) in CCl₄ (20 mL) under nitrogen was added NBS (34 g, 195 mmol) followed by benzoyl peroxide (1.7 g). The reaction mixture was refluxed for 12 hours and cooled at rt. The succininude was filtered off and the solvent was removed under reduced pressure. The residue was purified by flash chromatography (Pet Ether/EtOAc 9/1) to give 10 g (32%) of the title compound as a solid. TLC-Pet Ether/EtOAc (9/1): $R_f$=0.7.

Step c) Formation of 2,2-dimethyl-4-oxo-4H-1,3-benzodioxine-7-carbaldehyde

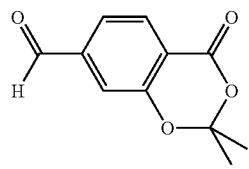

To a solution of 7-(dibromomethyl)-2,2-dimethyl-4H-1,3-benzodioxin-4-one (6.0 g, 17 mmol) in acetone (20 mL) and water (40 mL) under nitrogen was added AgNO₃ (6.0 g, 35 mmol). The reaction mixture was stirred at rt for 14 hours, then filtered through a pad of Celite. The solvents were removed under reduced pressure. The residue was purified by chromatography (pet ether/EtOAc 9/1) to give 2.0 g (57%) of the titled compound as a solid. TLC-Pet Ether/EtOAc (7/3): $R_f$=0.7.

Step d) Formation of 4-[(4-hexylphenyl)ethynyl]aniline

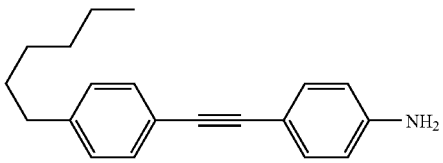

To a stirred solution of 4-iodoaniline (10.0 g, 45.6 mmol, Aldrich) and 1-eth-1-ynyl-4-hexylbenzene (10.0 g, 53.0 mol, Maybridge) in anhydrous acetonitrile (200 mL) under nitrogen was added CuI (0.43 g, 2.2 mmol), TEA (14.0 g, 138 mmol) followed by Pd(PPh₃)₂Cl₂ (1.6 g, 2.2 mmol). The reaction mixture was stirred at 85° C. for 22 hours. The solvent was removed under reduced pressure. The residue was diluted with Et₂O (200 mL) 20 and washed with water and brine. The organic layer was dried (MgSO₄) and the solvent was removed under reduced pressure. The crude product was purified by chromatography Wet ether/EtOAc 4/1) to give 11.0 g (87%) of the title compound as a pale yellow solid. TLC-Pet ether/EtOAc (4/1): $R_f$=0.4. HPLC purity >98%.

Step e) Formation of 7-({4-[(4-hexylphenyl)ethynyl]anilino}methyl)-2,2-dimethyl-4H-1,3-benzodioxin-4-one

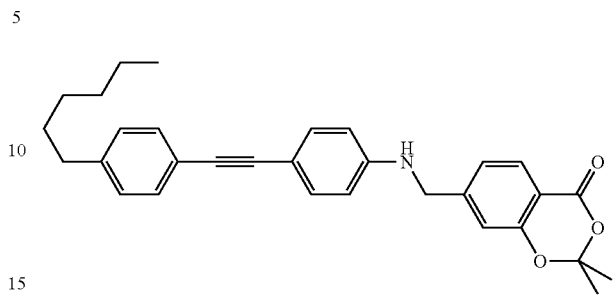

A solution of 2,2-dimethyl-4-oxo-4H-1,3-benzodioxine-7-carbaldehyde (700 mg; 3.38 mmol) and 4-[(4-hexylphenyl)ethynyl]aniline (940 mg; 3.38 mmol) in toluerene (40 mL) was refluxed for 48 hours with azeotropic removal of water. The solvent was removed under reduced pressure and the residue was taken up in a mixture of MeOH (20 mL) and THF (20 mL). NaBH₄ (130 mg, 3.38 mmol) was added and the resulting mixture was stirred at rt for 8 hours. The solvents were removed under reduced pressure. The residue was taken up in EtOAc and washed with a saturated aqueous solution of NaACO₃ and brine. The organic layer was dried (Na₂SO₄) and the solvent was removed under reduced pressure to give a brown oil. Purification by flash chromatography on silica (EtOAc:c-Hex 1:9 then 1:4) gave 466 mg (30%) of the title compound as a pale yellow oil. HPLC, Rt: 6.1 min (purity: 95.6%). LC/MS, M⁺(ESI): 468.0, M⁻(ESI): 466.1.

Step f) Formation of N-[(2,2-dimethyl-4-oxo-4H-1,3-benzodioxin-7-yl)methyl]-N-{4-[(4-hexylphenyl)ethynyl]phenyl}-3,3-dimethylbutanamide

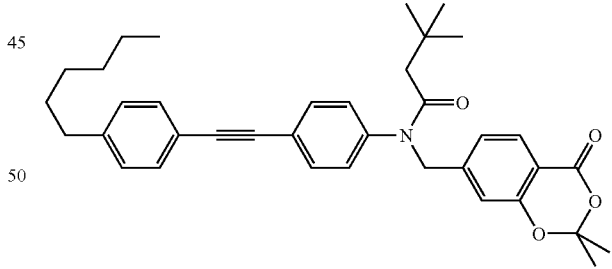

A solution of 7-({4-[(4-hexylphenyl)ethynyl]anilino}methyl)-2,2-dimethyl-4H-1,3-benzodioxin-4-one (227 mg; 0.49 mmol) was prepared in anhydrous THF (15.00 mL) and cooled at 0° C. DIEA (0.20 mL; 0.58 mmol) and tert-butylacetyl chloride (0.15 mL; 0.53. mmol) were added. The reaction mixture was then stirred at rt overnight. The solvent was removed under reduced pressure and the residue was taken up in Et₂O. The organic layer was washed with an aqueous solution of HCl (1N), a saturated aqueous solution of NaHCO₃ and brine. The organic layer was dried (MgSO₄) and the solvent was removed under reduced pressure. Purification by flash chromatography on silica (EtOAc:c-Hex 1:4)

gave 215 mg (78%) of the title compound as a pale yellow oil. HPLC, Rt: 6.5 min (purity: 100%). LC/MS, M+(ESI): 566.1.

Step g) Formation of 4-({(3,3-dimethylbutanoyl)-4-[(4-hexylphenyl)ethynyl]anilino}methyl)-2-hydroxybenzoic acid

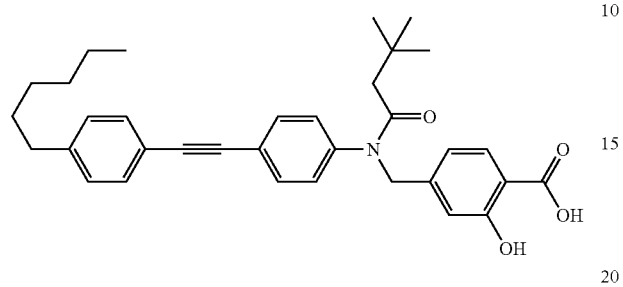

The title compound was prepared following procedure described in Example 19, step c) from N-[(2,2-dimethyl-4-oxo-4H-1,3-benzodioxin-7-yl)methyl]-N-{4-[(4-hexylphenyl)ethynyl]phenyl}-3,3-dimethylbutanamide (215 mg; 0.38 mmol). The title compound was isolated as a beige solid (170 mg, 85%). HPLC, Rt: 6.3 min (purity: 98.9%). LC/MS, M+(ESI): 526.4, M−(ESI): 524.3.

Step h) Formation of 4-({(3,3-dimethylbutanoyl)-4-[(4-hexylphenyl)ethynyl]anilino}methyl)-2-hydroxybenzoic acid, N-methyl-D-glucamine (i.e. 1-deoxy-1-(methylamino)glucitol) salt

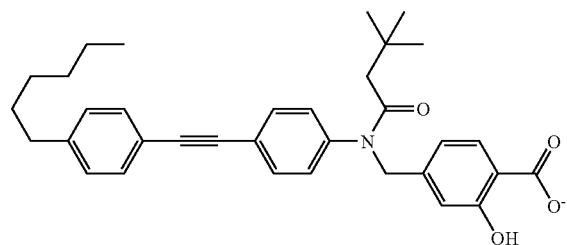

The title compound was prepared following procedure described in Example 1, step g) from 4-({(3,3-dimethylbutanoyl)-4-[(4-hexylphenyl)ethynyl]anilino}methyl)-2-hydroxybenzoic acid (170 mg; 0.32 mmol) and N-methyl-D-glucamine (63 mg; 0.32 mmol). The title compound was isolated as a beige powder (199 mg, 85%). HPLC, Rt: 6.3 min (purity: 98.8%). LC/MS, M+(ESI): 526.3, M−(ESI): 524.1.

Example 53

5-[{4-[(4-butylphenyl)ethynyl]benzyl}(isobutyl)amino]-2-fluorobenzoic acid, N-methyl-D-glucamine (i.e. 1-deoxy-1-(methylamino)glucitol)salt Step a) Formation of methyl 5-[{4-[(4-butylphenyl)ethynyl]benzyl)(isobutyl)amino]-2-fluorobenzoate

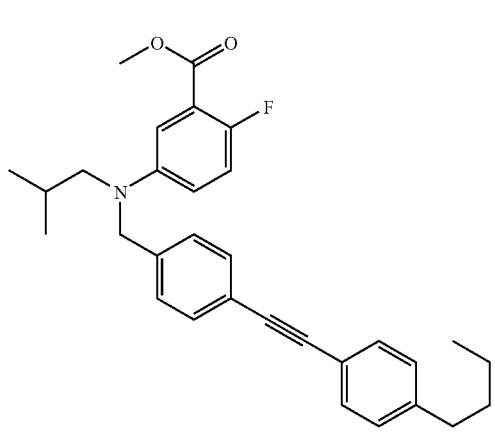

To a solution of methyl 5-({4-[(4-butylphenyl)ethynyl]benzyl}amino)-2-fluorobenzoate (300 mg; 0.72 mmol) in DCE (15 mL) were added isobutyraldehyde (Aldrich, 0.16 ml, 1.81 mmol) and triacetoxyborohydride (229 mg; 1.08 mmol). The reaction mixture was stirred at 60° C. under $N_2$ atmosphere for 4 hours. The mixture was poured into $NaHCO_3$ (100 mL), then the product was extracted with DCM (2×100 mL), washed with brine (100 mL), dried over magnesium sulfate and filtrated. The solvents were removed under reduced pressure. Purification of this crude by flash chromatography on silicagel (c-Hex/EtOAc, gradient 8:2 to 5:5 to 3:7) then by HPLC preparative with a X-Terra column gave 62 mg (19%) of the title compound as a brown oil. HPLC: 6.19 min (purity=96.4%), LC/MS: M+(ESI): 472.4. $^1$H NMR (CDCl$_3$) δ: 7.44 (d, J=5.6 Hz, 2H), 7.41 (d, J=5.3 Hz, 2H), 7.25 (m, 1H), 7.14 (t, J=7.5 Hz, 4H), 6.94 (t, J=9.6 Hz, 1H), 6.80 (m, 1H), 4.57 (s, 2H), 3.90 (s, 3H), 3.45 (m, 1H), 3.25 (d, J=7.2 Hz, 2H), 2.61 (t, J=7.7 Hz, 2H), 2.05 (m, 1H), 1.60 (m, 2H), (s, J=7.4 Hz, 2H), 0.95 (m, 9H).

Step b) Formation of the methyl5-[{4-[(4-butylphenyl)ethynyl]benzyl}(isobutyl)amino]-2-fluorobenzoique acid

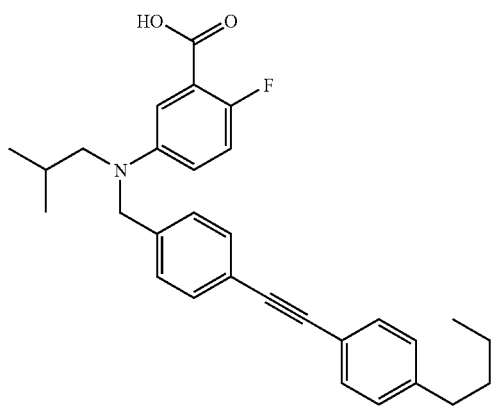

To a solution of methyl 5-[{4-[(4-butylphenyl)ethynyl]benzyl}(isobutyl)amino]-2-fluorobenzoate (62 mg; 0.13 mmol) in THF (3 mL) were added lithium hydroxide monohydrate (49 mg; 1.17 mmol) and water (2 mL). The reaction mixture was stirred at 100° C. for 2500 s under MW. The mixture was poured into HCl 1N (10 mL) and extracted with EtOAc (2×25 mL). Combined organic layers were washed with brine (50 mL), dried over magnesium sulfate and filtrated. The solvent was removed under reduced pressure to give 40 mg of the title compound as an orange solid. HPLC: Rt=5.8 min (purity=93.49%), LC/MS: M⁻(ESI): 456.2, ¹H NMR (MeOD) δ: 7.43 (t J=8.5 Hz, 4H), 7.35 (m, 1H), 7.14 (d, J=7.9 Hz, 4H), 6.96 (t, J=9.9 Hz, 1H), 7.85 (m, 1H), 4.58 (s, 2H), 3.24 (d, J=7.2 Hz, 2H), 2.61 (t, J=7.7 Hz, 2H), 2.1 (m, 1H), 1.59 (q, J=7.6 Hz, 2H), 1.31 (m, 2H), 0.95 (m, 10H).

Example 54

5-{[{4-[(4-butylphenyl)ethynyl]benzyl}(hexyl)amino]carbonyl}-2-fluorobenzoic acid, N-methyl-D-glucamine (i.e. 1-deoxy-1-(methylamino)glucitol) salt Step a) Formation of 4-fluoro-3-(methoxycarbonyl)benzoic acid

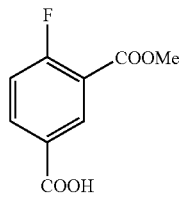

To a solution of methyl-2-fluoro-5-formylbenzoate (2 g, 0.0109 mol) in dry DMF (75 mL) was added oxone (Aldrich, 6.75 g, 0.0109 mol) and the reaction mixture was stirred for 3 h at room temperature. The reaction mixture was then quenched with 1.5M.HCl (50 mL) and the product was extracted with ethyl acetate (2×50 mL). The combined organic layers were washed with water, brine, dried over magnesium sulfate filtrated and concentrated to give 1.7 g (78%) of the titled compound as a solid. TLC: Chloroform/methanol (9/1), R$_f$=0.2, HPLC purity >99%. ¹H NMR (DMSO) δ: 8.44 (m, 1H), 8.19 (m, 1H), 7.48 (m 1H), 3.88 (s, 1H).

Step b) Formation of methyl 5-{[{4-[(4-butylphenyl)ethynyl]benzyl}(hexyl)amino]carbonyl}-2-fluorobenzoate

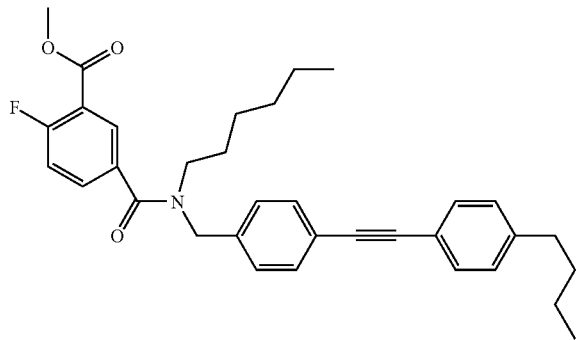

The title compound was prepared following procedure described in Example 19, step c) from 4-fluoro-isophtalic acid-3-methylester (199 mg; 1.01 mmol), EDC.HCl (212 mg; 1.11 mmol) and N-{4-[(4-butylphenyl)ethynyl]benzyl}-1-hexanamine (350 mg, 1.01 mmol). Purification of the crude (503 mg) by flash chromatography using silicagel (EtOAc/c-Hex, 20:80) afforded 394 mg (74%) of the title compound as a colorless oil. HPLC, Rt: 6.19 min (purity: 99.8%), LC/MS, M⁺(ESI): 528.4. ¹HN (CDCl₃) δ: 7.99 (d, J=5.1 Hz, 1H), 7.98 (m, 1H), 7.49 (d, J=8.1 Hz, 2H), 7.42 (d, J=8.1 Hz, 2H), 7.31 (m, 1H), 7.15 (d, J=8.1 Hz, 4H), 4.73 (s, 1H), 4.48 (s, 1H), 3.91 (s, 3H), 3.44 (s, 1H), 3.11 (s, 1H), 2.60 (t, J=7.6 Hz, 2H), 1.35 (m, 4H), 1.08-1.37 (m, 8H), 0.90 (t, J=7.3 Hz, 3H), 0.83 (m, 3H).

Step c) Formation of 5-{[{4-[(4-butylphenyl)ethynyl]benzyl}(hexyl)amino]carbonyl}-2-fluorobenzoic acid

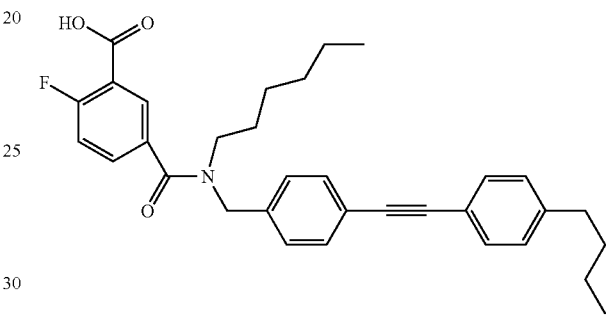

The title compound was prepared following procedure described in Example 36, step c) from methyl 5-{[{4-[(4-butylphenyl)ethynyl]benzyl}(hexyl)amino]carbonyl}-2-fluorobenzoate (394 mg; 0.75 mmol) and was isolated as a colorless oil (364 mg, 95%). HPLC, Rt: 5.66 min (purity: 97.7%), LC/MS, M⁻(ESI): 512.2, M⁺(ESI):514.4, ¹H NMR (CDCl₃) δ: 8.06 (dd, J=6.8, 2.3 Hz, 1H), 7.65 (m, 1H), 7.50 (d, J=7.9 Hz, 2H), 7.42 (d, J=8.1 Hz, 2H), 7.34 (m, 1H), 7.14 (d, J=8.1 Hz, 4H), 4.75 (s, 5H), 4.52 (s, 5H), 3.48 (s, 5H), 3.13 (s, 5H), 2.59 (t, J=7.8 Hz, 2H), 1.61 (m, 4H), 1.19-1.41 (m, 10H), 0.91 (t, J=7.3 Hz, 3H), 0.82 (m, 3H).

Step d) Formation of 5-{[{4-[(4-butylphenyl)ethynyl]benzyl}(hexyl)amino]carbonyl}-2-fluorobenzoic acid, N-methyl-D-glucamine (i.e. 1-deoxy-1-(methylamino)glucitol)salt

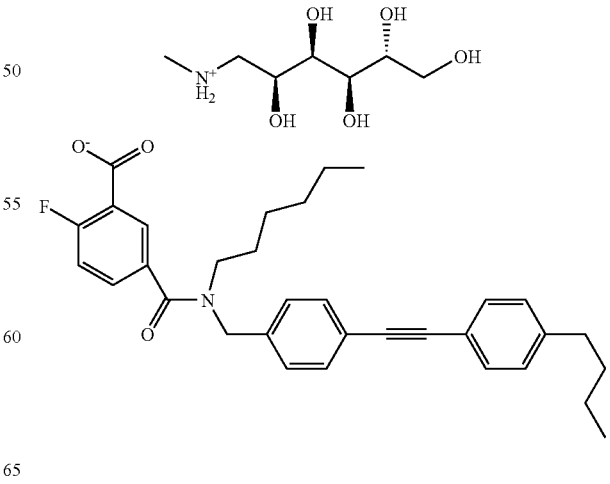

The title compound was prepared following procedure described in Example 24 from 5-{[{4-[(4-butylphenyl)ethynyl]benzyl})(hexyl)amino]carbonyl}-2-fluorobenzoic acid (360 mg; 0.70 mmol) and N-methyl-D-glucamine (136 mg; 0.70 mmol). It was isolated as a white powder (470 mg, 94.6%). HPLC, Rt: 5.63 min (purity: 100%). LC/MS, M⁺ESI): 514.3, M⁻(ESI): 512.3. Analysis calculated for $C_{33}H_{36}NO_3F$—$C_7H_{17}NO_5$·1.6H$_2$O calculated C, 65.13; H, 7.68; N, 3.80%; Found: C, 65.08; H, 7.72; N, 3.76.

Example 55

5-[{4-[(4-butylphenyl)ethynyl]benzoyl}(hexyl)amino]-2-fluorobenzoic acid, N-methyl-D-glucamine (i.e. 1-deoxy-1-(methylamino)glucitol)salt Step a) Formation of 4-[(4-butylphenyl)ethynyl]benzoyl chloride

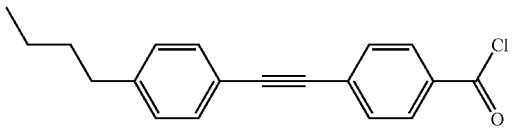

To a solution of 4-(4-butylphenylethynyl)benzoic acid (300 mg; 1.08 mmol) in anhydrous toluene (10 mL) was added thionyl chloride (0.39 ml; 5.39 mmol). The reaction mixture was stirred overnight at 60° C. under N$_2$ atmosphere. The solvent and thionyl chloride were removed under reduced pressure to give 296 mg of the title compound as a green solid. $^1$H NMR (CDCl$_3$) δ: 8.09 (d, J=8.7 Hz, 2H), 7.62 (d, J=8.7 Hz, 2H), 7.47 (d, J=8.3 Hz, 2H), 7.19 (d, J=8.3 Hz, 2H), 2.64 (t, J=8.7 Hz, 2H), 1.61 (q, J=7.6 Hz, 2H), 1.37 (q, J=7.8 Hz, 2H), 0.93 (t, J=7.3 Hz, 3H).

Step b) Formation of methyl 5-[{4-[(4-butylphenyl)ethynyl]benzoyl}(hexyl)amino]-2-fluorobenzoate

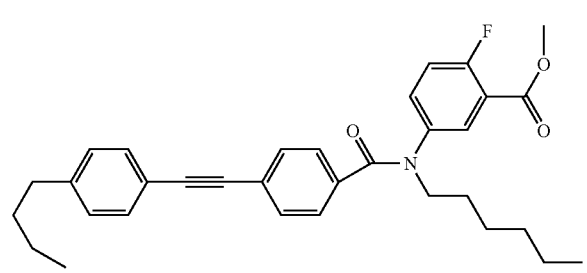

To a solution of methyl 2-fluoro-5-(hexylamino)benzoate (185 mg; 0.73 mmol) in THF (15 mL) were added 4-[(4-butylphenyl)ethynyl]benzoyl chloride (260 mg; 0.88 mmol), DIEA (0.15 mL; 0.88 mmol) and DMAP (20 mg). The mixture was stirred at 60° C. under N$_2$ atmosphere for 1 hour. It was then diluted with DCM (100 mL), washed with HCl 0.1N (50 mL) and a saturated solution of NaHCO$_3$ (100 mL). The organic layer was dried over magnesium sulfate, filtrated and the solvent was removed under reduced pressure to give 480 mg of a brown solid. Purification by flash chromatography on silicagel (c-Hex/EtOAc, 90:10) gave 170 mg (45.3%) of the title compound as a white solid. HPLC, Rt: 6.14 min (purity=99.5%). LC/MS: M⁺(ESI): 514.3.

Step c) Formation of 5-[{4-[(4-butylphenyl)ethynyl]benzoyl}(hexyl)amino]-2-fluorobenzoic acid

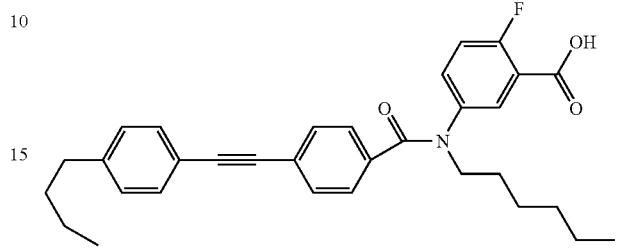

To a solution of methyl 5-[{4-[(4-butylphenyl)ethynyl]benzoyl}(hexyl)amino]-2-fluorobenzoate (170 mg; 0.33 mmol) in THF (7 mL) were added lithium hydroxide monohydrate (139 mg; 3.31 mmol) and water (3 mL). The reaction mixture was stirred under MW at 100° C. for 2500 s. Then an aqueous solution of HCl (1N) was added and the mixture extracted with EtOAc (2×50 mL). The combined organic layers were washed with brine, dried over magnesium sulfate and the solvent was removed under reduced pressure to give 147 mg (88.9%) of the title compound as a colorless solid. HPLC, Rt: 5.54 min (purity=98.4%), LC/MS: M⁻(ESI): 498.3. $^1$H NMR (MeOD) δ: 7.61 (m, 1H), 7.29 (d, J=7.9 Hz, 5H), 7.22 (d, J=7.9 Hz, 2H), 7.08 (d, J=7.9 Hz, 2H), 7.03 (s, 1H), 3.8 (m, 2H), 2.52 (t, J=7.5 Hz, 2H), 1.49 (q, J=7.4 Hz, 4H), 1.25 (m, 8H), 0.82 (m, 6H).

Step d) Formation of 5-[{4-[(4-butylphenyl)ethynyl]benzoyl}(hexyl)amino]-2-fluorobenzoic acid, N-methyl-D-glucamine (i.e. 1-deoxy-1-(methylamino)glucitol)salt

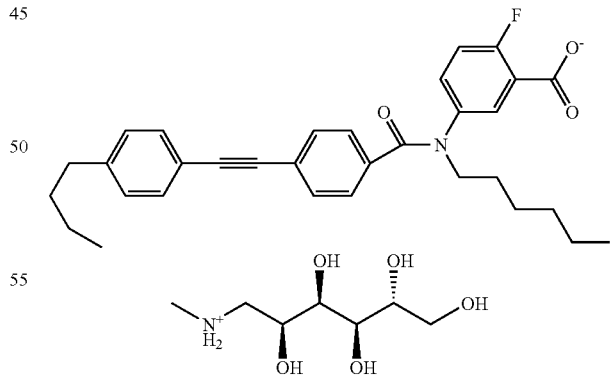

To a solution of 5-[{4-[(4-butylphenyl)ethynyl]benzoyl}(hexyl)amino]-2-fluorobenzoic acid (147 mg; 0.29 mmol) in MeOH (5 mL) was added a solution of N-methyl-D-glucamine (57 mg; 0.29 mmol) in water. The resulting solution was lyophilized to give 137 mg (93.2%) of the title compound as a white powder. HPLC, Rt: 5.53 min (purity=99.1%), LC/MS: M⁻(ESI): 498.2, Analysis calculated for $C_{32}H_{34}NO_3F$—$C_7H_{17}NO_5$-1.5 $H_2O$: calculated C, 64.89; H, 7.54; N, 3.88%; Found: C, 64.89; H, 7.70; N, 4.17%.

Example 56

5-[({4-[(4-butylphenyl)ethynyl]phenyl}sulfonyl)(hexyl)amino]-2-fluorobenzoic acid, N-methyl-1-D-glucamine (i.e. 1-deoxy-1-(methylamino)glucitol) salt Step a) Formation of methyl 5-[[(4-bromophenyl)sulfonyl](hexyl)amino]-2-fluorobenzoate

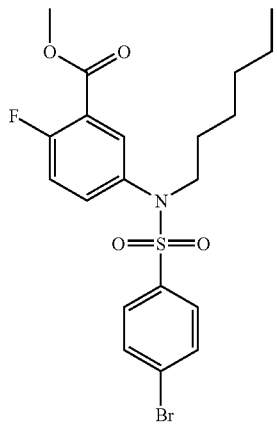

To a solution of methyl 2-fluoro-5-(hexylamino)benzoate (800 mg; 3.16 mmol) in anhydrous DCM (50 mL) were added 4-bromobenzenesulfonylchloride. (807 mg; 3.16 mmol) and TEA (0.53 mL). The reaction mixture was stirred overnight at 25° C. under $N_2$ atmosphere. Then the mixture was poured into a saturated solution of $NaHCO_3$ and extracted with DCM (2×200mL). The combined organic layers were washed with a saturated solution of $NH_4Cl$ followed by brine, dried over magnesium sulfate, filtrated and the solvent was removed under reduced pressure to give a brown cream. Purification by flash chromatography using silicagel (c-Hex/EtOAc, 95:5 then 90:10):gave 1.0 g (67.4%) of the title compound as a colorless cream. HPLC, Rt: 5.23 min (purity=97.13%). LC/MS,. $M^+$(ESI): 272.1. $^1H$ NMR ($CDCl_3$) δ: 7.63 (m, 2H), 7.52 (m, 1H), 7.43 (d, J=9.2 Hz, 2H), 7.25 (m, 2H), 7.13 (t, J=9.2 Hz, 1H), 3.91 (s, 3H), 3.49 (t, J=6.97 Hz, 2H), 1.25 (m, 8H), 0.85 (t, J=6.8 Hz, 3H).

Step b) Formation of methyl 5-[({4-[(4-butylphenyl)ethynyl]phenyl}sulfonyl)(hexyl)amino]-2-fluorobenzoate

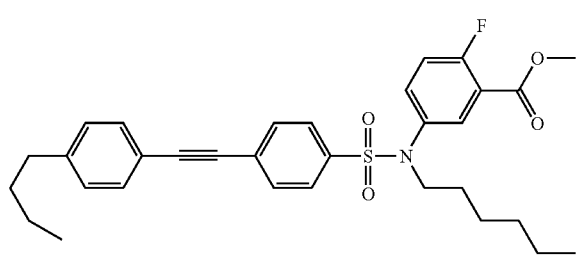

To a solution of 5-[({4-bromophenyl)sulfonyl](hexyl)amino]-2-fluorobenzoate (400 mg; 0.85 mmol) in DMF (15 mL) under nitrogen were added (p-butylphenyl)acetylene (0.16 mL; 0.93 mmol), bis(triphenylphosphine)palladium chloride (29.7 mg; 0.04 mmol), triphenylphosphine (44.4 mg; 0.17 mmol), copper iodine (8.1 mg; 0.04 mmol) and TEA (0.35 mL; 2.54 mmol). The reaction mixture was stirred under MW at 120° C. for 1500 s. The mixture was diluted with $Et_2O$ (75 mL) and the precipitate obtained filtrated off. Filtrate was washed with HCl 1N and with brine. The organic layer was dried over magnesium sulfate and the solvent was removed under reduced pressure. Purification by flash chromatography on silicagel (c-Hex/EtOAc, 95:5 then 90:10) gave 207 mg (44.5%) of the title compound as a yellow cream. HPLC, Rt: 6.17 min (purity=98.5%). LC/MS: $M^+$(ESI): 500.3, $^1H$ NMR ($CDCl_3$) δ: 7.55 (m, 6H), 7.32 (m, 1H), 7.10 (m, 4H), 3.91 (s, 3H), 3.52 (t, J=6.9 Hz, 2H), 2.63 (t, J=7.9 Hz, 2H), 1.30 (m, 12H), 0.95 (m, 3H), 0.85 (t, 3H.

Step c) Formation of 5-[({4-[(4-butylphenyl)ethynyl]phenyl}sulfonyl)(hexyl)amino]-2-fluorobenzoic acid

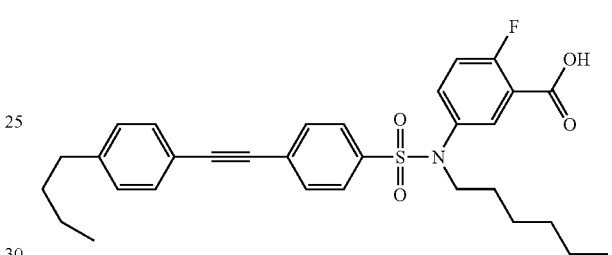

To a solution of methyl 5-[({4-[(4-butylphenyl)ethynyl]phenyl}sulfonyl)(hexyl)amino]-2-fluorobenzoate (207 mg; 0.38 mmol) in anhydrous THF (7 mL) were added lithium hydroxide monohydrate (158 mg; 3.77 mmol) and water (3 mL). The reaction mixture was stirred under MW at 100° C. for 2500 s. Then an aqueous solution of HCl (1N) was added and the mixture extracted with EtOAc (2×50 mL). The combined organic layers were washed with brine, dried over magnesium sulfate and the solvent was removed under reduced pressure to give 185 mg (91.7%) of the title compound as a brown cream. HPLC, Rt: 5.71 min (purity=98.5%). LC/MS, $M^-$(ESI): 534.3. $^1H$ NMR (MeOD) δ: 7.66 (d, J=8.66 Hz, 2H), 7.58 (d, J=8.66 Hz, 3H), 7.46 (d, J=7.91 Hz, 2H), 7.31. (m, 1H), 7.23 (m, 3H), 3.61 (m, 3H), 2.66 (t, J=7.53 Hz, 2H), 1.63 (qt, J=7.34 Hz, 2H), 1.35 (m, 12H), 0.96 (t, J=7.91 Hz, 3H), 0.87 (t, J=6.97 Hz, 3H).

Step d) Formation of 5-[({4-[(4-butylphenyl)ethynyl]phenyl}sulfonyl)(hexyl)amino]-2-fluorobenzoate, N-methyl-D-glucamine (i.e. 1-deoxy-1-(methylamino)glucitol)salt

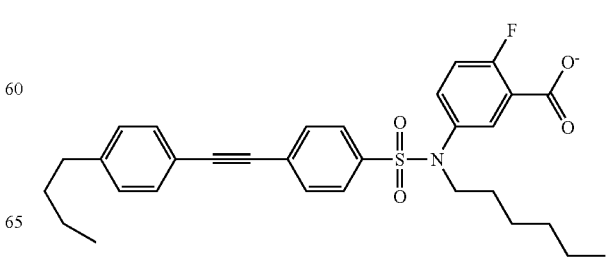

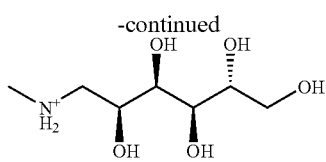

To a solution of 5-[({4-[(4-butylphenyl)ethynyl]phenyl}sulfonyl)(hexyl)amino]-2-fluorobenzoic acid (180 mg; 0.34 mmol) in MeOH (7 mL), was added a solution of N-methyl-D-glucamine (66 mg; 0.34 mmol) in water (20 mL). The resulting solution was lyophilized to give 195 mg (79.4%) of the title compound as a white powder. HPLC, Rt: 5.72 min (purity=98.50%). LC/MS, M(ESI): 536.2. Analysis calculated for $C_{31}H_{34}NO_4SF$—$C_7H_{17}NO_5$-1.6 $H_2O$: calculated C, 60.08; H, 7.19; N, 3.69%; Found: C, 59.93; H7.11; N3.82%.

Example 57

5-{[{4-[(4-butylphenyl)ethynyl]benzoyl}(hexyl)amino]methyl}-2-fluorobenzoic acid, N-methyl-D-glucamine (i.e. 1-deoxy-1-(methylamino)glucitol) salt Step a) Formation of methyl 2-fluoro-5-[(hexylamino)methyl]benzoate

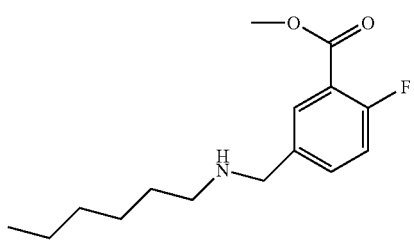

To solution of 2-fluoro-5-formylbenzoic acid methyl ester (1.0 g; 5.49 mmol) in anhydrous DCE (50 mL) were added hexylamine (Aldrich, 0.87 mL; 6.59 mmol), triacetoxyborohydride (1.74 g; 8.24 mmol) and acetic acid (0.47 mL; 8.24 mmol). The resulting mixture was stirred at room temperature under $N_2$ atmosphere for 5 hours. The mixture was poured into a saturated solution of $NaHCO_3$ and extracted with DCM (2×200 mL). The combined organic layers were washed with brine, dried over magnesium sulfate, filtrated and the solvent was removed under reduced pressure. Purification by flash chromatography on silica gel (DCM/MeOH/NH$_4$OH, 98:2:0.1) gave 920 mg (63%) of the title compound as a yellow cream. HPLC, Rt: 2.34 min (purity=94.9%), LC/MS: $M^+$(ESI): 268.1, $^1$H NMR (CDCl$_3$) δ: 7.8 (dd, J=2.2, 8.2 Hz, 1H), 7.42 (m, 1H), 7.00 (dd, J=8.2, 2.2 Hz, 1H), 3.91 (s, 3H), 3.76 (s, 2H), 2.58 (t, J=7.1 Hz, 2H), 1.46 (qt, J=6.7 Hz, 2H), 1.22 (m, 6H), 0.86 (t, J=6.7 Hz, 3H).

Step b) Formation of methyl 5-{[{4-[(4-butylphenyl)ethynyl]benzoyl}(hexyl)amino]methyl}-2-fluorobenzoate.

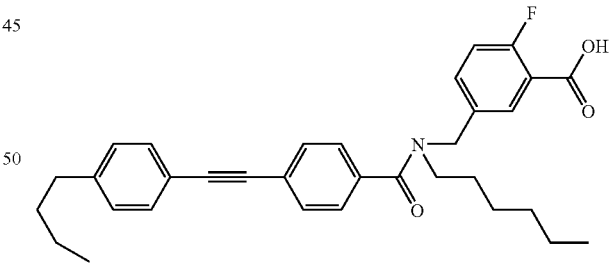

To a solution of 4-(4-butylphenylethynyl)benzoic acid (312 mg; 1.12 mmol) in DCM (15 mL) were added HOBT (181 mg; 1.35 mmol), EDC-HCl (258 mg; 1.35 mmol) and DIEA (362 mg; 2.81 mmol). The mixture was stirred for 10 min at room temperature under $N_2$ atmosphere before the addition of methyl 2-fluoro-5-[(hexylamino)methyl]benzoate (300 mg; 1.12 mmol). The reaction mixture was then stirred at 25° C. under $N_2$ atmosphere overnight. It was diluted in DCM (100 mL) and poured into NaOH (1N, 75 mL). The organic layer was washed with brine (100 mL), dried over magnesium sulfate, filtrated and the solvent was removed under reduced pressure. Purification by flash chromatography using silicagel (c-Hex/EtOAc, gradient from 9:1 to 1:1) gave 350 mg (59%) of the title compound as a white powder. HPLC, Rt: 6.19 min (purity=99.7%). LC/MS, $M^+$(ESI): 528.3. $^1$H NMR (CDCl$_3$) δ: 7.91 (m, 1H), 7.55 (m, 3H), 7.41 (m, 4H), 7.15 (m, 3H), 4.72 (m, 1H), 4.50 (m, 1H), 3.93 (s, 3H), 3.42 (m, 1H), 3.15 (m, 1H), 2.61 (t, J=5.5 Hz, 2H), 1.59 (qt, J=7.7 Hz, 2H), 1.2 (m, 10H), 0.92 (t, J=7.3 Hz, 3H), 0.8 (m, 3H).

Step c) Formation of 5-{[{4-[(4-butylphenyl)ethynyl]benzoyl}(hexyl)amino]methyl}-2-fluorobenzoic acid To a solution of methyl 5-{[{4-[(4-butylphenyl)ethynyl]benzoyl}(hexyl)amino]methyl}-2-fluorobenzoate (350 mg; 0.66 mmol) in THF (7 mL) were added lithium hydroxide monohydride (278 mg; 6.63 mmol) and water (3 mL).The reaction mixture was stirred under MW at 100° C. for 2500 s. Then an aqueous solution of HCl 1N (10 mL) was added and the mixture extracted with EtOAc (2×50 mL). The combined organic layers were washed with brine (100 mL), dried over magnesium sulfate and the solvent was removed under reduced pressure to give 316 mg (93%) of the title compound as a colorless oil. HPLC, Rt: 5.64 min (purity=98.7%). LC/MS: $M^+$(ESI): 514, $^1$H NMR (MeOD) δ: 7.88 (m, 1H), 7.50 (d, J=7.9 Hz, 2H), 7.33 (d, J=9.0 Hz, 5H), 7.1 (d, J=7.9 Hz, 3H), 4.78 (m, 1H), 4.60 (m, 1H), 2.54 (t, J=7.5 Hz, 2H), 1.51 (q, J=7.6 Hz, 5H), 1.38 (s, 3H), 1.14 (t, J=7.16 Hz, 4H), 1.02 (m, 3H).

Step d) Formation of 5-{[{4-[(4-butylphenyl)ethynyl]benzoyl}(hexyl)amino]methyl}-2-fluorobenzoic acid, N-methyl-D-glucamine (i.e. 1-deoxy-1-(methylamino)glucitol)salt

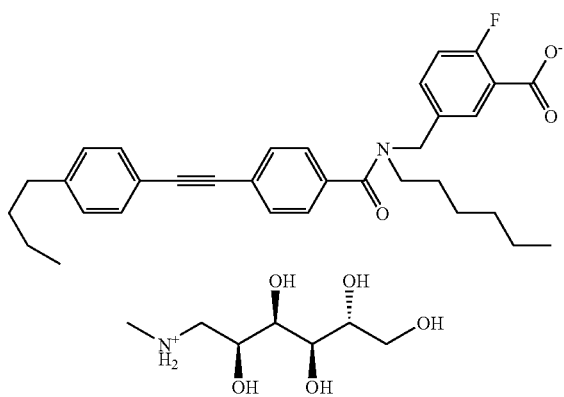

To a solution of 5-{[{4-[(4-butylphenyl)ethynyl]benzoyl}(hexyl)amino]methyl}-2-fluorobenzoic acid (316 mg; 0.62 mmol) in MeOH (5 mL) was added a solution of N-methyl-D-glucamine (120 mg; 0.62 mmol) in water. The resulting solution was lyophilized to give 312 mg (71%) of the title compound as a white powder. HPLC, Rt: 6.19 min (purity=99.7%, LCMS: M⁻(ESI): 514.5. Analysis calculated for $C_{33}H_{36}NO_3F$—$C_7H_{17}NO_5$-3.5 $H_2O$: C, 62.24; H, 7.83; N, 3.63; Exp.: C, 62.51; H, 7.54; N, 3.79.

Example 58

5-{[({4-[(4-butylphenol)ethynyl]phenyl}sulfonyl)(hexyl)amino]methyl}-2-fluorobenzoic acid Step a) Formation of methyl 5-{[[(4-bromophenyl)sulfonyl](hexyl)amino]methyl}-2-fluorobenzoate

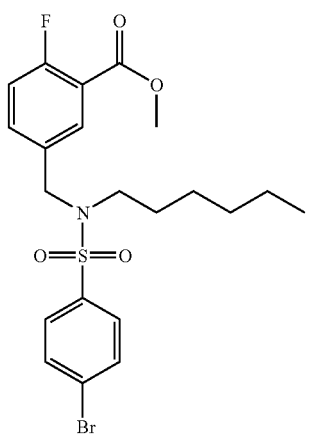

To a solution of methyl 2-fluoro-5-[(hexylamino)methyl]benzoate in DCM (13 mL) were added 4-bromobenzenesulfonyl chloride (200 mg; 0.79 mmol) and TEA (0.13 mL; 0.94 mmol). The reaction mixture was stirred at room temperature for 2 hours under $N_2$ atmosphere. The mixture was poured into a saturated solution of $NaHCO_3$ and extracted with DCM (2×100 mL). The combined organic layers were then washed with a saturated solution of $NH_4Cl$ (150 mL) and with brine (150 mL), dried over magnesium sulfate, filtrated and the solvent was removed under reduced pressure. Purification by flash chromatography on silica gel (c-Hex/EtOAc, 95:5) gave 96 mg (25%) of the title compound as a colorless oil. HPLC, Rt: 5.13 min (purity=99.1%). LC/MS: M⁺(ESI): 486.23; ¹H NMR (CDCl₃) δ: 7.78 (m, 1H), 7.72 (m, 4H), 7.55 (m, 1H), 7.12 (m, 1H), 4.31 (s, 2H), 3.93 (s, 3H), 3.09 (t, J=7.5 Hz, 2H), 1.85 to 1.05 (m, 8H), 0.81 (t, J=6.9 Hz, 3H).

Step b) Formation of methyl 5-{[({4-[(4-butylphenyl)ethynyl]phenyl}sulfonyl)(hexyl)amino]methyl}-2-fluorobenzoate

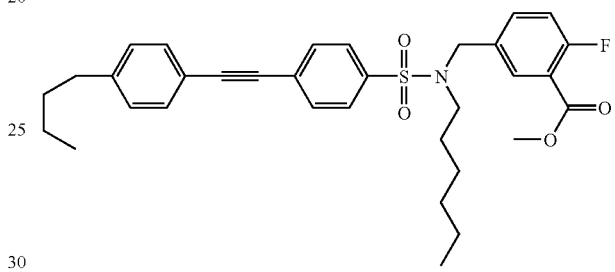

To a solution of methyl 5-{[[(4-bromophenyl)sulfonyl](hexyl)amino]methyl}-2-fluorobenzoate (96 mg; 0.20 mmol) in DMF (5 mL) were added (Aldrich, p-butylphenylacetylene (31 mg; 0.20 mmol), bis(triphenylphosphine) palladium (II) chloride (6.9 mg; 0.01 mmol), copper(I) iodide (1.9 mg; 0.01 mmol), triphenylphosphine (10.4 mg; 0.04 mmol) and TEA (0.08 mL; 0.59 mmol). The mixture was stirred for 1500 s at 150° C. under MW. The mixture was diluted with $Et_2O$ (50 mL) and the precipitate obtained filtrated off. Filtrate was washed with HCl 1N and with brine (75 mL). The organic layer was dried over magnesium sulfate and the solvent was removed under reduced pressure. Purification by flash chromatography using silicagel (c-Hex:EtOAc, 9:1 then 1:1) gave 66 mg (63.3%) of the title compound as a white solid. HPLC: Rt=6.12 min (purity=99.6%). LC/MS: M⁺(ESI): 564.4. ¹H NMR (CDCl₃) δ: 7.79 (d, J=8.3 Hz, 3H) 7.64 (d, J=8.7 Hz, 2H), 7.56 (m, 1H), 7.46 (d, J=8.3 Hz, 2H), 7.19 (d, J=7.9 Hz, 2H), 7.15 (s, 1H), 4.33 (s, 2H), 3.92 (s, 3H), 3.11 (t, J=7.5 Hz, 2H), 2.63 (t, J=7.7 Hz, 2H), 1.61 (t, J=7.7 Hz, 2H), 1.35 (m, 5H), 1.15 (m, 5H), 0.93 (t, J=7.3 Hz, 3H), 0.81 (t, J=6.9 Hz, 3H).

Step c) Formation of 5-{[({4-[(4-butylphenyl)ethynyl]phenyl}sulfonyl)(hexyl)amino]methyl)-2-fluorobenzoic acid

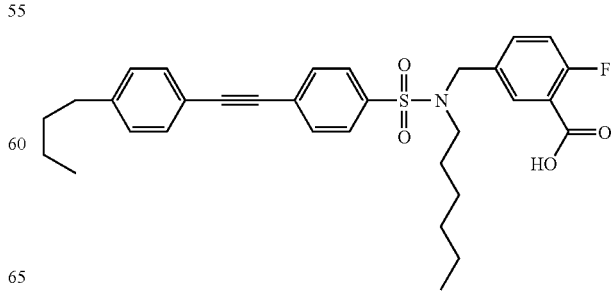

To a solution of methyl 5-{[({4-[(4-butylphenyl)ethynyl]phenyl}sulfonyl)(hexyl)amino]methyl}-2-fluorobenzoate (66 mg; 0.12 mmol) in THF (4 mL) were added lithium hydroxide monohydrate (49 mg; 1.17 mmol) and water (1 mL). The reaction mixture was stirred at 100° C. for 2500 s under MW. The mixture was poured into HCl 1N (10 mL) and extracted with EtOAc (2×75 mL). Combined organic layers were washed with brine (125 mL), dried over magnesium sulfate and filtrated. The solvent was removed under reduced pressure to give 57 mg (88.6%) of the title compound as a white powder. HPLC: Rt=5.71 min (purity=98.9%), LC/MS: M⁻(ESI): 548.3. ¹H NMR (MeOD) δ: 7.87 (d, J=8.6 Hz, 3H), 7.72 (d, J=8.6 Hz, 2H), 7.69 (m, 1H), 7.48 (d, J=7.9 Hz, 2H), 7.22 (d, J=8.2 Hz, 2H), 7.18 (s, 1H), 4.39 (s, 2H), 3.75 (m, 1H), 3.55 (t, J=4.3 Hz, 1H), 3.16 (t, J=7.3 Hz, 2H), 2.68 (t, J=7.7 Hz, 2H), 1.63 (q, J=7.5 Hz, 3H), 1.35 (m, 4H), 1.15 (m, 4H), 0.95 (t, J=7.3 Hz, 3H), 0.82 (t, J=7.0 Hz, 3H).

Example 59

5-{{4-[(4-butylphenyl)ethynyl]benzyl}[(propylamino)carbonyl]amino}-2-fluorobenzoic acid Step a) Formation of methyl 5-{{4-[(4-butylphenyl)ethynyl]benzyl}[(propylamino)carbonyl]amino}-2-fluorobenzoate

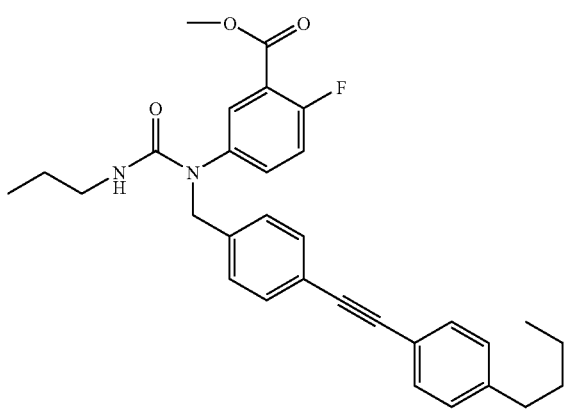

To a solution of methyl 5-({4-[(4-butylphenyl)ethynyl]benzyl}amino)-2-fluorobenzoate (150 mg; 0.36 mmol) in anhydrous DCM (12 mL) was added N-propylisocyanate (Aldrich, 0.39 mL; 4.16 mmol). The mixture was stirred at 100° C. for 1 h 30 min under MW. The reaction mixture was then treated with trisamine resin (Novabiochem HL, 941 mg, loading=3.2 mmol/g) and stirred at rt for 3 h. The resin was filtered off and the filtrate concentrated under reduced pressure. Purification by flash chromatography on silicagel (c-Hex-EtOAc, 90:10) gave 125 mg (69%) of the title compound as a white powder. HPLC: Rt=5.88 min (purity=99.3%), LC/MS: M⁺(ESI): 501.4. ¹H NMR (CDCl₃) δ: 7.71 (q, J=3.5 Hz, 1H), 7.43 (d, J=1.9 Hz, 4H), 7.15 (m, 5H), 7.06 (d, J=9.0 Hz, 1H), 4.84 (s, 2H), 3.92 (s, 3H), 3.75 (t, J=7.7 Hz, 2H), 2.61 (t, J=7.7 Hz, 2H), 1.7 to 1.2 (m, 6H), 0.92 (t, J=7.3 Hz, 3H), 0.83 (t, J=7.3 Hz, 3H).

Step b) Formation of 5-{4-[(4-butylphenyl)ethynyl]benzyl}(propylamino)carbonyl]amino}-2-fluorobenzoic acid

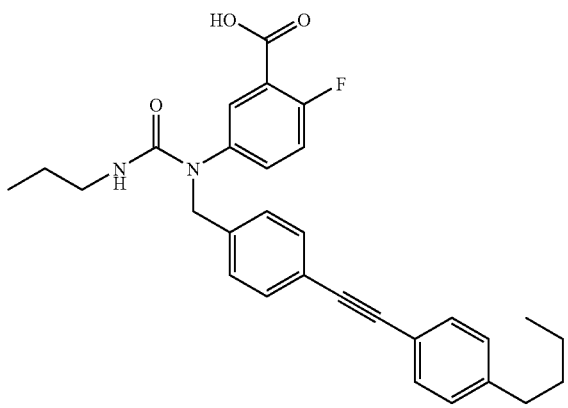

The title compound was prepared following the procedure described in Example 58 step c) using methyl 5-{{4-[(4-butylphenyl)ethynyl]benzyl}[(propylamino)carbonyl]amino}-2-fluorobenzoate (115 mg; 0.23 mmol).The title compound was obtained as a white solid (110 mg, 98.4%). HPLC, Rt: 5.39 min (purity: 98.9%). LC/MS, M⁻(ESI): 585.3. ¹H NMR (CDCl₃) δ: 7.61 (m, 1H), 7.43 (t, J=7.2 Hz, 4H), 7.22 (m, 6H), 3.71 (m, 1H), 3.25 (m, 1H), 3.09 (t, J=7.3 Hz, 2H), 2.63 (t, J=7.5 Hz, 2H), 1.59 (q, J=7.7 Hz, 2H), 1.38 (m, 4H), 0.95 (t, J=7.3 Hz, 2H), 0.86 (t, J=7.5 Hz, 2H).

Example 60

5-{{4-[(4-butylphenyl)ethynyl]benzyl}[(cyclohexylamino)carbonyl]amino}-2-fluorobenzoic acid Step a) Formation of methyl 5-{{4-[(4-butylphenyl)ethynyl]benzyl)[(cyclohexylamino)carbonyl]amino)-2-fluorobenzoate

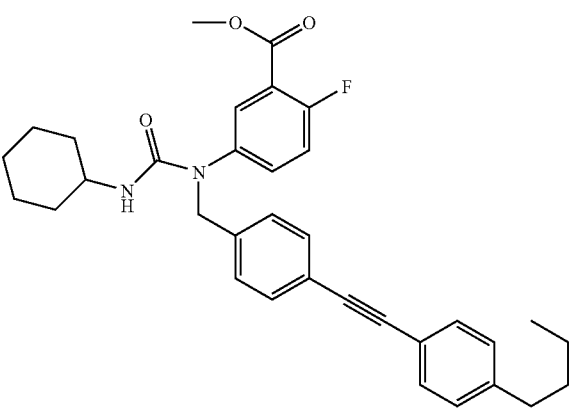

To a solution of methyl 5-({4-[(4-butylphenyl)ethynyl]benzyl}amino)-2-fluorobenzoate (142 mg; 0.34 mmol) in anhydrous DCM (15 mL) was added cyclohexylisocaynate (Aldrich, 0.51 mL, 3.93 mmol). The reaction mixture was stirred at 100° C. for 2500 s under MW. The solvent was removed under reduced pressure and the crude was purified by flash chromatography on silica (c-Hex/EtOAc, gradient from 9:1 to 1:1) to give 65 mg (35%) of the title compound as a colorless oil. HPLC: Rt=6.28 min (purity=99.6%), LC/MS: M+(ESI): 541.5.$^1$H NMR (CDCl$_3$) δ: 7.65 (dd, J=3.78, 2.65 Hz, 1H), 7.35 (d, J=7.5 Hz, 4H), 7.08 (m, 6H), 4.77 (s, 2H), 3.85 (s, 3H), 3.61 (m, 1H), 2.54 (t, J=8.1 Hz, 2H), 1.81 (m, 2H), 1.55 (m, 6H), 1.25 (m, 4H), 0.91 (m, 2H), 0.85 (t, 3H).

Step b) Formation of 5-{{4-[(4-butylphenyl)ethynyl]benzyl}[(cyclohexylamino)carbonyl]amino)-2-fluorobenzoic acid

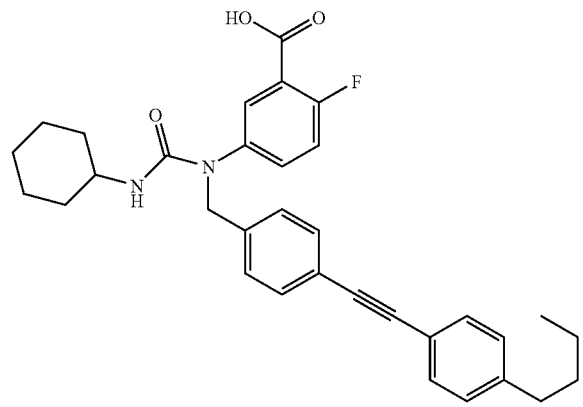

The title compound was prepared following procedure described in Example 58, step c) from methyl 5-{{4-[(4-butylphenyl)ethynyl]benzyl}[(cyclohexylamino)carbonyl]amino}-2-fluorobenzoate (65 mg; 0.12 mmol) and isolated as a white solid (51 mg, 81%). HPLC: Rt=5.74 min (purity=98.5%), LC/MS: M−(ESI): 525.5. $^1$H NMR (MeOD) δ: 7.62 (m, 1H), 7.41 (t, J=7.7 Hz, 4H), 7.21 (m, 6H), 3.58 (m, 2H), 2.63 (t, J=7.5 Hz, 2H), 1.85 (m, 2H), 1.65 (m, 5H), 1.35 (m, 5H), 1.15 (m, 2H), 0.95 (t, J=7.3 Hz, 3H).

Example 61

4-[{4-[(4-chlorophenyl)ethynyl]benzoyl}(3-cyclopentylpropyl)amino]-2-hydroxybenzoic acid, N-methyl-D-glucamine (i.e. 1-deoxy-1-(methylamino)glucitol)salt Step a) Formation of 4-[(4-chlorophenyl)ethynyl]-N-(3-cyclopentylpropyl)-N-(2,2-dimethyl-4-oxo-4H-1,3-benzodioxin-7-yl)benzamide

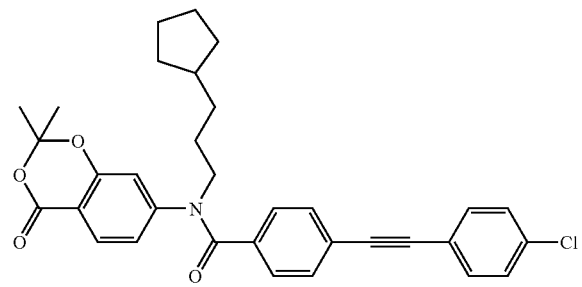

The title compound was prepared following procedure described in example 26, step d) from 4-bromo-N-(3-cyclopentylpropyl)-N-(2,2-dimethyl-4-oxo-4H-1,3-benzodioxin-7-yl)benzamide (437 mg, 0.90 mmol) and 4-chlorophenylacetylene (Apollo, 118 mg, 0.86 mmol). Purification by flash chromatography on silicagel (EtOAc/c-Hex 20:80) gave 373 mg (80%) of the title compound as a white foam. HPLC, Rt: 6.03 min (purity: 93.6%). LC/MS, M+(ESI): 541.9. $^1$H NMR (CDCl$_3$) δ: 7.78 (d, J=8.3 Hz, 1H), 7.24-7.45 (m, 8H), 6.74 (dd, J=8.4, 2.0 Hz, 1H), 6.58 (d, J=1.9 Hz, 1H), 3.90 (t, J=7.6 Hz, 2H), 1.46-1.86 (m, 9H), 1.40 (s, 6H), 1.36 (m, 2H), 1.03 (m, 2H).

Step b) Formation of 4-[{4-[(4-chlorophenyl)ethynyl]benzoyl}(3-cyclopentylpropyl)amino]-2-hydroxybenzoic acid

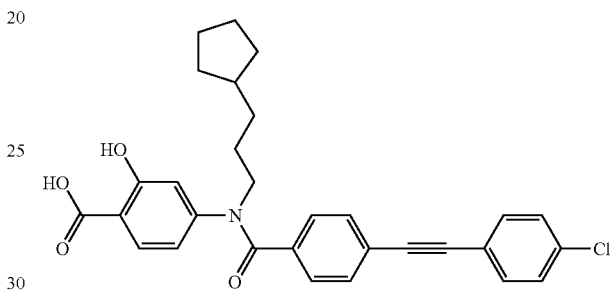

The title compound was prepared following the procedure described in example 19, step c) from 4-[(4-chlorophenyl)ethynyl]-N-(3-cyclopentylpropyl)-N-(2,2-dimethyl-4-oxo-4H-1,3-benzodioxin-7-yl)benzamide (374 mg, 0.69 mmol). Purification of the crude by preparative HPLC using a X-Terra column afforded 237 mg (68.4%) of the title compound. HPLC, Rt: 5.71 min (purity: 94.4%). LC/MS, M−(ESI): 521.9. $^1$H NMR (CDCl$_3$) δ: 10.51 (s, 1H), 7.69 (d, J=8.7 Hz, 1H), 7.27-7.70 (m, 8H), 6.71 (d, J=1.9 Hz, 1H), 6.48 (dd, J=1.9, 8.7 Hz, 1H), 3.91 (t, J=7.7 Hz, 2H), 1.63-1.71 (m, 9H), 1.34 (m, 2H), 1.03 (m, 2H).

Step c) Formation of 4-[{4-[(4-chlorophenyl)ethynyl]benzoyl}(3-cyclopentylpropyl)amino]-2-hydroxybenzoic acid, N-methyl-D-glucamine (i.e. 1-deoxy-1-(methylamino)glucitol) salt

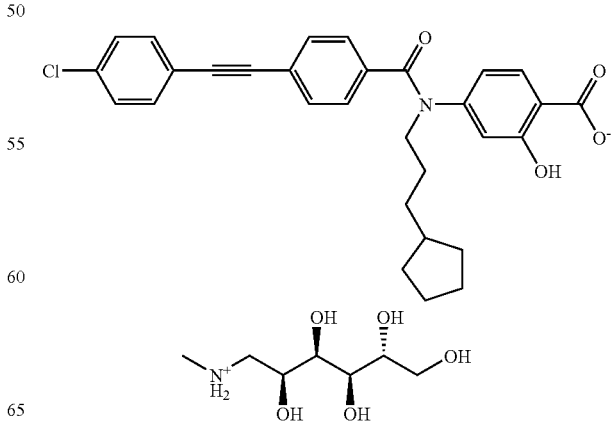

To a solution of 4-((3-cyclopentylpropyl){4-[(4-chlorophenyl)ethynyl]benzoyl}amino)-2-hydroxybenzoic acid (230 mg, 0.46 mmol) in MeOH (20 mL) was added a solution of N-methyl-D-glucamine (89 mg, 0.46 mmol) in water (4 mL). Water (20 mL) was added and the resulting solution was lyophilized to give 230 mg of the title compound as a white powder. HPLC, Rt: 5.48 min (purity: 100%). LC/MS, M$^+$(ESI):502.1, M$^-$(ESI): 500.0. Analysis calculated for $C_{30}H_{28}NO_4Cl \cdot C_7H_{17}NO_5 \cdot 1.5\ H_2O$: Calculated C, 61.36; H, 6.68; N, 3.87%. Found: C, 61.21; H, 6.68; N, 3.85%.

Example 62

Preparation of a Pharmaceutical Formulation

Formulation 1—Tablets
Carboxylic acid of formula (I) is admixed as a dry powder with a dry gelatin binder in an approximate 1:2 weight ration. A minor amount of magnesium stearate is added as a lubricant. The mixture is formed into 240-270 mg tablets (80-90 mg of active piperazine-2-carboxamide compound per tablet) in a tablet press.
Formulation 2—Capsules
Carboxylic acid of formula (I) is admixed as a dry powder with a starch diluent in an approximate 1:1 weight ratio. The mixture is filled into 250 mg capsules (125 mg of active piperazine-2-carboxamide compound per capsule).
Formulation 3—Liquid
Carboxylic acid of formula (I), sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.
Formulation 4—Tablets
Carboxylic acid of formula (I), is admixed as a dry powder with a dry gelatin binder in an approximate 1:2 weight ratio. A minor amount of magnesium stearate is added as a lubricant. The mixture is formed into 300-600 mg tablets (150-300 mg of active carboxylic acid derivative) in a tablet press.
Formulation 5—Injection
Carboxylic acid of formula (I), is dissolved in a buffered sterile saline injectable aqueous medium to a concentration of approximately 5 mg/ml.

Example 63

Biological Assays

The compounds of formula (I), may be subjected to the following assays:
(1) The PTP Enzyme Assay
(2) The in vivo assay in db/db mice
(1) The PTP Enzyme Assay (In Vitro Assay)
Assays for the determination of the PTP inhibitory activity of test compounds are well known to a person skilled in the art. An example of such an assay is described below:
The PTP Enzyme Assay aims at determining the extent of inhibition of PTP's, e.g. of PTP1B, SEP-1, SHP-2, GLEPP-1 or PTP-H1 in the presence of a test compound of lo formula (I). The inhibition is illustrated by IC$_{50}$ values which denote the concentration of test compound necessary to achieve an inhibition of 50% of said PTP's using the following concentration of the PTP substrate DiFMUP:
5 µM DiFMUP for PTP1B and PTP-H1;
20 µM DiFMUP for SHP-1 and SHP-2;
30 µM DiFMUP for GLEPP-1.

a) PTPs Cloning
The cloning and expression of the catalytic domain e.g. of PTP1B, may be performed as described in *J. Biol. Chem.* 2000, 275(13), pp 9792-9796.
b) Materials and Methods
The DiFMUP assay allows to follow the dephosphorylation of DiFMUP (6,8-DiFluoro-4-MethylUmbelliferyl Phosphate)—which is the PTP substrate—mediated by PTP into its stable hydrolysis product, i.e. DiFMU (6,8-difluoro-7-hydroxy coumarin). Due to its rather low pKa and its high quantum yield, DiFMU allows to measure both acidic and alkaline phosphatase activities with a great sensitivity.
Assays were performed in a 96 well plate format, using the catalytic core of a human recombinant PTP as the enzyme and 6,8-DiFluoro-4-MethylUmbelliferyl Phosphate (DiFMUP, Molecular Probes, D-6567) as a substrate. Compounds to be tested were dissolved in 100% DMSO at a concentration of 2 mM. Subsequent dilutions of the test compounds (to yield a concentration of 100, 30, 10, 3, 1,0.3, 0.1, 0.03, 0.01, 0.001 µM) were performed in 60% DMSO manually. 8 µl of diluted compound or vehicle (60% DMSO=control) was distributed to a black Costar 96 well plate. 42 µl of human recombinant PTP enzyme diluted in assay buffer (20 mM Tris HCl pH 7.5, 0.01% IGEPAL CA-630, 0.1 mM ethylenediaminetetracetic acid, 1 mM DL-Dithiothreitol) can be added to the dilutions of compound or vehicle (distributed to a black Costar 96-well plate), followed by 50 µl of DiFMUP diluted in the assay buffer. The reaction ran for 30 minutes at room temperature before reading the fluorescence intensity (integral or intensity) on a Perkin-Elmer Victor 2 spectrofluorimeter (excitation of 6,8-difluoro-7-hydroxy coumarin is at 355 nm, the emission at 460 nm, for 0.1 s). The percentage of inhibition is determined by measuring the relative fluorescence ion absence of a test compound (PTP inhibitor), i.e. with the solvent alone (5% DMSO). The IC$_{50}$ values for inhibition were determined in triplicates.
The tested compounds according to formula (I) display an inhibition (illustrated by IC$_{50}$ values) with regard to PTP of preferably less than 20 µM, more preferred less than 5 µM.
For instance, the compound of Example 8, i.e. {4-[({4-[(4-butylphenyl)ethynyl]benzyl}-{[(E)-2-phenylvinyl]sulfonyl}amino)methyl]phenoxy}acetic acid displays an IC$_{50}$ value of 0.51 µM in respect of PTP1B and an IC$_{50}$ value of 0.62 µM in respect of GLEPP-1, an IC$_{50}$ value of 0.82, 0.80 and 9.64 µM in respect of SHP-1, SHP-2 and PTP-H1. The compound of Examples 30 & 35 display an IC$_{50}$ value of 0.80 & 0.08 µM in respect of PTP1B and an IC$_{50}$ value of 0.86 & 0.21 µM in respect of GLEPP-1,
(2) In Vivo Assay in db/db Mice
The following assay aims at determining the anti-diabetic effect of the test compounds of formula (I) in a model of postprandial glycemia in db/db mice, in vivo.
The assay was performed as follows:
A total of 18 db/db mice (about 8-9 weeks; obtained from IFFACREDO, l'Arbreste, France) were fasted during 20 hours.
2 groups, each consisting of 6 animals were formed:
Group 1: The animals were administered (per os) a dose of 10 mL/kg of vehicle (control).
Group 2: The animals were administered (per os) a dose of 30 mg/kg of the test compound according to formula (I) solubilized in the vehicle.
After oral administration of the compounds of formula (I) solubilized or suspended in CarboxyMethylCellulose (0.5%), Tween 20 (0.25%) and water as vehicle, the animals had access to conmnercial food (D04, UAR, Villeinoisson/Orge, France) ad libitum. The diabetic state of the mice was verified by determining the blood glucose level before drug administration. Blood glucose and serum insulin levels were then determined 4 hrs after drug administration.

The determination of the blood glucose level was performed using a glucometer (Precision Q.I.D., Medisense, Abbot, ref. 212.62.31).

The determination of the Insulin level was performed using an ELISA kit (Crystal CHEM, Ref. INSK R020).

Changes in blood glucose and serum insulin of drug treated mice were expressed as a percentage of control (group 1: vehicle treated mice).

Treatment (per os) of the animals with carboxylic acid compounds of formula (I), at a dosage of 30 mg/kg, decreased the blood glucose level induced by food intake by about 20-40%.

For instance, upon using the compound of Example 16, i.e. 5-[(1-{4-[(4-butylphenyl)-ethynyl]phenyl}pentyl)oxy]-2-hydroxybenzoic acid, Example 19, i.e. 5-{[{4-[(4-butylphenyl)ethynyl]benzyl}(hexyl)amino]carbonyl}-2-hydroxybenzoic acid, N-methyl-D-, glucamine (i.e. 1-deoxy-1-(methylamino)glucitol) salt and Example 55, i.e. 5-[{4-[(4-butylphenyl)ethynyl]benzoyl}(hexyl)amino]-2-fluorobenzoic acid, N-methyl-D-glucamine (i.e. 1-deoxy-1-(methylamino)glucitol) salt, the following decrease in blood glucose level as well as insulin level was determined (difference in insulin & glucose levels compared to Group 1 animals), respectively:

| Example | Animal Group | Decrease in blood glucose | ±SEM | Decrease in serum insulin | ±SEM |
|---|---|---|---|---|---|
| 16 | 2 | 37 | 14 | 28 | 9 |
| 19 | 2 | 20 | 10 | 43 | 10 |
| 55 | 2 | 46 | 13 | 75 | 7 |

(SEM = Standard Error of the Mean)

LIST OF REFERENCES

*American Journal of Medicine*, 60, 80 (1976) by Reaven et al;
*Metabolism*, 34, 7 (1985) by Stout et al.;
*Diabetes/Metabolism Reviews*, 5, 547 (1989) by Pyorala et al;
*European Journal of Endocrinology* 138, 269-274 (1998) by A. Dunaif;
*Endocrine Reviews* 18(6), 774-800 (1997);
*Diabetes Care*, 14, 173 (1991) by DeFronzo and Ferrannini;
*J. Mol Med.* 78, 473-482 (2000) by A. Cheng et al.;
*Current Opinion in Drug Discovery & Development* 3(5), 527-540 (2000);,
*Molecular and Cellular Biology*, 5479-5489 (2000) by Lori Klaman et al.;
*Diabetes*, 40, 939 (1991) by McGuire et al.;
*J. Clinical Invest.*, 84, 976 (1989) by Meyerovitch et al;
*Metabolism*, 44, 1074, (1995) by Sredy et al.;
*Curr. Opin. Chem. Biol.*, 5(4), 416-23 (2001) by Zhang et al.;
*J. Biol. Chem.*, 275(52), 41439-46 (2000) by Bjorge J. D et al.;
*J. Neurosci. Res.*, 63(2), 143-150 (2001) by Pathre et al.;
*Mol. Brain. Res.*, 28(1), 110-16 (1995) by Shock L. P et al;
*Biochemical Pharmacology*, Vol. 60, 877-883, (2000) by Brian P. Kennedy et al.;
*Annu. Rev. Physiol.* 62 p. 413-437 (2000) by Ahima R. S. et al;
*Developmental Cell.*, vol. 2, p. 497-503 (2002);
WO 00/35859;
WO 00/15213;
WO 98/16503;
WO 00/35859;
WO 03/032999.
*Bioorg. Med. Chem. Lett.*, 2001,11(19), 2589-92);
*J. Chem. Soc. Perkin Trans. J*, 1975,1283-1284;
*J. Org. Chem.*, 1990, 2034-2044.
*J. Chem. Soc., Perkin Trans.* 1, 2000, 4265-4278

The invention claimed is:
1. A carboxylic acid of formula (I):

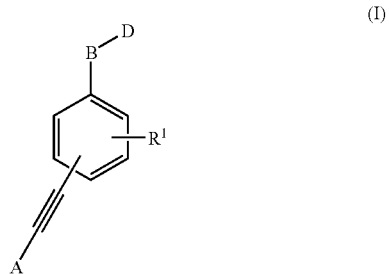

as well as its geometrical isomers, its optically active forms as enantiomers, diastereomers and its racemate forms, as well as pharmaceutically acceptable salts thereof, wherein A is selected from the group consisting of $C_1$-$C_6$-alkyl, $C_2$-$C_6$-alkenyl, $C_2$-$C_6$-alkynyl, $C_1$-$C_6$-alkyl amine, $C_1$-$C_6$-alkyl alkoxy, aryl, heteroaryl, saturated or unsaturated 3-8-membered cycloalkyl, 3-8-membered heterocycloalkyl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, $C_2$-$C_6$-alkynyl heterocycloalkyl;

$R^1$ is selected from the group consisting of H, $C_1$-$C_6$-alkyl, $C_1$-$C_6$-alkoxy, halogen;

B is selected from the group consisting of:

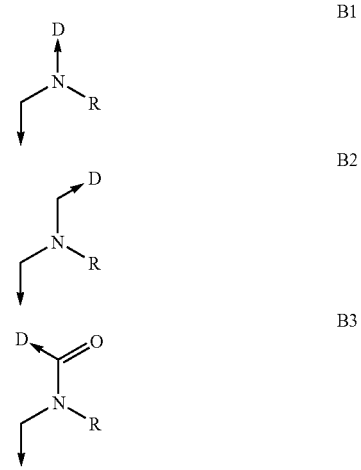

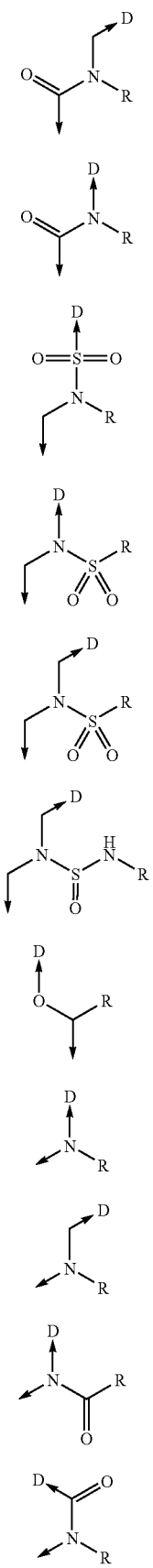
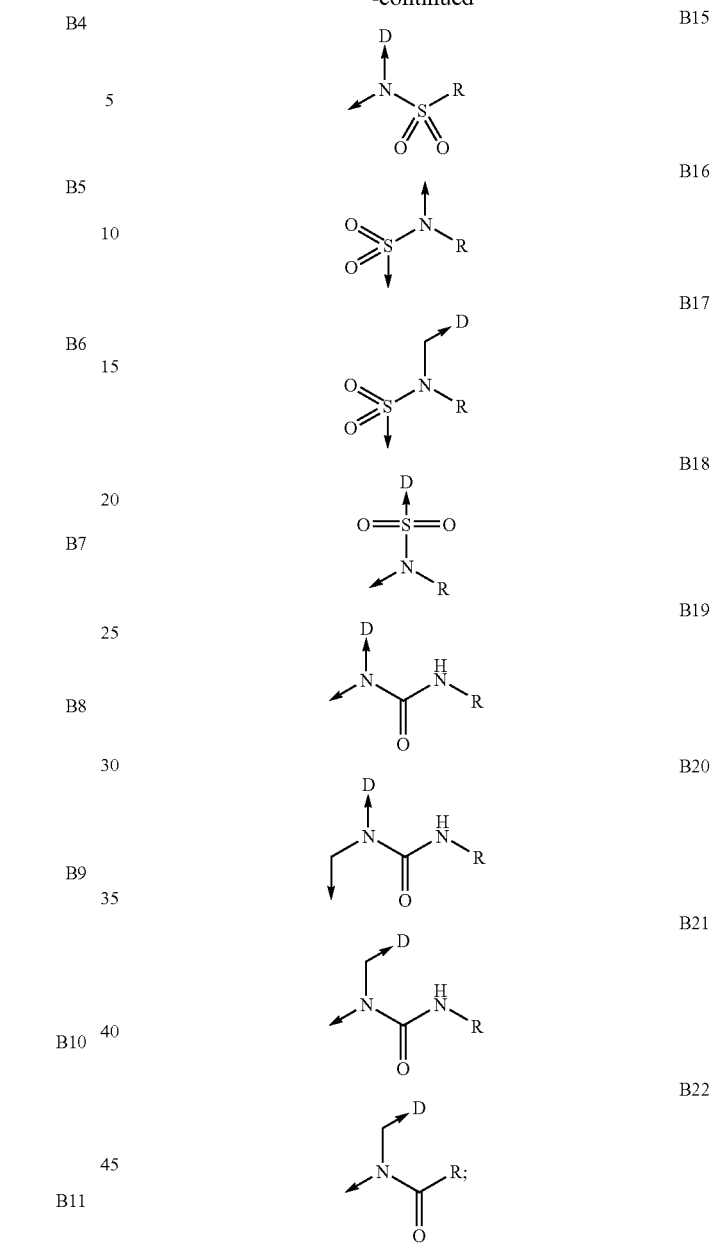
D is either selected from the group consisting of
with m being an integer selected from 0, 1 or 2 and n being an integer selected from 1 or 2; or D is
with n being an integer selected from 0 or 1;

R is selected from the group consisting of $C_1$-$C_8$-alkyl, $C_2$-$C_6$-alkenyl, $C_2$-$C_6$-alkynyl, $C_1$-$C_6$-alkoxy, $C_1$-$C_6$-alkyl amine, $C_1$-$C_6$-alkyl alkoxy, aryl, heteroaryl, saturated or unsaturated 3-8-membered cycloalkyl, 3-8-membered heterocycloalkyl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, $C_2$-$C_6$-alkynyl heterocycloalkyl; and $R^3$ is H, or $C_1$-$C_6$-alkyl;

with the proviso that when B is an amide B3, R is not be a phenyl—optionally fused with a heterocycloalkyl—substituted by one or 2 moieties selected from hydroxy, $C_1$-$C_6$ alkyl, carboxy, $C_1$-$C_6$ alkoxy, $C_1$-$C_3$ alkyl carboxy, $C_2$-$C_3$ alkenyl carboxy, $C_2$-$C_3$ alkynyl carboxy or amino.

2. A carboxylic acid according to claim 1, having the formula

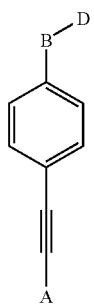

(I)

whereby A, B and D are as defined in claim 1.

3. A carboxylic acid according to claim 1, wherein $R^1$ is H.

4. A carboxylic acid according to claim 1, wherein A is an aryl moiety, in particular a phenyl group, optionally substituted by a $C_1$-$C_8$-alkyl, a halogen or an alkoxy.

5. A carboxylic acid according to claim 4, wherein A is a phenyl group substituted by a $C_1$-$C_4$-alkyl or a halogen.

6. A carboxylic acid according to claim 1, wherein B is any of

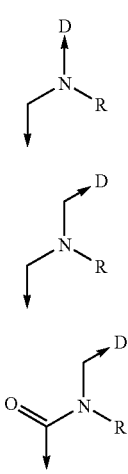

B1

B2

B4

-continued

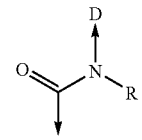

B5

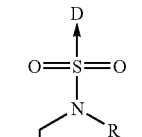

B6

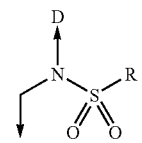

B7

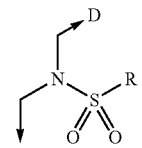

B8

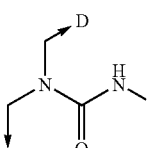

B9

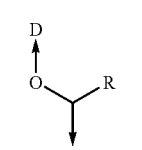

B10 whereby R is as defined in claim 1.

7. A carboxylic acid according to claim 6, wherein B is B1.

8. A carboxylic acid according to claim 1, wherein D is either of

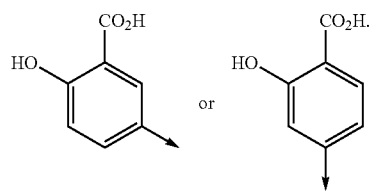

9. A carboxylic acid according to claim 1, wherein D is

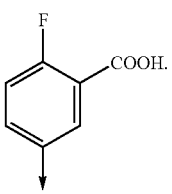

10. A carboxylic acid according to claim 1, wherein R is a $C_4$-$C_6$-alkyl.

11. A carboxylic acid according to claim 1, wherein A is a phenyl group substituted by a $C_1$-$C_4$-alkyl or a halogen, B is B1, R is a $C_4$-$C_6$-alkyl and D is

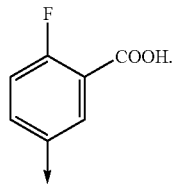

12. A carboxylic acid according to claim 1, selected from the group consisting of:
- 5-[{4-[(4-Butylphenyl)ethynyl]benzyl}(hexyl)amino]-2-hydroxybenzoic acid, N-methyl-D-glucamine (i.e. 1-deoxy-1-(methylamino)glucitol) salt,
- 5-[{4-[(4-Butylphenyl)ethynyl]benzyl}(hexyl)amino]-2-hydroxybenzoic acid, hydrochloride salts,
- 5-[{4-[(4-Butylphenyl)ethynyl]benzyl}(hexyl)amino]-2-hydroxybenzoic acid, lysine salt,
- 5-({4-[(4-Butylphenyl)ethynyl]benzyl}{[(E)-2-phenylvinyl]sulfonyl}amino)-2-hydroxybenzoic Acid,
- 4-({{4-[(4-Butylphenyl)ethynyl]benzyl}[2-(4-chlorophenyl)ethyl]amino}-methyl)benzoic acid, hydrochloride salt,
- {4-[({[(4-tert-Butylphenyl)amino]carbonyl}{4-[(4-butylphenyl)ethynyl]-benzyl}amino)methyl]phenoxy}acetic acid,
- 5-[{4-[(4-Butylphenyl)ethynyl]benzyl}(3-phenylpropyl)amino]-2-hydroxy-benzoic acid, hydrochloride salt,
- {4-[({4-[(4-Butylphenyl)ethynyl]benzyl}{[(E)-2-phenylvinyl]sulfonyl}-amino)methyl]phenoxy}acetic acid,
- 5-[{4-[(4-Butylphenyl)ethynyl]benzyl}(1-naphthylmethyl)amino]-2-hydroxy-benzoic acid, hydrochloride salt,
- [4-({{4-[(4-Butylphenyl)ethynyl]benzyl}[(cyclohexylamino)carbonyl]amino}methyl)phenoxy]acetic acid,
- [4-({{4-[(4-Butylphenyl)ethynyl]benzyl}[(cyclohexylamino)carbonyl]-amino}methyl)phenoxy]acetic acid, N-methyl-D-glucamine (i.e. 1-deoxy-1-(methylamino) glucitol) salt,
- [4-({{4-[(4-Butylphenyl)ethynyl]benzyl}[(propylamino)carbonyl]-amino}methyl)-phenoxy]acetic acid,
- {4-[({4-[(4-Butylphenyl)ethynyl]benzyl}{[(4-cyanophenyl)amino]carbonyl}amino)methyl]phenoxy}acetic acid,
- 5-((4-tert-Butylbenzyl){4-[(4-butylphenyl)ethynyl]benzyl}amino)-2-hydroxy-benzoic acid, hydrochloride salt,
- (4-{[{4-[(4-Butylphenyl)ethynyl]benzyl}(2-thienylsulfonyl)amino]methyl}phenoxy)acetic acid,
- 5-[(1-{4-[(4-Butylphenyl)ethynyl]phenyl}pentyl)oxy]-2-hydroxybenzoic acid,
- 7-[(1-{4-[(4-Butylphenyl)ethynyl]phenyl}pentyl)oxy]-2,2-dimethyl-4H-1,3-benzodioxin-4-one, N-methyl-D-glucamine (i.e. 1-deoxy-1-(methylamino)-glucitol) salt,
- (4-{[{4-[(4-Butylphenyl)ethynyl]benzyl}(ethylsulfonyl)amino]-methyl}phenoxy)-acetic acid,
- 5-{[{4-[(4-Butylphenyl)ethynyl]benzyl}(hexyl)amino]carbonyl}-2-hydroxy-benzoic acid, N-methyl-D-glucamine (i.e. 1-deoxy-1-(methylamino)-glucitol) salt,
- 5-{[{4-[(4-Butylphenyl)ethynyl]benzyl}(hexyl)amino]methyl}-2-hydroxybenzoic acid, N-methyl-D-glucamine (i.e. 1-deoxy-1-(methyl-amino)glucitol) salt,
- 5-{[{4-[(4-Butylphenyl)ethynyl]benzyl}(hexyl)amino]sulfonyl}-2-hydroxy-benzoic acid, N-methyl-D-glucamine (i.e. 1-deoxy-1-(methylamino)-glucitol) salt,
- 4-[{4-[(4-Butylphenyl)ethynyl]benzyl}(hexyl)amino]-2-hydroxybenzoic acid, N-methyl-D-glucamine (i.e. 1-deoxy-1-(methylamino)glucitol) salt,
- 5-[{4-[(4-Butylphenyl)ethynyl]benzyl}(hexyl)amino]-2-fluorobenzoic acid,
- 5-[{4-[(4-Butylphenyl)ethynyl]benzyl}(hexyl)amino]-2-fluorobenzoic acid, N-methyl-D-glucamine (i.e. 1-deoxy-1-(methylamino)glucitol) salt,
- 5-{[{2-[(4-Butylphenyl)ethynyl]benzyl}(hexyl)amino]carbonyl}-2-hydroxybenzoic acid,
- 4-((3-Cyclopentylpropyl){4-[(4-fluorophenyl)ethynyl]benzoyl}amino)-2-hydroxybenzoic acid, N-methyl-D-glucamine (i.e. 1-deoxy-1-(methyl-amino)glucitol) salt,
- 4-[{4-[(4-Butylphenyl)ethynyl]benzoyl}(3-cyclopentylpropyl)amino]-2-hydroxybenzoic acid, N-methyl-D-glucamine (i.e. 1-deoxy-1-(methyl-amino)glucitol) salt,
- 5-{[{4-[(4-Fluorophenyl)ethynyl]benzoyl}(hexyl)amino]methyl}-2-hydroxy-benzoic acid, N-methyl-D-glucamine (i.e. 1-deoxy-1-(methylamino)-glucitol) salt,
- 5-{[{4-[(4-Chlorophenyl)ethynyl]benzoyl}(hexyl)amino]methyl}-2-hydroxybenzoic acid, N-methyl-D-glucamine (i.e. 1-deoxy-1-(methyl-amino)glucitol) salt,
- 2-Fluoro-5-{hexyl[4-(phenylethynyl)benzyl]amino}benzoic acid, N-methyl-D-glucamine (i.e. 1-deoxy-1-(methylamino)glucitol) salt,
- 5-({4-[(4-Chlorophenyl)ethynyl]benzyl}(hexyl)amino)-2-hydroxybenzoic acid, N-methyl-D-glucamine (i.e. 1-deoxy-1-(methylamino)glucitol) salt,
- 5-(Hexyl{4-[(4-methoxyphenyl)ethynyl]benzyl}amino)-2-hydroxybenzoic acid, N-methyl-D-glucamine (i.e. 1-deoxy-1-(methylamino)glucitol)salt,
- 5-[Hexyl(4-{[4-(trifluoromethyl)phenyl]ethynyl}benzyl)amino]-2-hydroxybenzoic acid, N-methyl-D-glucamine (i.e. 1-deoxy-1-(methylamino)glucitol)salt,
- 5-[{4-[(4-Butylphenyl)ethynyl]benzyl}(cyclopentylmethyl)amino]-2-fluorobenzoic acid, N-methyl-D-glucamine (i.e. 1-deoxy-1-(methylamino)glucitol)salt,
- 5-[{4-[(4-Butylphenyl)ethynyl]benzyl}(3,3-dimethylbutyl)amino]-2-fluorobenzoic acid, N-methyl-D-glucamine (i.e. 1-deoxy-1-(methylamino)glucitol)salt,
- 5-((Cyclopentylmethyl){4-[(4-methoxyphenyl)ethynyl]benzyl}amino)-2-hydroxybenzoic acid, N-methyl-D-glucamine (i.e. 1-deoxy-1-(methylamino)glucitol)salt,
- 5-({4-[(4-Butylphenyl)ethynyl]benzyl}(ethyl)amino)-2-fluorobenzoic acid, N-methyl-D-glucamine (i.e. 1-deoxy-1-(methylamino)glucitol) salt,
- 5-(Hexyl{4-[(4-propylphenyl)ethynyl]benzyl}amino)-2-hydroxybenzoic acid, N-methyl-D-glucamine (i.e. 1-deoxy-1-(methylamino)glucitol)salt,
- 5-[{4-[(4-Butylphenyl)ethynyl]benzyl}(hexyl)amino]-2-fluorobenzoic acid, lysine salt,
- 5-[{4-[(4-Butylphenyl)ethynyl]benzyl}(hexyl)amino]-2-fluorobenzoic acid, tromethamine (i.e. (2-amino-2-hydroxymethyl)-1,3-propanediol) salt,
- 5-[{4-[(4-Butylphenyl)ethynyl]benzyl}(pentyl)amino]-2-fluorobenzoic acid, N-methyl-D-glucamine (i.e. 1-deoxy-1-(methylamino)glucitol) salt,
- 5-[{4-[(4-Butylphenyl)ethynyl]benzyl}(methyl)amino]-2-fluorobenzoic acid,
- 5-[{4-[(4-Butylphenyl)ethynyl]benzyl}(cyclopropylmethyl)amino]-2-fluorobenzoic acid, N-methyl-D-glucamine (i.e. 1-deoxy-1-(methylamino)glucitol)salt, 5-{Butyl[4-(phenylethynyl)benzyl]amino}-2-fluorobenzoic acid, N-methyl-D-glucamine (i.e. 1-deoxy-1-(methylamino)glucitol) salt, 2-Fluoro-5-{[4-(phenylethynyl)benzyl](propyl)amino}benzoic acid, N-methyl-D-glucamine (i.e. 1-deoxy-1-(methylamino)glucitol) salt, 2-Fluoro-5-[{4-[(4-fluorophenyl)ethynyl]benzyl}(hexyl)amino]benzoic acid, N-methyl-D-glucamine (i.e. 1-deoxy-1-(methylamino)glucitol)salt, 2-Fluoro-5-(hexyl{4-[(4-propylphenyl)ethynyl]benzyl}amino)benzoic acid, N-methyl-D-glucamine (i.e. 1-deoxy-1-(methylamino)glucitol)salt, 5-{{4-[(4-Butylphenyl)ethynyl]benzyl}[(2-carboxycyclopropyl)methyl]amino}-2-fluorobenzoic acid, N-methyl-D-glucamine (i.e. 1-deoxy-1-(methylamino)glucitol)salt, 5-[{4-[(4-Ethylphenyl)ethynyl]benzyl}(hexyl)amino]-2-fluorobenzoic acid, N-methyl-D-glucamine (i.e. 1-deoxy-1-(methylamino)glucitol)salt, 5-[{4-[(4-tert-Butylphenyl)ethynyl]benzyl}(hexyl)amino]-2-fluorobenzoic acid, N-methyl-D-glucamine (i.e. 1-deoxy-1-(methylamino)glucitol)salt, 5-{[{4-[(4-Butylphenyl)ethynyl]phenyl}(hexyl)amino]methyl}-2-fluorobenzoic acid, N-methyl-D-glucamine (i.e. 1-deoxy-1-(methylamino)glucitol)salt, 4-({(3,3-Dimethylbutanoyl)-4-[(4-hexylphenyl)ethynyl]anilino}methyl)-2-hydroxybenzoic acid, N-methyl-D-glucamine (i.e. 1-deoxy-1-(methylamino)glucitol) salt, 5-[{4-[(4-Butylphenyl)ethynyl]benzyl}(isobutyl)amino]-2-fluorobenzoic acid, N-methyl-D-glucamine (i.e. 1-deoxy-1-(methylamino)glucitol)salt, 5-{[{4-[(4-Butylphenyl)ethynyl]benzyl}(hexyl)amino]carbonyl}-2-fluorobenzoic acid, N-methyl-D-glucamine (i.e. 1-deoxy-1-(methylamino)glucitol)salt, 5-[{4-[(4-Butylphenyl)ethynyl]benzoyl}(hexyl)amino]-2-fluorobenzoic acid, N-methyl-D-glucamine (i.e. 1-deoxy-1-(methylamino)glucitol)salt, 5-[({4-[(4-Butylphenyl)ethynyl]phenyl}sulfonyl)(hexyl)amino]-2-fluorobenzoic acid, N-methyl-D-glucamine (i.e. 1-deoxy-1-(methylamino)glucitol)salt, 5-{[{4-[(4-Butylphenyl)ethynyl]benzoyl}(hexyl)amino]methyl}-2-fluorobenzoic acid, N-methyl-D-glucamine (i.e. 1-deoxy-1-(methylamino)glucitol)salt, 5-{[({4-[(4-Butylphenyl)ethynyl]phenyl}sulfonyl)(hexyl)amino]methyl}-2-fluorobenzoic acid, 5-{{4-[(4-Butylphenyl)ethynyl]benzyl}[(propylamino)carbonyl]amino}-2-fluorobenzoic acid, 5-{{4-[(4-Butylphenyl)ethynyl]benzyl}[(cyclohexylamino)carbonyl]amino}-2-fluorobenzoic acid, and 4-[{4-[(4-Chlorophenyl)ethynyl]benzoyl}(3-cyclopentylpropyl)amino]-2-hydroxybenzoic acid, N-methyl-D-glucamine (i.e. 1-deoxy-1-(methylamino)glucitol)salt.

13. A medicament comprising a carboxylic acid according to claim 1.

14. The medicament according to claim 13 for the modulation of the activity of PTPs.

15. The medicament according to claim 14 wherein the PTP is PTP1B, GLEPP-1.

16. The medicament according to claim 15 wherein said modulation consists in the inhibition of PTP1B.

17. A pharmaceutical composition containing at least one carboxylic acid according to claim 1 and a pharmaceutically acceptable carrier, diluent or excipient thereof.

18. A pharmaceutical composition according to claim 17 further comprising at least one supplementary drug selected from the group consisting of insulin, aldose reductase inhibitors, alpha-glucosidase inhibitors, sulfonyl urea agents, biguanides (e.g. metformin), thiazolidines, PPARs agonists, c-Jun Kinase or GSK-3 inhibitors.

19. A pharmaceutical composition according to claim 18 wherein said supplementary drug is selected from the group consisting of a rapid acting insulin, an intermediate acting insulin, a long acting insulin, a combination of intermediate and rapid acting insulins, Minalrestat, Tolrestat, Sorbinil, Methosorbinil, Zopolrestat, Epalrestat, Zenarestat, Imirestat, Ponalrestat, ONO-2235, GP-1447, CT-112, BAL-ARI 8, AD-5467, ZD5522, M-16209, NZ-314, M-79175, SPR-210, ADN 138, or SNK-860, Miglitol, Acarbose, Glipizide, Glyburide, Chlorpropamide, Tolbutamide, Tolaz-amide, or Glimepriride.

20. A method of preparing a carboxylic acid according to claim 1, comprising the step of:

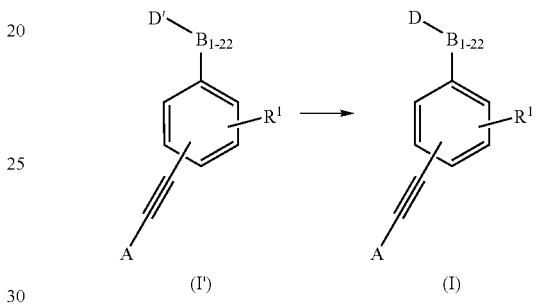

whereby the moieties A, $B_{1-22}$, $R^1$, D are as above defined and D' is a protected form of the moiety D.

21. An intermediate compound (I') selected from the group consisting of:
6-[{4-[(4-Butylphenyl)ethynyl]benzyl}(hexyl)amino]-2,2-dimethyl-4H-1,3-benzodioxin-4-one,
Methyl 5-[{4-[(4-butylphenyl)ethynyl]benzyl}(hexyl)amino]-2-hydroxybenzoate,
(E)-N-{4-[(4-Butylphenyl)ethynyl]benzyl}-N-(2,2-dimethyl-4-oxo-4H-1,3-benzodioxin-6-yl)-2-phenylethylenesulfonamide,
Methyl 4-({{4-[(4-butylphenyl)ethynyl]benzyl}[2-(4-chlorophenyl)ethyl]amino}-methyl)-benzoate,
Methyl {4-[({[(4-tert-butylphenyl)amino]carbonyl}{4-[(4-butylphenyl)ethynyl]-benzyl}amino)methyl]phenoxy}acetate,
6-[{4-[(4-Butylphenyl)ethynyl]benzyl}(3-phenylpropyl)amino]-2,2-dimethyl-4H-1,3-benzodioxin-4-one,
Methyl {4-[({4-[(4-butylphenyl)ethynyl]benzyl}{[(E)-2-phenylvinyl]sulfonyl}-amino)methyl]phenoxy}acetate,
6-[{4-[(4-Butylphenyl)ethynyl]benzyl}(1-naphthylmethyl)amino]-2,2-dimethyl-4H-1,3-benzodioxin-4-one,
Methyl [4-({{4-[(4-butylphenyl)ethynyl]benzyl}[(cyclohexylamino)carbonyl]-amino}-methyl)phenoxy]acetate,
Methyl [4-({{4-[(4-butylphenyl)ethynyl]benzyl}[(propylamino)carbonyl]amino}-methyl)phenoxy]acetate,
Methyl [4-({{4-[(4-butylphenyl)ethynyl]benzyl}[(4-cyanoanilino)carbonyl]amino}-methyl)phenoxy]acetate,
6-((4-tert-Butylbenzyl){4-[(4-butylphenyl)ethynyl]benzyl}amino)-2,2-dimethyl-4H-1,3-benzodioxin-4-one,
Methyl (4-{[{4-[(4-butylphenyl)ethynyl]benzyl}(2-thienylsulfonyl)amino]methyl}-phenoxy)acetate, 6-[(1-{4-[(4-Butylphenyl)ethynyl]phenyl}pentyl)oxy]-2,2-dimethyl-4H-1,3-benzodioxin-4-one,
Methyl (4-{[{4-[(4-butylphenyl)ethynyl]benzyl}(ethylsulfonyl)amino]methyl}-phenoxy)acetate,
N-{4-[(4-Butylphenyl)ethynyl]benzyl}-N-hexyl-2,2-dimethyl-4-oxo-4H-1,3-benzodioxine-6-carboxamide,
4-[(4-Butylphenyl)ethynyl]-N-[(2,2-dimethyl-4-oxo-4H-1,3-benzodioxin-6-yl)methyl]-N-hexylbenzamide,
7-[{4-[(4-Butylphenyl)ethynyl]benzyl}(hexyl)amino]-2,2-dimethyl-4H-1,3-benzodioxin-4-one,
Methyl 5-[{4-[(4-butylphenyl)ethynyl]benzyl}(hexyl)amino]-2-fluorobenzoate,
N-{2-[(4-Butylphenyl)ethynyl]benzyl}-N-hexyl-2,2-dimethyl-4-oxo-4H-1,3-benzodioxine-6-carboxamide,
4-Bromo-N-(3-cyclopentylpropyl)-N-(2,2-dimethyl-4-oxo-4H-1,3-benzodioxin-7-yl)benzamide,
N-(3-Cyclopentylpropyl)-N-(2,2-dimethyl-4-oxo-4H-1,3-benzodioxin-7-yl)-4-[(4-fluorophenyl)ethynyl]benzamide,
4-[(4-Butylphenyl)ethynyl]-N-(3-cyclopentylpropyl)-N-(2,2-dimethyl-4-oxo-4H-1,3-benzodioxin-7-yl)benzamide,
N-[(2,2-Dimethyl-4-oxo-4H-1,3-benzodioxin-6-yl)methyl]-4-[(4-fluorophenyl)-ethynyl]-N-hexylbenzamide,
4-[(4-Chlorophenyl)ethynyl]-N-[(2,2-dimethyl-4-oxo-4H-1,3-benzodioxin-6-yl)methyl]-N-hexylbenzamide,
Methyl 2-fluoro-5-{hexyl[4-(phenylethynyl)benzyl]amino}benzoate,
6-({4-[(4-Chlorophenyl)ethynyl]benzyl}(hexyl)amino)-2,2-dimethyl-4H-1,3-benzodioxin-4-one,
6-(Hexyl{4-[(4-methoxyphenyl)ethynyl]benzyl}amino)-2,2-dimethyl-4H-1,3-benzodioxin-4-one,
6-[Hexyl(4-{[4-(trifluoromethyl)phenyl]ethynyl}benzyl)amino]-2,2-dimethyl-4H-1,3-benzodioxin-4-one,
5-{[4-(4-Butyl-phenylethynyl)-benzyl]-cyclopentylmethyl-amino}-2-fluoro-benzoic acid methyl ester,
Methyl 5-[{4-[(4-butylphenyl)ethynyl]benzyl}(3,3-dimethylbutyl)amino]-2-fluorobenzoate,
6-((Cyclopentylmethyl){4-[(4-methoxyphenyl)ethynyl]benzyl}amino)-2,2-dimethyl-4H-1,3-benzodioxin-4-one,
Methyl 5-((cyclopentylmethyl){4-[(4-methoxyphenyl)ethynyl]-benzyl}amino)-2-hydroxybenzoate,
Methyl 5-({4-[(4-butylphenyl)ethynyl]benzyl}(ethyl)amino)-2-fluorobenzoate,
6-(Hexyl{4-[(4-propylphenyl)ethynyl]benzyl}amino)-2,2-dimethyl-4H-1,3-benzodioxin-4-one,
Methyl 5-(hexyl{4-[(4-propylphenyl)ethynyl]benzyl}amino)-2-hydroxybenzoate,
Methyl 5-[{4-[(4-butylphenyl)ethynyl]benzyl}(pentyl)amino]-2-fluorobenzoate,
Methyl 5-[{4-[(4-butylphenyl)ethynyl]benzyl}(methyl)amino]-2-fluorobenzoate,
Methyl 5-[{4-[(4-butylphenyl)ethynyl]benzyl}(cyclopropylmethyl)amino]-2-fluorobenzoate,
Methyl 5-{butyl[4-(phenylethynyl)benzyl]amino}-2-fluorobenzoate,
Methyl 2-fluoro-5-{[4-(phenylethynyl)benzyl](propyl)amino}benzoate,
Methyl 2-fluoro-5-[{4-[(4-fluorophenyl)ethynyl]benzyl}-(hexyl)amino]benzoate,
Methyl 2-fluoro-5-(hexyl{4-[(4-propylphenyl)ethynyl]benzyl}amino) benzoate,
Methyl 5-({4-[(4-butylphenyl)ethynyl]benzyl}{[2-(ethoxycarbonyl) cyclopropyl]methyl}amino)-2-fluorobenzoate,
Methyl 5-[{4-[(4-ethylphenyl)ethynyl]benzyl}(hexyl)amino]-2-fluorobenzoate,
Methyl 5-[{4-[(4-tert-butylphenyl)ethynyl]benzyl}(hexyl)amino]-2-fluorobenzoate,
Methyl 5-{[4-[(4-butylphenyl)ethynyl](hexyl)anilino]methyl}-2-fluorobenzoate,
N-[(2,2-Dimethyl-4-oxo-4H-1,3-benzodioxin-7-yl)methyl]-N-{4-[(4-hexylphenyl)ethynyl]phenyl}-3,3-dimethylbutanamide,
Methyl 5-[{4-[(4-butylphenyl)ethynyl]benzyl}(isobutyl)amino]-2-fluorobenzoate,
Methyl 5-{[{4-[(4-butylphenyl)ethynyl]benzyl}(hexyl)amino]carbonyl}-2-fluorobenzoate,
Methyl 5-[{4-[(4-butylphenyl)ethynyl]benzoyl}(hexyl)amino]-2-fluorobenzoate,
Methyl 5-[({4-[(4-butylphenyl)ethynyl]phenyl}sulfonyl)(hexyl)amino]-2-fluorobenzoate,
Methyl 5-{[{4-[(4-butylphenyl)ethynyl]benzoyl}(hexyl)amino]methyl}-2-fluorobenzoate,
Methyl 5-{[({4-[(4-butylphenyl)ethynyl]phenyl}sulfonyl)(hexyl)amino]methyl)-2-fluorobenzoate,
Methyl 5-{{4-[(4-butylphenyl)ethynyl]benzyl}[(propylamino)carbonyl]amino}-2-fluorobenzoate,
Methyl 5-{{4-[(4-butylphenyl)ethynyl]benzyl}[(cyclohexylamino)carbonyl]amino}-2-fluorobenzoate, and
4-[(4-Chlorophenyl)ethynyl]-N-(3-cyclopentylpropyl)-N-(2,2-dimethyl-4-oxo-4H-1,3-benzodioxin-7-yl)benzamide.

* * * * *